US012178910B2

(12) United States Patent
MacKay et al.

(10) Patent No.: US 12,178,910 B2
(45) Date of Patent: *Dec. 31, 2024

(54) REDUCING THE ENVIRONMENTAL IMPACT OF FARMING USING BIOCHAR

(71) Applicant: Carbon Technology Holdings, LLC, Oakdale, MN (US)

(72) Inventors: Juliette MacKay, Newbury Park, CA (US); Richard Wilson Belcher, Oxnard, CA (US); Wesley J. Bolsen, Parker, CO (US); Brian Buege, Centennial, CO (US); Daren Einar Daugaard, Aurora, CO (US); Han Suk Kim, Thousand Oaks, CA (US)

(73) Assignee: Carbon Technology Holdings, LLC, Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/835,900

(22) Filed: Jun. 8, 2022

(65) Prior Publication Data

US 2023/0125341 A1    Apr. 27, 2023

Related U.S. Application Data

(63) Continuation of application No. 16/059,008, filed on Aug. 8, 2018, now Pat. No. 11,426,350, which is a
(Continued)

(51) Int. Cl.
*A61K 9/16*      (2006.01)
*A01K 1/015*     (2006.01)
(Continued)

(52) U.S. Cl.
CPC ........... *A61K 9/1611* (2013.01); *A01K 1/015* (2013.01); *A23K 10/18* (2016.05); *A23K 20/10* (2016.05);
(Continued)

(58) Field of Classification Search
None
See application file for complete search history.

(56) References Cited

U.S. PATENT DOCUMENTS

| 1,369,428 A | 2/1921 | Hawley |
| 3,841,974 A | 10/1974 | Osborne |

(Continued)

FOREIGN PATENT DOCUMENTS

| CN | 1997590 | 7/2007 |
| CN | 103053244 | 4/2013 |

(Continued)

OTHER PUBLICATIONS

Ahmad et al. Biochar as a Sorbent for Contaminant Management in Soil and Water: A Review, Chemosphere, vol. 99, pp. 19-33 (Nov. 27, 2013).

(Continued)

*Primary Examiner* — Wayne A Langel
(74) *Attorney, Agent, or Firm* — Perkins Coie LLP

(57) ABSTRACT

A method for using treated biochar to reduce the overall environmental impact of farming and minimize the carbon footprint of farms is provided. The method comprising engaging in one or more of the following practices: (1) combining treated biochar with feed or using biochar as feed for animals to reduce methane from enteric fermentation and increase animal health and nutrition; (2) combining treated biochar with compost, animal bedding or manure piles to reduce odor and increase nutrient retention; (3) applying treated biochar to lagoons to reduce odor and treat water; (4) applying treated biochar to pastures to increase pasture health; (5) applying treated biochar to crops to increase crop productivity, healthier roots and prevent fertilizer leaching; and (6) using the carbon negativity of a produced biochar to reduce the overall farm or ranch carbon footprint.

20 Claims, 53 Drawing Sheets

Related U.S. Application Data continuation-in-part of application No. 15/973,191, filed on May 7, 2018, now Pat. No. 10,543,173, and a continuation of application No. 15/792,486, filed on Oct. 24, 2017, now Pat. No. 10,301,228, and a continuation-in-part of application No. 15/641,040, filed on Jul. 3, 2017, now Pat. No. 11,214,528, and a continuation-in-part of application No. 15/429,104, filed on Feb. 9, 2017, now Pat. No. 10,472,297, and a continuation-in-part of application No. 15/423,563, filed on Feb. 2, 2017, now Pat. No. 10,322,389, said application No. 15/973,191 is a continuation of application No. 15/419,976, filed on Jan. 30, 2017, now Pat. No. 9,980,912, said application No. 16/059,008 is a continuation-in-part of application No. 15/393,214, filed on Dec. 28, 2016, now Pat. No. 10,173,937, and a continuation-in-part of application No. 15/393,176, filed on Dec. 28, 2016, now Pat. No. 10,118,870, and a continuation-in-part of application No. 15/268,383, filed on Sep. 16, 2016, now Pat. No. 10,059,634, said application No. 15/792,486 is a continuation of application No. 15/156,256, filed on May 16, 2016, now Pat. No. 9,809,502, said application No. 16/059,008 is a continuation-in-part of application No. 14/873,053, filed on Oct. 1, 2015, now Pat. No. 10,252,951.

(60) Provisional application No. 62/542,528, filed on Aug. 8, 2017, provisional application No. 62/432,253, filed on Dec. 9, 2016, provisional application No. 62/357,668, filed on Jul. 1, 2016, provisional application No. 62/344,865, filed on Jun. 2, 2016, provisional application No. 62/293,160, filed on Feb. 9, 2016, provisional application No. 62/290,026, filed on Feb. 2, 2016, provisional application No. 62/290,285, filed on Feb. 2, 2016, provisional application No. 62/288,068, filed on Jan. 28, 2016, provisional application No. 62/271,486, filed on Dec. 28, 2015, provisional application No. 62/219,501, filed on Sep. 16, 2015, provisional application No. 62/162,219, filed on May 15, 2015, provisional application No. 62/058,472, filed on Oct. 1, 2014, provisional application No. 62/058,445, filed on Oct. 1, 2014.

(51) Int. Cl.
| | | |
|---|---|---|
| *A23K 10/18* | (2016.01) | |
| *A23K 20/10* | (2016.01) | |
| *A23K 20/163* | (2016.01) | |
| *A23K 20/20* | (2016.01) | |
| *A23K 40/00* | (2016.01) | |
| *A23K 40/30* | (2016.01) | |
| *A23K 50/10* | (2016.01) | |
| *A23K 50/20* | (2016.01) | |
| *A23K 50/30* | (2016.01) | |
| *A23K 50/75* | (2016.01) | |
| *A23K 50/80* | (2016.01) | |
| *A61K 9/50* | (2006.01) | |
| *A61K 33/44* | (2006.01) | |
| *A61K 47/02* | (2006.01) | |
| *A61L 9/012* | (2006.01) | |
| *A61L 9/014* | (2006.01) | |
| *C02F 1/28* | (2023.01) | |
| *C05B 17/00* | (2006.01) | |
| *C05C 5/00* | (2006.01) | |
| *C05D 9/00* | (2006.01) | |
| *C05F 3/00* | (2006.01) | |
| *C05F 17/10* | (2020.01) | |
| *C05G 3/80* | (2020.01) | |
| *C09K 17/00* | (2006.01) | |
| *C09K 17/04* | (2006.01) | |
| *A23K 20/142* | (2016.01) | |
| *A23K 20/158* | (2016.01) | |
| *A23K 20/174* | (2016.01) | |
| *A23K 20/189* | (2016.01) | |
| *A61K 9/00* | (2006.01) | |

(52) U.S. Cl.
CPC ............ *A23K 20/163* (2016.05); *A23K 20/20* (2016.05); *A23K 40/00* (2016.05); *A23K 40/30* (2016.05); *A23K 50/10* (2016.05); *A23K 50/20* (2016.05); *A23K 50/30* (2016.05); *A23K 50/75* (2016.05); *A23K 50/80* (2016.05); *A61K 9/167* (2013.01); *A61K 9/1682* (2013.01); *A61K 9/5036* (2013.01); *A61K 33/44* (2013.01); *A61K 47/02* (2013.01); *A61L 9/012* (2013.01); *A61L 9/014* (2013.01); *C02F 1/281* (2013.01); *C05B 17/00* (2013.01); *C05C 5/00* (2013.01); *C05D 9/00* (2013.01); *C05F 3/00* (2013.01); *C05F 17/10* (2020.01); *C05G 3/80* (2020.02); *C09K 17/00* (2013.01); *C09K 17/04* (2013.01); *A23K 20/142* (2016.05); *A23K 20/158* (2016.05); *A23K 20/174* (2016.05); *A23K 20/189* (2016.05); *A23K 20/30* (2016.05); *A61K 9/0056* (2013.01); *Y02P 20/145* (2015.11); *Y02W 30/40* (2015.05)

(56) References Cited

U.S. PATENT DOCUMENTS

| | | |
|---|---|---|
| 4,153,514 A | 5/1979 | Garrett et al. |
| 4,268,275 A | 5/1981 | Chittick |
| 4,383,391 A | 5/1983 | Thomas et al. |
| 4,421,524 A | 12/1983 | Chittick |
| 4,487,958 A | 12/1984 | Ream et al. |
| 4,495,165 A | 1/1985 | Gurza |
| 4,497,637 A | 2/1985 | Purdy et al. |
| 4,501,644 A | 2/1985 | Thomas |
| 4,530,702 A | 7/1985 | Fetters et al. |
| 4,618,735 A | 10/1986 | Bridle et al. |
| 4,861,351 A | 8/1989 | Nicholas |
| 4,992,480 A | 2/1991 | Mahajan et al. |
| 5,015,423 A | 5/1991 | Eguchi et al. |
| 5,032,618 A | 7/1991 | Marchionna et al. |
| 5,087,786 A | 2/1992 | Nubel et al. |
| 5,204,102 A | 4/1993 | Coles et al. |
| 5,221,290 A | 6/1993 | Dell |
| 5,462,908 A | 10/1995 | Liang et al. |
| 5,504,259 A | 4/1996 | Diebold et al. |
| 5,508,060 A | 4/1996 | Perman et al. |
| 5,756,194 A | 5/1998 | Shogren et al. |
| 5,820,640 A | 10/1998 | Ikura et al. |
| 5,857,807 A | 1/1999 | Longo, Sr. |
| 5,863,467 A | 1/1999 | Mariner et al. |
| 6,133,328 A | 10/2000 | Lightner |
| 6,227,473 B1 | 5/2001 | Arnold |
| 6,228,806 B1 | 5/2001 | Mehta |
| 6,339,031 B1 | 1/2002 | Tan |
| 6,548,026 B1 | 4/2003 | Dales et al. |
| 6,747,067 B2 | 6/2004 | Melnichuk et al. |
| 6,811,703 B2 | 11/2004 | Elliott |
| 6,841,085 B2 | 1/2005 | Werpy et al. |
| 6,923,838 B2 | 8/2005 | Maubert et al. |
| 6,946,496 B2 | 9/2005 | Mankiewicz et al. |
| 6,994,827 B2 | 2/2006 | Safir et al. |
| 7,033,972 B2 | 4/2006 | Shikada et al. |
| 7,226,566 B2 | 6/2007 | Beierle |

(56) References Cited

U.S. PATENT DOCUMENTS

| | | |
|---|---|---|
| 7,282,189 B2 | 10/2007 | Zauderer |
| 7,458,999 B2 | 12/2008 | Schenck |
| 7,596,906 B2 | 10/2009 | Gold |
| 7,846,979 B2 | 12/2010 | Rojey et al. |
| 7,888,540 B2 | 2/2011 | Deluga et al. |
| 7,947,155 B1 | 5/2011 | Green et al. |
| 8,173,044 B1 | 5/2012 | Cheiky et al. |
| 8,197,573 B2 | 6/2012 | Scharf |
| 8,236,085 B1 | 8/2012 | Cheiky et al. |
| 8,317,891 B1 | 11/2012 | Cheiky et al. |
| 8,317,892 B1 | 11/2012 | Cheiky et al. |
| 8,318,997 B2 | 11/2012 | McAlister |
| 8,361,186 B1 | 1/2013 | Shearer et al. |
| 8,430,937 B2 | 4/2013 | Cheiky et al. |
| 8,431,757 B2 | 4/2013 | Cheiky et al. |
| 8,568,493 B2 | 10/2013 | Cheiky et al. |
| 8,747,797 B2 | 6/2014 | Shearer et al. |
| 8,986,581 B2 | 3/2015 | Eddy et al. |
| 9,260,666 B2 | 2/2016 | Aelion et al. |
| 9,478,324 B1 | 10/2016 | Favetta et al. |
| 9,493,379 B2 | 11/2016 | Cheiky et al. |
| 9,527,780 B2 | 12/2016 | Wilson et al. |
| 9,809,502 B2 | 11/2017 | Bontchev et al. |
| 9,873,639 B1 | 1/2018 | Doccola et al. |
| 9,919,976 B1 | 3/2018 | Joblin, Jr. et al. |
| 9,968,911 B2 | 5/2018 | Eddy et al. |
| 9,980,912 B2 | 5/2018 | Belcher et al. |
| 10,023,503 B2 | 7/2018 | Bontchev et al. |
| 10,059,634 B2 | 8/2018 | Jarand et al. |
| 10,065,163 B2 | 9/2018 | Malyala et al. |
| 10,093,588 B2 | 10/2018 | Cheiky et al. |
| 10,118,870 B2 | 11/2018 | Bontchev et al. |
| 10,173,937 B2 | 1/2019 | Belcher et al. |
| 10,233,129 B2 | 3/2019 | Kim et al. |
| 10,252,951 B2 | 4/2019 | Bontchev et al. |
| 10,301,228 B2 | 5/2019 | Bontchev et al. |
| 10,322,389 B2 | 6/2019 | Malyala et al. |
| 10,543,173 B2 | 1/2020 | Belcher et al. |
| 10,640,429 B2 | 5/2020 | Kim |
| 10,696,603 B2 | 6/2020 | Belcher et al. |
| 10,870,608 B1 | 12/2020 | Smith et al. |
| 11,053,172 B2 | 7/2021 | Wilson et al. |
| 11,214,528 B2 | 1/2022 | Malyala et al. |
| 11,312,666 B2 | 4/2022 | Belcher et al. |
| 11,384,031 B2 | 7/2022 | Belcher et al. |
| 11,426,350 B1 * | 8/2022 | MacKay ............ C05F 3/00 |
| 2002/0012725 A1 | 1/2002 | Carlson |
| 2003/0119552 A1 | 6/2003 | Laumen et al. |
| 2004/0111968 A1 | 6/2004 | Day et al. |
| 2004/0128909 A1 | 7/2004 | Smiley |
| 2006/0225345 A1 | 10/2006 | Westrate et al. |
| 2007/0123420 A1 | 5/2007 | Hayashi et al. |
| 2007/0287068 A1 | 12/2007 | Shimizu et al. |
| 2008/0003166 A1 | 1/2008 | Maletin et al. |
| 2008/0006519 A1 | 1/2008 | Badger |
| 2008/0016769 A1 | 1/2008 | Pearson |
| 2008/0047313 A1 | 2/2008 | Johnson et al. |
| 2008/0093209 A1 | 4/2008 | Noto |
| 2008/0216391 A1 | 9/2008 | Cortright et al. |
| 2008/0223269 A1 | 9/2008 | Paoluccio |
| 2008/0300435 A1 | 12/2008 | Cortright et al. |
| 2008/0317657 A1 | 12/2008 | Hall et al. |
| 2008/0317907 A1 | 12/2008 | Thomas et al. |
| 2009/0007484 A1 | 1/2009 | Smith |
| 2009/0081292 A1 | 3/2009 | Otomo et al. |
| 2009/0126433 A1 | 5/2009 | Piskorz et al. |
| 2009/0139139 A1 | 6/2009 | Tilman et al. |
| 2009/0151251 A1 | 6/2009 | Manzer et al. |
| 2009/0183430 A1 | 7/2009 | Schubert et al. |
| 2009/0196816 A1 | 8/2009 | Yamamoto et al. |
| 2009/0217575 A1 | 9/2009 | Raman et al. |
| 2009/0217584 A1 | 9/2009 | Raman et al. |
| 2009/0253947 A1 | 10/2009 | Brandvold et al. |
| 2009/0308787 A1 | 12/2009 | O'Connor et al. |
| 2010/0040510 A1 | 2/2010 | Randhava et al. |
| 2010/0162780 A1 | 7/2010 | Scharf |
| 2010/0180805 A1 | 7/2010 | Cheiky et al. |
| 2010/0218417 A1 | 9/2010 | Bauldreay et al. |
| 2010/0223839 A1 | 9/2010 | Garcia-Perez et al. |
| 2010/0236309 A1 | 9/2010 | Celia |
| 2010/0236987 A1 | 9/2010 | Kreis |
| 2010/0240900 A1 | 9/2010 | Zhang |
| 2010/0257775 A1 | 10/2010 | Cheiky |
| 2010/0270505 A1 | 10/2010 | Gallaspy et al. |
| 2010/0300866 A1 | 12/2010 | van Aardt et al. |
| 2010/0310447 A1 | 12/2010 | Yaniv et al. |
| 2010/0311157 A1 | 12/2010 | Van Alstyne et al. |
| 2011/0003693 A1 | 1/2011 | Spittle |
| 2011/0023566 A1 | 2/2011 | Lodwig et al. |
| 2011/0081336 A1 | 4/2011 | Medoff |
| 2011/0092726 A1 | 4/2011 | Clarke |
| 2011/0100359 A1 | 5/2011 | North |
| 2011/0172092 A1 | 7/2011 | Lee et al. |
| 2011/0177466 A1 | 7/2011 | Cheiky |
| 2011/0209386 A1 | 9/2011 | Cheiky et al. |
| 2011/0212004 A1 | 9/2011 | Cheiky et al. |
| 2011/0258912 A1 | 10/2011 | O'Connor et al. |
| 2012/0103040 A1 | 5/2012 | Wolf et al. |
| 2012/0125064 A1 | 5/2012 | Joseph et al. |
| 2012/0208254 A1 | 8/2012 | Smith et al. |
| 2012/0220454 A1 | 8/2012 | Chen et al. |
| 2012/0237994 A1 | 9/2012 | Das et al. |
| 2012/0283493 A1 | 11/2012 | Olson et al. |
| 2012/0286209 A1 | 11/2012 | Cheiky et al. |
| 2012/0304718 A1 | 12/2012 | Cheiky et al. |
| 2012/0304719 A1 | 12/2012 | Cheiky et al. |
| 2013/0025188 A1 | 1/2013 | Cheiky et al. |
| 2013/0025190 A1 | 1/2013 | Cheiky et al. |
| 2013/0055635 A1 | 3/2013 | Harman |
| 2013/0123103 A1 | 5/2013 | Anderson et al. |
| 2013/0211158 A1 | 8/2013 | Romanos et al. |
| 2013/0213101 A1 | 8/2013 | Shearer et al. |
| 2014/0016709 A1 | 1/2014 | Ko et al. |
| 2014/0024528 A1 | 1/2014 | Smith et al. |
| 2014/0030250 A1 | 1/2014 | Eddy et al. |
| 2014/0037536 A1 | 2/2014 | Reimerink-Schats et al. |
| 2014/0161709 A1 | 6/2014 | Karthikeyan |
| 2014/0177136 A1 | 6/2014 | Kim et al. |
| 2014/0295161 A1 | 10/2014 | MacLachlan et al. |
| 2014/0345341 A1 | 11/2014 | Fiato et al. |
| 2014/0345343 A1 | 11/2014 | Wilson et al. |
| 2014/0349847 A1 | 11/2014 | Schrader |
| 2014/0352378 A1 | 12/2014 | Shearer et al. |
| 2015/0040624 A1 | 2/2015 | Devine et al. |
| 2015/0101372 A1 | 4/2015 | Cheiky et al. |
| 2015/0128672 A1 | 5/2015 | Shearer et al. |
| 2015/0144564 A1 | 5/2015 | Moller et al. |
| 2015/0155549 A1 | 6/2015 | Moganty et al. |
| 2015/0157661 A1 | 6/2015 | Eddy et al. |
| 2015/0203414 A1 | 7/2015 | Cook |
| 2015/0232349 A1 | 8/2015 | Peltz |
| 2015/0361369 A1 | 12/2015 | Tait et al. |
| 2016/0023959 A1 | 1/2016 | Bontchev et al. |
| 2016/0096746 A1 | 4/2016 | Feng |
| 2016/0100587 A1 | 4/2016 | Bywater-Ekegard et al. |
| 2016/0101990 A1 | 4/2016 | Traxler et al. |
| 2016/0102024 A1 | 4/2016 | Schrader et al. |
| 2016/0229709 A1 | 8/2016 | Beierwaltes et al. |
| 2016/0238317 A1 | 8/2016 | Heimann et al. |
| 2016/0362607 A1 | 12/2016 | Weaver et al. |
| 2016/0368831 A1 | 12/2016 | Bontchev et al. |
| 2017/0008769 A1 | 1/2017 | Otter et al. |
| 2017/0173562 A1 | 6/2017 | Dimiev |
| 2017/0334797 A1 | 11/2017 | Belcher et al. |
| 2019/0256431 A1 | 8/2019 | Zaseybida et al. |

FOREIGN PATENT DOCUMENTS

| | | |
|---|---|---|
| GB | 2479469 | 10/2011 |
| KR | 100819505 | 4/2008 |
| WO | WO 82/04223 | 12/1982 |
| WO | WO 89/09809 | 10/1989 |
| WO | WO 2004/037747 | 5/2004 |
| WO | WO 2005/030641 | 4/2005 |

(56) References Cited

FOREIGN PATENT DOCUMENTS

| | | |
|---|---|---|
| WO | WO 2008/058231 | 5/2008 |
| WO | WO 2009/004652 | 1/2009 |
| WO | WO 2010/084230 | 7/2010 |
| WO | WO 2010/129988 | 11/2010 |
| WO | WO 2011/006717 | 1/2011 |
| WO | WO 2011/014916 | 2/2011 |
| WO | WO 2011/019871 | 2/2011 |
| WO | WO 2011/097183 | 8/2011 |
| WO | WO 2011/143380 | 11/2011 |
| WO | WO 2011/143718 | 11/2011 |
| WO | WO 2011/159154 | 12/2011 |
| WO | WO 2012/094736 | 7/2012 |
| WO | WO 2014/060508 | 4/2014 |
| WO | WO 2014/091279 | 6/2014 |
| WO | WO 2014/146205 | 9/2014 |
| WO | WO 2015/055729 | 4/2015 |
| WO | WO 2016/054431 | 4/2016 |
| WO | WO 2016/187161 | 11/2016 |

OTHER PUBLICATIONS

Beesley et al., "A review of Biochars? Potential Role in the Remediation, Revegetation and Restoration of Contaminated Soils," Environmental Pollution 159, pp. 3269-3282 (Jul. 23, 2011).
Berek et al., "Improving Soil Productivity with Biochar," ICGAI, Yogyakarta, Indonesia, 23 pgs. (Nov. 11-14, 2013).
Biliaderis et al., "Functional Food Carbohydrates," CRC Press 2006, Ch. 16, pp. 517-518.
Bucheli et al., "Polycyclic Aromatic Hydrocarbons and Polychlorinated Aromatic Compounds in Biochar," Biochar for Environmental Management, Ch 21, pp. 595-622 (Jan. 2015).
Buerschaper, R. et al., "Thermal & Electrical Conductivity of Graphite & Carbon at Low Temperatures," Jour. of App. Physics, pp. 452-454 (1944).
Cheng et al., "Stability of Black Carbon in Soils Across a Climatic Gradient," Jour. of Geophysical Research Biogeosciences, vol. 113, G02027, pp. 1-10 (2008).
Chew, T.L. and Bhatia, S., "Catalytic Processes Towards the Production of Biofuelsin in a Palm Oail and Oil Palm Biomass-based biorefinery," Bioresource Tech., vol. 99, pp. 7911-8922 (2008).
Demirbas, A., "Effects of Temperature & Particle Size on Bio-Char Yield from Pyrolysis of Agricultural Residues," J. Anal. Pyrolysis, vol. 72, pp. 243-248 (2004).
Downie: Biochar Production and Use: Environmental Risks and Rewards: PhD Thesis: The University of New South Wales; Sydney, Australia, p. 1-16, p. 155-168 (2011).
Elliott, D.C. and Neuenschwander, G.G., "Liquid Fuels by Low-Severity Hydrotreating of Biocrude," Dev. in Thermochemical Biomass Conversion, vol. 1, pp. 611-621 (1996).
EPO; Supplementary European Search Report; May 17, 2018; 8 pages.
Extended European Search Report issued by the European Patent Office for European Patent Application No. 12797129.9 dated Mar. 6, 2015 (7 pgs).
Extended European Search Report issued by the European Patent Office for European Patent Application No. 12817137.8 dated Jul. 13, 2015 (8 pgs).
Faludi, J., "World Changing Change Your Thinking a Carbon-Negative Fuel," Oct. 16, 2007; www.worldchanging.com (9 pgs).
Gehrer R. and Hayek, K., "A Fully Programmable System for the Study of Catalytic Gas Reactions," J. Physc. E: Sci. Instrum., vol. 18, pp. 836-838 (1985).
Gray et al., "Water uptake in Biochars: The Roles of Porosity and Hydrophobicity; Biomass and Bioenergy," Vo. 6, No. 1, pp. 196-205 (Jan. 23, 2014).
Greenfacts, "Facts on Health and the Environment," Dioxins, Apr. 13, 2017, 3 pp.; retrieved from https://www.greenfacts.org/en/d on Aug. 15, 2004.
Hadjittofi et al., "Activated Biochar Derived from Cactus Fibres—Preparation, Characterization and Application on CU(II) Removal from Aqueous Solutions," Bioresource Technology, vol. 159, pp. 460-464 (May 2014).
Hua et al., "Impacts Upon Soil Quality and Plant Growth of Bamboo Charcoal Addition to Composted Sludge," Environmental Technology, vol. 33, No. 1, pp. 61-68 (Jan. 18, 2012).
Innovation Fluides Supercritiques, Explore, Use, Make the Most of Supercritical Fluids, Nov. 27, 2015. Online, retrieved from the Internet on Mar. 6, 2017; <http://web/20151127045828/http://www.supercriticalfluid.org/supercritical-fluids.146.0>html; 2 pp.
Jindo et al., "Biochar Influences the Microbial Community Structure During Manure Composting with Agricultural Wastes," Science of the Total Environment, vol. 416, pp. 476-481 (Feb. 2012).
Karmaker et al., "Plant Defence Activators Inducing Systematic Resistance in Zingiber Officinale Rosc. Against Pythium Aphanidermatum (Edson) Fitz.," Indian Journal of Biotechnology, vol. 2, pp. 591-595 (2003).
Kim et al., "Characteristics of Crosslinked Potato Starch & Starch-Filled Linear Low-Density Polyethylene Films," Carbohydrate Polymers, vol. 50, pp. 331-337 (2002).
Kolton et al., "Impact of Biochar Applications to Soil on the Root-Associated Bacterial Community Structure of Fully Developed Greenhouse Pepper Plants," Appl. Env. Micro., pp. 4924-4930, Abstract (Jul. 2011).
Laird, D., "The Charcoal Vision: A Win Win Scenario," Agron, J., vol. 100, No. 1, pp. 178-181 (2008).
Lashari, et al., "Effect of Amendment of Biochar-manure Compost in Conjunction with Pryroligneous Solution on Soil Quality and Wheat Yield of a salt-stressed Cropland from Central China Great Plain," Field Crops Research, vol. 144, pp. 113-118 (Mar. 20, 2013).
Lehmann, J., "Nutrient Avail. & Leaching in an Archaeological Anthrosol & Ferraisol of the Central Amazon Basin: Fertilizer, Manure and Charcoal Amendments," Plant Soil, vol. 249, pp. 343-357 (2003).
Lima et al., "Physiochemical and Adsorption Properties of Fast-Pyrolysis Bio Chars and their Steam Activated Counterparts," J. Chem. Tech. Biotechnical, vol. 85, pp. 1515-1521 (2010).
Liu et al., "An Experimental Study of Rheological Properties and Stability Characteristics of Biochar-Glycerol-Water Slurry Fuels," Fuel Processing Technology, vol. 153, Issue 1, pp. 37-42 (Aug. 5, 2016).
Matthews, J.A., "Carbon-negative Biofuels," Energy Policy, vol. 36, pp. 940-945 (2008).
McHenry, Mark P., "Agricultural Bio-char Production, Renewable Energy Generation and Farm Carbon Sequestration in Western Australia: Certainty, Uncertainty and Risk," Agriculture, Ecosystems and Environments, vol. 129, pp. 1-7 (2009).
Mohan et al., "Pyrolysis of Wood/Biomass for Bio-Oil: A Critical Review," Energy & Fuels, vol. 20, pp. 848-889 (2006).
Norman et al., "Best Management Practices for Reclaiming Surface Mines in Washington and Oregon," Open-File Report 0-92-2, revised Dec. 1997; www.oregongeology.org Feb. 9, 2010 (128 pgs).
Ogawa et al., "Carbon Sequestration by Carbonization of Biomass and Forestation: Three Case Studies," Mitigation and Adaptation Strategies for Global Change (2006) 11:429-444; 16 pp.
Oh et al., "Utilization of Biochar Impregnated with Anaerobically Digested Slurry as Slow-Release Fertilizer," Journal of Plant Nutrition and Soil Science, vol. 177, Issue 1, pp. 97-103 (Feb. 2014).
Omata et al., "Optimization of Cu Oxide Catalyst for Methanol Synthesis under High C02 Partial Pressure Using Combinatorial Tools," App. Catalyst A: General, vol. 262, pp. 207-214 (2004).
Preston, C.M. et al., "Black (Pyrogenic) Carbon; a Synthesis of Current Knowledge & Uncertainties with Special Consideration of Boreal Regions," Biogeosciences, vol. 3 pp. 397-420 (2006).
Rosenberg et al., "More on Commercial Carbon Resistors as Low Pressure Gauges," Intl. Jour of Impat. Engl, vol. 34, pp. 732-742 (2007).
Schmidt et al., "Biochar and Biochar-compost as Soil Amendments to a Vineyard Soil: Influence on Plant Growth Nutrient Update, Plant Health and Grape Equality," Agricuture, Ecosystems and Environment, vol. 191, Issue 15, pp. 117-123 (Jun. 2014).
Sharma, R.K. and Bakhshi, N.N., "Catalytic Upgrading of Pyrolysis Oil," Energy & Fuels, vol. 7, pp. 306-314 (1993).

(56) References Cited

OTHER PUBLICATIONS

Shivaram et al., "Flow and Yield Behavior of Ultrafine Mallee Biochar Slurry Fuels: The Effect of Particle Size Distribution and Additives," 10th Japan/China Symposium on Coal and C1 Chemistry, vol. 104, pp. 326-332 (Feb. 2013).

Sorrenti, G. (Doctoral Thesis): "Biochar in Perennial Crops: Nutritional, Agronomical and Environmental Implications," University of Bologna, Abstract, Chs. 4, 5, 7, p. 101 Table 4.2 (Mar. 1, 2015).

Takeishi, K., "Dimethy Ether & Catalyst Development for Production of Syngas," Biofuels, vol. 1(1), pp. 217-226 (2010).

Tryon, E.H., "Effect of Charcoal on Certain Physical, Chemical, & Biological Properties of Forest Soils," Ecological Monographs, vol. 18, No. 1, pp. 81-115 (Jan. 1948).

Wikipedia; Bacillus Thuringiensis; Dec. 27, 2015; online, retrieved from the Internet on Mar. 6, 2017; <https://en/wikipedia.org/w/index.php?title=bacillus+thuringiensis&oldid=69697011>; 6 pp.

Xusheng, et al., "Implications of Production and Agricultural Utilization of Biochar and its International Dynamic," Transaction of the CSAE, vol. 27, No. 2, 7 pgs. (2011) with English Abstract.

\* cited by examiner

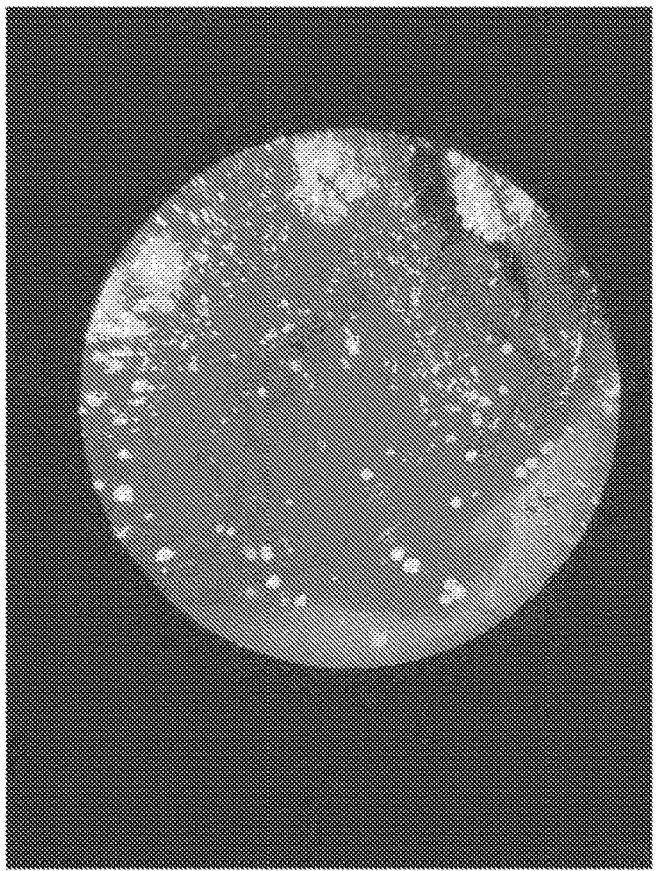
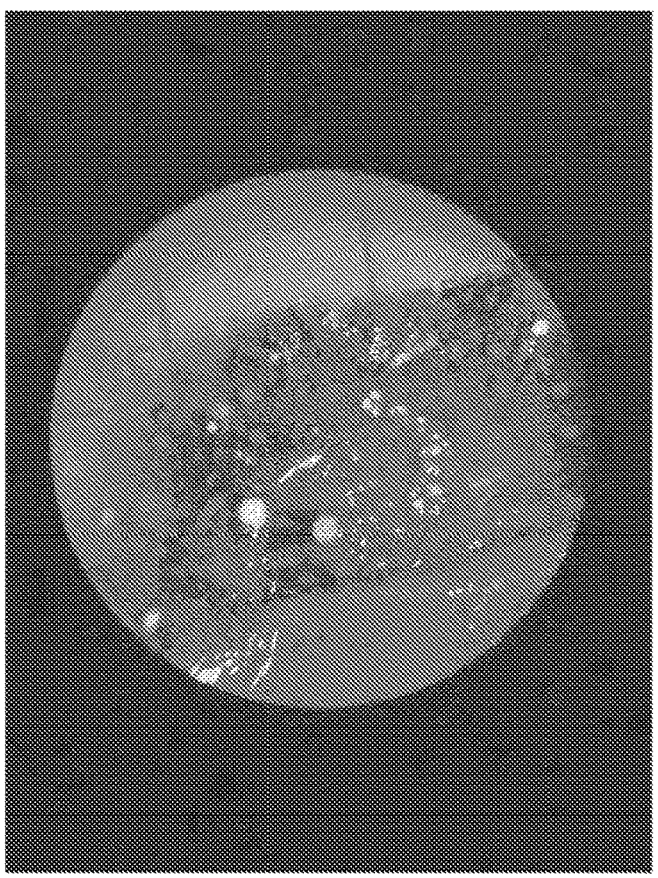
FIG. 27

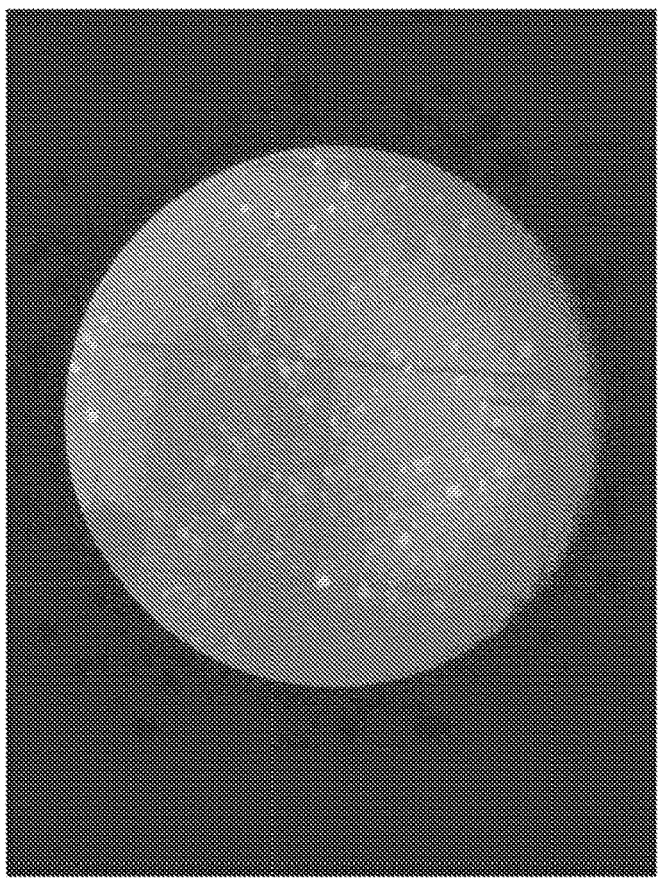
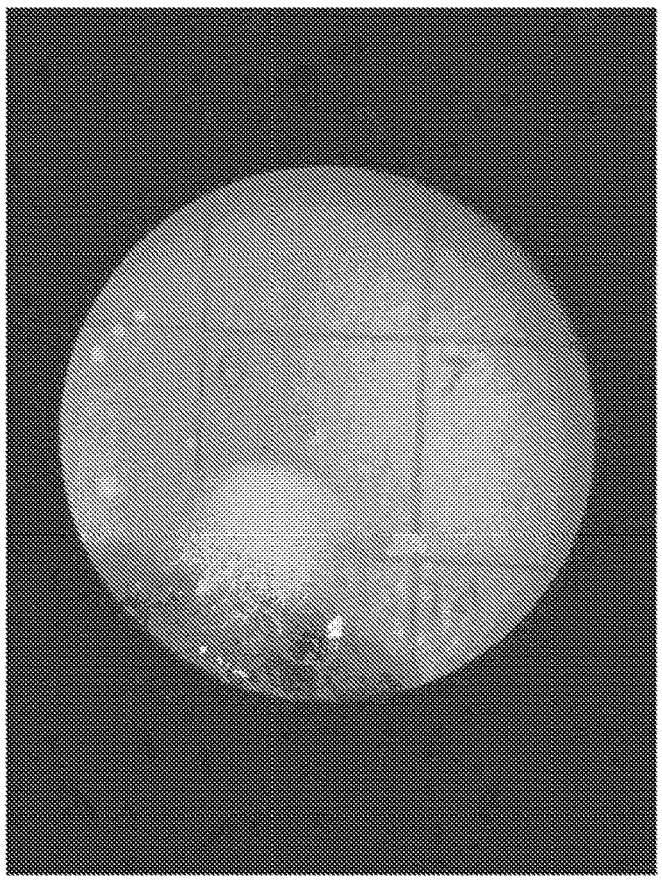
FIG. 28

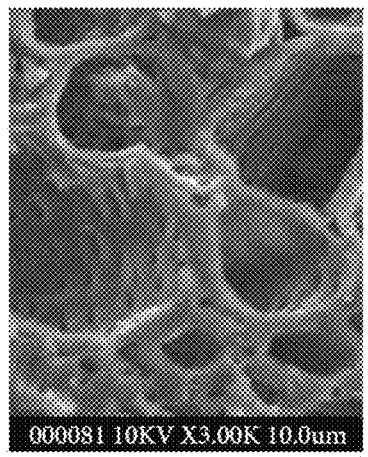 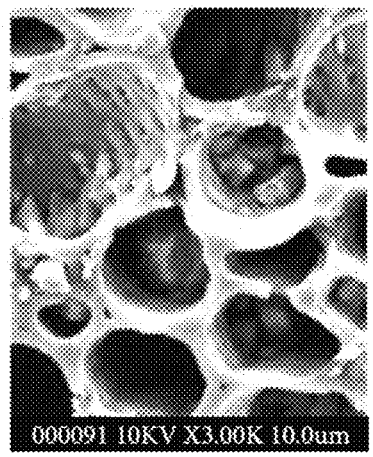 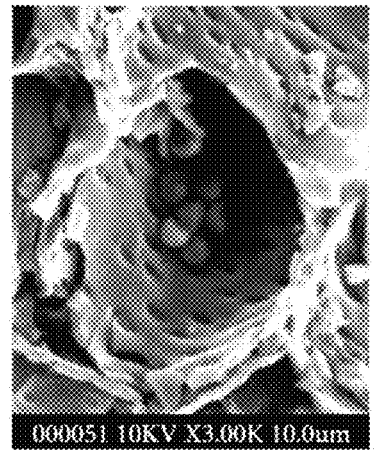
*FIG. 38A*  *FIG. 38B*  *FIG. 38C*

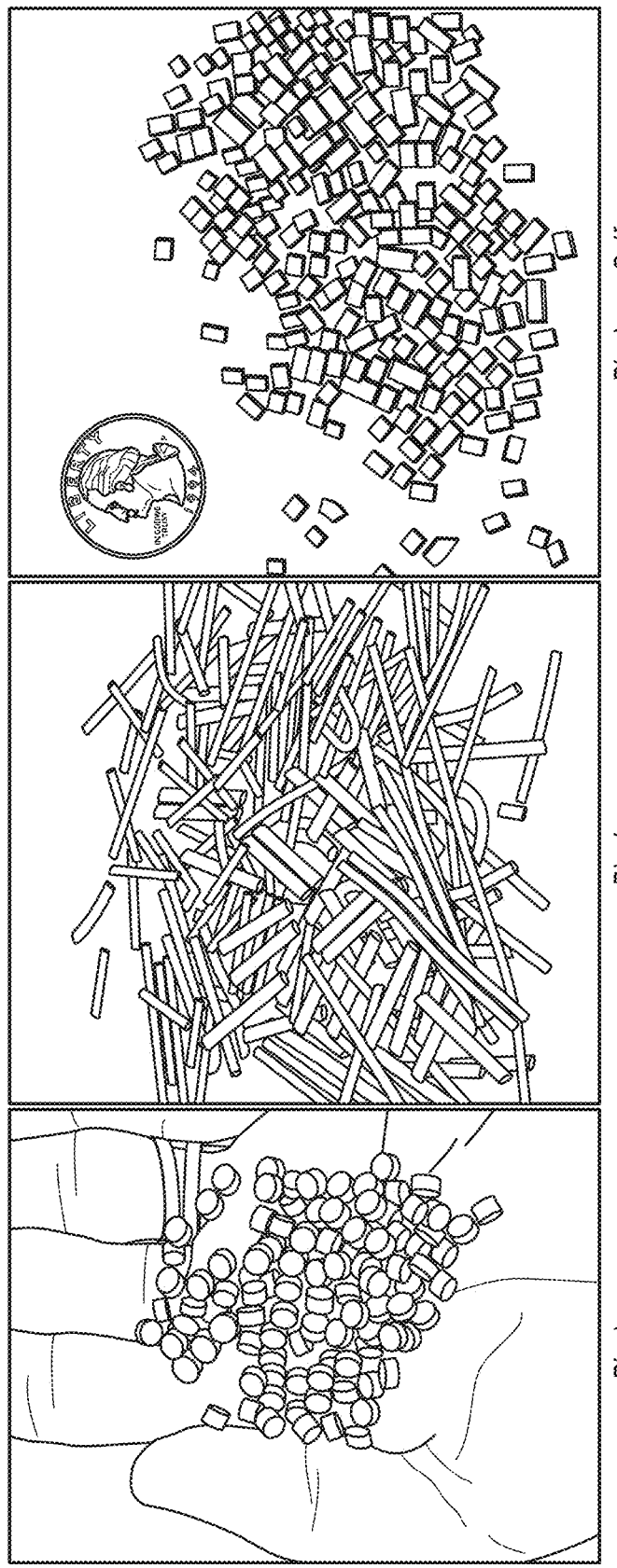
FIG. 39A  Biochar Pellets
FIG. 39B  Biochar Extrudates
FIG. 39C  Biochar + Sulfur Prills <0.05 mm 0.05-0.1 mm 0.1-0.3 mm Sieved Ground and Sieved

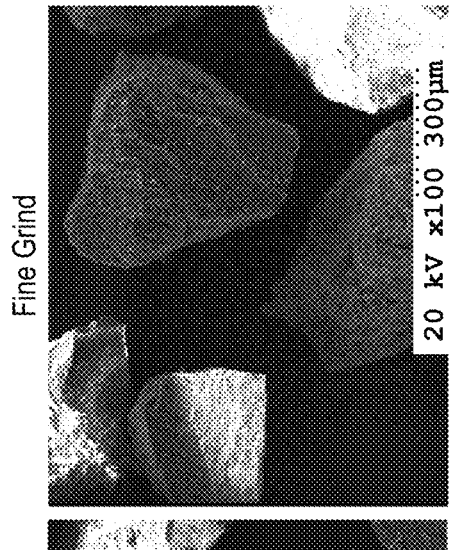
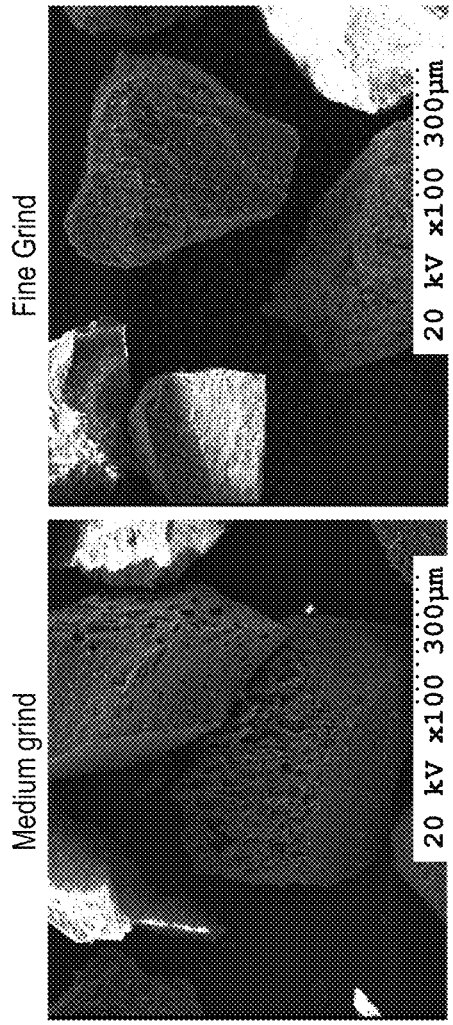
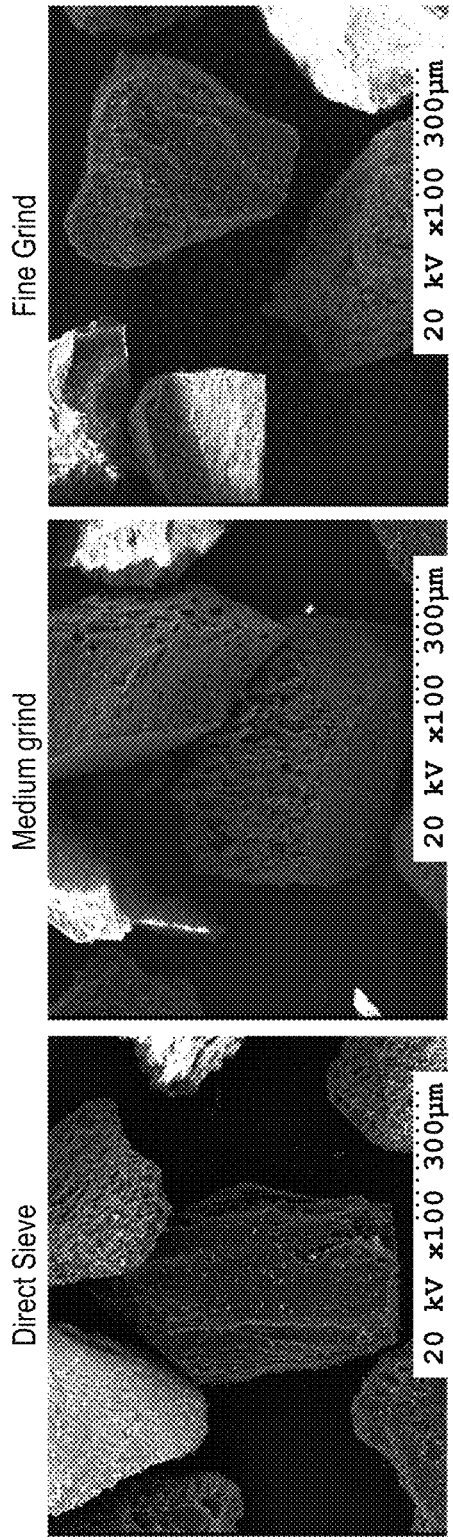
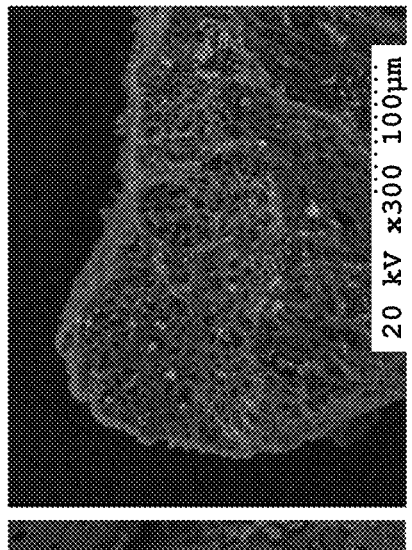
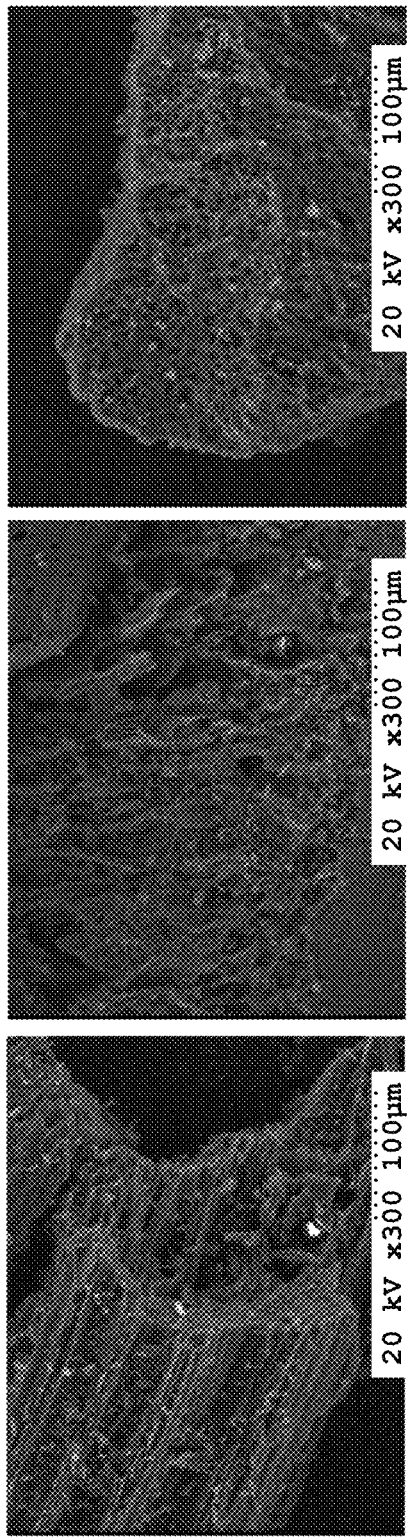
FIG. 42A  FIG. 42B  FIG. 42C  FIG. 42D  FIG. 42E  FIG. 42F

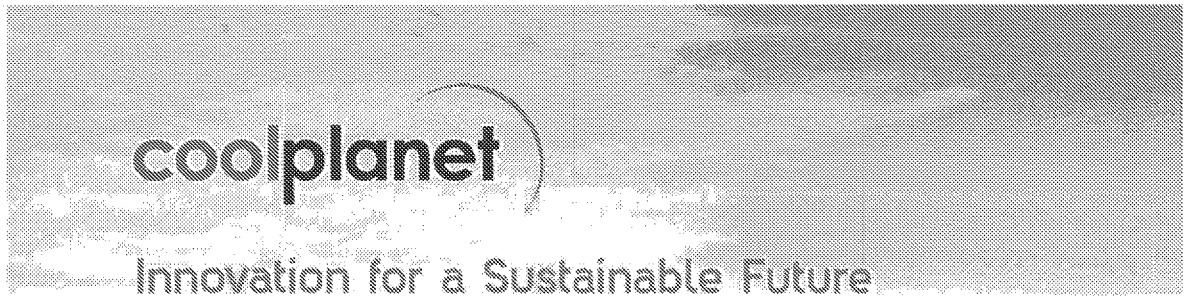

Cool Planet + Sustainability

Cool Planet provides an engineered biocarbon platform that significantly improves soil health while sequestering carbon. The result is more sustainable agriculture production practices and a healthier planet, feeding more people with higher grower profitability.

At Cool Planet, our products are designed with these sustainable agriculture practices in mind:

- Sequestering carbon
- Reducing fertilizer runoff
- Optimizing water efficiency
- Nurturing microbial life
- Improving soil health

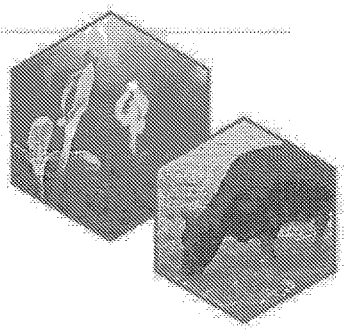

Produced with sustainability in mind, Cool Terra is a durable, porous, organic material that helps:

- Sequester carbon from the atmosphere
- Improve fertilizer efficiency by reducing leaching and run off
- Reduce water use in drought prone regions
- Reduce odor and retain nutrients in manure
- Increase plant growth and productivity
- Put plantation-grown biomass to its best use

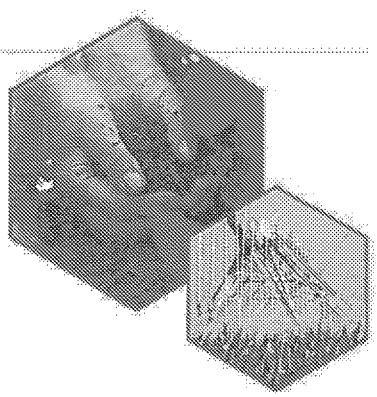

Cool Planet + Soil Health

The USDA defines soil as a vital, living ecosystem that sustains plants, animals and humans. By helping increase the health of soil, Cool Terra can promote a diverse soil microbiome that results in fewer plant stressors and diseases, enhances plant growth and increases yield potential.

FIG. 50a

Learn more at ...planet.com

% Removal of Initial Metal Concentrations in SPLP Extract of Missouri Mine Soil After 24 Hour Contact with Treated Biochar Formulations

| | Mean Metal Concentrations (mg/L) | | |
|---|---|---|---|
| | Cadmium | Copper | Zinc |
| Initial Missouri Mine Soil SPLP Solution | 0.20 | 0.02 | 6.63 |

| Biochar | % Cd Removal | % Cu Removal | % Zn Removal |
|---|---|---|---|
| Formulation #1 | 96.08 | 100.00 | 93.57 |
| Formulation #2 | 92.52 | 100.00 | 86.20 |
| Formulation #3 | 99.64 | 100.00 | 99.69 |

FIG. 51

REDUCING THE ENVIRONMENTAL IMPACT OF FARMING USING BIOCHAR

CROSS-REFERENCE TO RELATED APPLICATIONS

This application is a continuation of U.S. patent application Ser. No. 16/059,008, filed Aug. 8, 2018, which claims priority to U.S. Provisional Patent Application Ser. No. 62/542,528, filed Aug. 8, 2017; is a continuation-in-part of U.S. patent application Ser. No. 15/973,191, filed May 7 (now U.S. Pat. No. 10,543,173), which is a continuation of U.S. patent application Ser. No. 15/419,976 filed on Jan. 30, 2017 (now U.S. Pat. No. 9,980,912), which claims priority to U.S. Provisional Patent Application Ser. No. 62/288,068, filed Jan. 28, 2016; is a continuation-in-part of U.S. patent application Ser. No. 15/429,104, filed on Feb. 9, 2017 (now U.S. Pat. No. 10,472,297), which claims priority to U.S. Provisional Patent Application Ser. No. 62/293,160, filed on Feb. 9, 2016 and U.S. Provisional Patent Application Ser. No. 62/344,865, filed on Jun. 2, 2016; is a continuation-in-part of U.S. patent application Ser. No. 15/393,176, filed on Dec. 30, 2016, which claims priority to U.S. Provisional Patent Application Ser. No. 62/271,486, filed on Dec. 28, 2015, U.S. Provisional Patent Application Ser. No. 62/290,285, filed on Feb. 2, 2016, and U.S. Provisional Patent Application Ser. No. 62/344,865 filed on Jun. 2, 2016; is a continuation-in-part of U.S. patent application Ser. No. 15/641,040, filed Jul. 3, 2017 (now U.S. Pat. No. 11,214,528), which claims priority to U.S. Provisional Patent Application Ser. No. 62/357,668 filed Jul. 1, 2016 and U.S. Provisional Patent Application Ser. No. 62/432,253 filed on Dec. 9, 2016; is a continuation-in-part of U.S. patent application Ser. No. 15/423,563, filed Feb. 2, 2017 (now U.S. Pat. No. 10,322,389), which claims priority to U.S. Provisional Patent Application Ser. No. 62/290,026, filed on Feb. 2, 2016, U.S. Provisional Patent Application Ser. No. 62/293,160, filed on Feb. 9, 2016; is also a continuation-in-part of U.S. patent application Ser. No. 15/393,214, filed on Dec. 28, 2016 (now U.S. Pat. No. 10,173,937), which claims priority to U.S. Provisional Patent Application Ser. No. 62/271,486, filed on Dec. 28, 2015, U.S. Provisional Patent Application Ser. No. 62/290,285, filed on Feb. 2, 2016, U.S. Provisional Patent Application Ser. No. 62/344,865, filed on Jun. 2, 2016 and U.S. Provisional Patent Application Ser. No. 62/432,253 filed on Dec. 9, 2016; is also a continuation-in-part of U.S. patent application Ser. No. 15/268,383, filed on Sep. 16, 2016 (now U.S. Pat. No. 10,059,634), which claims priority to U.S. Provisional Patent Application Ser. No. 62/219,501 filed Sep. 16, 2015 and U.S. Provisional Patent Application Ser. No. 62/290,026 filed on Feb. 2, 2016; this application is also a continuation-in-part of U.S. patent application Ser. No. 15/792,486 filed Oct. 24, 2017 (now U.S. Pat. No. 10,301,228), which is a continuation of U.S. patent application Ser. No. 15/156,256, filed on May 16, 2016 (now U.S. Pat. No. 9,809,502), which claims priority to U.S. Provisional Patent Application No. 62/162,219, filed on May 15, 2015; and this application is also a continuation-in-part of U.S. patent application Ser. No. 14/873,053 filed on Oct. 1, 2015 (now U.S. Pat. No. 10,252,951), which claims priority to U.S. Provisional Patent Application No. 62/058,445, filed on Oct. 1, 2014 and U.S. Provisional Patent Application No. 62/058,472, filed on Oct. 1, 2014, all of the above of which are incorporated by reference herein in their entirety.

FIELD OF THE INVENTION

The present invention relates to the use of biochar and, in particular, treated and/or processed biochar having enhanced physical and chemical properties that increase the usefulness, predictability and efficacy of the treated biochar, in order to reduce the environmental impact of farming.

BACKGROUND

Biochar has been known for many years as a soil enhancer. Biochar is defined by the International Biochar Initiative ("IBI") as "a solid material obtained from thermochemical conversion of biomass in an oxygen-limited environment. Biochar can be used for a range of applications as an agent for soil improvement, improved resource use efficiency, remediation and/or protection against particular environmental pollution and as an avenue for greenhouse gas (GHG) mitigation. In addition, to be recognized as biochar, the material has to pass a number of material property definitions that relate both to its value (e.g., $H/C_{org}$ ratios relate to the degree of charring and therefore mineralization in soil) and its safety (e.g., heavy metal content)."

Biochar is defined by the American Association of Plant Food Control Officials ("AAPFCO") as "a solid material obtained from thermochemical conversion of biomass in an oxygen-limited environment (pyrolysis) containing at least 60% carbon. Feedstocks may be composed of crop residue, wood or other forest waste, and animal manures. Materials transported in salt water, painted, or treated with preservatives are not permitted. When listing biochar in an ingredient statement, the feedstock shall be designated by prefixing the term biochar with the feedstock from which it was produced; i.e. poultry litter biochar, green waste biochar, papermill biochar, etc. When more than one feedstock is involved, all feedstocks greater than 10% of the total volume are to be listed by decreasing volume."

Biochar is created by the pyrolysis of biomass, which generally involves heating and/or burning of organic matter, in a reduced oxygen environment, at a predetermined rate. Such heating and/or burning is stopped when the matter reaches a charcoal-like stage. The resulting biochar consists of various pieces of residual solid material full of crevices, pores and holes that help store water, microorganisms and other nutrients that promote plant growth. For purposes of this application, the resulting pyrolyzed biomass will be referred to as "raw or untreated biochar."

Raw biochar, while known for its soil enhancing characteristics, does not always benefit soil and, depending upon the biomass from which the biochar is produced, could potentially be harmful to the soil, making it unsuitable for various types of crops or other productive uses. In particular, biochar can be detrimental, or even toxic, to 1) soil microbes involved in nutrient transport to the plant; 2) plants and 3) humans. Raw biochars derived from different biomass will have different physical and chemical properties and will behave quite differently. For example, raw biochar having pH levels too high, containing too much ash, too much of other inorganic materials which can cause toxicity at elevated levels, or containing toxins or heavy metal content too high can be harmful and/or have minimal benefit to the soil and the plant life it supports. Raw biochar can also contain unacceptable levels of residual organic compounds such as acids, esters, ethers, ketones, alcohols, sugars, phenyls, alkanes, alkenes, phenols, polychlorinated biphenyls or poly or mono aromatic hydrocarbons which are either toxic or not beneficial to plant or animal life.

While some attention has been focused on the use of raw biochar in conjunction with controlling and regulating the growth of plants and vegetation, e.g., crops, the commercial and widespread adoption of biochar as a soil amendment or for other agricultural purposes has not occurred. There are several reasons for these failures. As described above, biochar may be derived from varied and different sources. As a result, these materials have very inconsistent and unpredictable properties. These inconsistencies and lack of predictability make their use difficult and in many cases problematic. Jeffery et al. in *Agriculture, Ecosystems, and Environment* (2011) ("Jeffery") compiled the results from several biochar field trials from around the globe. The trials show at best a modest improvement with biochar applications and the application rates required to achieve these modest results is significant. (See Jeffery, at page 175 and FIG. 1). Even more recently, Spokas et al. published *Biochar: A Synthesis of Its Agronomic Impact beyond Carbon Sequestration*, in the Journal of Environmental Quality (July 2012), which demonstrated the how untreated biochar may yield vastly different economic and agronomic results when added to soil, from strongly positive to strongly negative. See, also, Buss et al., *Inherent organic compounds in biochar—Their content, composition and potential toxic effects*, Journal of Environmental Management 156 (2015).

In Lehmann, et al, *Biochar for Environmental Management* (2006)("Lehmann") a pioneer researcher, Lehmann, is quoted about biochar that " . . . variability is high and it is not yet clear under what soil and climatic conditions high or low yields can be expected." (Lehmann, Chp. 12, at page 207). It is believed that these inconsistencies and lackluster outcomes are common among biochar work. Since most cannot produce biochar with predictable properties and outcomes, the use of these materials, e.g., biochar, can have limited, sporadic or little to no beneficial effect. In certain cases, the use may be problematic and detrimental, e.g., lower crop yield, and in some situations, increased mortality rate and/or death of the crops.

Currently, biochar has mostly been a scientific curiosity, not found wide spread use, not found large scale commercial application, and has been relegated to small niche applications. Prior to the present inventions, biochar having predictable, controllable, and beneficial results have not been obtained, thereby prohibiting large scale applications. In general, the art has focused on the failings, and problems, of biochars by attempting to better select or sort the starting material or to refine the pyrolysis or other processes used to make the untreated biochar, without identifying, controlling, or enhancing the properties of a biochar that make it effective. Typically, these attempts were done with the hope that increased process control, material selection and refinements would overcome the unpredictable nature, inconsistencies, and harmful effects found with existing biochars. It is believed that these attempts have been to a lesser or greater extent failures. A need remains for producing biochars that can be used in large scale applications and that have certain generally sustainable, controllable and/or particular physical and chemical properties known to have the highest positive impact on soils, to counteract or ameliorate the impact of toxic or noxious substances in the environment or for other beneficial uses, including the present invention.

Additionally, since it is typically derived from organic plant matter, and because much of the carbon contained in biochar is fixed carbon, biochar has been recognized by the World Bank and others as a major form of agricultural carbon sequestration. The potential to impact plant and animal systems, while reducing waterborne pollutants and sequestering atmospheric carbon is timely, significant, and relevant to many of the pressing environmental issues facing both agriculture and modern civilization.

In particular, the large and ever growing industries based upon large-scale farming, both for crops and for the breeding, maintenance, care, feeding and treatment of animals, particularly livestock (i.e. dairy and beef cattle, sheep, goats and horses), present ever-increasing challenges to the environment. Indeed, in 2006, the Food and Agriculture Organization of the United Nations, in its landmark report assessing the impacts of animal agriculture, concluded that the livestock sector alone was one of the top two or three most significant contributors to the most serious environmental problems at every scale from local to global, and that animal agriculture accounts for 18% of global, human-induced greenhouse gas emissions.

Another significant environmental impact is the issue of nutrient and effluent buildup on the sea floor below cages used in aquaculture. Because the fish are contained in one place at high densities, their waste—which includes both solids and dissolved nutrients like nitrogen—has the potential to build up below the cages and in the surrounding area. This creates the potential for algal blooms, which deplete the water of oxygen and can create damaging dead zones near aquaculture sites.

There is thus a pressing need to deal responsibly with the many harmful effects of farming on the environment, whether from the leaching of harmful chemicals found in fertilizers into waterways, manure build up and spills, decreased land fertility and toxicity to local fauna. This need is satisfied by the present invention.

SUMMARY

The present invention relates to the use of biochar that is treated or processed to have certain chemical and physical properties found to reduce the negative environmental impact of farming, and in particular, large-scale industrial farming, and to reduce the leaching of harmful chemicals found in fertilizers, antibiotics and other harmful compounds, to provide better management of manure lagoons, control of emissions of greenhouse gases and volatile organic compounds (VOCs), to reduce carbon footprint and other environmentally beneficial results. For purposes of this application, when the biochar is referred to as "treated" or undergoes "treatment," it shall mean raw biochar that has undergone additional physical and/or chemical processing.

In particular, the following physical and/or chemical properties, among others, of a biochar have been identified as critical properties to control for in the selection of biomass feedstock, pyrolysis conditions and/or enhancing treatment to increase biochar performance: (i) bulk density (ii) impregnation capacity; (iii) particle size distribution; (iv) solid particle density; (v) surface area; (vi) porosity; (vii) total porosity; (viii) ratio of macroporosity to total porosity; (ix) content of residual organic compounds; (x) content of VOCs; (xii) ash content; (xiii) water holding capacity; (xiv) water retention capabilities; (xv) levels of dioxins and other potentially hazardous byproducts of pyrolysis; and (xvi) pH. Treatment can also modify and preferably increase hydrophilicity/decrease hydrophobicity, remove dioxins from the raw biochar, modify electrical conductivity and/or surface charge, modify cation exchange capacity and modify anion exchange capacity, among other things.

For purposes of this application, these properties will be known as "performance properties." The list above of properties is not exhaustive and shall include any property of the biochar that enhances performance of treated biochar over raw biochar for a specified purpose. Those skilled in the art will recognize the certain performance properties may be more desirable than others for different applications, including, but not limited to, the reduction of the harmful impact of farming on the environment. Further, treatment of raw biochar may be tailored such that certain of these performance properties are targeted to be present in the resulting treated biochar. The treatment process selected and utilized for treating the raw biochar may also be tailored to allow certain of these performance properties to be sustained for certain periods of time after treatment to boost long-term performance of the treated biochar.

The raw biochar of the present invention is obtained from the pyrolysis of biomass. The resulting biochar is then treated in a manner that causes the infusion and/or effusion of liquids into and out of the biochar pores or infiltration and/or exfiltration of liquids, gases, nutrients and/or other additives ("additives) into and out of the biochar pores, which process may be caused by the rapid, forced or rapid and forced infusion and/or effusion of additives into and out of the biochar pores. While those skilled in the art may recognize other methods for treating the biochar that causes the rapid, forced infusion and effusion of additives into and out of the biochar pores, one such treatment process that can be used is a process that changes the pressure differential surrounding the biochar, such as vacuum impregnation, optionally following additional vacuum extraction and/or centrifuge extraction.

An additional relevant technique is treatment with a solution containing either organic or inorganic surfactant or detergent. The solution to which the surfactant or detergent is added may optionally be heated or may be ambient temperature or less. The combination of pressure changes or vacuum treatment with one or more surfactant or detergent treatments either prior to, simultaneous with, or following vacuum treatment is also a possible treatment method. Optionally, treatment may include subjecting the biochar to temperatures during vacuum treatment from ambient to about 250° C. Since research associated with the present invention has identified what physical and chemical properties have the highest impact on particular end uses, the treatment process can be modified to treat different forms of raw biochar to achieve treated biochar properties known to enhance the ensilage process. For example, if the pH of the biochar needs to be adjusted to enhance the raw biochar performance properties, the treatment may be the impregnation of an acidic solution into the pores of the biochar or similarly removal of basic or alkaline compounds from the pores or surface of the raw biochar. This treatment of impregnation or infiltration, impregnation or infiltration with additional additives to assist the process, or both, followed optionally by extraction of the infiltrate has further been proven to sustain the pH levels of the treated biochar for much longer periods than biochar that is simply immersed in an acid solution or washed with water or some other solvent.

Treatment also allows for the impregnation or inoculation of the pores of the biochar with additives that can introduce greater efficiencies in crop production or animal growth, better promote or control various agricultural processes or to reduce the risk of leaching of harmful substances into the environment. These additives might include fertilizers, nutrients, additional foodstuffs, vitamins or other substances that promote plant or animal health, as well as medications, microbes such as probiotics and other forms of microbial life. The above describes a few examples of treatment that results in treated biochar having desired performance properties identified to introduce efficiencies into agriculture that are environmentally friendly, promote plant and animal health and reduce or minimize the environmental impact of farming.

The resulting infused biochar provides for gradual, steady, more controlled and/or efficient delivery of the additives, either to the root zone of plants or to the care and maintenance of animals. When used as an enhancement to animal feed, biochar may increase the animals' uptake of foodstuffs and the energy contained within them, reducing the amount of nutrients lost into excrement and manure. The biochar may also act to detoxify the animal while enriching the beneficial microbes in the digestive track that are key to maintaining an animal's metabolism and helping them to resist dangerous pathogens.

Biochar can also be used to improve the overall environment of animal stalls, pens, cages and swine lagoons, as well as paddocks, corrals and other animal enclosures, by promoting beneficial effects such as odor control, ammonia and nitrate management, and moisture absorption. As an additional benefit, manure produced by an animal that consumes biochar will contain biochar, making this manure better for agricultural purposes than ordinary manure as well as impacting the actual soil characteristics where the manure is applied.

Treated biochar can also be used to reduce the overall environmental impact of farming and minimize the carbon footprint of farms is provided. For example, the present invention further teaches a method for reducing the overall environmental impact of farming and minimize the carbon footprint of farms by engaging in one or more of the following practices: (1) combining treated biochar with feed or using biochar as feed for animals to reduce methane from enteric fermentation and increase animal health and nutrition; (2) combining treated biochar with compost, animal bedding or manure piles to reduce odor and increase nutrient retention; (3) applying treated biochar to lagoons to reduce odor and treat water; (4) applying treated biochar to pastures to increase pasture health; (5) applying treated biochar to crops to increase crop productivity, healthier roots and prevent fertilizer leaching and (6) using the carbon negativity of a produced biochar to reduce the overall farm or ranch carbon footprint.

Other devices, apparatus, systems, methods, features and advantages of the invention are or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention. In the figures, like reference numerals designate corresponding parts throughout the different views.

FIGS. 27 and 28 illustrate improved growth rates of colonies of *Streptomyces lydicus* using biochars.

FIG. 38a is a SEM (10 KV×3.00K 10.0 µm) of pore morphology of raw biochar.

FIG. 38b is a SEM (10 KV×3.00K 10.0 µm) of pore morphology of raw biochar of FIG. 38a after it has been infused with microbial species.

FIG. 38c is a SEM (10 KV×3.00K 10.0 µm) of a pore morphology of another example of raw biochar of FIG. 38a after it has been infused with microbial species.

FIG. 39a is an image of biochar aggregate particles of the present invention made in the form pellets.

FIG. 39b is an image of biochar aggregate particles of the present invention made in the form an extrudates.

FIG. 39c is an image of the biochar aggregate particles made in the form of biochar sulfur prills.

FIGS. 42a-f illustrates the effects of size and grinding on particle structure of a biochar derived from a second biomass.

FIGS. 50a, 50b and 50c illustrate how biochar can be used to improve productivity of the entire farm or ranch system.

FIG. 51 is a chart illustrating the percentage removal of initial metal concentrations in SPLP Extract of Missouri mine soil after twenty-four hours of contact with treated biochar formulations.

DESCRIPTION OF THE INVENTION

Figure 1:
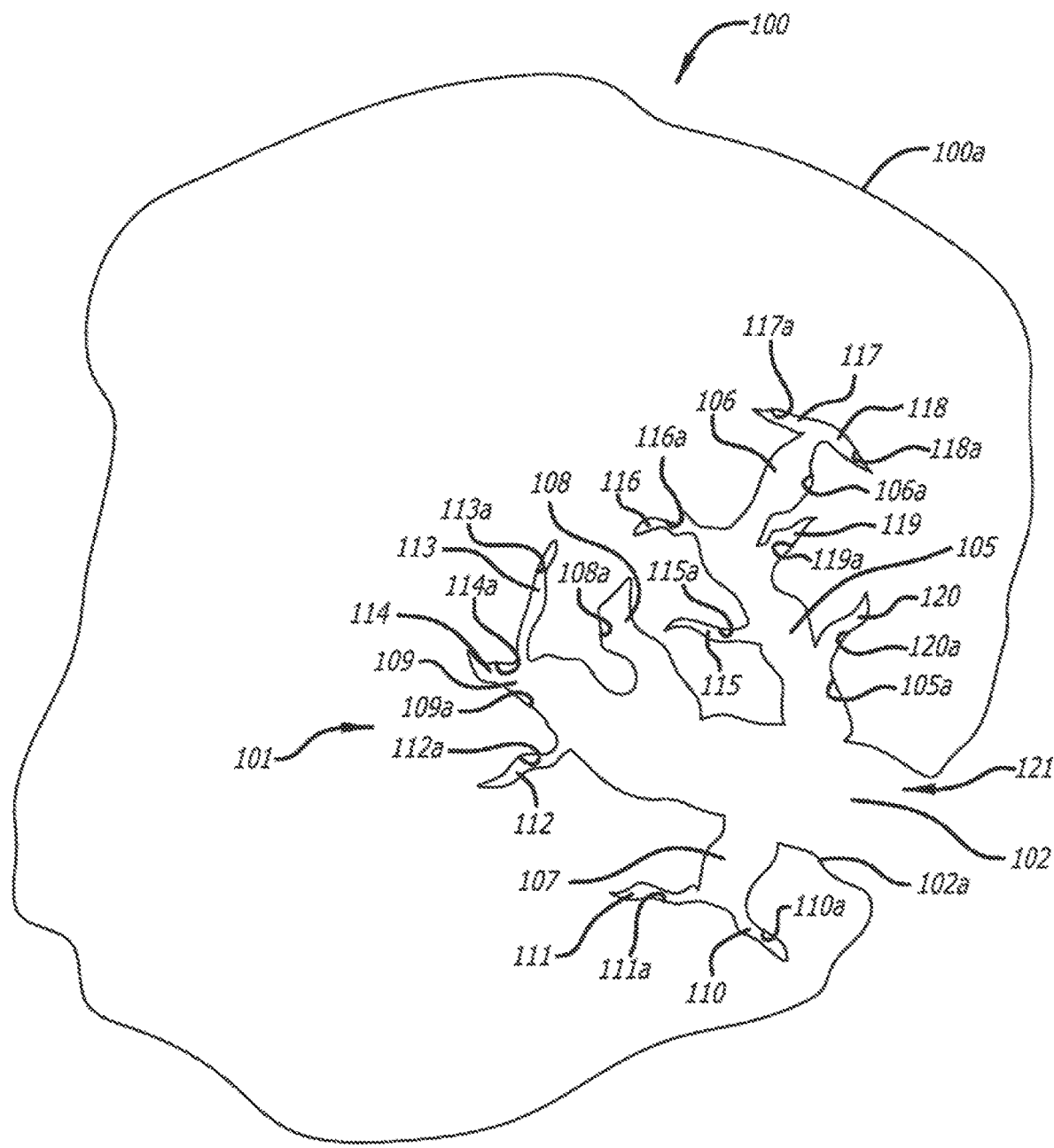
FIG. 1 illustrates a cross-section of one example of a raw biochar particle.

Biochar has been shown to have positive impacts in cropping systems, animal health, nutrient runoff/leaching scenarios, and carbon sequestration. While many inventions have been directed towards these uses, however, little work has been done to determine how biochar can be produced, treated, and deployed to optimize its impact on a full farm/ranch system. Like many other fields of study, optimizing to solve a localized problem can actually lead to a less than optimal result in the overall system. As an example, one way to optimize an internal combustion engine for fuel economy is to reduce the displacement of the engine. However, reducing the displacement (all other things being equal) will likely lead to less power, and if a specific level of power is necessary for the motor to successfully function in and power a specific automobile, the local optimization of the engine will deoptimize the larger system (the automobile). Many similar challenges are faced in a typical agricultural environment. This invention, and the subject matter disclosed here, is focused on producing and utilizing biochar in such a way that it can add greater value to an entire farm or ranch system—in many cases, by preparing and deploying materials that can add value at many points in the system. For example, if the same material can increase animal growth, reduce toxicity, enrich manure, improve growth where the manure is applied and sequester environmental carbon, then one product is producing many benefits. However, the methods and mechanisms to construct, formulate, treat, and apply this material are not obvious, and are provably different than if the material was only targeted towards a single outcome.

Whether biochar is harmful or helpful to soil health, plant growth and yield and/or useful for other farm-related applications, including but not limited to animal-related applications, depends largely on the chemical and physical properties of the biochar. In general, the present invention relates to biochar that is treated to have certain chemical and physical properties found to have the greatest efficacy in ameliorating the negative environmental impact of farming by influencing temperature, moisture, acid levels, pH levels, air emissions (e.g., VOCs, ammonia and methane), odors, and microbial profile. These properties or characteristics can be further enhanced and sustained for longer periods of time with the utilization of certain treatment processes and through the biomass processing and/or raw biochar selection. As explained further below, the resulting properties of the treated biochar can be tailored through biochar production, selection and treatment to achieve treated biochar having chemical and physical properties useful for specific applications.

Testing was performed on a variety of types of raw and treated biochar. The testing involved full lab scale evaluation of the properties of raw biochar produced from over 40 biomass sources. Testing studied the properties possessed by the different raw biochar in light of the source biomass and the pyrolysis process used to produce the biochar. Batches of the raw biochar were treated utilizing different treatment methods and the toxicity of and properties of the raw and treated biochar were evaluated. In particular, elemental, polyaromatic hydrocarbon, pathogen, and phytotoxicity analyses were performed. The physical and chemical properties of the raw and treated biochar were compared, tested for performance and the changes in pH over time were studied.

Testing revealed that the following properties (among others) impact the performance of raw or treated biochar:

Bulk density
Impregnation Capacity
Particle Size & Particle Size Distribution
Surface Area
Total porosity
Ratio of Macroporosity to Total Porosity
pH
Water Holding Capacity (WHC)
Residual Organic Compounds (ROCs)
VOCs
Ash Content
Water Retention Capacity
Dioxin Content
Hydrophobicity
Electrical Conductivity
Cation and Anion Exchange Capacity (CEC and AEC)

Testing further demonstrated that many of the above properties can be altered in biochar, when compared to its raw state, to be more beneficial or suitable for specific applications through treating the raw biochar with processes designed to achieve the desired proven high impact properties.

As described below, raw biochar may be first treated to increase properties favorable for applications intended to reduce the environmental impact of farming, such as water holding, water retention and pH, although for purposes of these applications, treatment of the raw biochar is not required as part of the production of biochar packets or capsules made from biodegradable materials. However, through treatment, the properties of the raw biochar can be modified to significantly increase the biochar's ability to retain water and/or nutrients while also, in many cases, creating an environment beneficial to microorganisms. The processing of the biochar can also ensure that the pH of biochar used in the present applications is suitable for creating soil conditions beneficial for plant growth, which has been a challenge for raw biochars. In certain applications, it may be desirable to produce the biochar aggregate particles from treated biochars or the fines of treated biochars.

For purposes of this application, the term "biochar" shall be given its broadest possible meaning and shall include any solid materials obtained from the pyrolysis, torrefaction, gasification or any other thermal and/or chemical conversion of a biomass, where the biochar contains at least 55% carbon based upon weight. Pyrolysis is generally defined as a thermochemical decomposition of organic material at elevated temperatures in the absence of, or with reduced levels of oxygen.

For purposes of this application, biochar may include, but not be limited to, BMF char disclosed and taught by U.S. Pat. No. 8,317,891, which is incorporated into this application by reference, and those materials falling within the IBI and AAPFCO definition of biochar. When the biochar is referred to as "treated" or undergoes "treatment," it shall mean raw, pyrolyzed biochar that has undergone additional physical, biological, and/or chemical processing.

As used herein, unless specified otherwise, the terms "carbonaceous", "carbon based", "carbon containing", and similar such terms are to be given their broadest possible meaning, and would include materials containing carbon in various states, crystallinities, forms and compounds.

As used herein, unless stated otherwise, room temperature is 25° C. And, standard temperature and pressure is 25° C. and 1 atmosphere. Unless stated otherwise, generally, the term "about" is meant to encompass a variance or range of ±10%, the experimental or instrument error associated with obtaining the stated value, and preferably the larger of these.

Generally, treated biochar of the present invention can be used throughout the world, in numerous applications related to the care and feeding of animals or the production/growth of plants. As described below, treated biochar, when added to the green vegetation used as feedstock, has proved to improve fermentation and better control pH levels, temperature, moisture, odors and emissions (e.g. ammonia and VOCs).

A. Biochars

Typically, biochars include porous carbonaceous materials, such as charcoal, that are used as soil amendments or other suitable applications. Biochar most commonly is created by pyrolysis of a biomass. In addition to the benefits to plant growth, yield and quality, etc.; biochar provides the benefit of reducing carbon dioxide ($CO_2$) in the atmosphere by serving as a method of carbon sequestration. Thus, biochar has the potential to help mitigate climate change, via carbon sequestration. However, to accomplish this important, yet ancillary, benefit to any meaningful extent, the use of biochar in agricultural applications must become widely accepted, e.g., ubiquitous. Unfortunately, because of the prior failings in the biochar arts, this has not occurred. It is believed that with the solutions of the present invention may this level of use of biochar be achieved; and more importantly, yet heretofore unobtainable, realize the benefit of significant carbon sequestration.

In general, one advantage of putting biochar in soil includes long term carbon sequestration. It is theorized that as worldwide carbon dioxide emissions continue to mount, benefits may be obtained by controlling, mitigating and reducing the amount of carbon dioxide in the atmosphere and the oceans. It is further theorized that increased carbon dioxide emissions are associated with the increasing industrial development of developing nations, and are also associated with the increase in the world's population. In addition to requiring more energy, the increasing world population will require more food. Thus, rising carbon dioxide emissions can be viewed as linked to the increasing use of natural resources by an ever increasing global population. As some suggest, this larger population brings with it further demands on food production requirements. Biochar uniquely addresses both of these issues by providing an effective carbon sink, e.g., carbon sequestration agent, as well as, an agent for improving and increasing agricultural output. In particular, biochar is unique in its ability to increase agricultural production, without increasing carbon dioxide emission, and preferably reducing the amount of carbon dioxide in the atmosphere. However, as discussed above, this unique ability of biochar has not been realized, or seen, because of the inherent problems and failings of prior biochars including, for example, high pH, phytotoxicity due to high metals content and/or residual organics, and dramatic product inconsistencies.

In addition, another factor slowing widespread adoption of biochar has been the unattractive return on investment (ROI) from biochar production given the limited applications to which biochar has been historically put. Producing biochar on a large scale has not been widely viewed as an attractive investment because of, among other things, the transportation costs associated with bringing the organic feedstock from different parts of the world to a single biochar plant and costs associated with production and treatment. However, this limitation can be overcome through systemwide applications, which can dramatically increase ROI.

Biochar can be made from basically any source of carbon, for example, from hydrocarbons (e.g., petroleum based materials, coal, lignite, peat) and from a biomass (e.g., woods, hardwoods, softwoods, waste paper, coconut shell, manure, chaff, food waste, etc.). Combinations and variations of these starting materials, and various and different members of each group of starting materials can be, and are, used. Thus, the large number of vastly different starting materials leads to biochars having different properties.

Many different pyrolysis or carbonization processes can be, and are used to create biochars. In general, these processes involve heating the starting material under positive pressure, reduced pressure, vacuum, inert atmosphere, or flowing inert atmosphere, through one or more heating cycles where the temperature of the material is generally brought above about 400° C., and can range from about 300° C. to about 900° C. The percentage of residual carbon formed and several other initial properties are strong functions of the temperature and time history of the heating cycles. In general, the faster the heating rate and the higher the final temperature the lower the char yield. Conversely, in general, the slower the heating rate or the lower the final temperature the greater the char yield. The higher final temperatures also lead to modifying the char properties by changing the inorganic mineral matter compositions, which in turn, modify the char properties. Ramp, or heating rates, hold times, cooling profiles, pressures, flow rates, and type of atmosphere can all be controlled, and typically are different from one biochar supplier to the next. These differences potentially lead to a biochar having different properties, further framing the substantial nature of one of the problems that the present inventions address and solve. Generally, in carbonization most of the non-carbon elements, hydrogen and oxygen are first removed in gaseous form by the pyrolytic decomposition of the starting materials, e.g., the biomass. The free carbon atoms group or arrange into crystallographic formations known as elementary graphite crystallites. Typically, at this point the mutual arrangement of the crystallite is irregular, so that free interstices exist between them. Thus, pyrolysis involves thermal decomposition of carbonaceous material, e.g., the biomass, eliminating non-carbon species, and producing a fixed carbon structure.

As noted above, raw or untreated biochar is generally produced by subjecting biomass to either a uniform or varying pyrolysis temperature (e.g., 300° C. to 550° C. to 750° C. or more) for a prescribed period of time in a reduced oxygen environment. This process may either occur quickly, with high reactor temperature and short residence times, slowly with lower reactor temperatures and longer residence times, or anywhere in between. To achieve better results, the biomass from which the char is obtained may be first stripped of debris, such as bark, leaves and small branches, although this is not necessary. The biomass may further include feedstock to help adjust the pH and particle size distribution in the resulting raw biochar. In some applications, it is desirous to have biomass that is fresh, less than six months old, and with an ash content of less than 3%. Further, by using biochar derived from different biomass, e.g., pine, oak, hickory, birch and coconut shells from different regions, and understanding the starting properties of the raw biochar, the treatment methods can be tailored to ultimately yield a treated biochar with predetermined, predictable physical and chemical properties. Additionally, the biomass may be treated with various organic or inorganic substances prior to pyrolysis to impact the reactivity of the material during pyrolysis and/or to potentially be fixed in place and available for reaction with various substances during the treatment process after pyrolysis. Trace materials, usually in gaseous form, but potentially in other forms, may also be injected during the pyrolysis process with the intention of either modifying the characteristics of the raw biochar produced, or for potential situation on the raw biochar so that those materials, or a descendant material created by thermal or chemical reaction during pyrolysis, may be reacted with other compounds during the treatment process.

In general, biochar particles can have a very wide variety of particle sizes and distributions, usually reflecting the sizes occurring in the input biomass. Additionally, biochar can be ground, sieved, strained, or crushed after pyrolysis to further modify the particle sizes. Typically, for agricultural uses, biochars with consistent, predictable particle sizes are more desirable. By way of example, the biochar particles can have particle sizes as shown or measured in Table 1 below. When referring to a batch having ¼ inch particles, the batch would have particles that will pass through a 3 mesh sieve, but will not pass through (i.e., are caught by or sit atop) a 4 mesh sieve.

TABLE 1

| U.S. Mesh (i.e., mesh) | Inches | Microns (μm) | Millimeters (mm) |
|---|---|---|---|
| 3 | 0.2650 | 6730 | 6.370 |
| 4 | 0.1870 | 4760 | 4.760 |
| 5 | 0.1570 | 4000 | 4.000 |
| 6 | 0.1320 | 3360 | 3.360 |
| 7 | 0.1110 | 2830 | 2.830 |
| 8 | 0.0937 | 2380 | 2.380 |
| 10 | 0.0787 | 2000 | 2.000 |
| 12 | 0.0661 | 1680 | 1.680 |
| 14 | 0.0555 | 1410 | 1.410 |
| 16 | 0.0469 | 1190 | 1.190 |
| 18 | 0.0394 | 1000 | 1.000 |
| 20 | 0.0331 | 841 | 0.841 |
| 25 | 0.0280 | 707 | 0.707 |
| 30 | 0.0232 | 595 | 0.595 |
| 35 | 0.0197 | 500 | 0.500 |
| 40 | 0.0165 | 400 | 0.400 |
| 45 | 0.0138 | 354 | 0.354 |
| 50 | 0.0117 | 297 | 0.297 |
| 60 | 0.0098 | 250 | 0.250 |
| 70 | 0.0083 | 210 | 0.210 |
| 80 | 0.0070 | 177 | 0.177 |
| 100 | 0.0059 | 149 | 0.149 |
| 120 | 0.0049 | 125 | 0.125 |
| 140 | 0.0041 | 105 | 0.105 |
| 170 | 0.0035 | 88 | 0.088 |
| 200 | 0.0029 | 74 | 0.074 |
| 230 | 0.0024 | 63 | 0.063 |
| 270 | 0.0021 | 53 | 0.053 |
| 325 | 0.0017 | 44 | 0.044 |
| 400 | 0.0015 | 37 | 0.037 |

For most basic agricultural applications, it is desirable to use biochar particles having particle sizes from about 3/4 mesh to about 60/70 mesh, about 4/5 mesh to about 20/25 mesh, or about 4/5 mesh to about 30/35 mesh. However, for applications such as seed treatment, or microbial carriers, smaller mesh sizes ranging from 200, to 270, to 325, to 400 mesh or beyond may be desirable. It is understood that the desired mesh size, and mesh size distribution can vary depending upon a particular application for which the biochar is intended.

FIG. 1 illustrates a cross-section of one example of a raw biochar particle. As illustrated in FIG. 1, a biochar particle 100 is a porous structure that has an outer surface 100a and a pore structure 101 formed within the biochar particle 100. As used herein, unless specified otherwise, the terms "porosity", "porous", "porous structure", and "porous morphology" and similar such terms are to be given their broadest possible meaning, and would include materials having open pores, closed pores, and combinations of open and closed pores, and would also include macropores, mesopores, and micropores and combinations, variations and continuums of these morphologies. Unless specified otherwise, the term "pore volume" is the total volume occupied by the pores in a particle or collection of particles; the term "inter-particle void volume" is the volume that exists between a collection of particle; the term "solid volume or volume of solid means" is the volume occupied by the solid material and does not include any free volume that may be associated with the pore or inter-particle void volumes; and the term "bulk volume" is the apparent volume of the material including the particle volume, the inter-particle void volume, and the internal pore volume.

The pore structure 101 forms an opening 121 in the outer surface 100a of the biochar particle 100. The pore structure 101 has a macropore 102, which has a macropore surface 102a, and which surface 102a has an area, i.e., the macropore surface area. (In this diagram only a single micropore is shown. If multiple micropores are present than the sum of their surface areas would equal the total macropore surface area for the biochar particle.) From the macropore 102, several mesopores 105, 106, 107, 108 and 109 are present, each having its respective surfaces 105a, 106a, 107a, 108a and 109a. Thus, each mesopore has its respective surface area; and the sum of all mesopore surface areas would be the total mesopore surface area for the particle. From the mesopores, e.g., 107, there are several micropores 110, 111, 112, 113, 114, 115, 116, 117, 118, 119 and 120, each having its respective surfaces 110a, 11a, 112a, 113a, 114a, 115a, 116a, 117a, 118a, 119a and 120a. Thus, each micropore has its respective surface area and the sum of all micropore surface areas would be the total micropore surface area for the particle. The sum of the macropore surface area, the mesopore surface area and the micropore surface area would be the total pore surface area for the particle.

Macropores are typically defined as pores having a diameter greater than 300 nm, mesopores are typically defined as diameter from about 1-300 nm, and micropores are typically defined as diameter of less than about 1 nm, and combinations, variations and continuums of these morphologies. The macropores each have a macropore volume, and the sum of these volumes would be the total macropore volume. The mesopores each have a mesopore volume, and the sum of these volumes would be the total mesopore volume. The micropores each have a micropore volume, and the sum of these volumes would be the total micropore volume. The sum of the macropore volume, the mesopore volume and the micropore volume would be the total pore volume for the particle.

Additionally, the total pore surface area, volume, mesopore volume, etc., for a batch of biochar would be the actual, estimated, and preferably calculated sum of all of the individual properties for each biochar particle in the batch.

It should be understood that the pore morphology in a biochar particle may have several of the pore structures shown, it may have mesopores opening to the particle surface, it may have micropores opening to particle surface, it may have micropores opening to macropore surfaces, or other combinations or variations of interrelationship and structure between the pores. It should further be understood that the pore morphology may be a continuum, where moving inwardly along the pore from the surface of the particle, the pore transitions, e.g., its diameter becomes smaller, from a macropore, to a mesopore, to a micropore, e.g., macropore 102 to mesopore 109 to micropore 114. It should also be understood that the pores can be terminal as depicted in FIG. 1, where the pore ends somewhere in the particle or open-ended where the pore ends at one or more other pore openings. In other words, terminal pores have only one opening to the external surface of the particle and open-ended pores have two or more openings to the external surface of the particle.

In general, most biochars have porosities that can range from 0.2 $cm^3/cm^3$ to about 0.8 $cm^3/cm^3$ and more preferably about 0.2 $cm^3/cm^3$ to about 0.5 $cm^3/cm^3$. (Unless stated otherwise, porosity is provided as the ratio of the total pore volumes (the sum of the micro+meso+macro pore volumes) to the solid volume of the biochar. Porosity of the biochar particles can be determined, or measured, by measuring the micro-, meso-, and macro pore volumes, the bulk volume, and the inter particle volumes to determine the solid volume by difference. The porosity is then calculated from the total pore volume and the solid volume.

Figure 2A:
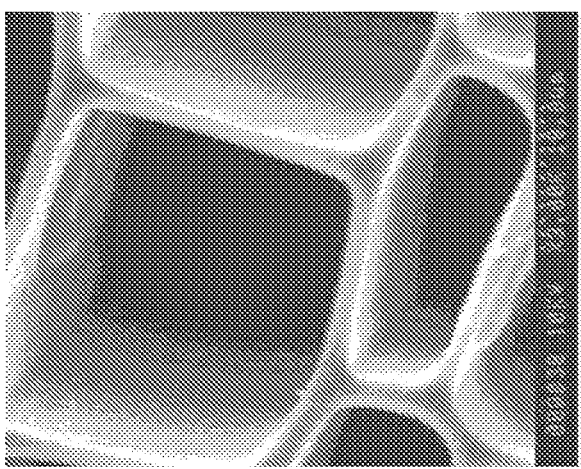
FIG. 2a is a SEM (10 KV×3.00K 10.0 μm) of pore morphology of treated biochar made from pine.
Figure 2B:
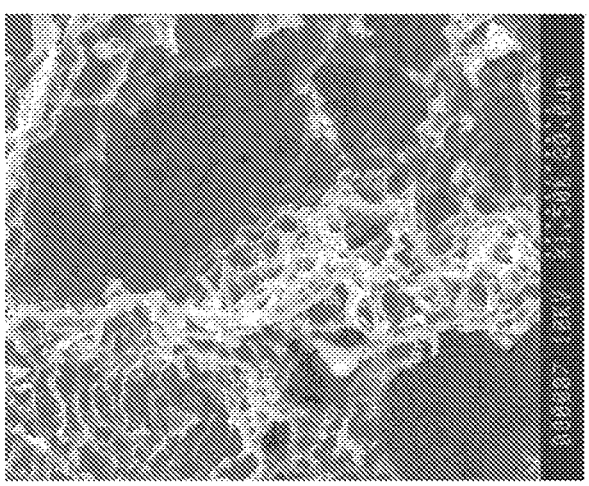
FIG. 2b is a SEM (10 KV×3.00K 10.0 μm) of pore morphology of treated biochar made from birch.
Figure 2C:
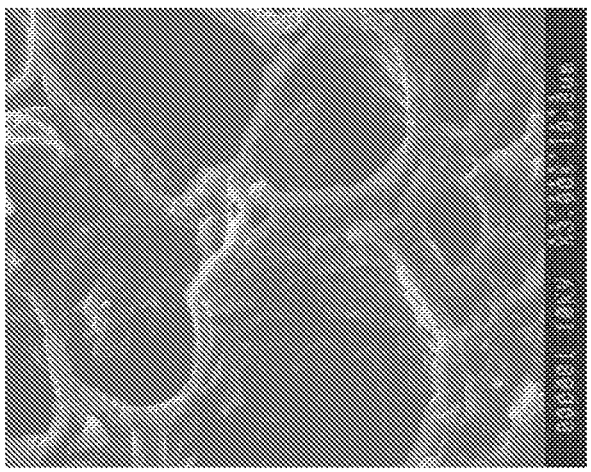
FIG. 2c is a SEM (10 KV×3.00K 10.0 μm) of pore morphology of treated biochar made from coconut shells.

As noted above, the use of different biomass potentially leads to biochars having different properties, including, but not limited to different pore structures. By way of example, FIGS. 2A, 2B and 2C illustrate Scanning Electron Microscope ("SEM") images of various types of treated biochars showing the different nature of their pore morphology. FIG. 2A is biochar derived from pine. FIG. 2B is biochar derived from birch. FIG. 2C is biochar derived from coconut shells.

The surface area and pore volume for each type of pore, e.g., macro-, meso- and micro- can be determined by direct measurement using $CO_2$ adsorption for micro-, $N_2$ adsorption for meso- and macro pores and standard analytical surface area analyzers and methods, for example, particle analyzers such as Micrometrics instruments for meso- and micro pores and impregnation capacity for macro pore volume. Mercury porosimetry, which measures the macroporosity by applying pressure to a sample immersed in mercury at a pressure calibrated for the minimum pore diameter to be measured, may also be used to measure pore volume.

Figure 3:
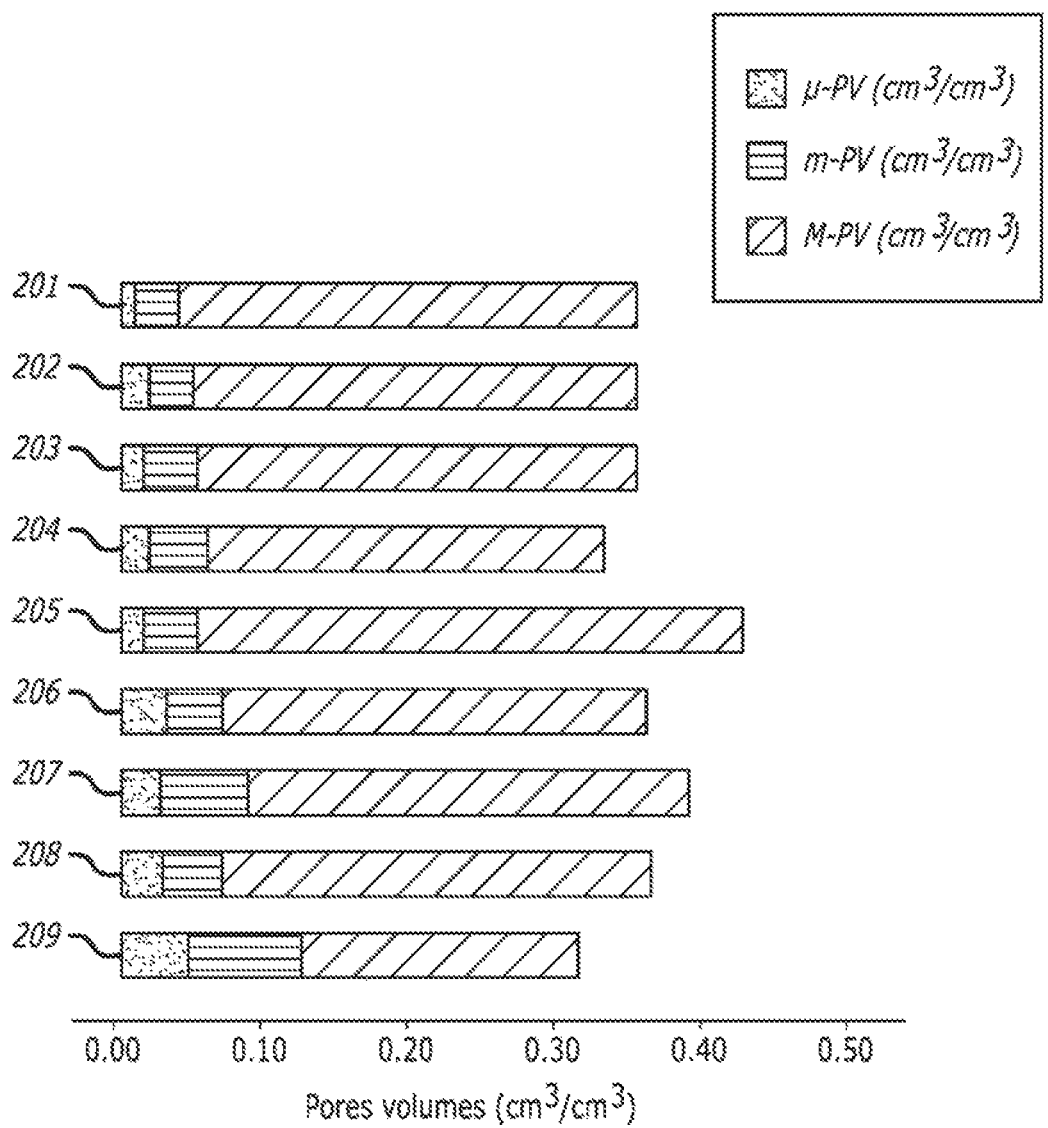
FIG. 3 is a chart showing porosity distribution of various biochars.

The total micropore volume can be from about 2% to about 25% of the total pore volume. The total mesopore volume can be from about 4% to about 35% of the total pore volume. The total macropore volume can be from about 40% to about 95% of the total pore volume. By way of example, FIG. 3 shows a bar chart setting out examples of the pore volumes for sample biochars made from peach pits 201, juniper wood 202, a first hard wood 203, a second hard wood 204, fir and pine waste wood 205, a first pine 206, a second pine 207, birch 208 and coconut shells 209.

As explained further below, treatment can increase usable pore volumes and, among other things, remove obstructions in the pores, which leads to increased retention properties and promotes further performance characteristics of the biochar. Knowing the properties of the starting raw biochar, one can treat the biochar to produce controlled, predictable and optimal resulting physical and chemical properties.

B. Treatment

The rationale for treating the biochar after pyrolysis is that given the large internal pore volume and large interior surface are of the biochars, it is most efficient to make significant changes in the physical and chemical properties of the biochar by treating both the internal and external surfaces and internal pore volume of the char. Testing has demonstrated that if the biochar is treated, at least partially, in a manner that causes the forced infusion and/or diffusion of liquids and/or vapors into and/or out of the biochar pores (through mechanical, physical, or chemical means), certain properties of the biochar can be altered or improved over and above simply contacting these liquids with the biochar. By knowing the properties of the raw biochar and the optimal desired properties of the treated biochar, the raw biochar can then be treated in a manner that results in the treated biochar having controlled optimized properties.

For purposes of this application, treating and/or washing the biochar in accordance with the present invention involves more than simply contacting, washing or soaking, which generally only impacts the exterior surfaces and a small percentage of the interior surface area. "Washing" or "treating" in accordance with the present invention, and as used below, involves treatment of the biochar in a manner that causes the forced, accelerated or assisted infusion and/or diffusion of liquids, vapors, and/or additivities into and/or out of the biochar pores (through mechanical, physical, biological, or chemical means) such that certain properties of the biochar can be altered or improved over and above simply contacting these liquids with the biochar or so that treatment becomes more efficient or rapid from a time standpoint over simple contact or immersion.

In particular, effective treatment processes can mitigate deleterious pore surface properties, remove undesirable substances from pore surfaces or volume, and impact anywhere from between 10% to 99% or more of pore surface area of a biochar particle. By modifying the usable pore surfaces through treatment and removing deleterious substances from the pore volume, the treated biochars can exhibit a greater capacity to retain water and/or other nutrients as well as being more suitable habitats for some forms of microbial life. Through the use of treated biochars, agricultural applications can realize increased moisture control, increased nutrient retention, reduced water usage, reduced water requirements, reduced runoff or leaching, increased nutrient efficiency, reduced nutrient usage, increased yields, increased yields with lower water requirements and/or nutrient requirements, increases in beneficial microbial life, improved performance and/or shelf life for inoculated bacteria, and any combination and variation of these and other benefits.

Treatment further allows the biochar to be modified to possess certain known properties that enhance the benefits received from the use of biochar. While the selection of feedstock, raw biochar and/or pyrolysis conditions under which the biochar was manufactured can make treatment processes less cumbersome, more efficient and further controlled, treatment processes can be utilized that provide for the biochar to have desired and generally sustainable resulting properties regardless of the biochar source or pyrolysis conditions. As explained further below, treatment can (i) repurpose problematic biochars, (ii) handle changing biochar material sources, e.g., seasonal and regional changes in the source of biomass, (iii) provide for custom features and functions of biochar for particular soils, regions or agricultural purposes; (iv) increase the retention properties of biochar, (v) provide for large volumes of biochar having desired and predictable properties, (vi) provide for biochar having custom properties, (vii) handle differences in biochar caused by variations in pyrolysis conditions or manufacturing of the "raw" biochar; and (viii) address the majority, if not all, of the problems that have, prior to the present invention, stifled the large scale adoption and use of biochars.

Treatment can impact both the interior and exterior pore surfaces, remove harmful chemicals, introduce beneficial substances, and alter certain properties of the biochar and the pore surfaces and volumes. This is in stark contrast to simple washing, contact, or immersion which generally only impacts the exterior surfaces and a small percentage of the interior surface area. Treatment can further be used to coat substantially all of the biochar pore surfaces with a surface modifying agent or impregnate the pore volume with additives or treatment to provide a predetermined feature to the biochar, e.g., surface charge and charge density, surface species and distribution, targeted nutrient addition, magnetic modifications, root growth facilitator, and water absorptivity and water retention properties. Just as importantly, treatment can also be used to remove undesirable substances from the biochar, such as dioxins or other toxins either through physical removal or through chemical reactions causing neutralization.

Figure 4:
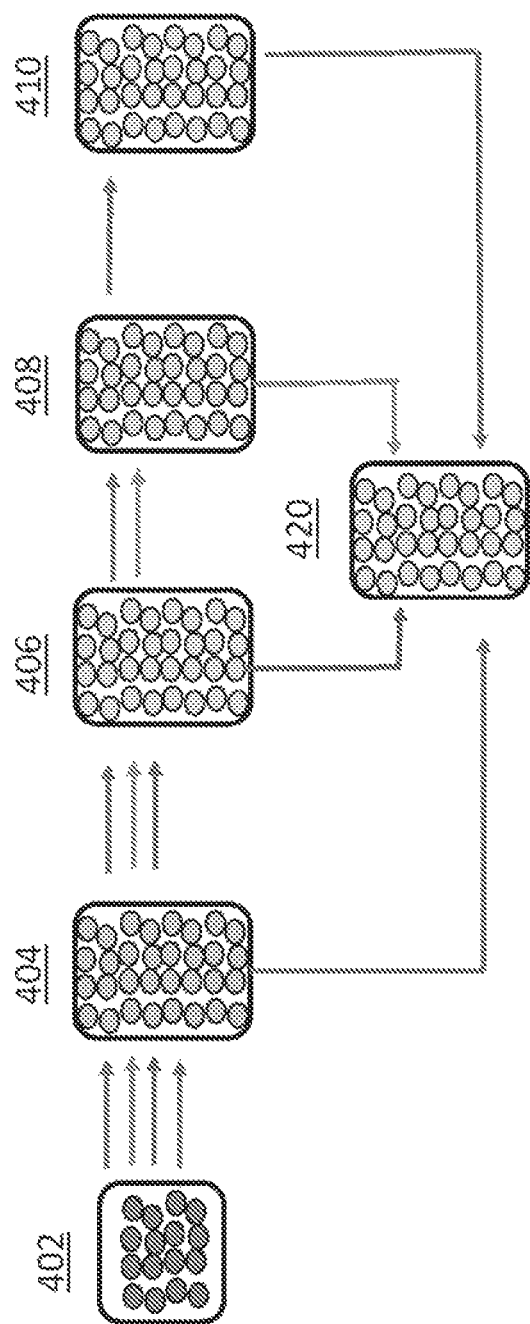
FIG. 4 is a flow chart process diagram of one implementation of a process for treating the raw biochar in accordance with the invention.

FIG. 4 is a schematic flow diagram of one example treatment process 400 for use in accordance with the present invention. As illustrated, the treatment process 400 starts with raw biochar 402 that may be subjected to one or more reactors or treatment processes prior to bagging 420 the treated biochar for resale. For example, 404 represents reactor 1, which may be used to treat the biochar. The treatment may be a simple water wash or may be an acid wash used for the purpose of altering the pH of the raw biochar particles 402. Optionally, the treatment may also contain a solvent suited to remove any soluble substances which are undesirable in the final product, such as VOCs, or other residual organic or inorganic compounds. The treatment may also contain a surfactant or detergent to aid the penetration of the treatment solution into the pores of the biochar. The treatment may optionally be heated, cooled, or may be used at ambient temperature or any combination of the three. For some applications, depending upon the properties of the raw biochar, a water and/or acid/alkaline wash 404 (the latter for pH adjustment) may be the only necessary treatment prior to bagging the biochar 420. If, however, the moisture content of the biochar needs to be adjusted, the treated biochar may then be put into a second reactor 406 for purposes of reducing the moisture content in the washed biochar. From there, the treated and moisture adjusted biochar may be bagged 420.

Again, depending upon the starting characteristics of the raw biochar and the intended application for the resale product, further processing may still be needed or desired. In this case, the treated moisture adjusted biochar may then be passed to a third reactor 408 for inoculation, which may include the impregnation of biochar with beneficial additives, such as nutrients, bacteria, microbes, fertilizers or other additives. Thereafter, the inoculated biochar may be bagged 420, or may be yet further processed, for example, in a fourth reactor 410 to have further moisture removed from or added to the biochar. Further moisture adjustment may be accomplished by placing the inoculated biochar in a fourth moisture adjustment reactor 410 or circulating the biochar back to a previous moisture adjustment reactor (e.g. reactor 406). Those skilled in the art will recognize that the ordering in which the raw biochar is processed and certain processes may be left out, depending on the properties of the starting raw biochar and the desired application for the biochar. For example, the treatment and inoculation processes may be performed without the moisture adjustment step, inoculation processes may also be performed with or without any treatment, pH adjustment or any moisture adjustment. All the processes may be completed alone or in conjunction with one or more of the others. It should also be noted that microbes themselves may be part of the process, not simply as an inoculant, but as an agent to convey materials into or out of the pore volume of the biochar.

Figure 4A:
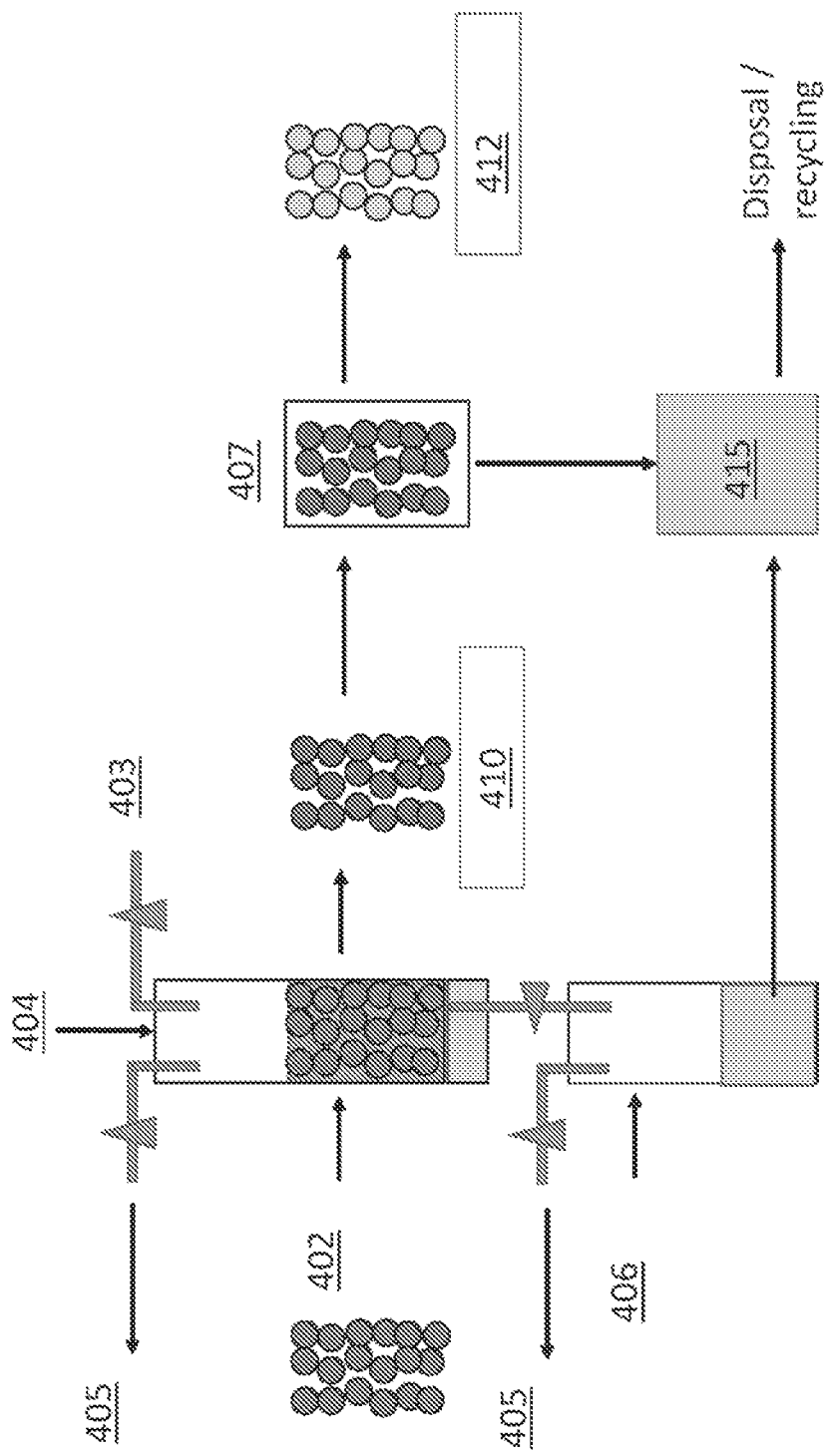
FIG. 4a illustrates a schematic of one example of an implementation of a biochar treat processes that that includes washing, pH adjustment and moisture adjustment.
Figure 4B:
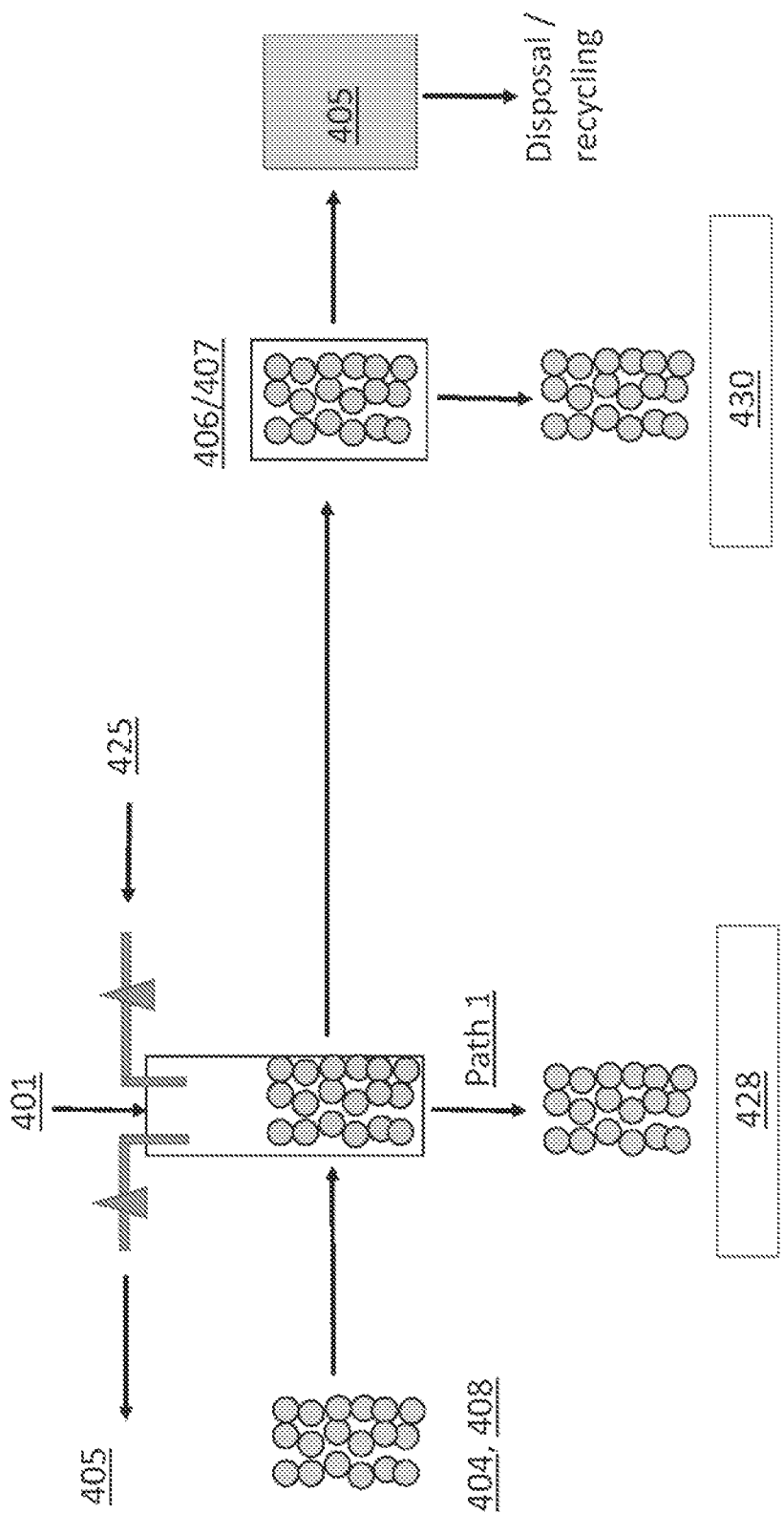
FIG. 4b illustrates yet another example of an implementation of a biochar treatment processing that includes inoculation.

For example, FIG. 4a illustrates a schematic of one example of an implementation of biochar processing that includes washing the pores and both pH and moisture adjustment. FIG. 4b illustrates yet another example of an implementation of biochar processing that includes inoculation.

As illustrated in FIG. 4a, raw biochar 402 is placed into a reactor or tank 404. A washing or treatment liquid 403 is then added to a tank and a partial vacuum, using a vacuum pump, 405 is pulled on the tank. The treating or washing liquid 403 may be used to clean or wash the pores of the biochar 402 or adjust the chemical or physical properties of the surface area or pore volume, such as pH level, usable pore volume, or VOC content, among other things. The vacuum can be applied after the treatment liquid 403 is added or while the treatment liquid 403 is added. Thereafter, the washed/adjusted biochar 410 may be moisture adjusted by vacuum exfiltration 406 to pull the extra liquid from the washed/moisture adjusted biochar 410 or may be placed in a centrifuge 407, heated or subjected to pressure gradient changes (e.g., blowing air) for moisture adjustment. The moisture adjusted biochar 412 may then be bagged or subject to further treatment. Any excess liquids 415 collected from the moisture adjustment step may be disposed of or recycled, as desired. Optionally, biochar fines may be collected from the excess liquids 415 for further processing, for example, to create a slurry, cakes, or biochar extrudates. It should be noted that in any of these steps, the residual gaseous environment in the tanks or centrifuges may be either ambient air, or a prescribed gas or combination of gasses to impact (through assistance or attenuation) reactivity during the process.

Optionally, rather than using a vacuum pump 405, a positive pressure pump may be used to apply positive pressure to the tank 404. In some situations, applying positive pressure to the tank may also function to force or accelerate the washing or treating liquid 403 into the pores of the biochar 402. Any change in pressure in the tank 404 or across the surface of the biochar could facilitate the exchange of gas and/or moisture into and out of the pores of the biochar with the washing or treating liquid 403 in the tank. Accordingly, changing the pressure in the tank and across the surface of the biochar, whether positive or negative, is within the scope of this invention. The atmosphere of the tank may be air or other gaseous mixture, prior to the intuition of the pressure change.

As illustrated FIG. 4b, the washed/adjusted biochar 410 or the washed/adjusted and moisture adjusted biochar 412 may be further treated by inoculating or impregnating the pores of the biochar with an additive 425. The biochar 410, 412 placed back in a reactor 401, an additive solution 425 is placed in the reactor 401 and a vacuum, using a vacuum pump, 405 is applied to the tank. Again, the vacuum can be applied after the additive solution 425 is added to the tank or while the additive solution 425 is being added to the tank. Thereafter, the washed, adjusted and inoculated biochar 428 can be bagged. Alternatively, if further moisture adjustment is required, the biochar can be further moisture adjusted by vacuum filtration 406 to pull the extra liquid from the washed/moisture adjusted biochar 410 or may be placed in a centrifuge 407 for moisture adjustment. The resulting biochar 430 can then be bagged. Any excess liquids 415 collected from the moisture adjustment step may be disposed of or recycled, as desired. Optionally, biochar particulates or "fines" which easily are suspended in liquid may be collected from the excess liquids 415 for further processing, for example, to create a slurry, biochar extrudates, or merely a biochar product of a consistently smaller particle size. Similarly, the flow rates, viscosity, and flow patterns of the liquid may be adjusted to capture particles of various geometries, drag coefficients, and weights using hydrodynamic principles. As described above, both processes of the FIGS. 4a and 4b can be performed with a surfactant solution in place of, or in conjunction with, the vacuum 405.

While known processes exist for the above described processes, research associated with the present invention has shown improvement and the ability to better control the properties and characteristics of the biochar if the processes are performed through the infusion and diffusion of liquids into and out of the biochar pores. One such treatment process that can be used is vacuum impregnation and vacuum and/or centrifuge extraction. Another such treatment process that can be used is the addition of a surfactant to infused liquid, which infused liquid may be optionally heated, cooled, or used at ambient temperature or any combination of the three.

Since research associated with the present invention has identified what physical and chemical properties have the highest impact on plant growth and/or soil health, the treatment process can be geared to treat different forms of raw biochar to achieve treated biochar properties known to enhance these characteristics. For example, if the pH of the biochar needs to be adjusted to enhance the raw biochar performance properties, the treatment may be the infusion of an acid solution into the pores of the biochar using vacuum, surfactant, or other treatment means. This treatment of pore infusion through, for example, the rapid, forced infusion of liquid into and out of the pores of the biochar, has further been proven to sustain the adjusted pH levels of the treated biochar for much longer periods than biochar that is simply immersed in an acid solution for the same period of time. By way of another example, if the moisture content needs to be adjusted, then excess liquid and other selected substances (e.g. chlorides, dioxins, and other chemicals, to include those previously deposited by treatment to catalyze or otherwise react with substances on the interior or exterior surfaces of the biochar) can be extracted from the pores using vacuum and/or centrifuge extraction or by using various heating techniques. The above describes a few examples of treatment that result in treated biochar having desired performance properties identified to enhance soil health and plant life or other applications.

Figure 5:
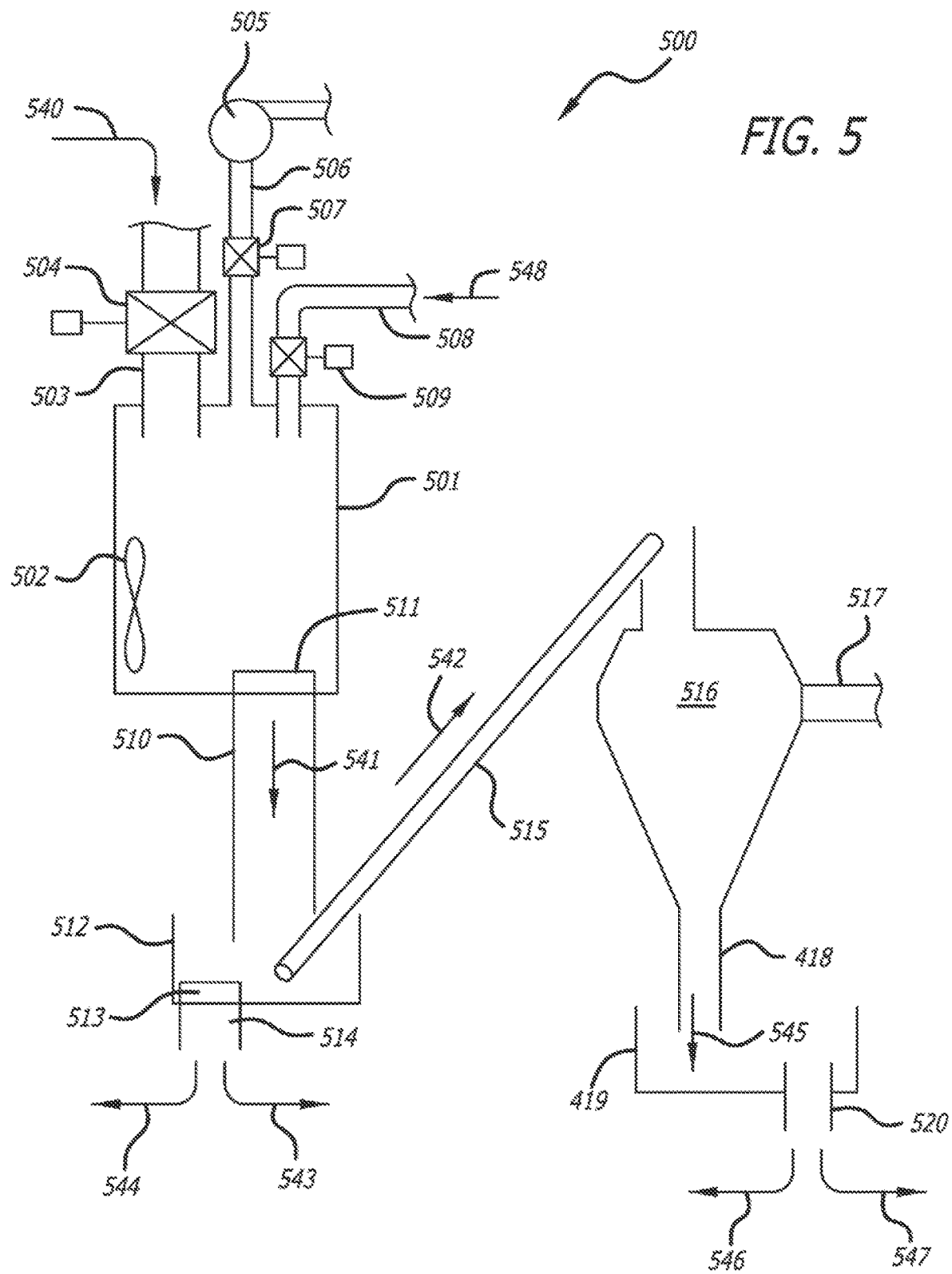
FIG. 5 is a schematic flow diagram of one example of a treatment system for use in accordance with the present invention.

FIG. 5 illustrates one example of a system 500 that utilizes vacuum impregnation to treat raw biochar. Generally, raw biochar particles, and preferably a batch of biochar particles, are placed in a reactor, which is connected to a vacuum pump, and a source of treating liquid (i.e. water or acidic/basis solution). When the valve to the reactor is closed, the pressure in the reactor is reduced to values ranging from 750 Torr to 400 Torr to 10 Torr or less. The biochar is maintained under vacuum ("vacuum hold time") for anywhere from seconds to 1 minute to 10 minutes, to 100 minutes, or possibly longer. By way of example, for about a 500-pound batch of untreated biochar, a vacuum hold time of from about 1 to about 5 minutes can be used if the reactor is of sufficient size and sufficient infiltrate is available to adjust the necessary properties. While under the vacuum the treating liquid may then be introduced into the vacuum chamber containing the biochar. Alternatively, the treating liquid may be introduced into the vacuum chamber before the biochar is placed under a vacuum. Optionally, treatment may also include subjecting the biochar to elevated temperatures from ambient to about 250° C. or reduced temperatures to about −25° C. or below, with the limiting factor being the temperature and time at which the infiltrate can remain flowable as a liquid or semi-liquid.

The infiltrate or treating liquid is drawn into the biochar pore, and preferably drawn into the macropores and mesopores. Depending upon the specific doses applied and pore structure of the biochar, the infiltrate can coat anywhere from 10% to 50% to 100% of the total macropore and mesopore surface area and can fill or coat anywhere from a portion to nearly all (10%-100%) of the total macropore and mesopore volume.

As described above, the treating liquid can be left in the biochar, with the batch being a treated biochar batch ready for packaging, shipment and use in an agricultural or other application. The treating liquid may also be removed through drying, treatment with heated gases, subsequent vacuum processing, centrifugal force (e.g., cyclone drying machines or centrifuges), dilution, or treatment with other liquids, with the batch being a treated biochar batch ready for packaging, shipment and use in an agricultural application. A second, third or more infiltration, removal, infiltration and removal, and combinations and variations of these may also be performed on the biochar with optional drying steps between infiltrations to remove residual liquid from and reintroduce gasses to the pore structure if needed. In any of these stages the liquid may contain organic or inorganic surfactants to assist with the penetration of the treating liquid.

As illustrated in FIG. 5, a system 500 for providing a biochar, preferably having predetermined and generally uniform properties. The system 500 has a vacuum infiltration tank 501. The vacuum infiltration tank 501 has an inlet line 503 that has a valve 504 that seals the inlet line 503. In operation, the starting biochar is added to vacuum infiltration tank 501 as shown by arrow 540. Once the tank is filled with the starting biochar, a vacuum is applied to the tank, by a vacuum pump connected to vacuum line 506, which also has valve 507. The starting biochar is held in the vacuum for a vacuum hold time. Infiltrate, as shown by arrow 548 is added to the tank 501 by line 508 having valve 509. The infiltrate is mixed with the biochar in the tank 501 by agitator 502. The mixing process is done under vacuum for a period of time sufficient to have the infiltrate fill the desired amount of pore volume, e.g., up to 100% of the macropores and mesopores.

Alternatively, the infiltrate may be added to the vacuum infiltration tank 501 before vacuum is pulled on the tank. Optionally, one or more selected gasses may be added to the tank. In this manner, infiltrate is added in the tank in an amount that can be impregnated into the biochar and optionally, the gasses introduced can also potentially impact the reactivity of the liquid as well as any organic or inorganic substances on the surface or in the pore volume of the biochar. As the vacuum is applied, the biochar is circulated in the tank to cause the infiltrate to fill the pore volume. To one skilled in the art, it should be clear that the agitation of the biochar during this process can be performed through various means, such as a rotating tank, rotating agitator, pressure variation in the tank itself, or other means. Additionally, the biochar may be dried using conventional means before even the first treatment. This optional pre-drying can remove liquid from the pores and in some situations, may increase the efficiency of impregnation due to pressure changes in the tank.

Pressure is then restored in the tank 501 with either ambient air or a prescribed selection of gasses, and the infiltrated biochar is removed, as shown by arrow 541, from the tank 501 to bin 512, by way of a sealing gate 511 and removal line 510. The infiltrated biochar is collected in bin 512, where it can be further processed in several different ways. The infiltrated biochar can be shipped for use as a treated biochar as shown by arrow 543. The infiltrated biochar can be returned to the tank 501 (or a second infiltration tank). If returned to the tank 501 the biochar can be processed with a second infiltration step, a vacuum drying step, a washing step, or combinations and variations of these. The infiltrated biochar can be moved by conveyor 514, as shown by arrow 542, to a drying apparatus 516, e.g., a centrifugal dryer or heater, where water, infiltrate or other liquid is removed by way of line 517, and the dried biochar leaves the dryer through discharge line 518 as shown by arrow 545, and is collected in bin 519. The biochar is removed from the bin by discharge 520. The biochar may be shipped as a treated biochar for use in an agriculture application, as shown by arrow 547. The biochar may also be further processed, as shown by 546. Thus, the biochar could be returned to tank 501 (or a second vacuum infiltration tank) for a further infiltration step. The drying step may be repeated either by returning the dry biochar to the drying apparatus 516, or by running the biochar through a series of drying apparatus, until the predetermined dryness of the biochar is obtained, e.g., between 50% to less than 1% moisture.

The system 500 is illustrative of the system, equipment and processes that can be used for, and to carry out the present inventions. Various other implementations and types of equipment can be used. The vacuum infiltration tank can be a sealable off-axis rotating vessel, chamber or tank. It can have an internal agitator that also, when reversed, can move material out, empty it, (e.g., a vessel along the lines of a large cement truck, or ready-mix truck, that can mix and move material out of the tank, without requiring the tank's orientation to be changed). Washing equipment may be added or utilized at various points in the process, or may be carried out in the vacuum tank, or drier, (e.g., wash fluid added to biochar as it is placed into the drier for removal). Other steps, such as bagging, weighing, the mixing of the biochar with other materials, e.g., fertilized, peat, soil, etc. can be carried out. In all areas of the system referring to vacuum infiltration, optionally positive pressure can be applied, if needed, to enhance the penetration of the infiltrate or to assist with re-infusion of gaseous vapors into the treated char. Additionally, where feasible, especially in positive pressure environments, the infiltrate may have soluble gasses added which then can assist with removal of liquid from the pores, or gaseous treatment of the pores upon equalization of pressure.

As noted above, the biochar may also be treated using a surfactant. The same or similar equipment used in the vacuum infiltration process can be used in the surfactant treatment process. Although it is not necessary to apply a vacuum in the surfactant treatment process, the vacuum infiltration tank or any other rotating vessel, chamber or tank can be used. In the surfactant treatment process, a surfactant, such as yucca extract, is added to the infiltrate, e.g., acid wash or water. The quantity of the surfactant added to the infiltrate may vary depending upon the surfactant used. For example, organic yucca extract can be added at a rate of between 0.1-20%, but more preferably 1-5% by volume of the infiltrate. The infiltrate with surfactant is then mixed with the biochar in a tumbler for several minutes, e.g., 3-5 minutes, without applied vacuum. Optionally, a vacuum or positive pressure may be applied with the surfactant to improve efficiency and penetration, but is not strictly necessary. Additionally, infiltrate to which the surfactant or detergent is added may be heated or may be ambient temperature or less. Similarly, the mixture of the surfactant or detergent, as well as the char being treated may be heated, or may be ambient temperature, or less. After tumbling, excess free liquid can be removed in the same manner as described above in connection with the vacuum infiltration process. Drying, also as described above in connection with the vacuum infiltration process, is an optional additional step. Besides yucca extract, a number of other surfactants may be used for surfactant treatment, which include, but are not limited to, the following: nonionic types, such as, ethoxylated alcohols, phenols-lauryl alcohol ethoxylates, Fatty acid esters-sorbitan, tween 20, amines, amides-imidazoles; anionic types, such as sulfonates-arylalkyl sulfonates and sulfate-sodium dodecyl sulfate; cationic types, such as alkyl-amines or ammoniums-quaternary ammoniums; and amphoteric types, such as betaines-cocamidopropyl betaine. Additionally, biosurfactants, or microbes which produce biosurfactants such as *Flavobacterium* sp., may also be used.

Optionally, the biochar may also be treated by applying ultrasonics. In this treatment process, the biochar may be contacted with a treating liquid that is agitated by ultrasonic waves. By agitating the treating liquid, contaminants may be dislodged or removed from the biochar due to bulk motion of the fluid in and around the biocarbon, pressure changes, including cavitation in and around contaminants on the surface, as well as pressure changes in or near pore openings (cavitation bubbles) and internal pore cavitation.

In this manner, agitation will cause contaminants of many forms to be released from the internal and external structure of the biochar. The agitation also encourages the exchange of water, gas, and other liquids with the internal biochar structure. Contaminants are transported from the internal structure to the bulk liquid (treating fluid) resulting in biochar with improved physical and chemical properties. The effectiveness of ultrasonic cleaning is tunable as bubble size and number is a function of frequency and power delivered by the transducer to the treating fluid.

In one example, applying ultrasonic treatment, raw wood based biochar between about 10 microns to 10 mm with moisture content from 0% to 90% may be mixed with a dilute mixture of acid and water (together the treating liquid) in a processing vessel that also translates the slurry (the biochar/treating liquid mixture). During translation, the slurry passes near an ultrasonic transducer to enhance the interaction between the fluid and biochar. The biochar may experience one or multiple washes of dilute acid, water, or other treating fluids. The biochar may also make multiple passes by ultrasonic transducers to enhance physical and chemical properties of the biochar. For example, once a large volume of slurry is made, it can continuously pass an ultrasonic device and be degassed and wetted to its maximum, at a rapid processing rate. The slurry can also undergo a separation process in which the fluid and solid biochar are separated at 60% effectiveness or greater.

Through ultrasonic treatment, the pH of the biochar, or other physical and chemical properties may be adjusted and the mesopore and macropore surfaces of the biochar may be cleaned and enhanced. Further, ultrasonic treatment can be used in combination with bulk mixing with water, solvents, additives (fertilizers, etc.), and other liquid based chemicals to enhance the properties of the biochar. After treatment, the biochar may be subject to moisture adjustment, further treatment and/or inoculation using any of the methods set forth above. In certain applications, ultrasonic technology may also be used to modify (usually reduce) the size of the biochar particles while retaining much, most, or nearly all of the porosity and pore structure. This yields smaller size particles with different morphologies than other methods of sizing such as grinding, crushing, sieving, or shaking.

C. Impact of Treatment

As illustrated above, the treatment process, whether using pressure changes (e.g. vacuum), surfactant or ultrasonic treatment, or a combination thereof, may include two steps, which in certain applications, may be combined: (i) washing and (ii) inoculation of the pores with an additive. When the desired additive is the same and that being inoculated into the pores, e.g., water, the step of washing the pores and inoculating the pores with an additive may be combined.

While not exclusive, washing is generally done for one of three purposes: (i) to modify the surface of the pore structure of the biochar (i.e., to allow for increased retention of liquids); (ii) to modify the pH of the biochar; and/or (iii) to remove undesired and potentially harmful compounds or gases.

Testing has further demonstrated that if the biochar is treated, at least partially, in a manner that causes the infusion and/or effusion of liquids and/or vapors into and/or out of the biochar pores (through mechanical, physical, biological, or chemical means), certain beneficial properties of the biochar can be altered, enhanced or improved through treatment. By knowing the properties of the raw biochar and the optimal desired properties of the treated biochar, the raw biochar can then be treated in a manner that results in the treated biochar having controlled optimized properties and greater levels of consistency between batches as well as between treated biochars arising from various feedstocks.

Using the treatment processes described above, or other treatments that provide, in part, for the infusion and/or effusion of liquids and/or vapors into and/or out of the biochar pores, biochars can have improved physical and chemical properties over raw biochar.

The table below, illustrates some of the important physical and chemical properties of biochar that can be achieved through treatment methods of the present invention:

| PROPERTY | NUMERIC VALUES |
|---|---|
| Bulk Density | 0.1-0.6 g/cm$^3$ |
| Solid Particle Density | 0.2-1.2 g/cm$^3$ |
| Impregnation/Absorption Capacity (IC) | 0.2-0.8 cm$^3$/cm$^3$ |
| Water Holding Capacity (WHC)/Water Retention Capacity (WRC) | Volumetric: Above 30% (volume of water/volume biochar) Gravimetric: 100-400% (wet weigh-dry weight/dry weight) |
| Plant Available Water | ≥35 wt % |
| Surface Area | 200-600 m2/g |
| TGA (H2O) | 0% ≤ x ≤ 80% by weight Preferred: 20% ≤ x ≤ 80% by weight |
| Percentage Total Residual Organic Compound Content | 0-30 wt. % |
| Percentage Heavy ROC Content | 0-20 wt. % |
| Percentage VOC Content | Less than 5% |
| Acidity (pH) | pH < 8.5, optimal 6.5 < pH < 5 |
| Percentage of pore volume > 300 nm to total pore volume | 50% |
| Ash Content | 0.1-5 wt. % |
| Remaining Water Content | 100-650 mL/kg; 45-150 mL/L; 12-30 gal/ton; 3-10 gal/yd3 after 360 hours (15 days) of exposure to the environment |
| Electrical conductivity | >0.2 ds/m |
| Cation Exchange Capacity | ≥5 millieq/l |
| Anion Exchange Capacity | ≥5 millieq/l |
| Dioxins TEQ | <0.75 ng/kg WHO-PCDD/F-TEQ//kg (with <0.5 ng/kg WHO-PCDD/F-TEQ//kg optimal) |
| Hydrophilicity | 0-4 (Indexed by MED testing) 0-4 (Indexed by Infiltrometer testing) |

The above data has been verified by the testing set forth herein using treated biochars containing mostly particle sizes less than or equal to 10 mm and greater than 0.5 mm. In general, for most batches of biochar, greater than seventy-five percent (75%) of the biochars tested in batch by both volume and weight have particle sizes less than or equal to 10 mm, where approximately 75% of the biochars tested in batch have particles sizes less than or equal to 5 mm. As also set forth above, the biochars tested have at least 55% carbon content based upon weight. When measuring particle size, as particle size distribution in a batch, a cumulative method of measure is used. When measured in a batch of particles, the cumulative particle size distribution is the percentage of the particles in the batch that will pass through a uniform sieve of a given size.

Regarding measurement of the above properties, the properties are defined and measured as set forth below:

| Attribute | Definition | Unit of Measure | Method of Measure |
|---|---|---|---|
| Impregnation Capacity | The amount of water that can be held internally within the porous structure (micro, meso, and macro pores) of a given particle or batch of particles, measured by the amount of liquid that can be infused into biochar by vacuum impregnation. | Either volumetric (cm$^3$ liquid per cm$^3$ particles) or gravimetric (gm liquid per gm particles) | Example measurement techniques: Measure specific amount (grams or mL) of biochar; dry the sample at 120 C. for 2 hrs.; transfer the sample into sealed vacuum reactor and apply vacuum of 15 to 30 inches Hg; start adding water drop wise to the biochar under vacuum; at the first sight of water not impregnated into the pores |

| Attribute | Definition | Unit of Measure | Method of Measure |
| --- | --- | --- | --- |
| | | | (incipient wetness) stop and measure the amount of water added up to this point; this water amount divided by the samples mass or volume will give the impregnation capacity. Alternative measurement: Dry substance completely (through heating or other means); weigh substance; expose substance to water while removing adsorbed gasses with partial vacuum by apply vacuum of 15 to 30 inches Hg; remove interspatial water by centrifuge or other surface drying technology. Do not heat to remove water in pores; weigh substance; the difference in the two weights of the substance of the initial dry weigh of the substance measures impregnation capacity. |
| Water Holding Capacity/Water Retention Capacity | The amount of water that can be held both internally within the porous structure, sorbed onto the particle surface and in the interparticle void spaces in a given batch of particles without forced infusion techniques. | Volumetric: (ml liquid/ml particles or L liquid/L particles) Gravimetric (wet weight-dry weight/dry weight) | 1. Dry sample of biochar 2. Place sample in a container 3. Fill container with water 4. Drain container 5. Measure mass of sample (i.e., wet weight) 6. Dry sample (preferably by exposure to heat at or above boiling point of water) 7. Measure mass of sample (i.e., dry weight) and/or determine sample volume |
| Plant Available Water | The difference of water content at field capacity from the water content at the permanent wilting point, which is the point when no water is available for the plants | % mass by weight | A pressure plate extractor is used to measure plant available water |
| HO (TGA) | HO (TGA) represents the mass of water contained in the sample measured through Thermogravimetric analysis ("TGA"). | % mass by weight | Thermogravimetric analysis of a given sample indicating % water in a sample is determined by % mass loss measured between standard temperature and 150 degrees C. |
| Total ROC (TGA) | Total ROC (TGA) represents the mass of residual organic compounds (light and heavy) contained in a sample. | % mass by weight | Thermogravimetric analysis of a given sample indicating % of residual organic compounds is measured by % mass loss sustained between 150 degrees C and 950 degrees C. |
| VOC % (TGA) | Total ROC (TGA) represents the mass of residual light organic compounds (volatiles) contained in the sample. | % mass by weight | Thermogravimetric analysis of a given sample indicating % of light organic compounds (volatiles) is measured by % mass loss sustained between 150 degrees C. and 550 degrees C. |
| Heavy ROC % (TGA) | TGA (Total ROC) represents the mass of mass of residual heavy organic compounds contained in the sample. | % mass by weight | Thermogravimetric analysis of a given sample indicating % of heavy organic compounds is measured by % mass loss sustained between 550 degrees C and 950 degrees C. |
| PH | The acidity of the biochar | pH | Mix biochar into deionized water at a ratio of 1 part BC to 5 parts water [mass : volume] ratio, for example, 50 g biochar + 250 mL DI water. Still slurry for 10 minutes using a standard magnetic stirrer. Measure pH of the slurry using standard pH measurement technology (i.e., a standard laboratory pH meter). |

-continued

| Attribute | Definition | Unit of Measure | Method of Measure |
|---|---|---|---|
| Porosimetry-Volume of Meso and Macro pores (3 nm-360,000 nm) | Mesopore and Macropore volume (pores between 3 nm and 360,000 nm) in a material sample over total sample volume | Weight based porosity (pore volume/weight) cc/g or Volume based porosity (pore volume/bulk volume) cc/ml | Determined by mercury porosimetry, which measures the meso & macro porosity by applying pressure to a sample immersed in mercury at a pressure calibrated for the desired minimum pore diameter to be measured. |
| Percentage of pore volume > 300 nm to total pore volume | Percentage of macropore volume in a sample greater than 300 nm in diameter over total pore volume | ml pores >300 nm/ml substance/ ml total pores/ml substance | Macropore volume is determined by mercury porosimetry, which measures the macroporosity by applying pressure to a sample immersed in mercury at a pressure calibrated for the minimum pore diameter (300 nm) to be measured.<br>Total volume of pores per volumetric unit of substance is measured using gas expansion method. |
| Remaining Water Content | The total amount of water that remains held by the biochar after exposure to the enviro nment for certain amount of time. | mL/kg; mL/L | 1. Create a sample of biochar where the biochar has reached its maximum water holding capacity;<br>2. Determine (using a portion of the sample) the total water content by thermogravimetric analysis (H2O (TGA))<br>3. Expose the biochar (in the remaining sample) to the enviro nment for a period of 2 weeks, 1 day (15 days, 360 hrs.);<br>4. Determine the remaining water content by thermogravimetric analysis (H2O (TGA)); and<br>5. Normalizing the remaining (retained) water in mL to 1 kg or 1 L biochar. |
| Electrical Conductivity | Electrical conductivity is the measure of the amount of electrical current a material can carry. | ds/m | Following the USDA Soil Quality Test Kit Guide, material is mixed with deionized water on a 1:1 material to water ratio on a volume basis. The electrical conductivity is then measured using a commonly available EC meter-consisting of two electrodes and a constant current flowing through the material between the electrodes. |
| Cation Exchange Capacity | Cation exchange capacity (CEC) is the total capacity of a soil to hold exchangeable cations. CEC is an inherent soil characteristic and is difficult to alter significantly. It influences the soil's ability to hold onto essential nutrients and provides a buffer against soil acidification. | millieq/l | CEC may be determined through the use of ammonium acetate buffered at pH 7.0. The material is saturated with 1M ammonium acetate, (NHOAc), followed by the release of the $NH_4^+$ ions and its measurement in meq/100 g (milliequivalents of charge per 100 g of dry soil) or cmolc/kg (centimoles of charge per kilogram of dry soil).<br>Instead of ammonium acetate another method uses barium chloride. 0.1 M BaCl is used to saturate the exchange sites followed by replacement with either $MgSO_4$ or $MgCl_2$. Indirect methods for CEC calculation involves the |

| Attribute | Definition | Unit of Measure | Method of Measure |
|---|---|---|---|
| | | | estimation of extracted Cat, $Mg_2^+$, $K^+$, and $Na^+$ in a standard soil test using Mehlich 3 and accounting for the exchangeable acidity (sum of $H^+$, $Al_3^+$, $Mn_2^+$, and $Fe_2^+$) if the pH is below 6.0 |
| Anion Exchange Capacity | AEC is the degree to which a soil can adsorb and exchange anions. AEC increases as soil pH decreases. The pH of most productive soils is usually too high (exceptions are for volcanic soils) for full development of AEC and thus it generally plays a minor role in supplying plants with anions. | millieq/1 | AEC is calculated directly or indirectly by saturated paste extraction of exchangeable anions, $Cl^-$, $NO_3^-$, $SO_4^{2-}$, and $PO4^{3-}$ to calculate anion sum or the use of potassium bromide to saturate anions sites at different pHs and repeated washings with calcium chloride and final measurement of bromide |
| Dioxins TEQ | Polychlorinated dibenzo-p-dioxins (PCDDs) (i.e., 75 congeners (10 are specifically toxic)); Polychlorinated dibenzofurans (PCDFs) (i.e., 135 congeners (7 are specifically toxic)) and Polychlorinated biphenyls (PCBs) (Considered dioxin-like compounds (DLCs)) | ng/kg WHO-PCDD/F-TEQ//kg | Two methods are used: EPA Method 8290 (for research and understanding at low levels (ppt-ppq); and EPA Method 1613B (for regulatory compliance). Both are based on high resolution gas chromatography (HRGC)/high resolution mass spectrometry (HRMS). |
| Hydrophilicity | Measure of the affinity of the material to absorb or associate with water (the lower the indexed number the more affinity the biochar has to absorb water and thus the more hydrophillic) | Indexed | Molarity of Ethanol Drop Test ("MED Test")<br>1. Make seven solutions of deionized ("DI") water with the following respective percentages of ethanol: 3, 5, 11, 13, 18, 24 and 36. The test started with a mixture having no DI.<br>2. Place biochar in container prepared for testing<br>3. Start with DI water testing (solution 0-no ethanol); Test multiple drop laid onto the substrate surface from low height. If drops soak in less than 3 seconds, record substrate as "0." If drops take longer than 3 seconds or don't soak in, go to test solution 1.<br>4. Test Solution 1; Test multiple drops from dropper laid onto the surface from low height. If drops soak into the substrate in less than 3 seconds, record material as "1" If drops take longer than 3 seconds, or don't soak in, go to test solution 2.<br>5. Test solution 2; Test multiple drops from dropper laid onto the surface from low height. If drops soak into the substrate in less than 3 seconds, record material as "2." If drops take longer than 3 seconds, or don't soak in, go to test solution 3.<br>Proceed as above, testing progressively higher numbered MED solutions until you find the solution that soaks into the substrate in 3 seconds or less. The substrate is recorded as having that Hydrophobicity Index number assigned to it (0-7, with 0 being very hydrophilic and 7 strongly hydrophobic). |

| Attribute | Definition | Unit of Measure | Method of Measure |
|---|---|---|---|
| Hydrophilicity | Measure of the affinity of the material to absorb or associate with water (the lower the indexed number the more affinity the biochar has to absorb water and thus the more hydrophillic) | Indexed | Infiltrometer Testing<br>1. Fill the bubble chamber three quarters full with tap water for both water and ethanol sorptivity tests. Do NOT use distilled or DI water.<br>2. Once the upper chamber is full, invert the infiltrometer and fill the water reservoir with 80 mL.<br>3. Carefully set the position of the end of the mariotte tube with respect to the porous disk to ensure a zero suction offset while the tube bubbles. If this dimension is changed accidentally, the end of the mariotte tube should be reset to 6 mm from the end of the plastic water reservoir tube.<br>4. Replace the bottom elastomer, making sure the porous disk is firmly in place.<br>5. If the infiltrometer is held vertically using a stand and clamp, no water should leak out.<br>6. Set the suction rate of 1 cm for all samples.<br>7. If the surface of the sample is not smooth, a thin layer of fine biochar being tested can be applied to the area directly underneath the infiltrometer stainless steel disk. This ensures good contact between the samples and the infiltrometer.<br>8. When we take the reading, the interval is 1 min for both water and ethanol sorptivity test.<br>9. To be accurate, 20 mL water or 95% ethanol needs to be infiltrated into the samples.<br>10. Record time and water/ethanol volume.<br>Data Processing<br>1. Input the volume levels and time to the corresponding volume column<br>2. Use the following equation to calculate the hydrophobicity index of R<br>$I = at + b\sqrt{t}$<br>a: Infiltration Rate, cm/s<br>b: Sorptivity, cm/s$^{1/2}$<br><br>$$R = 1.95 * \frac{b_{ethanol}}{b_{water}}$$ |

1. Impregnation Capacity

As illustrated above, "impregnation capacity" is defined as the amount of water that can be held internally within the porous structure (micro, meso, and macro pores) of a given particle or batch of particles. This is measured by determining the maximum amount of liquid that can be infused into biochar by vacuum impregnation. The measurement can be taken either volumetric (ml liquid per ml particles) or gravimetric (gin liquid per gm particles). More than one measurement technique can be used to determine the impregnation capacity. In one example, the measurement is determined by the following procedure: (i) measure a specific amount (grams or mL) of biochar; (ii) dry the sample at 120° C. for 2 hrs.; (iii) transfer the sample into sealed vacuum reactor and apply vacuum of 15 to 30 inches Hg; (iv) start adding water drop wise to the biochar under vacuum; (v) at the first sight of water not impregnated into the pores (incipient wetness) stop and measure the amount of water added up to this point; (vi) this water amount divided by the samples mass or volume will give the impregnation capacity.

In another example, impregnation capacity is measured by the following procedure: (i) measure a specific amount of biochar (grams or mL); (ii) dry the biochar by, for example, heating the biochar under a temperature of 120° C. for a period of 2 hours or until mass loss is below 0.1% in a 5 minute period, or by using another acceptable technique to reduce the moisture content of the biochar to less than 2% and preferably less than 1%; (ii) weigh the biochar; (iii) expose the biochar to water while removing the absorbed gasses with a partial vacuum of 15 to 30 inches Hg; (iv) removing interspatial water by centrifuge or other surface drying technology (excluding heat); and (v) weighing the biochar. The difference in weight of the substance in step (ii) from step (v) over the total weight of the substance from step (ii) determines the impregnation capacity of the biochar. This number can be then be presented as a measurement by mass or volume.

2. Increases Water Holding Capacity/Water Retention Capacity

As demonstrated below, the treatment processes of the invention modify the surfaces of the pore structure to provide enhanced functionality and to control the properties of the biochar to achieve consistent and predicable performance. Using the above treatment processes, anywhere from at least 10% of the total pore surface area up to 90% or more of the total pore surface area may be modified. In some implementations, it may be possible to achieve modification of up to 99% or more of the total pore surface area of the biochar particle. Using the processes set forth above, such modification may be substantially and uniformly achieved for an entire batch of treated biochar.

For example, it is believed that by treating the biochar as set forth above, the hydrophilicity of the surface of the pores of the biochar is modified, allowing for a greater water retention capacity. Further, by treating the biochars as set forth above, gases and other substances are also removed from the pores of the biochar particles, also contributing to the biochar particles' increased water holding capacity. Thus, the ability of the biochar to retain liquids, whether water or additives in solution, is increased, which also increases the ability to load the biochar particles with large volumes of inoculant, infiltrates and/or additives.

A batch of biochar has a bulk density, which is defined as weight in grams (g) per $cm^3$ of loosely poured material that has or retains some free space between the particles. The biochar particles in this batch will also have a solid density, which is the weight in grams (g) per $cm^3$ of just particles, i.e., with the free space between the particles removed. The solid density includes the air space or free space that is contained within the pores, but not the free space between particles. The actual density of the particles is the density of the material in grams (g) per $cm^3$ of material, which makes up the biochar particles, i.e., the solid material with pore volume removed.

In general, as bulk density increases the pore volume is expected to decrease. When the pore volume is macro or mesoporous, the ability of the material to hold infiltrate, e.g., inoculant is directly proportional to the pore volume, thus it is also expected to decrease as bulk density increases. With the infiltration processes, the treated biochars can have impregnation capacities that are larger than could be obtained without infiltration, e.g., the treated biochars can readily have 30%, 40%, 50%, or most preferably, 60%-100% of their total pore volume filled with an infiltrate, e.g., an inoculant. The impregnation capacity is the amount of a liquid that a biochar particle, or batch of particles, can absorb. The ability to make the pores surface hydrophilic, and to infuse liquid deep into the pore structure through the application of positive or negative pressure and/or a surfactant, alone or in combination, provides the ability to obtain these high impregnation capabilities. The treated biochars can have impregnation capabilities, i.e., the amount of infiltrate that a particle can hold on a volume held/total volume of a particle basis, that is greater than 0.2 $cm^3/cm^3$ to 0.8 $cm^3/cm^3$. Resulting bulk densities of treated biochar can range from 0.1-0.6 $g/cm^3$ and sometimes preferably between 0.3-0.6 $g/cm^3$ and can have solid densities ranging from 0.2-1.2 $g/cm^3$.

Figure 6:
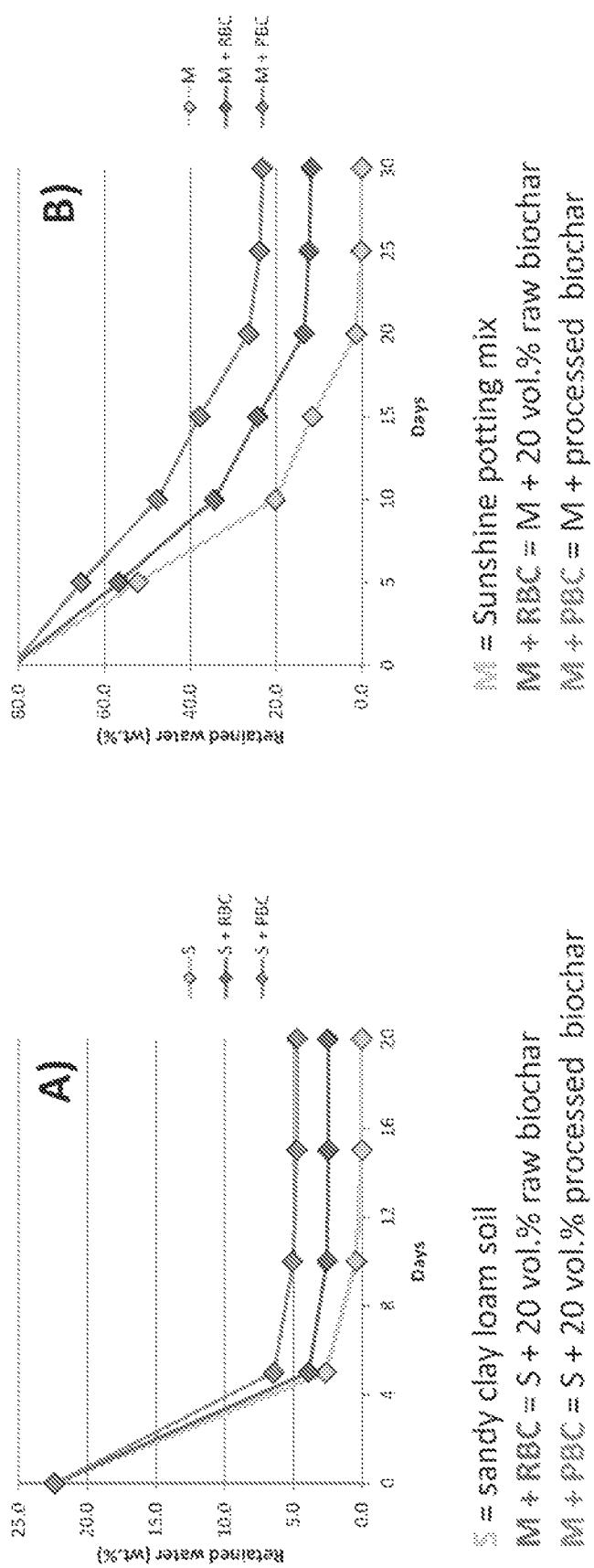
FIG. 6 is a chart showing the water holding capacities of treated biochar as compared to raw biochar and sandy clay loam soil and as compared to raw biochar and sunshine potting soil.

Accordingly, by using the treatment above, the water retention capacity of biochar can be greatly increased over the water retention capacities of various soil types and even raw biochar, thereby holding water and/or nutrients in the plant's root zone longer and ultimately reducing the amount of applied water (through irrigation, rainfall, or other means) needed by up to 50% or more. FIG. 6 is a chart showing the water retention capacities of soils versus raw and treated biochar. The soils sampled are loam and sandy clay soil and a common commercial horticultural mix. The charts show the retained water as a function of time.

In chart A, the bottom line represents the retained water in the sandy claim loam soil over time. The middle line represents the retained water in the sandy clay soil with 20% by volume percent of unprocessed raw biochar. The top line represents the retained water in the sandy clay loam soil with 20% by volume percent of treated biochar (adjusted and inoculated biochar). Chart B represents the same using a soilless potting mix rather than sandy clay loam soil.

Figure 7:
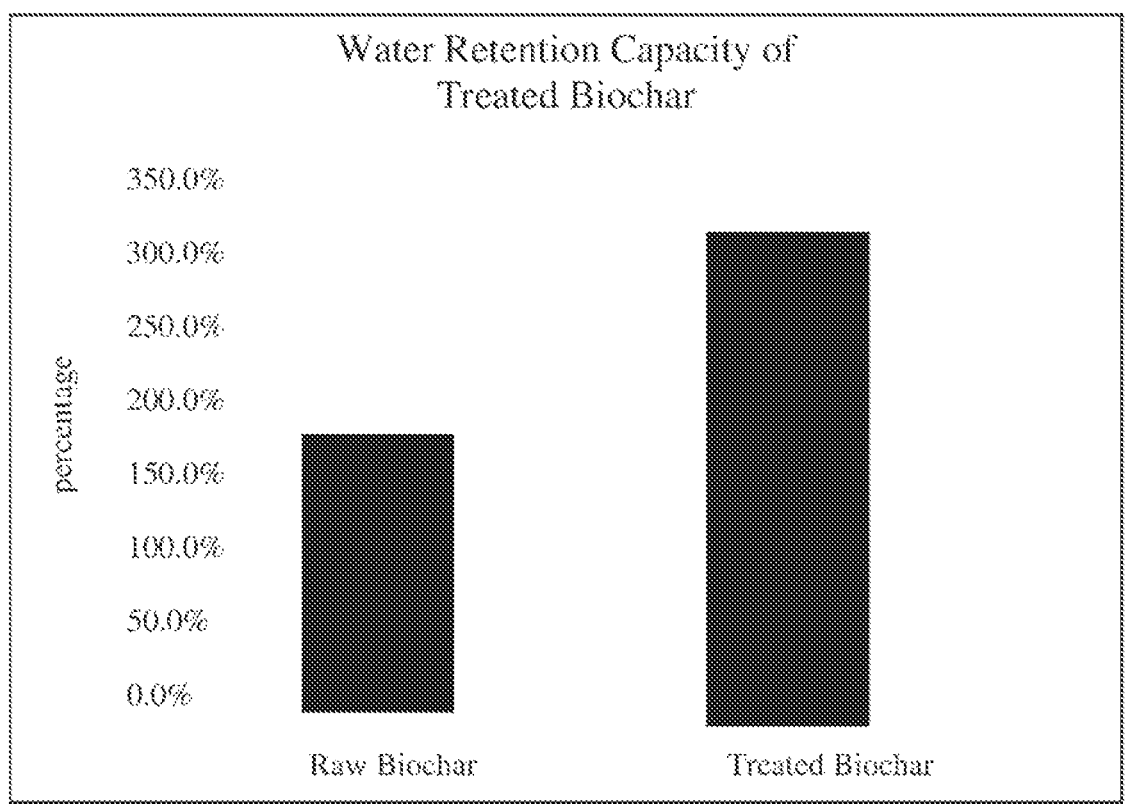
FIG. 7 illustrates the different water retention capacities of raw biochar versus treated biochar measured gravimetrically.

As illustrated in FIG. 7, testing showed a treated biochar had an increased water retention capacity of approximately 1.5 times that of the raw biochar from the same feedstock. Similar results have been seen with biochars derived from various feedstocks. With certain biochar types, the water retention capacity of treated biochar could be as great as three times that of raw biochar.

"Water holding capacity," which may also be referred to as "Water Retention Capacity," is the amount of water that can be held both internally within the porous structure and in the interparticle void spaces in a given batch of particles. While a summary of the method of measure is provided above, a more specific method of measuring water holding capacity/water retention capacity is measured by the following procedure: (i) drying a sample of material under temperatures of 105° C. for a period of 24 hours or using another scientifically acceptable technique to reduce the moisture content of the material to less than 2%, less than 1%; and preferably less than 0.5% (ii) placing a measured amount of dry material in a container; (iii) filling the container having the measured amount of material with water such that the material is completely immersed in the water; (iv) letting the water remain in the container having the measured amount of material for at least ten minutes or treating the material in accordance with the invention by infusing with water when the material is a treated biochar; (v) draining the water from the container until the water ceases to drain; (vi) weighing the material in the container (i.e., wet weight); (vii) again drying the material by heating it under temperatures of 105° C. for a period of 24 hours or using another scientifically acceptable technique to reduce the moisture content of the material to less than 2% and preferably less than 1%; and (viii) weighing the dry material again (i.e., dry weight) and, for purposes of a volumetric measure, determining the volume of the material.

Figure 8:
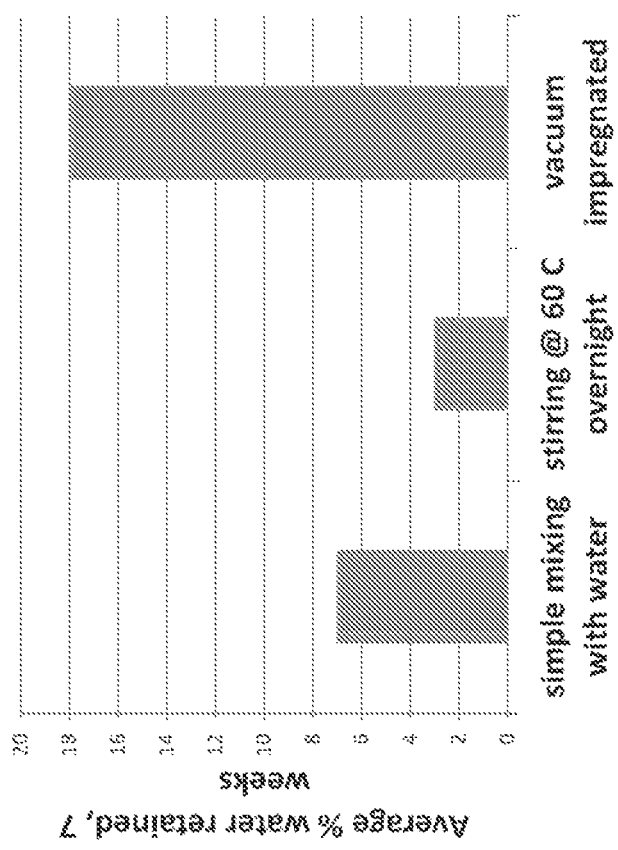
FIG. 8 is a chart showing the retained water in vacuum impregnated biochar over other biochars after a seven week period.

Measured gravimetrically, the water holding/water retention capacity is determined by measuring the difference in weight of the material from step (vi) to step (viii) over the weight of the material from step (viii) (i.e., wet weight-dry weight/dry weight). FIG. 8 illustrates the different water retention capacities of raw biochar versus treated biochar measured gravimetrically. As illustrated, water retention capacity of raw biochar can be between 100-200%, whereas treated biochar can have water retention capacities measured gravimetrically between 200-400%.

Water holding capacity can also be measured volumetrically and represented as a percent of the volume of water retained in the biochar after gravitationally draining the excess water/volume of biochar The volume of water retained in the biochar after draining the water can be determined from the difference between the water added to the container and water drained off the container or from the difference in the weight of the wet biochar from the weight of the dry biochar converted to a volumetric measurement. This percentage water holding capacity for treated biochar may be 50-55 percent and above by volume.

Given biochar's increased water retention capacity, the application of the treated biochar and even the raw biochar can greatly assist with the reduction of water and/or nutrient application. It has been discovered that these same benefits can be imparted to agricultural growth.

Treated biochar of the present invention has also demonstrated the ability to retain more water than raw biochar after exposure to the environment for defined periods of time. For purposes of this application "remaining water content" can be defined as the total amount of water that remains held by the biochar after exposure to the environment for certain amount of time. Exposure to environment is exposure at ambient temperature and pressures. Under this definition, remaining water content can be measured by (i) creating a sample of biochar that has reached its maximum water holding capacity; (ii) determining the total water content by thermogravimetric analysis ($H_2O$ (TGA)), as described above on a sample removed from the output of step (i) above, (iii) exposing the biochar in the remaining sample to the environment for a period of 2 weeks (15 days, 360 hrs.); (iv) determining the remaining water content by thermogravimetric analysis ($H_2O$ (TGA)); and (v) normalizing the remaining (retained) water in mL to 1 kg or 1 L biochar. The percentage of water remaining after exposure for this two-week period can be calculated by the remaining water content of the biochar after the predetermined period over the water content of the biochar at the commencement of the two-week period. Using this test, treated biochar has shown to retain water at rates over 4× that of raw biochar. Testing has further demonstrated that the following amount of water can remain in treated biochar after two weeks of exposure to the environment: 100-650 mL/kg; 45-150 mL/L; 12-30 gal/ton; 3-10 gal/yd$^3$ after 360 hours (15 days) of exposure to the environment. In this manner, and as illustrated in FIG. 8, biochar treated with a process consistent with those described in this disclosure can increase the amount of retained water in biochar about 3 times compared to other methods even after seven weeks. In general, the more porous and the higher the surface area of a given material, the higher the water retention capacity. Further, it is theorized that by modifying the hydrophilicity/hydrophobicity of the pore surfaces, greater water holding capacity and controlled release may be obtained. Thus, viewed as a weight percent, e.g., the weight of retained water to weight of biochar, examples of the present biochars can retain more than 5% of their weight, more than 10% of their weight, and more than 15% of their weight, and even more than 50% of their weight compared to an average soil which may retain 2% or less, or between 100-600 ml/kg by weight of biochar.

Tests have also shown that treated biochars that show weight loss of >1% in the interval between 43-60° C. when analyzed by the Thermal Gravimetric Analysis (TGA) (as described below) demonstrate greater water holding and content capacities over raw biochars. Weight loss of >5%-15% in the interval between 38-68° C. when analyzed by the Thermal Gravimetric Analysis (TGA) using sequences of time and temperature disclosed in the following paragraphs or others may also be realized. Weight percentage ranges may vary from between >1%-15% in temperature ranges between 38-68° C., or subsets thereof, to distinguish between treated biochar and raw biochar.

Figure 9:
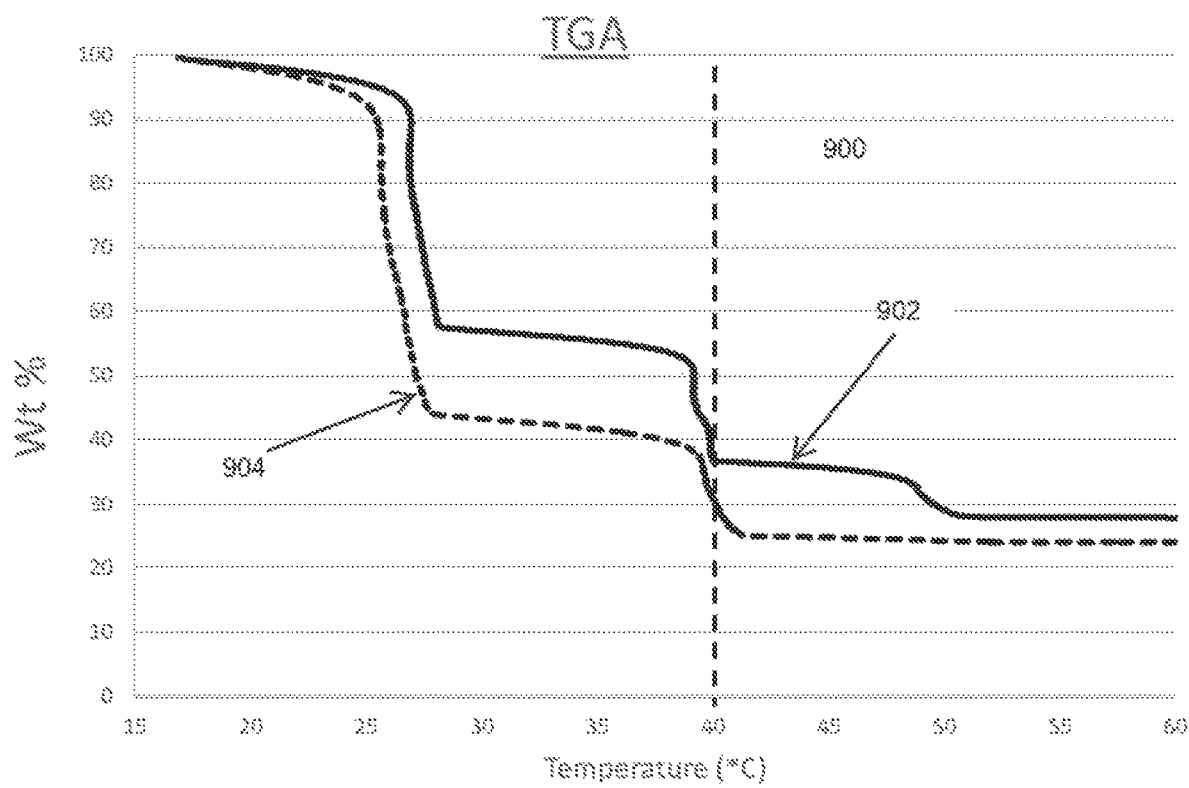
FIG. 9 is a chart showing the weight loss of treated biochars versus raw biochar samples when heated at varying temperatures using a TGA testing method.

FIG. 9 is a chart 900 showing the weight loss of treated biochars 902 versus raw biochar samples 904 when heated at varying temperatures using the TGA testing described below. As illustrated, the treated biochars 902 continue to exhibit weight loss when heated between 40-60° C. when analyzed by the Thermal Gravimetric Analysis (TGA) (described below), whereas the weight loss in raw biochar 804 between the same temperature ranges levels off. Thus, testing demonstrates the presence of additional moisture content in treated biochars 902 versus raw biochars 904.

In particular, the treated biochars 902 exhibit substantial water loss when heated in inert gas such as nitrogen following treatment. More particularly, when heated for 25 minutes at each of the following temperatures 20, 30, 40, 50 and 60° C. the treated samples lose about 5-% to 15% in the interval 43-60° C. and upward of 20-30% in the interval between 38-68° C. The samples to determine the water content of the raw biochar were obtained by mixing a measured amount of biochar and water, stirring the biochar and water for 2 minutes, draining off the water, measuring moisture content and then subjecting the sample to TGA. The samples for the treated biochar were obtained by using the same measured amount of biochar as used in the raw biochar sample and using treatment process consistent with those described in this disclosure. The moisture content is then measured and the sample is subjected to TGA described above.

The sequences of time and temperature conditions for evaluating the effect of biochars heating in inert atmosphere is defined in this application as the "Bontchev-Cheyne Test" ("BCT"). The BCT is run using samples obtained, as described above, and applying Thermal Gravimetric Analysis (TGA) carried out using a Hitachi STA 7200 analyzer under nitrogen flow at the rate of 110 mL/min. The biochar samples are heated for 25 minutes at each of the following temperatures: 20, 30, 40, 50 and 60° C. The sample weights are measured at the end of each dwell step, at the beginning and at the end of the experiment. The analyzer also continually measures and records weight over time. Biochars treated with a process consistent with those described in this disclosure to enhance water holding or retention capacities typically exhibit weight loss of >5% in the interval between 38-68° C., >1% in the interval between 43-60° C. Biochars with greater water holding or retention capacities can exhibit >5% weight loss in the interval between 43-60° C. measured using the above described BCT.

Figure 10:
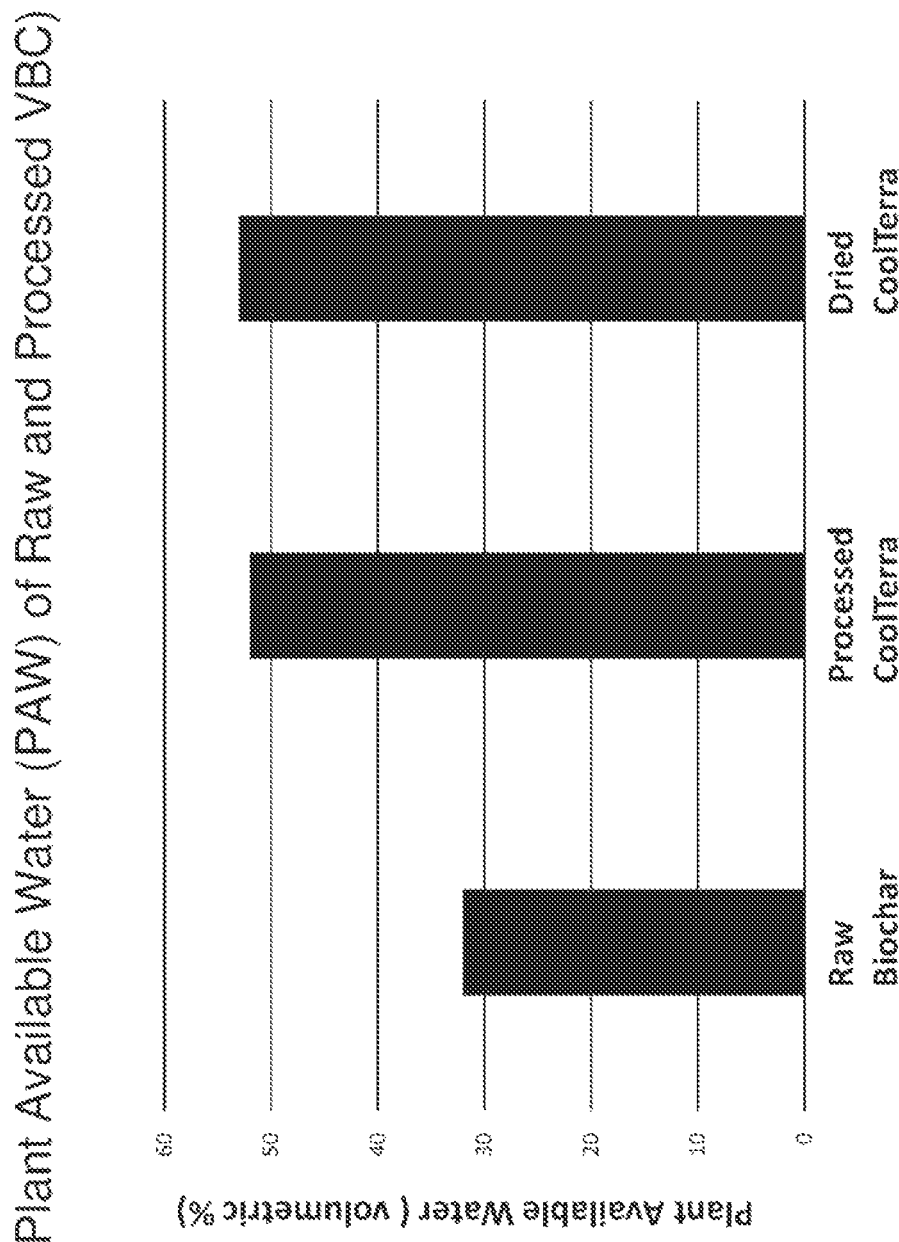
FIG. 10 illustrates the plant available water in raw biochar, versus treated biochar and treated dried biochar.

Lastly, as illustrated in FIG. 10, plant available water is greatly increased in treated biochar over that of raw biochar. FIG. 10 illustrates the plant available water in raw biochar, versus treated biochar and treated dried biochar and illustrates that treated biochar can have a plant available water percent of greater than 35% by volume.

"Plant Available Water" is the amount of unbound water in a material available for plants to uptake. This is calculated by subtracting the volumetric water content at the permanent wilting point from the volumetric water content at field capacity, which is the point when no water is available for the plants. Field capacity is generally expressed as the bulk water content retained in at −33 J/kg (or −0.33 bar) of hydraulic head or suction pressure. Permanent wilting point is generally expressed as the bulk water content retained at −1500 J/kg (or −15 bar) of hydraulic head or suction pressure. Methods for measuring plant available water are well-known in the industry and use pressure plate extractors, which are commercially available or can be built using well-known principles of operation.

3. Adjusts pH

Figure 11:
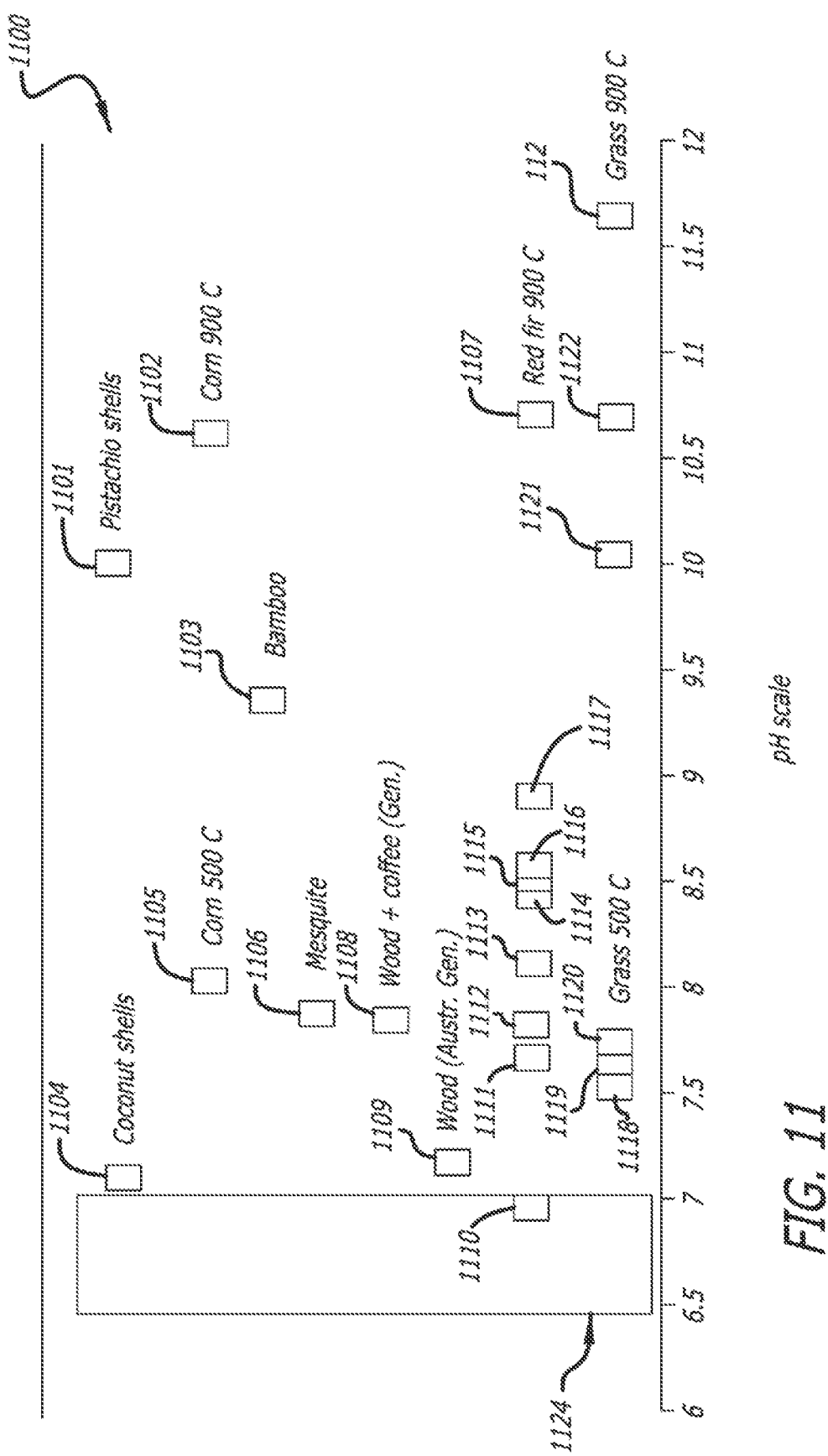
FIG. 11 is a graph showing the pH of various starting biochars that were made from different starting materials and pyrolysis process temperatures.
Figure 12:
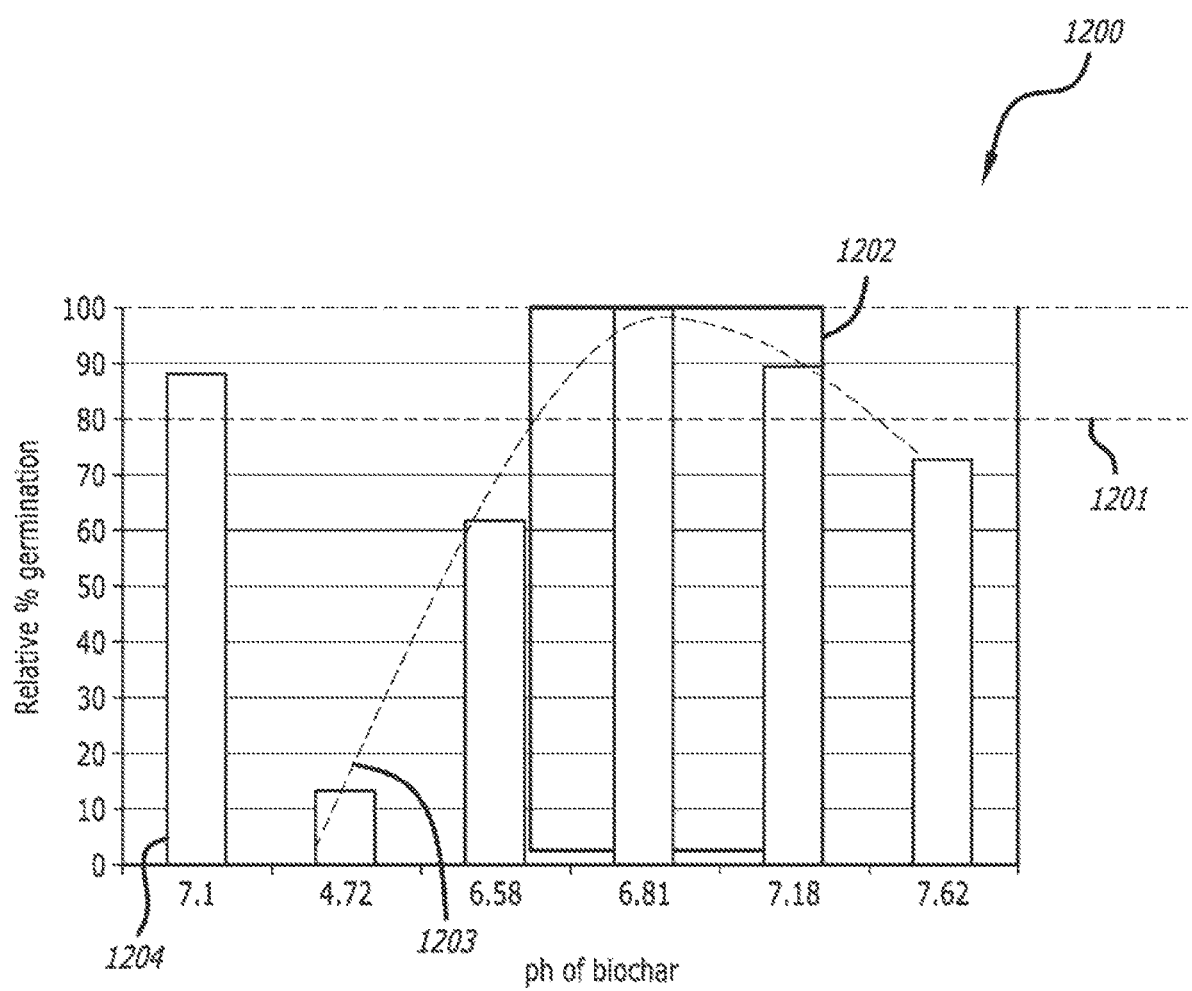
FIG. 12 is a chart showing various pH ranges and germination for treated biochars.

With regard to treatment for pH adjustment, the above described vacuum infiltration processes and/or surfactant treatment processes have the ability to take raw biochars having detrimental or deleterious pHs and transform those biochars into a treated biochar having pH that is in an optimal range for most plant growth, and soil health. Turning to FIG. 11, a graph 1100 is provided that shows the pH of various starting raw biochars that were made from different starting materials and pyrolysis process temperatures, including coconut shells 1104, pistachio shells 1101, corn at 500° C. 1105, corn at 900° C. 1102, bamboo 1103, mesquite 1106, wood and coffee 1108, wood (Australia) 1109, various soft woods 1110, 1111, 1112, 1113, 1114, 1115, 1116, 1117, red fir at 900° C. 1107, various grasses at 500° C. 1118, 1119, 1120, grass 1121, and grass at 900° C. 1123. The treatment processes described in this disclosure, can be used to alter the pH from the various undesirable pH levels and bring the pH into the preferred, optimal range 1124 for most plant growth, soil health and combinations of these. FIG. 12 is a chart 1200 showing percentage of germination for lettuce plants for particular pHs, and a desired germination range 1201. A control 1204 is compared with an optimal pH range 1202, and a distribution 1203 of growth rates across pHs is shown.

If treated for pH adjustment, the treated biochar takes a few days after treatment for the pH to normalize. Once normalized, tests have proven that pH altered biochar remains at a stable pH, typically the treatment is used to lower the stable pH to below that of the raw biochar, for up to 12 months or more after treatment. Although in certain situations, the pH could be altered to be higher than the raw biochar when needed.

For example, the treatment process of the present invention can remove and/or neutralize inorganic compounds, such as the calcium hydroxide $((CaOH)_2)$, potassium oxide $(K_2OK_2OK_2O)$, magnesium oxide (MgO), magnesium hydroxide $(Mg(OH)_2)$, and many others that are formed during pyrolysis, and are fixed to the biochar pore surfaces. These inorganics, in particular calcium hydroxide, adversely affect the biochar's pH, making the pH in some instances as high as 8.5, 9.5, 10.5 and 11.2. These high pH ranges are deleterious, detrimental to crops, and may kill or adversely affect the plants, sometimes rendering an entire field a loss.

The calcium hydroxide, and other inorganics, cannot readily and quickly be removed by simple washing of the biochar, even in an acid bath. It cannot be removed by drying the biochar, such as by heating or centrifugal force. It is theorized that these techniques and methodologies cannot reach or otherwise affect the various pore surfaces, e.g., macro-, meso- and micro- in any viable or efficacious manner; and thus cannot remove or otherwise neutralize the calcium hydroxide.

Upon modification of the pore surface area by removal and/or neutralization of deleterious substances, such as calcium hydroxide, the pH of the biochar can be reduced to the range of about pH 5 to about pH 8, and more preferably from about pH 6.4 to about 7.2, and still more preferably around 6.5 to 6.8, recognizing that other ranges and pHs are contemplated and may prove useful, under specific environmental or agricultural situations or for other applications. Thus, the present treated biochars, particles, batches and both, have most, essentially all, and more preferably all, of their pore surfaces modified by the removal, neutralization and both, of the calcium hydroxide that is present in the starting biochar material. These treated biochars have pHs in the range of about 5 to about 8, about 6.5 to about 7.5, about 6.4 to about 7, and about 6.8. Prior to and before testing, biochar is passed through a 2 mm sieve before pH is measured. All measurements are taken according to Rajkovich et. al, *Corn growth and nitrogen nutrition after additions of biochars with varying properties to a temperate soil*, Biol. Fertil. Soils (2011), from which the International Biochar Initiative (IBI) method is based.

There are a wide variety of tests, apparatus and equipment for making pH measurements. For example, and preferably when addressing the pH of biochar, batches, particles and pore surfaces of those particles, two appropriates for measuring pH are the Test Method for the US Composting Council ("TMCC") 4.11-A and the pH Test Method promulgated by the International Biochar Initiative. The test method for the TMCC comprises mixing biochar with distilled water in 1:5 [mass:volume] ratio, e.g., 50 grams of biochar is added to 250 ml of pH 7.0±0.02 water and is stirred for 10 minutes; the pH is then the measured pH of the slurry. The pH Test Method promulgated by the International Biochar Initiative comprises 5 grams of biochar is added to 100 ml of water pH=7.0±0.02 and the mixture is tumbled for 90 minutes; the pH of the slurry is measured at the end of the 90 minutes of tumbling.

4. Removing/Neutralizing Deleterious Materials

Further, the treatment processes are capable of modifying the pore surfaces to remove or neutralize deleterious materials that are otherwise difficult, if not for all practical purpose, impossible to mitigate. For example, heavy metals, transition metals, sodium and phytotoxic organics, polycyclic aromatic hydrocarbons, volatile organic compounds (VOCs), and perhaps other phytotoxins. Thus, by treating the biochar in accordance with the treatment processes set forth and described above, the resulting treated biochar has essentially all, and more preferably all, of their pore surfaces modified by the removal, neutralization and both, of one or more deleterious, harmful, or potentially harmful material that is present in the starting biochar material.

For example, treatment can reduce the total percentage of residual organic compounds (ROC), including both the percentage of heavy ROCs and percentage of VOCs. Through treatment, the total ROC can be reduced to 0-25% wt. %, percentage heavy ROC content can be reduced to 0-20% wt. % and VOC content can be reduced to less than 5% wt. %. For purposes of this application, "Residual organic compounds" (ROCs) are defined as compounds that burn off during thermogravimetric analysis, as defined above, between 150 degrees C. and 950 degrees C. Residual organic compounds include, but are not limited to, phenols, polyaromatic hydrocarbons, monoaromatic hydrocarbons, acids, alcohols, esters, ethers, ketones, sugars, alkanes and alkenes. Of the ROCs, those that burn off using thermogravimetric analysis between 150 degrees C. and 550 degrees are considered light organic compounds (volatiles or VOCs), and those that burn off between 550 degrees C. and 950 degrees C. are heavy residual organic compounds. It should be noted that there may be some inorganic compounds which also are burned off during TGA analysis in these temperature ranges, but these are generally a very low percentage of the total emission and can be disregarded in the vast majority of cases as slight variations. In any of these measurements, a gas chromatograph/mass spectrometer may be used if needed for higher degrees of precision.

Figure 13:
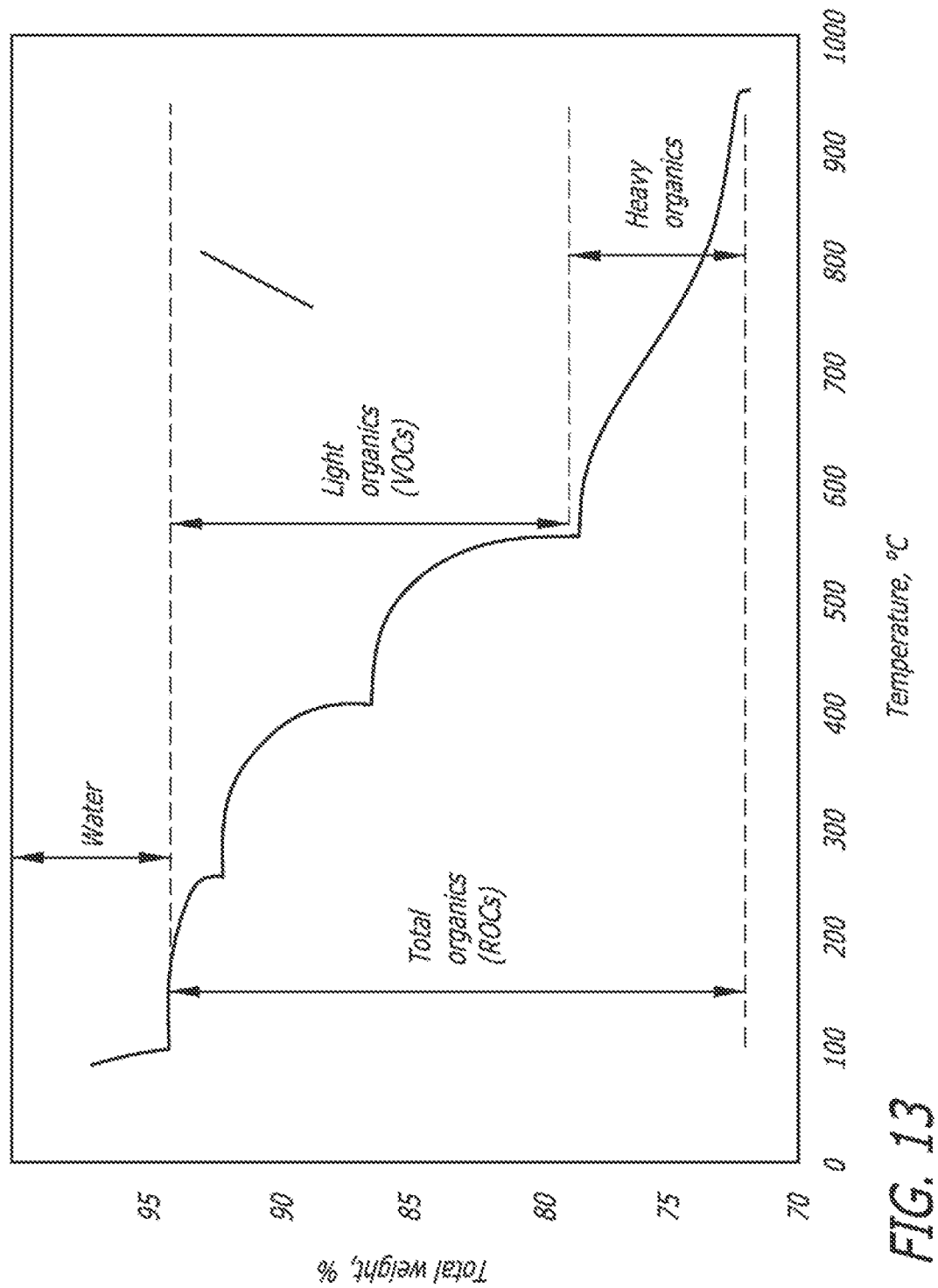
FIG. 13 is a Thermogravimetric Analysis (TGA) plot showing the measurement of water content, heavy organics and light organics in a sample.

The percent water, total organic compounds, total light organic compounds (volatiles or VOC) and total heavy organic compounds, as referenced in this application as contained in a biochar particle or particles in a sample may all be measured by thermogravimetric analysis. Thermogravimetric analysis is performed by a Hitachi STA 7200 analyzer or similar piece of equipment under nitrogen flow at the rate of 110 mL/min. The biochar samples are heated for predetermined periods of time, e.g., 20 minutes, at a variety of temperatures between 10° and 950° C. The sample weights are measured at the end of each dwell step and at the beginning and at the end of the experiment. Thermogravimetric analysis of a given sample indicating percentage water in a sample is determined by % mass loss measured between standard temperature and 150 degrees C. Thermogravimetric analysis of a given sample indicating percentage of residual organic compounds is measured by percentage mass loss sustained between 150 degrees C. and 950 degrees C. Thermogravimetric analysis of a given sample indicating percentage of light organic compounds (volatiles) is measured by percentage mass loss sustained between 150 degrees C. and 550 degrees C. Thermogravimetric analysis of a given sample indicating percentage of heavy organic compounds is measured by percentage mass loss sustained between 550 degrees C. and 950 degrees C. FIG. 13 is an example of a Thermogravimetric Analysis (TGA) plot outlining the above explanation and the measure of water, light organics and heavy organics.

As noted above, treatment can remove or neutralize heavy metals, transition metals, sodium and phytotoxic organics, polycyclic aromatic hydrocarbons, volatile organic compounds (VOCs), other phytotoxins, and even dioxins. Thus, by treating the biochar in accordance with the treatment processes set forth and described above, the resulting treated biochar has essentially all, and more preferably all, of their pore surfaces modified by the removal, neutralization or both, of one or more deleterious, harmful, or potentially harmful material that is present in the starting biochar material.

Dioxins may also be removed through the treatment processes of the present invention. Dioxins are released from combustion processes and thus are often found in raw biochar. Dioxins include polychlorinated dibenzo-p-dioxins (PCDDs) (i.e., 75 congeners (10 are specifically toxic)); polychlorinated dibenzofurans (PCDFs) (i.e., 135 congeners (7 are specifically toxic)) and polychlorinated biphenyls (PCBs) (Considered dioxin-like compounds (DLCs)).

Since some dioxins may be carcinogenic even at low levels of exposure over extended periods of time, the FDA views dioxins as a contaminant and has no tolerances or administrative levels in place for dioxins in animal feed. Dioxins in animal feed can cause health problems in the animals themselves. Additionally, the dioxins may accumulate in the fat of food-producing animals and thus consumption of animal derived foods (e.g. meat, eggs, milk) could be a major route of human exposure to dioxins. Thus, if biochar is used in animal applications, where the animals ingest the biochar, the ability to remove dioxins from the raw biochar prior to use is of particular significance.

Results have proven the removal of dioxins from raw biochar by applying the treatment process of the present invention. To demonstrate the removal of dioxins, samples of both raw biochar and biochar, treated within the parameters set forth above, were sent out for testing. The results revealed that the dioxins in the raw biochar were removed through treatment as the dioxins detected in the raw biochar sample were not detected in the treated biochar sample. Below is a chart comparing the test results of measured dioxins in the raw verses the treated biochar.

| Dioxins | Amount Detected in Raw Biochar Sample | Amount Detected in Treated Biochar Sample |
| --- | --- | --- |
| Tetradioxins | 26.4 ng/Kg-dry | Not detectable |
| Pentadioxins | 5.86 ng/Kg-dry | Not detectable |
| Hexadioxins | 8.41 ng/Kg-dry | Not detectable |

A number of different dioxins exist, several of which are known to be toxic or undesirable for human consumption. Despite the test results above, it is possible that any number of dioxins could be present in raw biochar depending on the biomass or where the biomass is grown. It is shown, however, in the above testing, that the treatment process of the present invention can be used to eliminate dioxins present in raw biochar.

Seventeen tetra-octo dioxins and furan congeners are the basis for regulatory compliance. Other dioxins are much less toxic. Dioxins are generally regulated on toxic equivalents (TEQ) and are represented by the sum of values weighted by Toxic Equivalency Factor (TEF)

$$TEQ = \Sigma [C_i] \times TEF_i$$

2,3,7,8-TCDD has a TEF of 1 (most toxic). TEQ is measured as ng/kg WHO-PCDD/F-TEQ//kg NDs are also evaluated. Two testing methods are generally used to determine TEQ values: EPA Method 8290 (for research and understanding at low levels (ppt-ppq); and EPA Method 1613B (for regulatory compliance). Both are based on high resolution gas chromatography (HRGC)/high resolution mass spectrometry (HRMS).

The required EU Feed Value is equal to or less than 0.75 ng/kg WHO-PCDD/F-TEQ//kg. Treated biochar, in accordance with the present invention, has shown to have TEQ dioxins less than 0.5 ng/kg WHO-PCDD/F-TEQ//kg, well below the requirement for EU Feed limits of 0.75 ng/kg WHO-PCDD/F-TEQ//kg. As further set forth above, treatment can reduce the amount of detectable dioxins from raw biochar such that the dioxins are not detectible in treated biochar. Two methods are used: EPA Method 8290 (for research and understanding at low levels (ppt-ppq); and EPA Method 1613B (for regulatory compliance). Both are based on high resolution gas chromatography (HRGC)/high resolution mass spectrometry (HRMS).

5. Pore Volume

Generally, a treated biochar sample has greater than 50% by volume of its porosity in macropores (pores greater than 300 nanometers). Further, results indicate that greater than 75% of pores in treated biochar are below 50,000 nanometers. Also, results indicate that greater than 50% by volume of treated biochar porosity are pores in the range of 500 nanometers and 100,000 nanometers. Bacterial sizes are typically 500 nanometers to several thousand nanometers.

Bacteria and other microbes have been observed to fit and colonize in the pores of treated biochar, thus supporting the pore size test results.

Macropore volume is determined by mercury porosimetry, which measures the meso and/or macro porosity by applying pressure to a sample immersed in mercury at a pressure calibrated for the minimum pore diameter to be measured (for macroporosity this is 300 nanometers). This method can be used to measure pores in the range of 3 nm to 360,000 nm. Total volume of pores per volumetric unit of substance is measured using gas expansion method.

Depending upon the biomass from which the biochar is derived, mercury porosimetry testing has shown that washing under differential pressure, using the processes described above, can increase the number of both the smallest and larger pores in certain biochar (e.g., pine) and can increase the number of usable smaller pores. Treatment of biochar using either vacuum or surfactant does alter the percentage of total usable pores between 500 to 100,000 nanometers and further has varying impact on pores less than 50,000 nanometers and less than 10,000 nanometers.

Figure 14:
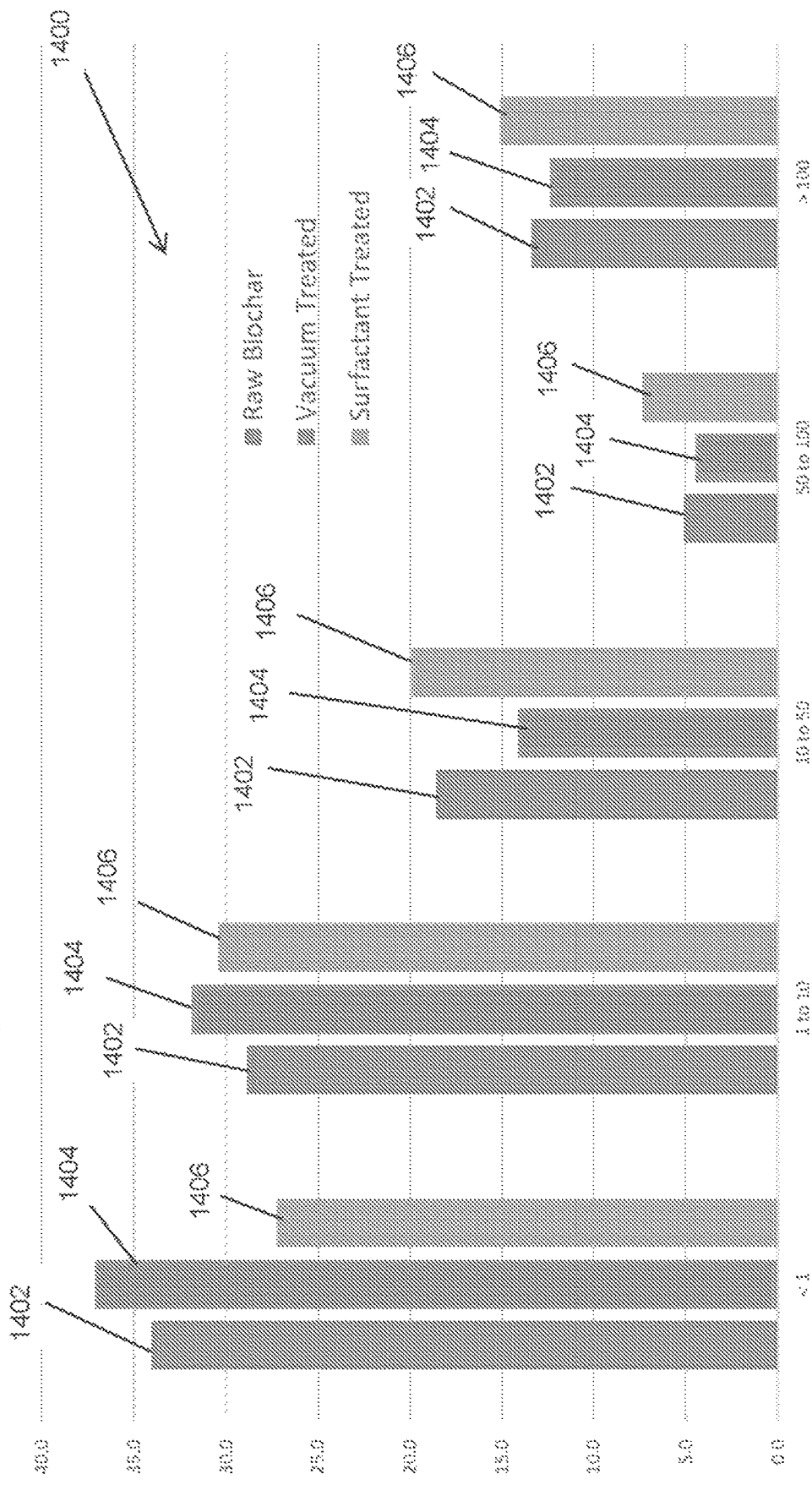
FIG. 14 is a chart showing the impact of treatment on pores sizes of biochar derived from coconut.

FIG. 14 is a chart 1400 showing the impact of treatment on pores sizes of biochar derived from coconut. The majority of the coconut based biochar pores are less than 10 microns. Many are less than 1 micron. Vacuum processing of the biochar results in small reduction of 10 to 50 micron pores, with increase of smaller pores on vacuum processing. The mercury porosimetry results of the raw biochar are represented by 1402 (first column in the group of three). The vacuum treated biochar is represented by 1404 (second column in the group of three) and the surfactant treated biochar is 1406 (third column in the group of three).

Figure 15:
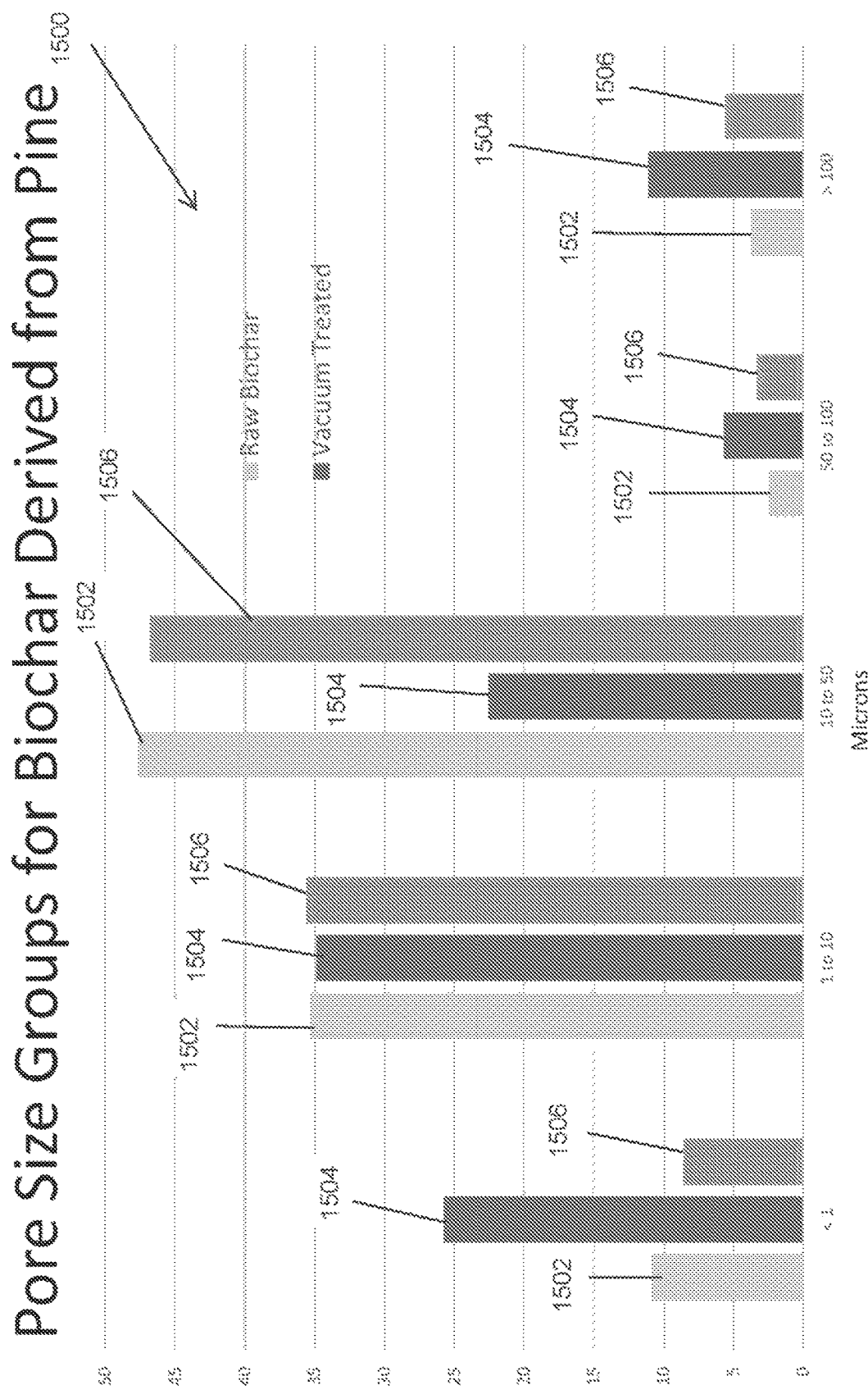
FIG. 15 is a chart showing the impact of treatment on pores sizes of biochar derived from pine.

FIG. 15 is a chart 1500 showing the impact of treatment on pores sizes of biochar derived from pine. The majority of the pine based biochar pores are 1 to 50 microns, which is a good range for micro-biologicals. Vacuum processing results in significant reduction of the 10 to 50 micron pores, with an increase of smallest and largest pores. The mercury porosimetry results of the raw biochar are represented by 1502 (first column in the group of three). The vacuum treated biochar is represented by 1504 (second column in the group of three) and the surfactant treated biochar is 3006 (third column in the group of three).

6. Electrical Conductivity

The electrical conductivity (EC) of a solid material-water mixture indicates the amount of salts present in the solid material. Salts are essential for plant growth. The EC measurement detects the amount of cations or anions in solution; the greater the amount of ions, the greater the EC. The ions generally associated with salinity are $Ca^{2+}$, $Mg^{2+}$, $K^+$, $Na^+$, $H^+$, $NO_3^-$, $SO_4^{2-}$, $Cl^-$, $HCO_3^-$, $OH^-$. Electrical conductivity testing of biochar was done following the method outlined in the USDA's Soil Quality Test Kit Guide and using a conventional EC meter. The biochar sample is mixed with DI water in a 1:1 biochar to water ratio on a volume basis. After thorough mixing, the EC (dS/m) is measured while the biochar particles are still suspended in solution. Treatment, as outlined in this disclosure can be used to adjust the ions in the char. Testing of treated biochar shows its EC is generally greater than 0.2 dS/m and sometimes greater than 0.5 dS/m.

7. Cation Exchange Capacity

One method for cation exchange capacity ("CEC") determination is the use of ammonium acetate buffered at pH 7.0 (see Schollenberger, C. J. and Dreibelbis, E R. 1930, *Analytical methods in base-exchange investigations on soils*, Soil Science, 30, 161-173). The material is saturated with 1M ammonium acetate, ($NH_4OAc$), followed by the release of the $NH_4^+$ ions and its measurement in meq/100 g (milliequivalents of charge per 100 g of dry soil) or cmole/kg (centimoles of charge per kilogram of dry soil). Instead of ammonium acetate another method uses barium chloride according to Mehlich, 1938, *Use of triethanolamine acetate-barium hydroxide buffer for the determination of some base exchange properties and lime requirement of soil*, Soil Sci. Soc. Am. Proc. 29:374-378. 0.1 M $BaCl_2$ is used to saturate the exchange sites followed by replacement with either $MgSO_4$ or $MgCl_2$.

Indirect methods for CEC calculation involves the estimation of extracted $Ca_2^+$, $Mg_2^+$, $K^+$, and $Na^+$ in a standard soil test using Mehlich 3 and accounting for the exchangeable acidity (sum of $H^+$, $Al_3^+$, $Mn_2^+$, and $Fe_2^+$) if the pH is below 6.0 (see Mehlich, A. 1984, *Mehlich-3 soil test extractant: a modification of Mehlich-2 extractant*, Commun. Soil Sci. Plant Anal. 15(12): 1409-1416). When treated using the above methods, including but not limited by washing under a vacuum, treated biochars generally have a CEC greater than 5 millieq/l and some even have a CEC greater than 25 (millieq/l). To some extent, treatment can be used to adjust the CEC of a char.

8. Anion Exchange Capacity

Similar to CEC measurements, anion exchange capacity ("AEC") may be calculated directly or indirectly-saturated paste extraction of exchangeable anions, $Cl^-$, $NO_3^-$, $SO_4^{2-}$, and $PO4^{3-}$ to calculate anion sum or the use of potassium bromide to saturate anions sites at different pHs and repeated washings with calcium chloride and final measurement of bromide (see Rhoades, J. D. 1982, *Soluble salts*, p. 167-179. In: A. L. Page et al. (ed.) Methods of soil analysis: Part 2: Chemical and microbiological properties; and Michael Lawrinenkoa and David A. Laird, 2015, *Anion exchange capacity of biochar*, Green Chem., 2015, 17, 4628-4636). When treated using the above methods, including but not limited by washing under a vacuum, treated biochars generally have an AEC greater than 5 millieq/l and some even have an AEC greater than 20 (millieq/l). To some extent, treatment can be used to adjust the CEC of a char.

9. Hydrophilicity/Hydrophobicity

The ability to control the hydrophilicity of the pores provides the ability to load the biochar particles with larger volumes of inoculant. The more hydrophilic the more the biochars can accept inoculant or infiltrate. Tests show that biochar treated in accordance with the above processes, using either vacuum or surfactant treatment processes increase the hydrophilicity of raw biochar. Two tests may be used to test the hydrophobicity/hydrophilicity of biochar: (i) the Molarity of Ethanol Drop ("MED") Test; and (ii) the Infiltrometer Test.

The MED test was originally developed by Doerr in 1998 and later modified by other researchers for various materials. The MED test is a timed penetration test that is noted to work well with biochar soil mixtures. For 100% biochar, penetration time of different mixtures of ethanol/water are noted to work better. Ethanol/Water mixtures verses surface tension dynes were correlated to determine whether treated biochar has increased hydrophilicity over raw biochar. Seven mixtures of ethanol and deionized water were used with a sorption time of 3 seconds on the biochar.

Seven solutions of deionized ("DI") water with the following respective percentages of ethanol: 3, 5, 11, 13, 18, 24 and 36, were made for testing. The test starts with a mixture having no DI. If the solution is soaked into the biochar in 3 seconds for the respective solution, it receives the corresponding Hydrophobicity Index value below.

| Ethanol % | Hydrophobicity Index | |
|---|---|---|
| 0: DI Water | 0 | Very Hydrophilic |
| 3% | 1 | |
| 5% | 2 | |
| 11% | 3 | |
| 13% | 4 | |
| 18% | 5 | |
| 34% | 6 | |
| 36% | 7 | Strongly Hydrophobic |

To start the test the biochar ("material/substrate") is placed in convenient open container prepared for testing. Typically, materials to be tested are dried 110° C. overnight and cooled to room temperature. The test starts with a deionized water solution having no ethanol. Multiple drips of the solution are then laid onto the substrate surface from low height. If drops soak in less than 3 seconds, test records substrate as "0". If drops take longer than 3 seconds or don't soak in, go to test solution 1. Then, using test solution 1, multiple drops from dropper are laid onto the surface from low height. If drops soak into the substrate in less than 3 seconds, test records material as "1". If drops take longer than 3 seconds, or don't soak in, go to test solution 2. Then, using test solution 2, multiple drops from dropper laid onto the surface from low height. If drops soak into the substrate in less than 3 seconds, test records material as "2". If drops take longer than 3 seconds, or don't soak in, go to test solution 3. Then, using test solution 3, multiple drops from dropper laid onto the surface from low height. If drops soak into the substrate in less than 3 seconds, test records material as "3". If drops take longer than 3 seconds, or don't soak in, go to solution 4.

The process above is repeated, testing progressively higher numbered MED solutions until the tester finds the solution that soaks into the substrate in 3 seconds or less. The substrate is recorded as having that hydrophobicity index number that correlates to the solution number assigned to it (as set forth in the chart above).

Example test results using the MED test method is illustrated below.

| MATERIAL | HYDROPHOBICITY INDEX |
|---|---|
| Raw Biochars | 3 to 5 |
| Treated Biochars | 1 to 3 |

Another way to measure and confirm that treatment decreases hydrophobicity and increases hydrophilicity is by using a mini disk infiltrometer. For this test procedure, the bubble chamber of the infiltrometer is filled three quarters full with tap water for both water and ethanol sorptivity tests. Deionized or distilled water is not used. Once the upper chamber is full, the infiltrometer is inverted and the water reservoir on the reserve is filled with 80 mL. The infiltrometer is carefully set on the position of the end of the mariotte tube with respect to the porous disk to ensure a zero suction offset while the tube bubbles. If this dimension is changed accidentally, the end of the mariotte tube should be reset to 6 mm from the end of the plastic water reservoir tube. The bottom elastomer is then replaced, making sure the porous disk is firmly in place. If the infiltrometer is held vertically using a stand and clamp, no water should leak out.

The suction rate of 1 cm is set for all samples. If the surface of the sample is not smooth, a thin layer of fine biochar can be applied to the area directly underneath the infiltrometer stainless steel disk. This ensures good contact between the samples and the infiltrometer. Readings are then taken at 1 min intervals for both water and ethanol sorptivity test. To be accurate, 20 mL water or 95% ethanol needs to be infiltrated into the samples. Record time and water/ethanol volumes at the times are recorded.

The data is then processed to determine the results. The data is processed by the input of the volume levels and time to the corresponding volume column. The following equation is used to calculate the hydrophobicity index of R $$I = at + b\sqrt{t}$$

$a$:Infiltration Rate, cm/s $b$:Sorptivity, cm/s$^{1/2}$ $$R = 1.95 * \frac{b_{ethanol}}{b_{water}}$$

Figure 16:
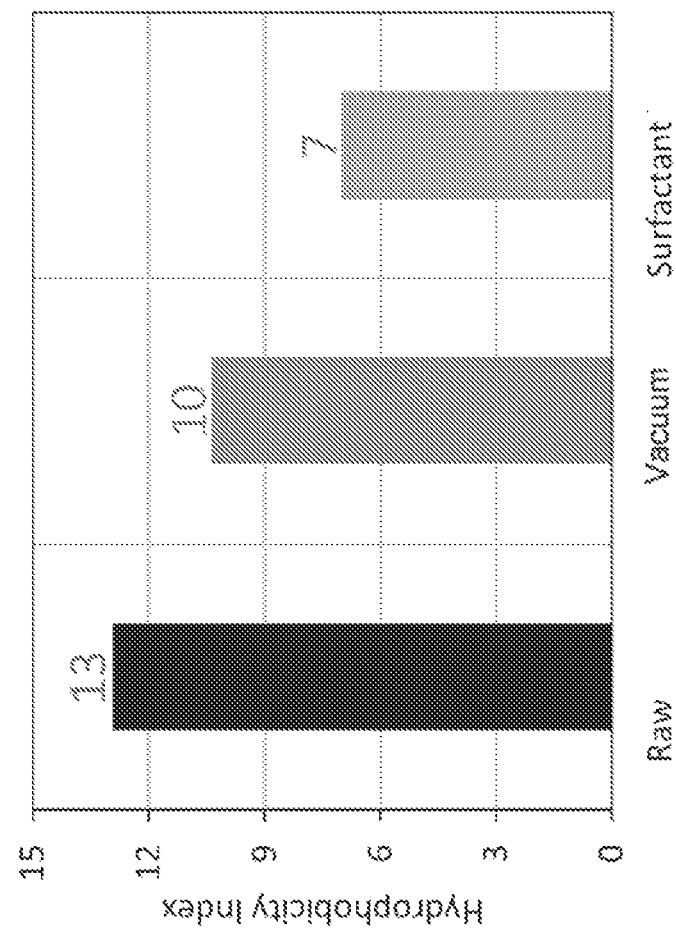
FIG. 16 is a chart showing the measured hydrophobicity index raw biochar, vacuum treated biochar and surfactant treated biochar.

FIG. 16 illustrates one example of the results of a hydrophobicity test performed on raw biochar, vacuum treated biochar and surfactant treated biochar. As illustrated, both the vacuum treated and surfactant treated biochar are more hydrophilic than the raw biochar based upon the lower Index rating. In accordance with the test data in FIG. 16, the hydrophobicity of raw biochar was reduced 23% by vacuum processing and 46% by surfactant addition.

As an example, raw biochar and treated biochar were tested with ethanol and water, five times for each. The results below show that the hydrophobicity index of the treated biochar is lower than the raw biochar. Thus, tests demonstrate that treating the biochar, using the methods set forth above, make the biochar less hydrophobic and more hydrophilic.

| MATERIAL | HYDROPHOBICITY INDEX |
|---|---|
| Dried Raw Biochar | 12.9 |
| Dried Vacuum Treated Biochar | 10.4 |
| Dried Surfactant Treated Biochar | 7.0 |
| As Is Raw Biochar | 5.8 |
| As Is Vacuum Treated Biochar | 2.9 |

Further, through the treatment processes of the present invention, the biochar can also be infused with soil enhancing agents. By infusing liquid into the pore structure through the application of positive or negative pressure and/or a surfactant, alone or in combination, provides the ability to impregnate the macropores of the biochar with soil enhancing solutions and solids. The soil enhancing agent may include, but not be limited to, any of the following: water, water solutions of salts, inorganic and organic liquids of different polarities, liquid organic compounds or combinations of organic compounds and solvents, mineral and organic oils, slurries and suspensions, supercritical liquids, fertilizers, plant growth promoting rhizobacteria, free-living and nodule-forming nitrogen fixing bacteria, organic decomposers, nitrifying bacteria, phosphate solubilizing bacteria, biocontrol agents, bioremediation agents, saprotrophic fungi, ectomycorrhizae and end mycorrhizae, among others.

D. Impregnation and/or Inoculation with Infiltrates or Additives

In addition to mitigating or removing deleterious pore surface properties, by treating the pores of the biochar through a forced, assisted, accelerate or rapid infiltration process, such as those described above, the pore surface properties of the biochar can be enhanced. Such treatment processes may also permit subsequent processing, may modify the pore surface to provide predetermined properties to the biochar, and/or provide combinations and variations of these effects. For example, it may be desirable or otherwise advantageous to coat substantially all, or all of the biochar macropore and mesopore surfaces with a surface modifying agent or treatment to provide a predetermined feature to the biochar, e.g., surface charge and charge density, surface species and distribution, targeted nutrient addition, magnetic modifications, root growth facilitator, and water absorptivity and water retention properties.

By infusing liquids into the pores of biochar, it has been discovered that additives infused within the pores of the biochar provide a time release effect or steady flow of some beneficial substances to the root zones of the plants and also can improve and provide a more beneficial environment for microbes which may reside or take up residence within the pores of the biochar. In particular, additive infused biochars placed in the soil prior to or after planting can dramatically reduce the need for high frequency application of additives, minimize losses caused by leaching and runoff and/or reduce or eliminate the need for controlled release fertilizers. They can also be exceptionally beneficial in animal feed applications by providing an effective delivery mechanism for beneficial nutrients, pharmaceuticals, enzymes, microbes, or other substances.

For purposes of this application, "infusion" of a liquid or liquid solution into the pores of the biochar means the introduction of the liquid or liquid solution into the pores of the biochar by a means other than solely contacting the liquid or solution with the biochar, e.g., submersion. The infusion process, as described in this application in connection with the present invention, includes a mechanical, chemical or physical process that facilitates or assist with the penetration of liquid or solution into the pores of the biochar, which process may include, but not be limited to, positive and negative pressure changes, such as vacuum infusion, surfactant infusion, or infusion by movement of the liquid and/or biochar (e.g., centrifugal force, steam and/or ultrasonic waves) or other method that facilitates, assists, forces or accelerates the liquid or solution into the pores of the biochar.

Figure 17:
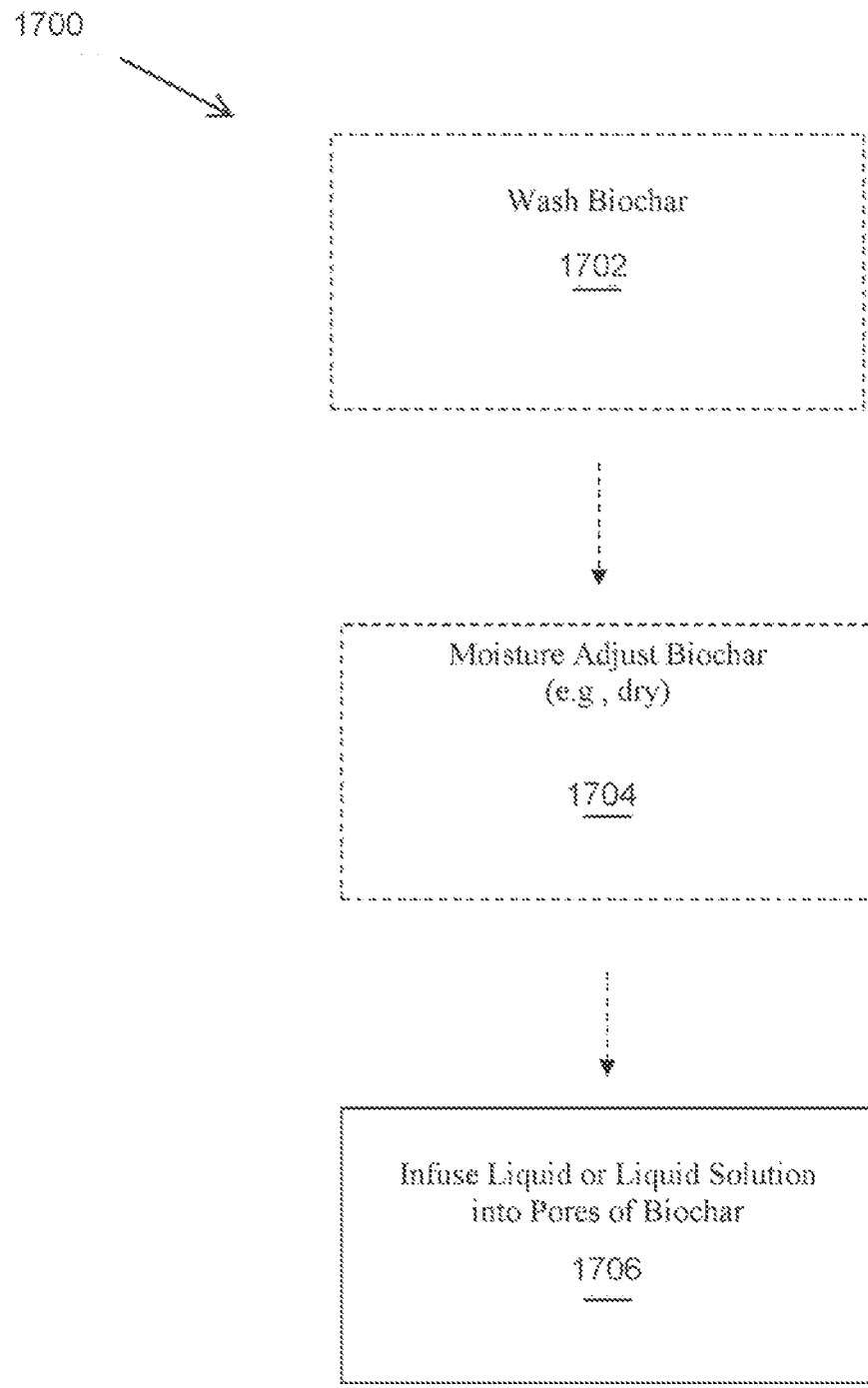
FIG. 17 is a flow diagram showing one example of a method for infusing biochar.

Prior to infusing the biochar, the biochar, as described in detail above, may be washed and/or moisture adjusted. FIG. 17 is a flow diagram 1700 of one example of a method for infusing biochar with an additive. Optionally, the biochar may first be washed or treated at step 1702, the wash may adjust the pH of the biochar, as described in more detail above, or may be used to remove elemental ash and other harmful organics that may be unsuitable for the desired infused fertilizer or animal feed. Optionally, the moisture content of the biochar may then be adjusted by drying the biochar at step 1704, also as described in further detail above, prior to infusion of the additive or inoculant at step 1706.

In summary, the infusion process may be performed with or without any washing, prior pH adjustment or moisture content adjustment. Optionally, the infusion process may be performed with the wash and/or the moisture adjustment step. All the processes may be completed alone or in the conjunction with one or more of the others.

Through the above process of infusing the additive into the pores of the biochar, the pores of the biochar may be filled by 25%, up to 100%, with an additive solution, as compared to 1-20% when the biochar is only submerged in the solution or washed with the solution for a period of less than twelve hours. Higher percentages may be achieved by washing and/or drying the pores of the biochar prior to infusion.

Data have been gathered from research conducted comparing the results of soaking or immersion of biochar in liquid versus vacuum impregnation of liquid into biochar. These data support the conclusion that vacuum impregnation provides greater benefits than simple soaking and results in a higher percentage volume of moisture on the surface, interstitially and in the pores of the biochar.

Figure 18:
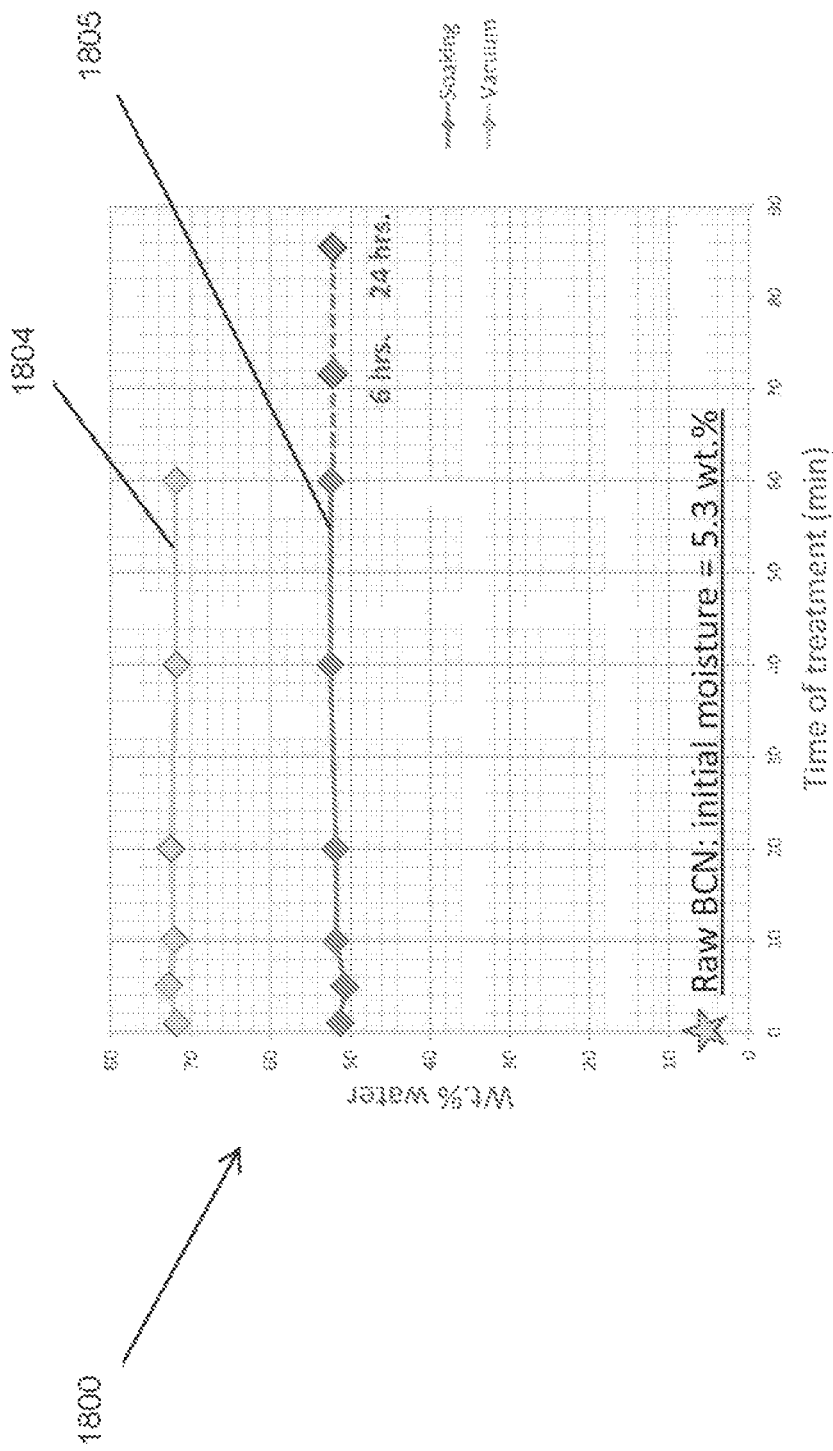
FIG. 18 illustrates the improved liquid content of biochar using vacuum impregnation as against soaking the biochar in liquid.

In one experiment, equal quantities of pine biochar were mixed with equal quantities of water, the first in a beaker, the second in a vacuum flask. The mixture in the beaker was continuously stirred for up to 24 hours, then samples of the suspended solid were taken, drained and/or dried on a paper towel and analyzed for moisture content. The mixture in the vacuum flask was connected to a vacuum pump and negative pressure of 15" was applied. Samples of the treated solid were taken, drained and analyzed for moisture content. FIG. 18 is a chart illustrating the results of the experiment. The lower graph 1802 of the chart, which shows the results of soaking over time, shows a Wt. % of water of approximately 52%. The upper graph 1804 of the chart, which shows the results of vacuum impregnation over time, shows a Wt. % of water of approximately 72%.

Figures 19A, 19B:
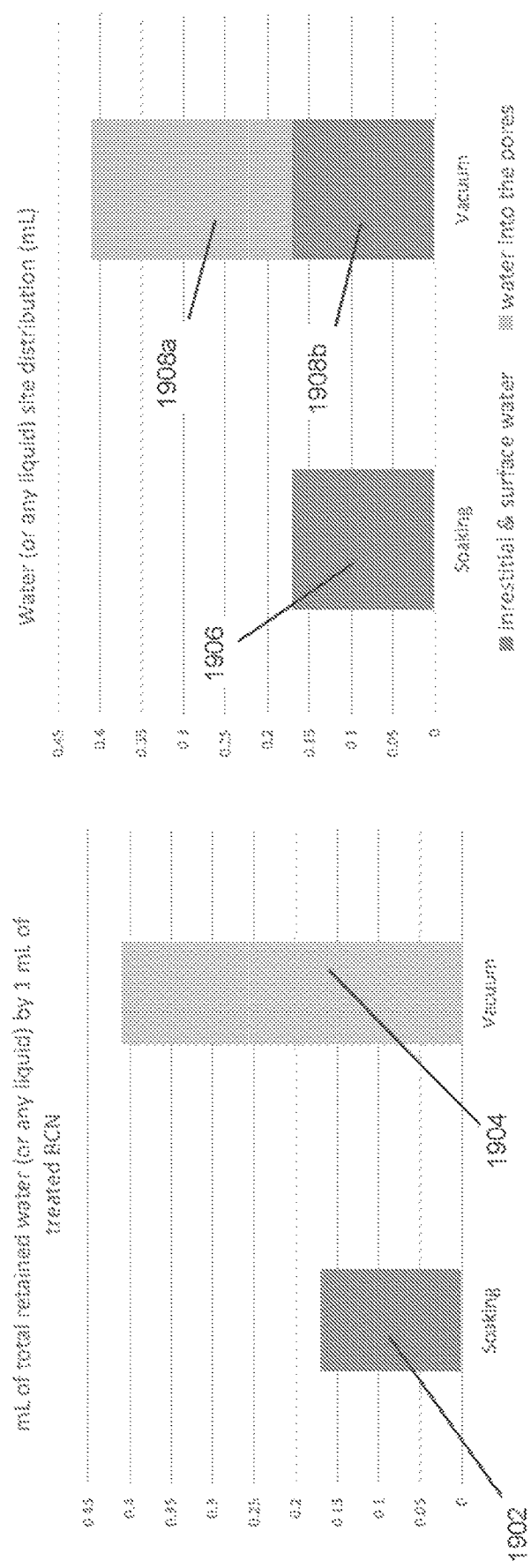
FIG. 19a is a chart comparing total retained water of treated biochar after soaking and after vacuum impregnation.
FIG. 19b is a chart comparing water on the surface, interstitially and in the pores of biochar after soaking and after vacuum impregnation.

FIGS. 19a and 19b show two charts that further illustrate that the total water and/or any other liquid content in processed biochar can be significantly increased using vacuum impregnation instead of soaking. FIG. 19a compares the mL of total water or other liquid by retained by 1 mL of treated pine biochar. The graph 1902 shows that approximately 0.17 mL of water or other liquid are retained through soaking, while the graph 1904 shows that approximately 0.42 mL of water or other liquid are retained as a result of vacuum impregnation. FIG. 19b shows that the retained water of pine biochar subjected to soaking consists entirely of surface and interstitial water 1906, while the retained water of pine biochar subjected to vacuum impregnation consists not only of surface and interstitial water 1908a, but also water impregnated in the pores of the biochar 1908b.

Figure 20:
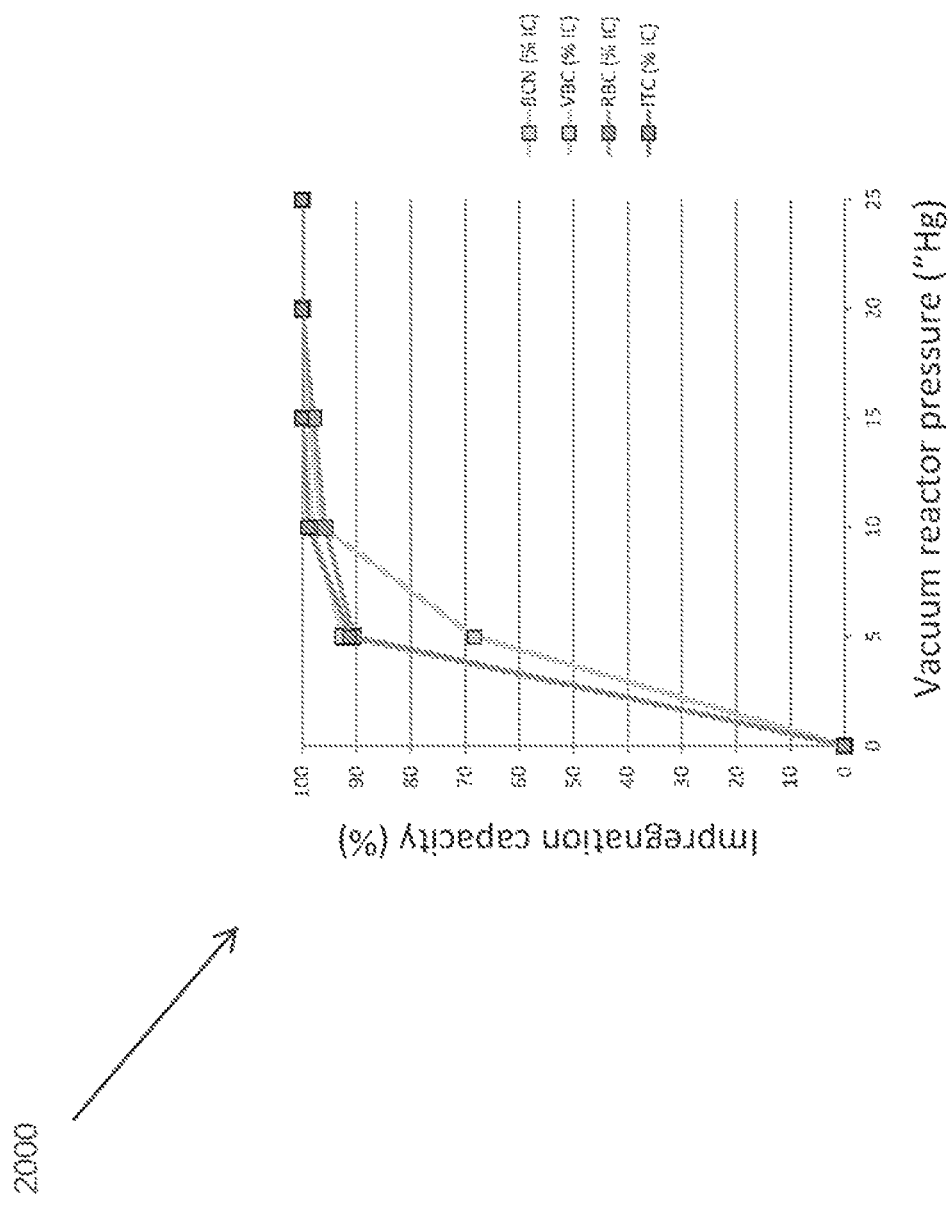
FIG. 20 illustrates how the amount of water or other liquid in the pores of vacuum processed biochars can be increased varied based upon the applied pressure.

In addition, as illustrated by FIG. 20, the amount of moisture content impregnated into the pores of vacuum processed biochars by varying the applied (negative) pressure during the treatment process. The graphs of four different biochars all show how the liquid content of the pours of each of them increase to 100% as vacuum reactor pressure is increased.

In another experiment, the percentage of water retained in the pores of pine derived biochar was measured to determine the difference in retained water in the pores of the biochar (i) soaked in water, and (ii) mixed with water subjected to a partial vacuum. For the soaking, 250 mL of raw biochar was mixed with 500 mL water in a beaker. Upon continuous stirring for 24 hrs., aliquots of the suspended solid were taken, drained on a paper towel and analyzed for moisture content. For the vacuum, 250 mL of raw biochar was mixed with 500 mL water in a vacuum flask. The flask was connected to a vacuum pump and negative pressure of 15" has been applied, aliquots of the treated solid were taken, drained on a paper towel and analyzed for moisture content.

The total retained water amounts were measured for each sample. For the soaked biochar, the moisture content of biochar remains virtually constant for the entire duration of the experiment, 52 wt. % (i.e. 1 g of "soaked biochar" contains 0.52 g water and 0.48 g "dry biochar"). Taking into account the density of raw biochar, 0.16 g/cm$^3$ (or mL), the volume of the 0.48 g "dry biochar" is 3.00 mL (i.e. 3 mL dry biochar can "soak" and retain 0.52 mL water, or 1 mL dry biochar can retain 0.17 mL water (sorbed on the surface and into the pores)).

For vacuum, the moisture content of the biochar remains virtually constant for the entire duration of the experiment, 72 wt. %, (i.e. 1 g of vacuum impregnated biochar contains 0.72 g water and 0.28 g "dry biochar"). Taking into account the density of raw biochar, 0.16 g/cm$^3$ (or mL), the volume of the 0.28 g "dry biochar" is 1.75 mL (i.e. 1.75 mL dry biochar under vacuum can "absorb" and retain 0.72 mL water, or 1 mL dry biochar can retain 0.41 mL water (sorbed on the surface and into the pores)).

It was next determined where the water was retained—in the pores or on the surface of the biochar. Capillary porosity ("CP") (vol % inside the pores of the biochar), non-capillary porosity ("NCP") (vol. % outside/between the particles), and the total porosity (CP+NCP)) were determined. Total porosity and non-capillary porosity were analytically determined for the dry biochar and then capillary porosity was calculated.

Since the dry biochar used in this experiment had a density less than water, the particles could be modeled and then tested to determine if soaking and/or treating the biochar could infuse enough water to make the density of the biochar greater than that of water. Thus, the dry biochar would float and, if enough water infused into the pores, the soaked or treated biochar would sink. Knowing the density of water and the density of the biochar, calculations were done to determine the percentage of pores that needed to be filled with water to make the biochar sink. In this specific experiment, these calculations determined that more than 24% of the pore volume would need to be filled with water for the biochar to sink. The two processed biochars, soaked and vacuum treated, were then immersed in water after 1 hour of said processing. The results of the experiment showed that the vast majority of the soaked biochar floated and remained floating after 3 weeks, while the vast majority of the vacuum treated biochar sank and remained at the bottom of the water column after 3 weeks.

Using the results of these experiments and model calculations, the biochar particles can be idealized to estimate how much more water is in the pores from the vacuum treatment versus soaking. Since the external surface of the materials is the same, it was assumed that the samples retain about the same amount of water on the surface. Then the most conservative assumption was made using the boundary condition for particles to be just neutral, i.e. water into pores equal 24%, the water distribution is estimated as follows:

| | DRY BIOCHAR | SOAKED BIOCHAR | VACUUM TREATED BIOCHAR |
|---|---|---|---|
| Experimental result | FLOATED | FLOATED | SANK |
| Total water (determined in first part of experiment) | 0% | 52% | 72% |
| Water in the pores (assumed for floating biochar to be boundary condition, calculated for biochar that sank) | 0% | 24% | 44% |
| Water on the surface (calculated for floating biochar, assumed to match floating biochar for the biochar that sank) | 0% | 28% | 28% |

In summary, these experimental tests and model calculations show that through vacuum treatment more than 24% of the pores of the biochar can be filled with water and in fact at least 1.8 times the amount of water can be infused into the pores compared to soaking. Vacuum treatment can impregnate almost two times the amount of water into the pores for 1 minute, while soaking does not change the water amount into the pores for three weeks.

The pores may be substantially filled or completely filled with additives to provide enhanced performance features to the biochar, such as increased plant growth, nutrient delivery, water retention, nutrient retention, disadvantageous species control, e.g., weeds, disease causing bacteria, insects, volunteer crops, etc. By infusing liquid into the pore structure through the application of positive or negative pressure, surfactant and/or ultrasonic waves, alone or in combination, provides the ability to impregnate the mesopores and macropores of the biochar with additives, that include, but are not limited to, soil enhancing solutions and solids.

The additive may be a soil enhancing agent that includes, but is not be limited to, any of the following: water, water solutions of salts, inorganic and organic liquids of different polarities, liquid organic compounds or combinations of organic compounds and solvents, mineral and organic oils, slurries and suspensions, supercritical liquids, fertilizers, PGPB (including plant growth promoting rhizobacteria, free-living and nodule-forming nitrogen fixing bacteria, organic decomposers, nitrifying bacteria, and phosphate solubilizing bacteria), biocontrol agents, bioremediation agents, saprotrophic fungi, ectomycorrhizae and endomycorrhizae, among others.

Fertilizers that may be infused into the biochar include, but are not limited to, the following sources of nitrogen, phosphorous, and potassium: urea, ammonium nitrate, calcium nitrate, sulfur, ammonium sulfate, monoammonium phosphate, ammonium polyphosphate, potassium sulfate, or potassium chloride.

Similar beneficial results are expected from other additives, such as: bio pesticides; herbicides; insecticides; nematicides; plant hormones; plant pheromones; organic or inorganic fungicides; algicides; antifouling agents; antimicrobials; attractants; biocides, disinfectants and sanitizers; miticides; microbial pesticides; molluscicides; bactericides; fumigants; ovicides; repellents; rodenticides, defoliants, desiccants; insect growth regulators; plant growth regulators; beneficial microbes; and, microbial nutrients or secondary signal activators, that may also be added to the biochar in a similar manner as a fertilizer. Additionally, beneficial macro- and micro-nutrients such as, calcium, magnesium, sulfur, boron, zinc, iron, manganese, molybdenum, copper and chloride may also be infused into the biochar in the form of a water solution or other solvent solution.

Examples of compounds, in addition to fertilizer, that may be infused into the pores of the biochar include, but are not limited to: phytohormones, such as, abscisic acid (ABA), auxins, cytokinins, gibberellins, brassinosteroies, salicylic acid, jasmonates, planet peptide hormones, polyamines, karrikins, strigolactones; 2,1,3-Benzothiadiazole (BTH), an inducer of systemic acquired resistance that confers broad spectrum disease resistance (including soil borne pathogens); signaling agents similar to BTH in mechanism or structure that protects against a broad range or specific plant pathogens; EPSPS inhibitors; synthetic auxins; photosystem I inhibitors photosystem II inhibitors; and HPPD inhibitors. Growth media, broths, or other nutrition to support the growth of microbes or microbial life may also be infused such as Lauryl Tryptose broth, glucose, sucrose, fructose, or other sugars or micronutrients known to be beneficial to microbes. Binders or binding solutions can also be infused into the pores to aid in the adhesion of coatings, as well as increasing the ability for the treated biochar to associate or bond with other nearby particles in seed coating applications. Infusion with these binders can also allow for the coating of the biochar particle itself with other beneficial organisms or substances.

In one example, a 1000 ppm $NO_3^-$ N fertilizer solution is infused into the pores of the biochar. As discussed above, the method to infuse biochar with the fertilizer solution may be accomplished generally by placing the biochar in a vacuum infiltration tank or other sealable rotating vessel, chamber or tank. When using vacuum infiltration, a vacuum may be applied to the biochar and then the solution may be introduced into the tank. Alternatively, the solution and biochar may both be introduced into the tank and, once introduced, a vacuum is applied. Based upon the determined total pore volume of the biochar or the incipient wetness, the amount of solution to introduce into the tank necessary to fill the pore of the biochar can be determined. When infused in this manner, significantly more nutrients can be held in a given quantity of biochar versus direct contact of the biochar with the nutrients alone.

When using a surfactant, the biochar and additive solution may be added to a tank along with 0.01-20% of surfactant, but more preferably 1-5% of surfactant by volume of fertilizer solution. The surfactant or detergent aids in the penetration of the wash solution into the pores of the biochar. The same or similar equipment used in the vacuum infiltration process can be used in the surfactant treatment process. Although it is not necessary to apply a vacuum in the surfactant treatment process, the vacuum infiltration tank or any other rotating vessel, chamber or tank can be used. Again, while it is not necessary to apply a vacuum, a vacuum may be applied or the pressure in the vessel may be changed. Further, the surfactant can be added with or without heat or cooling either of the infiltrate, the biochar, the vessel itself, or any combination of the three.

The utility of infusing the biochar with fertilizer is that the pores in biochar create a protective "medium" for carrying the nutrients to the soil that provides a more constant supply of available nutrients to the soil and plants and continues to act beneficially, potentially sorbing more nutrients or nutrients in solution even after introduction to the soil. By infusing the nutrients in the pores of the biochar, immediate oversaturation of the soil with the nutrients is prevented and a time released effect is provided. This effect is illustrated in connection with FIGS. 21 and 22 below. As demonstrated in connection with FIGS. 21 & 22 below, biochars having pores infused with additives, using the infusion methods described above, have been shown to increase nutrient retention, increase crop yields and provide a steadier flow of fertilizer to the root zones of the plants.

Figure 21:
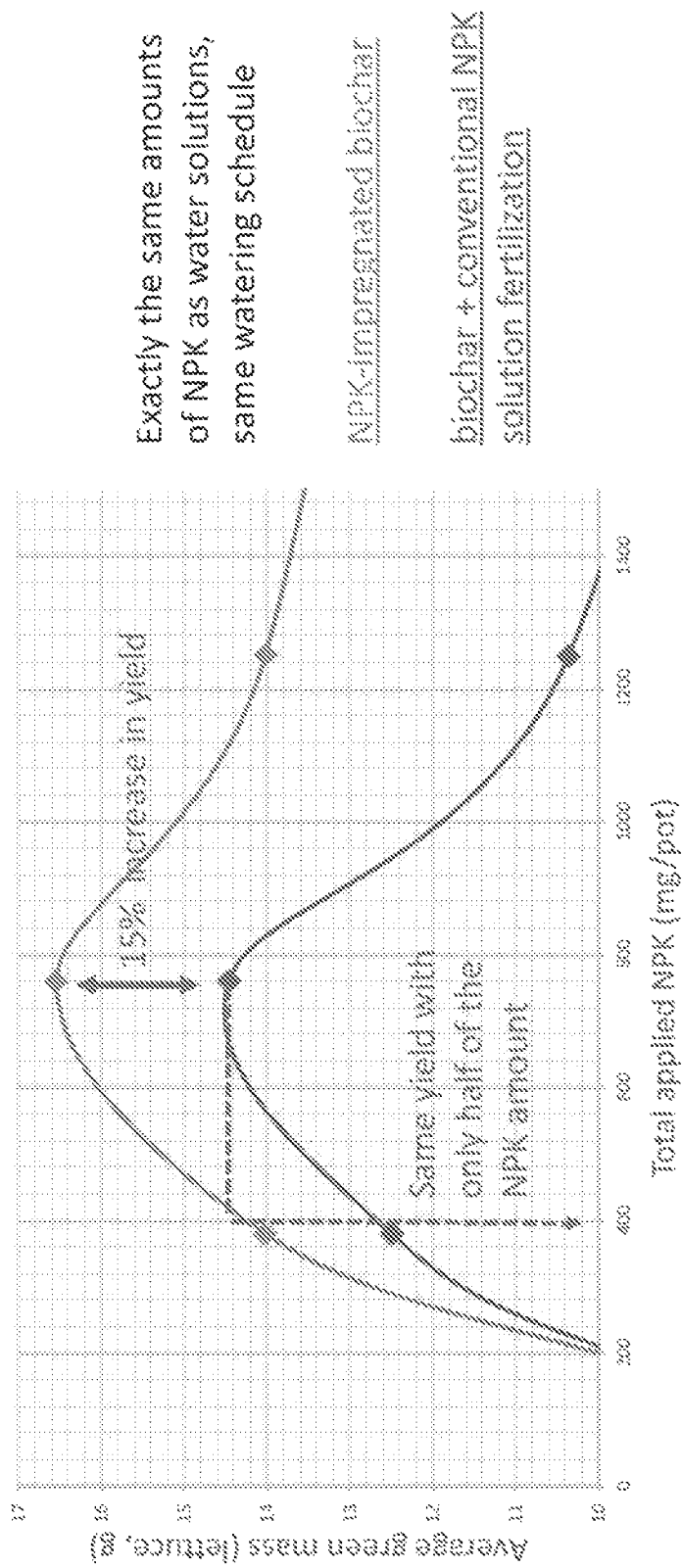
FIG. 21 illustrates the effects of NPK impregnation of biochar on lettuce yield.

FIG. 21 is a chart showing improved mass yield in lettuce with fertilizer infused biochar using vacuum impregnation. FIG. 21 compares the mass yield results of lettuce grown in different environments. One set of data measurements represents lettuce grown in soil over a certain set time period with certain, predetermined amounts of fertilizer infused into the biochar. A second set of data represents lettuce grown in soil over a certain set period of time with the same amount of unimpregnated biochar added at the beginning of the trial and certain predetermined amounts of NPK solution added to the soil over time. Growth comparisons were made between the same amount of fertilizer solution infused into the biochar as added directly to the soil, using the same watering schedule. As illustrated, the test results demonstrated a 15% yield increase in growth when infusing approximately 750 mg/pot of NPK into the biochar than when applying it directly to the soil. Similarly, the same mass yield of lettuce is achieved at 400 mg NPK/pot with infused biochar than at 750 mg/pot when adding the fertilizer solution directly to the soil.

Figure 22:
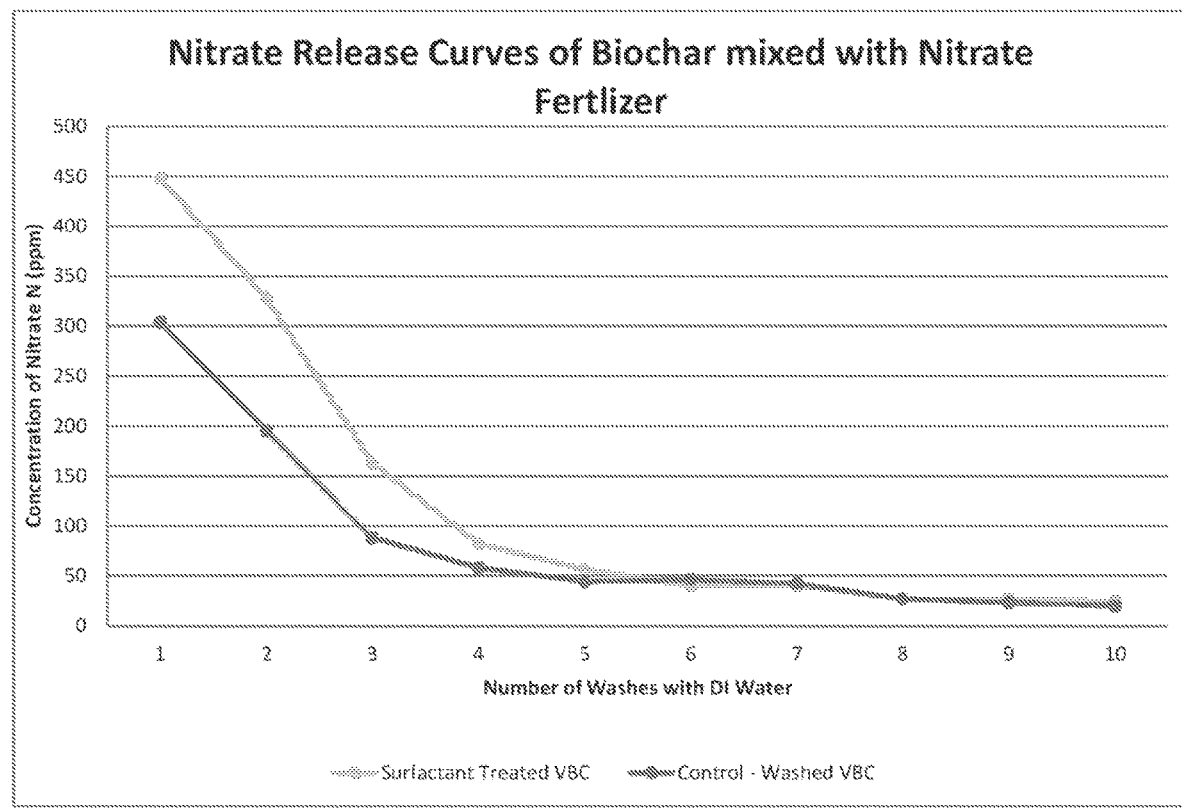
FIG. 22 is a chart showing nitrate release curves of treated biochars infused with nitrate fertilizer.

FIG. 22 is a chart illustrating the concentration of nitrate (N) found in distilled water after washing differentially treated biochar. In the illustrated example, two biochar samples (500 ml each) mixed with 1000 ppm $NO_3^-$ N fertilizer solution were washed with distilled water. The resulting wash was then tested for the presence of nitrate (N), measured in ppm. In one sample, the biochar was submerged in and mixed with the nutrient solution. In the other example, the biochar was mixed or washed with a nutrient solution augmented with 1% surfactant by volume (i.e., 1 ml of surfactant per 100 ml of fertilizer solution) in a tumbler. In both examples, the biochar was not dried completely before infusion with the $NO_3^-$ N fertilizer solution, but used as received with a moisture content of approximately 10-15%. In both examples, the biochar was mixed with solution and/or surfactant (in the case of a second sample) with a bench scale tumbler, rotating the drum for four (4) minutes without vacuum. The results demonstrate that the biochar treated with the 1% surfactant increases the efficiency of infiltrating nitrate fertilizer into biochar and then demonstrates the release of the nutrient over time. To yield the above data, the test was repeated six times for each treatment sample, with 10 washes for each sample per repeat test.

Adjusting the method of treatment (amount of vacuum, amount or residence time, addition of surfactant, additional substances infused, and optionally additional treatments after infusion) based on the substance being infused can modify and adjust the release characteristics of the material, either causing more rapid release, slower release, or a modification of the shape of the release curve over time.

In animal related applications, the additive may include, but not be limited to, water, water solutions of salts, inorganic and organic liquids of different polarities, liquid organic compounds or combinations of organic compounds and solvents, vitamins, supplements and/or medications, nutrients, minerals, oils, amino acids, fatty acids, supercritical liquids, growth promotants, proteins and enzymes, phytogenics, carbohydrates, antimicrobial additives and sensory additives (e.g. flavor enhancers salt or sweeteners or smell enhancers), among others, to provide nutrition, promote the overall health of the animal, and increase the animal's desire to ingest said biochar. Vitamins, supplements, minerals, nutritional and/or medications may be used to prevent, treat or cure animal illnesses and diseases and/or control the nutritional value of the animals overall diet.

For example, dietary supplementation with certain nutrients (e.g., arginine, glutamine, zinc, and conjugated linoleic acid) can regulate gene expression and key metabolic pathways to improve fertility, pregnancy outcome, immune function, neonatal survival and growth, feed efficiency, and meat quality. Such additives in the biochar can help provide the proper balance of protein, energy, vitamins and nutritionally important minerals in animal diets. Additionally, for poultry, the additive may include, for example, coccidiostats and/or histomonostats, which are both shown to control the health of the poultry. The present invention can be used to help correct deficiencies in basal diets (e.g., corn- and soybean meal-based diets for swine; milk replacers for calves and lambs; and available forage for ruminants).

Another example of additive infused biochar is a case when the beneficial inoculant contains microbes (fungi and/or PGPB) or microbial spores. These beneficial microbes interact with and enhance the performance of the plants' root systems when the so processed biochar is mixed with the soil in the root zone.

P G P B includes, for example, plant growth promoting rhizobacteria, free-living and nodule-forming nitrogen fixing bacteria, organic decomposers, nitrifying bacteria, MSM, biocontrol agents, bioremediation agents, archea, actinomycetes, thermophilic bacteria, purple sulfur bacteria, cyanobacteria, and combinations and variations of these. Beneficial fungi include, for example, saprotrophic fungi, ectomycorrhizae, endomycorrhizae, ericoid mycorrhizae, and combinations and variations of these.

Thus, treated biochar can have a microbial community in its pores (macro-, meso-, and combinations and variations of these), on its pore surfaces, embedded in it, located on its surface, and combinations and variations of these. The microbial community can have several different types, e.g., species, of biologics, such as different types of bacteria or fungi, or it may have only a single type. A primary purpose, among many purposes, in selecting the microbial population is looking toward a population that will initiate a healthy soil, e.g., one that is beneficial for, enhances or otherwise advance the desired growth of plants under particular environmental conditions.

A primary purpose, among many purposes, in selecting the microbial population in animal related applications is looking toward a population that will promote animal health either directly or through interactions with other microbes in the animals digestive tract. These types of beneficial microbes are essential to a functional gastrointestinal tract and immune system in many types of animals, serving many functional roles, including degradation of ingesta, pathogen exclusion, production of short-chain fatty acids, compound detoxification, vitamin supplementation, and immunodevelopment. Beneficial bacteria include *Lactobacillus acidophilus* LA1 (which decreases adhesion of diarrheagenic *Escherichia coli* to Caco-2 cells by 85% and prevents invasion of the same cells by *E. coli* (95%), *Yersinia* pseudo-tuberculosis (64%) and *Salmonella enterica* serovar *Typhimurium*) and *Lactobacillus rhamnosus* GG to prevent *E. coli* O157:H7-induced lesions in Caco-2 cells.

Further, biochar may be impregnated with probiotic bacteria to treat diseases in farm-raised fish. Infectious diseases pose one of the most significant threats to successful aquaculture. The maintenance of large numbers of fish crowded together in a small area provides an environment conducive for the development and spread of infectious diseases. In this crowded, relatively unnatural environment, fish are stressed and more susceptible to disease. Moreover, the water environment, and limited water flow, facilitates the spread of pathogens within crowded populations. There is thus an urgent need in aquaculture to develop microbial control strategies, since disease outbreaks are recognized as important constraints to aquaculture production and trade and since the development of antibiotic resistance has become a matter of growing concern. One alternative disease control relies on the use of probiotic bacteria as microbial control agents. Another implementation of the invention therefore involves the impregnation of biochar for consumption by aquatic animals as a treatment or preventative for disease.

Additionally, biochar may be infused with bacteria which prove helpful in methane reduction. An example of this is to infuse the biochar with methanotrophic bacteria (bacteria which are able to metabolize methane as a source of carbon and energy). Bacteria which metabolize methane are useful in two regards—they can reduce the environmental methane emissions from the rumen and they (the bacteria) also serve as nutrition for the animal itself, leading to increased weight gain. Infusing biocarbon with microbes such as these can lead to methane reduction in cattle applications that exceeds the methane reduction of solely untreated biochar itself.

Typically the prior art with respect to agricultural applications teaches placing biochar on soils without 'precharging' with bacteria or combining the biochar with compost and using this mixture as a soil amendment. The nature of the microbial population in this compost mixture is poorly disclosed by the prior art. Thus, through impregnation of the biochar particles, one can achieve a predetermined and controllable amount of a microbial community, e.g., population, into the soil. This integration of a microbial community with a biochar particle, and biochar batches provides the ability to have controlled addition, use and release of the microbes in the community. This integration further enhances, promotes and facilitates the growth of roots, e.g., micro-roots, in the biochar pores, e.g., pore morphology, pore volume.

With respect to animal applications, typically, the prior art teaches mixing raw biochar with animal feed without 'precharging' with nutrients, microbes, etc. Through impregnation of the biochar particles, one can achieve a predetermined and controllable amount of a particular nutrient, medication, foodstuff, microbial community, etc. being ingested by the animal. Once in the rumen, data indicates that these infused additives will also be released more slowly over time, yielding yet another benefit over additives mixed directly into the feed. This integration of a beneficial additive with a biochar particle and biochar batches provides the ability to have controlled addition, use and release of the additive or additives. This integration may further enhance, promote and facilitate animal growth and health, aid in digestion and digestibility of food, improvement hygiene, increase intestinal health, reduce the amount of nutrients lost into excrement and manure and reduce methane discharge.

Treatment can also impact the hydrophobicity of raw biochar (reduce it) which makes the biochar not only more suitable to house microbes, but also more able to associate with and interact with water and water soluble nutrients in the soil.

Additive infused biochar may be mixed with the animals regular feeds or may be included within a salt or mineral block and made available for animals to self-feed or self-administer the additives.

Other methods exist for integrating a microbial community with a previously infused biochar particle. Different manners and methods would be preferred depending on needs to minimize contamination, encourage biochar pore colonization/infiltration, minimize labor and cost and producing a uniform, or mostly uniform, product.

Methods for integrating a microbial community with a biochar particle may include, but are not be limited to the following: while under vacuum, pulling the microbial solution through a treated biochar bed that is resting on a membrane filter; spraying a microbial solution on top of a treated biochar bed; lyophilizing a microbial solution and then blending said freeze dried solution with the treated biochar; again infusing, as defined previously, the treated biochar with a microbial solution; adding treated biochar to a growth medium, inoculating with the microbe, and incubating to allow the microbe to grow in said biochar containing medium; infusing, as defined previously, the biochar with a food source and then introducing the substrate infused biochar to a microbe and incubating to allow the microbes to grow; blending commercially available strains in dry form with treated biochar; adding the treated biochar to a microbial solution and then centrifuging at a high speed, potentially with a density gradient in order to promote the biochar to spin down with the microbes; densely packing a column with treated biochar and then gravity flowing a microbial solution through the column and possibly repeating this multiple times; or adding the microbe to a solution based binder that is well known to enter the treated biochar pores and then adding said solution to the treated biochar. In order to insure the proper microbial community the treated biochar may need to be sterilized prior to these methods for integrating a microbial community. The sterilization can be done with standard methods including but not limited to thermal, radiation, or chemical. The sterilization method does not need to eliminate all microbial life. It can be a mild sterilization to reduce total populations or a method to target reduction or elimination of specific microbes. Instead of sterilization of the biochar itself the biochar can be handled via sterile or sanitary methods from pyrolysis through treatments including microbial community integration to limit contamination particularly of competing microbe communities or pathogenic microbes. All or parts of the above manners and methods may be combined to create greater efficacy. In addition, those skilled in the art will recognize that there may be additional manners or methods of infusing biochars with microbials, including those created by the combination of one or more of the manners and methods listed above, without departing from the scope of the present invention.

One manner in which the population of a microbial community can be determined is by PLFA (Phospholipid-derived fatty acids) analysis. Biological cell membranes are composed of a phospholipid bilayer with fatty acid side chains that are unique to certain families of organisms. PLFA analysis extracts the fatty acid side chains of phospholipid bilayers and measures the quantity of these biomarkers using GC-MS. An estimate of the microbial community population can thus be determined through PLFA analysis. The microbial activity may also be inferred through PLFA analysis by monitoring the transformation of specific fatty acids. Next generation sequencing of the conserved ribosomal RNA regions of the bacteria and fungi may allow for more direct and accurate measurements than PLFA.

Treated biochars can have a mixture of bacteria and fungi, or other microbes. For example, a preferred functional biochar, can have a preferred range for bacterial population of from about 50-5000000 micrograms/g biochar; and for fungi, from about 5 to 500000 micrograms/g biochar.

Compared to a biochar that has been bathed with a compost tea, which may have a relatively short, e.g., a few days for the life of the microbes, the impregnated populations of examples of the present treated biochars, are stable over substantially longer periods of time, e.g., at least an 8 week period and in some cases 1 year or more as measured by PLFA. Thus, the impregnation of the biochar with a microbial population provides for extended life of the microbes by at least 5×, 10×, or more over simple contact or immersion. In fact, some microbes may be better suited to surfactant infiltration versus vacuum infiltration and vice versa and this may impact the shelf life, penetration, viability, or other characteristics of the microbes.

Figure 23:
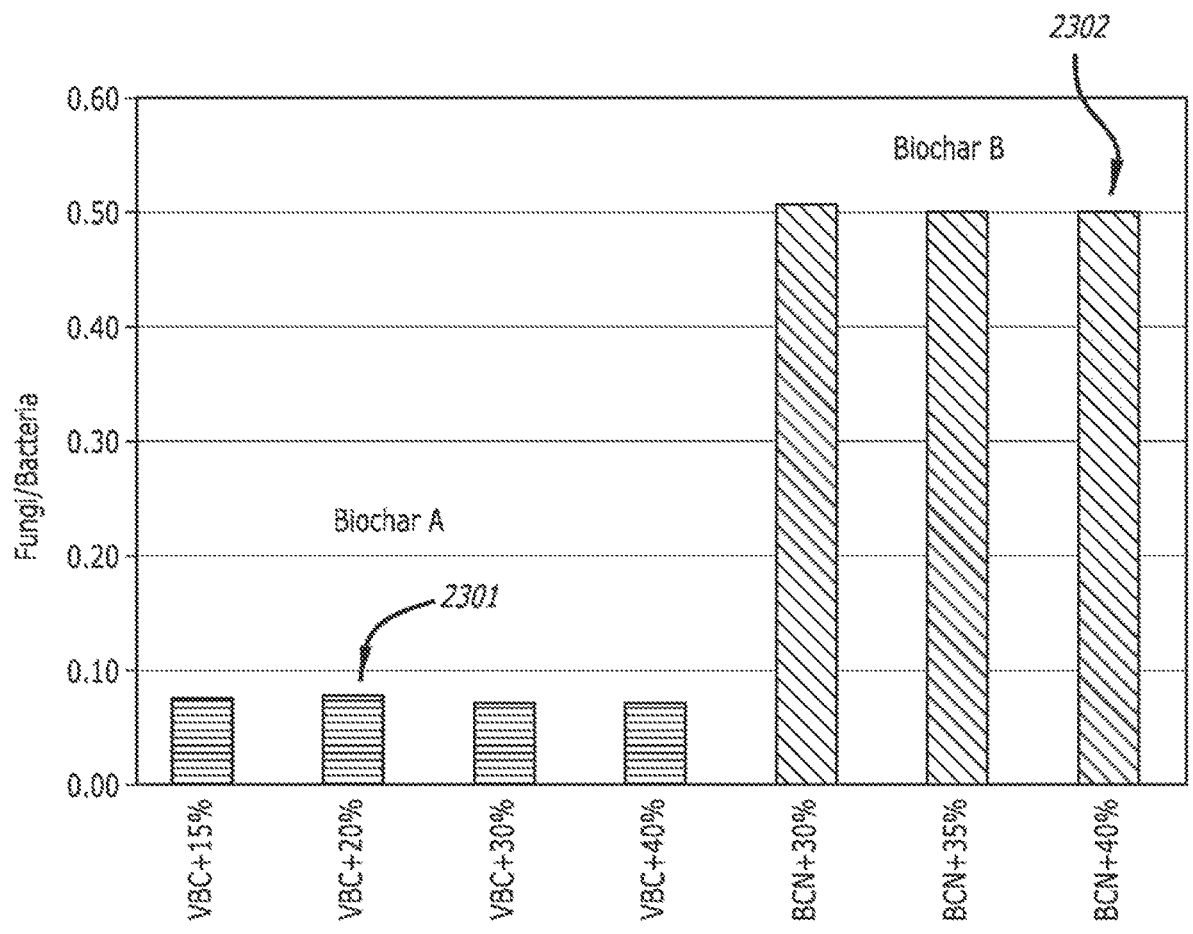
FIG. 23 is a chart comparing examples of biochars.

FIG. 23 shows the total fungi/bacteria ratio for two biochars derived from different biochar starting materials, e.g., feedstocks. Each biochar was loaded with different levels of moisture, and the total fungi/bacteria ratio was monitored during the first week. Biochar A 2301 showed a constant total fungi/bacteria ratio of 0.08 across moisture levels ranging from 15% to 40%, while Biochar B 2302 showed a constant total fungi/bacteria ratio of 0.50 for moisture levels ranging from 30% to 40%. It is theorized that, a fungi/bacteria ratio between 0.05 and 0.60 is an effective prescription for a stable biochar composition. This composition allows a commercially viable product, which has sufficient shelf life that it can be delivered to storage houses waiting for the proper planting window.

As used herein, unless stated otherwise, the stable shelf life of an example of a biochar product having a microbial population is the period of time over which the product can be stored in a warehouse, e.g., dry environment, temperature between 40° F.-90° F., with a less than 50% decrease in microbial population.

It is theorized that the difference in the observed total fungi/total bacteria ratios of may also be explainable by the structures of the biochars. Biochar's having an open pore structure, e.g., more interconnected pores, promotes more bacteria formation; while closed pores, e.g., relatively non-connected nature of the pores, tends to promote fungi formation. Biochars with differing microbial communities may be beneficial for specific applications in commercial agriculture. Thus, custom or tailored loading of the microbial population may be a desired implementation of the present invention.

Figure 24A:
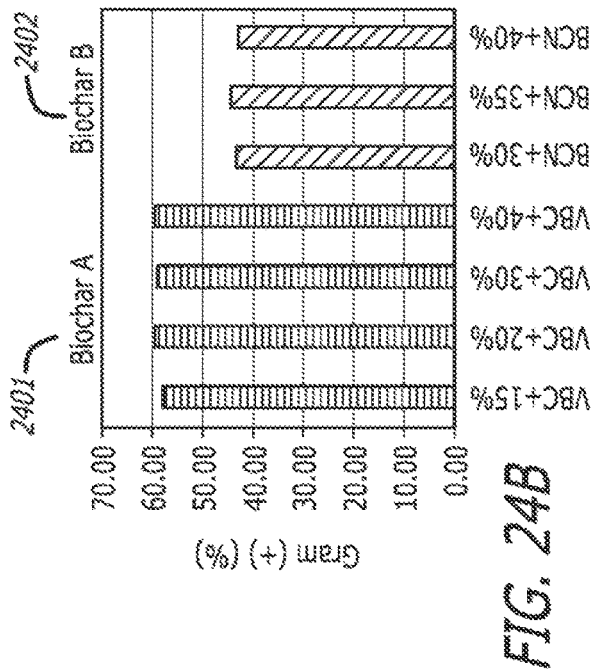
FIGS. 24a, 24b, 24c are charts comparing different examples of biochars.
Figure 24B:
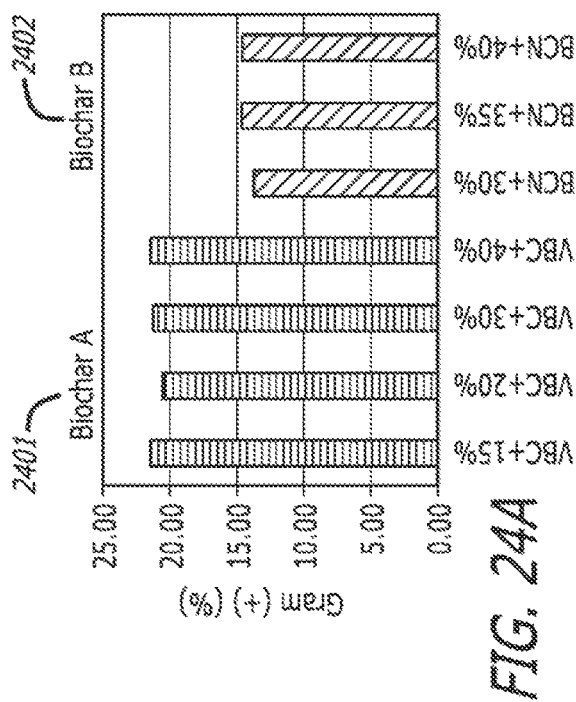
Figure 24C:
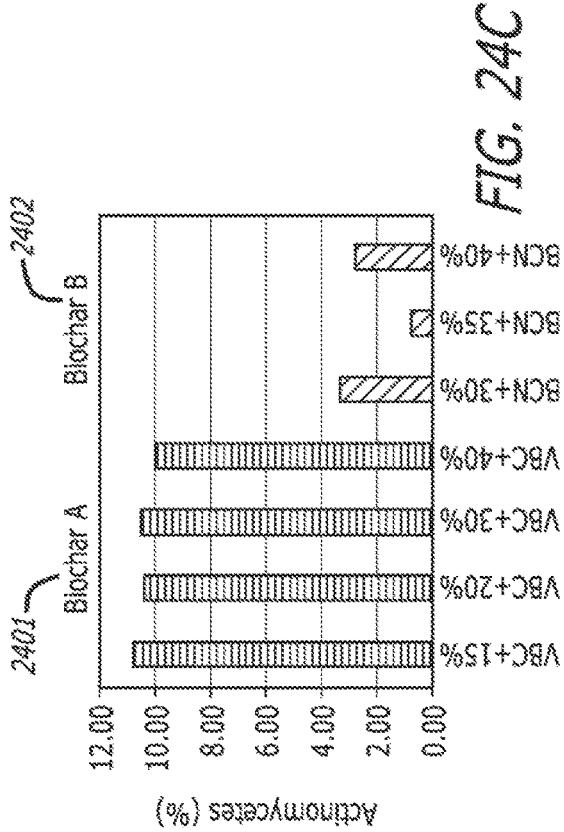

For example, as shown in FIGS. 24*a*, 24*b* and 24*c*, Biochar A 2401 shows that it has a greater population of, e.g., is inhabited by, more gram negative, gram positive and actinomycetes than Biochar B 2402. Thus, for example, Biochar A would be more applicable for use with certain agricultural crops in which PGPB species in the actinomycetes, gram (-) *pseudomonas*, and *bacillus* groups are used for nutrient utilization and uptake. Many vegetable and short cycle row crops such as tomatoes, lettuce, and celery form mutualistic relationships with bacteria that lead to the formation of biofilms on root hairs that function not only in nutrient uptake but also in plant pathogen resistance. The presence of biofilms in Biochar A would consequently promote bacterial colonization of plant root hairs as they encounter the biochar in the soil.

It is further theorized that, in general, biochars with greater fungal development may be better suited for perennial crops such as grapes, almonds, blueberries, and strawberries in which symbiotic relationships with arbuscular mycorrhizal fungi (AMF) are favored over PGPRs. The presence of high concentrations of AMF spores in biochars can therefore rapidly promote fungal colonization of plant root hairs leading to extensive mycelial development. Increased plant root associations with mycelial filaments would consequently increase nutrient and water uptake.

In general, bacteria communicate via the distribution of signaling molecules which trigger a variety of behaviors like swarming (rapid surface colonization), nodulation (nitrogen fixation), and virulence. Biochars can bind signaling molecules and in particular it is believed can bind a major signaling molecule to their surface. This binding ability can be dependent upon many factors including on the pyrolysis temperature. This dependency on pyrolysis temperature and other factors can be overcome, mitigated, by the use of examples of the present vacuum infiltration techniques. For example, a signaling molecule that is involved in quorum sensing-multicellular-like cross-talk found in prokaryotes can be bound to the surface of biochars. Concentration of biochars required to bind the signaling molecule decreased as the surface area of biochars increased. These signaling molecules may be added to the surface of a biochar and may be used to manipulate the behavior of the bacteria. An example of such a use would be to bind the molecules which inhibit cell-to-cell communication and could be useful in hindering plant pathogens; using techniques in the present invention signaling molecules may be added to the surface of a biochar to engineer specific responses from various naturally occurring bacteria.

For animal applications, in the same way that biochars are known to bind organic contaminants in soil environments due to hydrophobic-hydrophobic interactions, treated biochar may bind organic toxins as they pass through an animal's digestive system, for example, when cattle are suffering from botulism or diarrhea.

Further, a benefit of examples of biochars of the present inventions is the ability to provide an environment where bacteria communities can flourish. Bacterial communities can shift their morphology to increase nutritional access and decrease predation. One such modification is that the bacteria may attach to surfaces, such as those found in biochar, in a densely compacted community. In this compacted form they may form an extracellular polymeric substance (EPS) matrix called a biofilm. These communities can contain a few hundred different species which find shelter under the protective EPS coating from predatory protozoa, pathogens, contaminants, and other environmental stressors. Thus, examples of biochars produced in accordance with the vacuum infiltration methods may be used as carriers for established biofilms; and thus biochars with such films many used in agricultural settings.

The above are only a few examples of how additive infused biochar may be produced for different uses. Those skilled in the art will recognize that there may be other mechanisms for infusing fertilizer or other soil additives into the pores of the biochar without departing from the scope of the invention. Those skilled in the art will further recognize that the present invention can be used on any type of soil application, including, but not limited to, the following: crops, turf grasses, potted plants, flowering plants, annuals, perennials, evergreens and seedlings, and could also be applied more generally for veterinary purposes for many types of animals, including pets, as well as in a wide variety of environments and contexts, for example, for zoo or aquarium animals or for other penned or caged animals, or for wild animals.

Finally, in another implementation, additive infused biochar may be produced for use for consumption by humans. Biochar may be infused in the same manner as described above with nutrients (such as carbohydrates, minerals, proteins, lipids), vitamins, drugs and/or other supplements (such as enzymes or hormones, to name a few), or a combination of any of the foregoing, for consumption by humans. Coloring, flavor agents and/or coating may also be infused into the pores of the biochar or applied to the surface. The foregoing may be included to enhance the performance of the substance in the digestive tract or to ease or facilitate the ingestion of the biochar.

10. PGPB Infused Biochars

PGPB, includes, for example, plant growth promoting rhizobacteria, free-living and nodule-forming nitrogen fixing bacteria, organic decomposers, nitrifying bacteria, phosphate solubilizing bacteria, biocontrol agents, bioremediation agents, archea, actinomycetes, thermophilic bacteria, purple sulfur bacteria, cyanobacteria, and combinations and variations of these.

PGPB may promote plant growth either by direct stimulation such as iron chelation, phosphate solubilization, nitrogen fixation and phytohormone production or by indirect stimulation, such as suppression of plant pathogens and induction of resistance in host plants against pathogens. In addition, some beneficial bacteria produce enzymes (including chitinases, cellulases, -1,3 glucanases, proteases, and lipases) that can lyse a portion of the cell walls of many pathogenic fungi. PGPB that synthesize one or more of these enzymes have been found to have biocontrol activity against a range of pathogenic fungi including *Botrytis cinerea, Sclerotium rolfsii, Fusarium oxysporum, Phytophthora* spp., *Rhizoctonia solani*, and *Pythium ultimum*.

Currently, the most economic conventional solid carrier used to deliver microbes is peat. A solid carrier allows for a relatively long shelf life and a more direct application to a plants root system compared to a microbial liquid solution, which would be sprayed directly.

Figure 25:
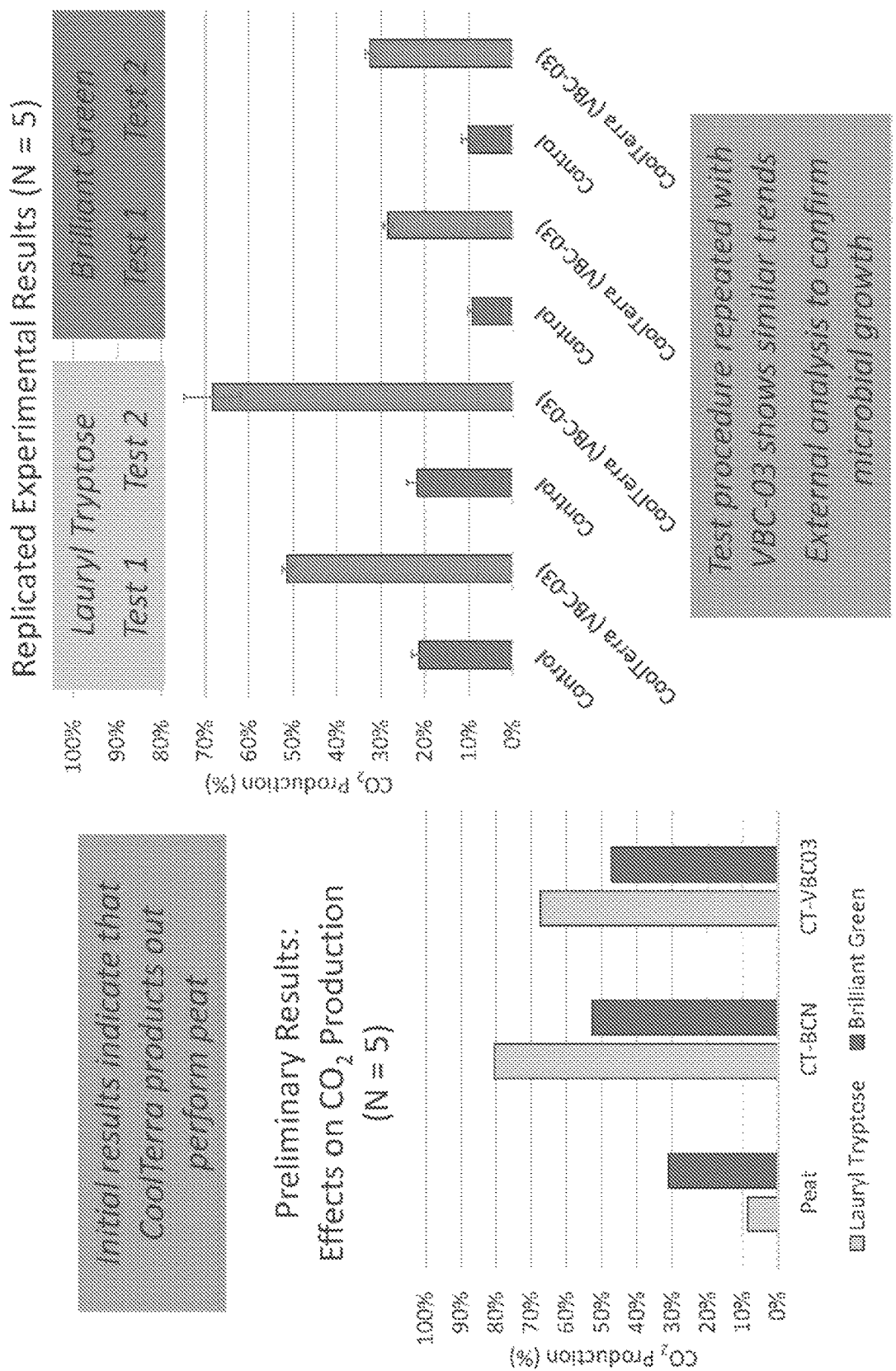
FIG. 25 contains charts illustrating improved results obtained through the use of biochars.

Research has shown a substantial increase in PGPB growth and distribution resulting from being infused in biochar. For example, data resulting from research conducted to compare the effects upon $CO_2$ production (an indicator of bacterial growth) using peat and biochars show the beneficial effects of using various biochars in promoting PGPB growth. As illustrated in the left-hand chart in FIG. 25, peat results in $CO_2$ production of between approximately 10% and 30% (depending upon the grown medium), whereas biochars result in $CO_2$ production of approximately 48% and 80%. Replicated experimental results using different biochars confirm $CO_2$ production of approximately 30% to 70% (depending on the grown medium), as compared to approximately 10% to 20% for the peat control.

Figure 26:
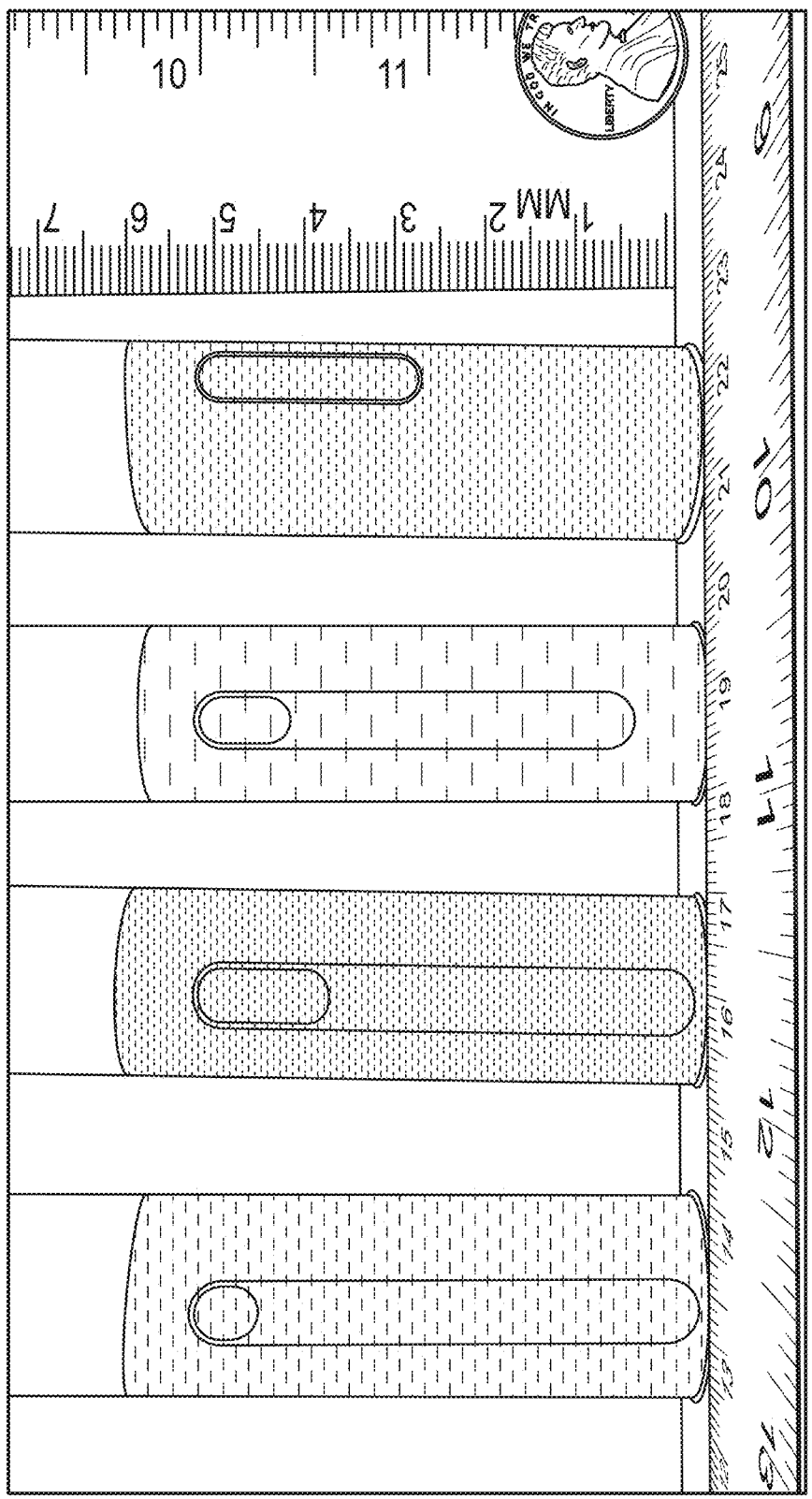
FIG. 26 is an example of carbon dioxide production captured as a continuous gas bubble in BGB (left two tubes) and LTB (right two tubes) growth medium.

The method developed for determining this $CO_2$ production as an indicator of bacterial growth consists of the following. The substrate (e.g., biochar or peat) is sterilized by heating at 110 C for 15 hours. A bacterial stock solution is then created. In this example, Tryptic Soy Broth was solidified with agar at 1.5% w/v in petri plates to isolate the gram negative non-pathogenic organism *Escherichia coli* ATCC 51813 (15 h growth at 37° C.). Then an isolated colony is captured with an inoculating loop and suspend in 10 ml sterile buffer (phosphate buffer saline or equivalent) to create the bacterial stock solution. Lactose containing assays are then used. In this example, test tubes that contain 13 ml of either Lauryl Tryptose Broth (LTB) or Brilliant Green Broth (BGB) that also contain a Durham tube were used. A negative control is generated by adding 10 μL of sterile buffer to triplicate sets of LTB and BGB tubes. A positive control is generated by adding 10 μL of bacterial stock solution to triplicate sets of LTB and BGB tubes. A negative substrate is generated by adding 1.25 ml (~1% v/v) of sterile substrate to triplicate sets of LTB and BGB tubes. A positive substrate is generated by adding 1.25 ml (~1% v/v) of sterile substrate and 10 μL of bacterial stock solution to triplicate sets of LTB and BGB tubes. The tubes of the four treatments are then incubated statically in a test tube rack at 37° C. for at least 15 h. The tubes are then carefully observed and any gas bubbles captured by the Durham tube within respective LTB or BGB tubes are closely measured with a ruler. Small bubbles <0.2 mm should not be considered. A continuous bubble as shown in individual tubes in FIG. 26 are what are observed and quantified. FIG. 26 is an example of carbon dioxide production captured as a continuous gas bubble in BGB (left two tubes) and LTB (right two tubes) growth medium. The percent carbon dioxide production is then calculated by dividing the recorded bubble length by the total Durham tube length and multiplying by 100.

Further tests were conducted using the *Streptomyces lidicus* WYEC 108 bacterium found in one of the commercially available products sold under the Actinovate brand. Actinovate products are biofungicides that protect against many common foliar and soil-borne diseases found in outdoor crops, greenhouses and nurseries. The formulations are water-soluble.

FIG. 27 illustrates the effects upon the growth of *Streptomyces* lidicus using conventional peat versus biochars. In the test illustrated by the photograph on the left of FIG. 27, an Actinovate powder was blended with peat, placed in an inoculated media and incubated at 25° C. The photograph shows the distribution and density of white colonies after 3 days. In the test illustrated by the photograph on the right of FIG. 27, an Actinovate powder was blended with the treated biochar, placed in an inoculated media and incubated at 25° C. The photograph also shows the distribution and density of white colonies after 3 days, the distribution and density of which are significantly greater than those achieved with peat.

FIG. 28 further illustrates the improved growth of the Actinovate bacterium using biochar versus peat. The left photograph shows only limited and restricted growth away from the peat carrier. The right photograph shows abundant growth of the bacterium spread much farther out from the biochar carrier.

Mycorrhizal fungi, including but not limited to Endomycorrhizae and Ectomycorrhizae, are known to be an important component of soil life. The mutualistic association between the fungi and the plant can be particularly helpful in improving plant survivability in nutrient-poor soils, plant resistance to diseases, e.g. microbial soil-borne pathogens, and plant resistance to contaminated soils, e.g. soils with high metal concentrations. Since mycorrhizal root systems significantly increase the absorbing area of plant roots, introducing mycorrhizal fungi may also reduce water and fertilizer requirements for plants.

Typically, mycorrhizae are introduced into soil as a liquid formulation or as a solid in powder or granular form and contain dormant mychorrhizal spores and/or colonized root fragments. Often the most economic and efficient method is to treat the seeds themselves, but dealing with traditional liquid and powder inoculums to coat the seed can be difficult. In accordance with the present invention, inoculated biochar may be used to coat the seeds by, for example, using a starch binder on the seeds and then subjecting the seeds to inoculated biochar fines or powder. Another method is by placing the mycorrhizae inoculum in the soil near the seeding or established plant but is more costly and has delayed response as the plants initial roots form without a mycorrhizal system. This is because the dormant mychorrhize are only activated when they come close enough to living roots which exude a signaling chemical. In addition, if the phosphorus levels are high in the soil, e.g. greater than 70 ppm, the dormant mycorrhizae will not be activated until the phosphorus levels are reduced. Thus applying inoculant with or near fertilizers with readily available phosphorus can impede the desired mycorrhizal fungi growth. A third option is to dip plant roots into an inoculant solution prior to replanting, but this is costly as it is both labor and time intensive and only applicable for transplanting.

If the colonization of mycorrhizae can be quickened and the density of the mycorrhizae's hyphal network can be increased, then the beneficial results of mycorrhizal root systems, e.g. increased growth, increased survivability, reduced water, and reduced fertilizer needs, can be realized sooner. Prior art shows that compost, compost teas, humates, and fish fertilizers can improve microbial activities and in more recent studies have shown physically combining arbuscular mycorrhizal fungi (AMF) inoculant with raw biochar has resulted in additional plant yield compared to each alone. See Hammer, et. al., *Biochar Increases Arbuscular Mycorrhizal Plant Growth Enhancement and Ameliorates Salinity Stress*, Applied Soil Ecology Vol 96, November 2015 (pg 114-121).

An ideal carrier for the mycorrhizae would have moisture, air, a neutral pH, a surface for the fungi to attach, and a space for the roots and fungi to meet. Thus a previously infused biochar created by the method disclosed above would be a better carrier than raw biochar alone. The infused biochar could be physically mixed with a solid mycorrhizal fungi inoculant or sprayed with a liquid mycorrhizal inoculant prior to or during application at seeding or to established plants. Additionally, the infused biochar and mycorrhizal fungi inoculant could be combined to form starter cubes, similar to Organo-Cubes, rockwool, oasis cubes, and peat pots.

The infused biochar could be further improved upon by initially or further infusing the biochar with micronutrients for mycorrhizal fungi, for example but not limited to humic acid, molasses, or sugar. The growth nutrient infused biochar would further expedite the colonization of the mycorrhizal fungi when physically combined with the inoculant and applied to seeds or plants.

Another improvement to the infused biochar would be to initially infusing or further infusing the biochar with the signaling molecules of mycorrhizal fungi. The signaling molecule infused biochar would further expedite the colonization of the mycorrhizal fungi when physically combined with the inoculant and applied to seeds or plants, as it would bring the mycorrhizae out of dormancy quicker and thus establish the mycorrhizal root system quicker.

Another method for establishing and improving mycorrhizal fungi colonies would be by growing mycorrhizae into the infused biochar and then applying the mycorrhizal fungi inoculated biochar to seeds or plants. Similar to a sand culture (see "Buying and Applying Mycorrhizal Fungi," by Lester, Donald, published by Maximum Yield USA, September 2009, pg. 128 citing Ojala and Jarrell 1980 (jhbiotech.com/docs/Mycorrhizae-Article.pdf), which article is incorporated herein by reference), a bed of infused biochar is treated with a recycled inoculated nutrient solution by passing it through the bed multiple times.

11. MSM Infused Biochars

The most important macro nutrients for healthy plant growth are nitrogen, phosphorus and potassium. Also needed are secondary macronutrients such as calcium, sulfur and magnesium, and trace minerals such as boron, chlorine, manganese, iron, zinc, copper, molybdenum and nickel. Among the macronutrients needed for animals are nitrogen, potassium, calcium, magnesium, phosphorus, sodium and chlorine; and micronutrients include copper, zinc, selenium and iodine.

Phosphorus is the second most important nutrient after nitrogen for healthy plant growth. While phosphorus is relatively abundant in most soils, its availability for plant uptake is restricted because of poor solubility and its fixation in soil. Poor availability or deficiency of phosphorus markedly reduces plant size and growth. Phosphorus accounts for about 0.2-0.8% of the plant dry weight.

To satisfy crop nutritional requirements, phosphorus is usually added to soil as chemical fertilizer; however synthesis of chemical phosphorus fertilizer is a highly energy intensive process, and has long term impacts on the environment in terms of eutrophication, soil fertility depletion, and carbon footprint. Moreover, plants can use only a small amount of this phosphorus since 75-90% of added phosphorus is precipitated by metal-cation complexes, and rapidly becomes fixed in soils. Such environmental concerns have led to the search for sustainable ways of making phosphorus available to plants. Mineral solubilizing microorganisms ("MSMs") are being increasingly viewed as the most eco-friendly means to accomplish this goal.

Potassium is a very important plant nutrient. Without adequate availability of potassium, plants will have poorly developed roots, grow slowly, produce small seeds and have lower yields, as well as increased susceptibility to diseases and pests. As with phosphorus, potassium is generally supplied as fertilizer, as large areas of the agricultural land of the world are deficient in potassium, and subject to the same environmental concerns expressed above. As with phosphorus, MSM is expected to play an ever-increasing role in making potassium available to plants in an eco-friendly manner.

MSM are able to release potassium from insoluble minerals. In addition, MSM can provide beneficial effects on plant growth through suppressing pathogens and improving soil nutrients and structure. For example, certain bacteria can weather silicate minerals to release potassium, silicon and aluminum, and secrete bio-active materials to enhance plant growth.

The major mechanism of mineral solubilization is the action of organic acids synthesized by MSM. Productions of organic acids results in acidification of the microbial cell and its surrounding environment that convert insoluble mineral compounds into soluble forms and make them available to the plants.

MSM that solubilize phosphorus or potassium include, but are not limited to, the following bacterial generas and species, *Bacillus* (for example *Bacillus mucilaginosus, Bacillus edaphicus, Bacillus circulans, Bacillus megaterium, Bacillus polymyxa, Paenibacillus* spp., *Acidothiobacillus, Bacilus subtilis, lysinibacillus sphaericus, lysinibacillus fusiformis*), *ferrooxidans, Pseudomonas* (for example *Pseudomonas striata, Pseudomonas fluorescens, Pseudomonas aeruginosa, Pseudomonas putida*), *Rhizobium, Cephalosporium, Klebsiella variicola, Arthrobacter* sp, *Pantoea agglomerans, Microbacterium laevaniformans, Micrococcus, Saccharomyces cerevisiae, Citrobacter* sp., *Burkholderia vietnamiensis, Acinetobacter rhizosphaera, Pantoea agglomerans, Achromobacter, Agrobacterium, Microccocus, Aereobacter, Flavobacterium, Erwinia, Klebsiella* (including *Klebsiella variicola*), and *Enterobacter* and *Burkholderia* (including *Burkholderia cepacia*); and fungi such as *Glomus* (e.g. *Glomus mosseae, Glomus intraradices*), *Penicillium* (e.g *Penicillium notatum*), *Aspergillus* (e.g. *Aspergillus terreus*, and *Aspergillus niger*) and *Tolypocladium geodes*. Additional phosphate solubilizing microbes can be found in Table 1 of "Phosphate Solubilizing Microbes: Sustainable Approach for Managing Phosphorus Deficiency in Agricultural Soils" by Sharma, Seema B., published by SpringerPlus, December 2013, 2:587, which article is incorporated herein in its entirety by reference (see link.springer.com/article/10.1186/2193-1801-2-587/fulltext.html).

Mineral intake of animals may also need to be supplemented. For example, grasses may not provide sufficient macro or micronutrients for grazing animals, resulting in mineral imbalances that can result in illnesses such as grass tetany, a magnesium deficiency that can occur in ruminants, as well as sheep, especially lactating ewes with twins that can result in animal death. Enhanced availability of nitrogen and potassium for forage, such as that produced by MSM-infused biochar, can minimize the risk of grass tetany. Restoring available soil phosphorus using MSM-infused biochar to concentrations adequate for good plant growth can also elevate magnesium and calcium concentrations in grass leaves.

In addition, where minerals are out of balance, this imbalance can directly or indirectly affect bioavailability of other minerals. This means that an animal may show signs of mineral deficiency even though it is getting the proper amount of that mineral. Use of biochar infused with both necessary minerals and MSM as a feed stock additive can counteract this situation.

An ideal carrier for the MSM would have moisture, air, a neutral pH, and a surface for the MSM to attach. Thus, a previously infused biochar created by the method disclosed above would be a better carrier than raw biochar alone. The infused biochar could be physically mixed with a liquid MSM inoculant prior to or during application at seeding or to established plants. Additionally, the infused biochar and MSM inoculant could be combined to form starter cubes, similar to Organo-Cubes, rockwool, oasis cubes, and peat pots.

The infused biochar could be further improved upon by initially or further infusing the biochar with micronutrients or growth media for MSM. The growth nutrient infused biochar would further expedite the colonization of the MSM when physically combined with the inoculant and applied to seeds or plants.

Another method for establishing and improving MSM colonies would be by growing MSM into the infused biochar and then applying the MSM inoculated biochar to seeds or plants. Similar to a sand culture (see above reference), a bed of infused biochar is treated with a recycled inoculated nutrient solution by passing it through the bed multiple times.

Additionally the MSM, minerals, and/or growth media could be infused with the method disclosed previously, using vacuum, surfactant, or ultrasound. All of the infusion methods listed could be used independently, in conjunction, in any order and even repeated as needed. These MSM-infused biochars can then be used to solubilize useful minerals for plants and animals in several different implementations.

In one implementation, the biochar to be infused with MSM already has the desired minerals in it. The biochar itself may have some minerals infused in it from the original biomass (e.g. organic phosphorus in the biomass) and the pyrolysis process (e.g. from the inorganic phosphates and pyrophosphates in the biomass) or minerals that were added to the biomass prior to pyrolysis or added into the biochar after the pyrolysis process itself or it could have acquired additional minerals as a result of being used for example in a water purification process, such as that taught by U.S. Patent application 2015/0144564 (Moller et al.), which is herein incorporated by reference in its entirety. Mineral levels of the biochar may include for example, at least 10 ppm or higher of phosphorous, nitrogen/nitrates, and/or potassium. In some applications, the minerals can be 50 ppm or greater or may be significantly greater when, for example, high levels of fertilizing minerals are desired. This application discloses embodiments of a system for treating water contaminated with, among other things, phosphates, nitrates and other minerals, using, in part, carbon capture, such as that provided by biochar. Modified biochar particulates form part of the reject stream resulting from the disclosed purification process. These modified particulates can, if large enough, then be infused with MSM (or if not, the particles can be pelletized and infused as part of the pellet creation process).

The MSM-infused biochar can then either be used as a soil enhancement in agricultural applications, or fed to animals. Research has indicated that the MSM will reproduce faster and more efficiently in the biochar environment, as disclosed above, and act to solubilize the minerals present.

In another implementation, biochar can be infused with MSM, and this MSM-infused biochar can be used as a soil amendment or fed to animals to act upon insoluble minerals either in the root zone of plants or in the ruminant or digestive system of animals.

In yet another implementation, biochar can be infused with potassium, phosphorous, or other minerals which MSM act upon, and then either mixed with, deployed with, or subsequently infused with MSM. This biochar infused with nutrients and either infused or deployed with MSM can then be used as a soil amendment, fed to animals, or used to yield many of the benefits already stated in this application.

In another implementation, biochar can be used to filter soluble nutrients from wastewater, stormwater, runoff, or other water in general. Then, the biochar laden with potentially useful, but usually immobile nutrients can be mixed with, deployed with, or infused with MSM to mobilize these nutrients. As the treated biochar is added to the soil, the MSM will mobilize the nutrients, allowing for true recycling of the nutrients retained in the biochar.

The above are only a few examples of how MSM infused biochar may be of beneficial use both for plant and animal health and growth, including humans, for whom minerals are an important nutrient and who can also benefit from the greater availability of those minerals provided by MSM. Those skilled in the art will recognize that there may be other ways that MSM-infused biochars may be useful without departing from the scope of the invention.

E. Biochar as a Habitat for Microorganisms

Biotechnology, specifically the use of biological organisms, usually microorganisms, to address chemical, industrial, medical, or agricultural problems is a growing field with new applications being discovered daily. To date, much research has focused on identifying, developing, producing and deploying microbes for various uses. However, despite much work on the microbes themselves, relatively little work has been performed on how to carry, deliver, and encourage the successful establishment of these microbes in their targeted environment. Most current technology for microbial carriers in agriculture is based on technologies or products that are highly variable and, in many cases, lead to highly unpredictable performance of microbes in the field. For example, many commercial microbes in agricultural settings are delivered on peat, clay, or other carriers derived from natural sources, accompanied by limited engineering or process control.

Biochar have a proclivity to interact positively with many microbes relevant to plant health, animal health, and human public health applications. In fact, there has been a level of initial research focused on inoculating biochar with microbes and/or using biochar in conjunction with microbes or materials with microbes, e.g. compost. See co-owned U.S. Pat. No. 8,317,891 Method for Enhancing Soil Growth Using Bio-char and Fischer et al., and *Synergisms between compost and biochar for sustainable soil amelioration* 2012 www.intechopen.com/source/pdfs/27163/InTech-Synergisms_between_compost_and_biochar_for_sustainable_soil_amelioration.pdf.

However, biochars, especially in raw form, often suffer from many characteristics which make their interaction with microbial organisms extremely unpredictable. Key among these undesirable characteristics is a high degree of variability. Because of this and other factors, biochar has been, to date, unused in large scale commercial biotechnology applications. There are several methods by which this variability can be ameliorated. At a high level, the methods to overcome these challenges fall into two categories: (i) making the biochar a more favorable habitat for the microbes—either by modifying its properties, adding materials beneficial to microbes, or removing materials deleterious to microbes, or (ii) inoculating, applying, or immobilizing the microbes on the biochar in ways that mitigate the underlying variability in the material. Both of these high-level methods can be used independently or in conjunction and have been shown to have a significant impact on the suitability of biochar in many biotechnology applications.

Before delving into the varying treatment methods that will turn the biochar into a microbial carrier or co-deploying with microbes, it is important to be able to view biochar as a habitat for microbes. Biochar, especially treated biochar, has many physical properties that make it interesting as a microbial habitat. The most obvious of these is its porosity (most biochars have a surface area of over 100 m2/g and total porosity of 0.10 cm3/cm3 or above). Furthermore, many biochars have significant water holding and nutrient retention characteristics which may be beneficial to microbes. Previous disclosure has outlined how these characteristics can be further improved with treatment, e.g., U.S. patent application Ser. No. 15/156,256, filed on May 16, 2016, and titled Enhanced Biochar.

However, recent data indicates that the Earth may be home to more than one trillion independent species of microbes (See Kenneth J. Locey and Jay T. Lennon, *Scaling laws predict global microbial diversity*, Proceedings of the National Academy of Science, vol. 113 no. 21 (see full text at www.pnas.org/content/113/21/5970.full). Clearly, each of these microbial species does not require an identical habitat. In fact, many have evolved in different conditions and thrive in different environments. Biochar, due to its organic origins, porosity, and amenability to treatment seems to be an extremely desirable base product to be used in the construction of microbial carriers or co-deployment of microbes. If the properties of the biochar can be made to match the properties expected by particular microbes, or groups of microbes, empirical data has shown that a much greater impact can be delivered in many applications—whether the targeted biochar is used as a carrier, substrate, co-deployed product, or merely is introduced into the same environment at a separate time. It stands to reason, as many real-world environments are composed of very complex microbial ecosystems. that giving certain microbes in these ecosystems a more favorable habitat, can ultimately help those microbes to become more successfully established, and potentially shift the entire ecosystem based on their improved ability to compete for resources. Clearly this is a very desirable characteristic when the successful deployment and establishment of a targeted microbe into a new environment is a desired outcome.

There are many properties of a habitat which may be important to certain microbes, but some of the most important are: pH, hydrophobicity or hydrophilicity, ability to hold moisture, ability to retain and exchange certain types of nutrients, ion exchange capacity (cationic and anionic), physical protection from predatory or competitive microbes or protozoa (usable and inhabitable porosity), presence or absence of nutrients, micronutrients, or sources of metabolic carbon, ability to host other symbiotic microbes or plant systems (such as plant root tissue), or others which may be important to various types or species of microbes. Ability to either enhance or suppress the availability of certain enzymes can also be an extremely important factor in building a viable habitat. This invention focuses on methods and systems that can be used to consistently produce biochar which has these targeted characteristics, methods that can be used to effectively create a particular formulation of biochar targeted to match a particular microbe or group of microbes, and techniques for deploying the desired microbes along with this targeted biochar, through inoculation, co-deployment, integrated growth/fermentation, or other methods.

By using treatment properties disclosed previously, proper feedstock selection, aid control of the pyrolysis process, the following are some, but not all, of the properties that can be consistently targeted and controlled at product ion scales to improve the biochar for use with microbes or as a microbial carrier. Examples of those properties include (1) pH, (2) hydrophobicity, (3) sodium levels, (4) usable pore size distribution and usable pore volume, (5) particle size and distribution, (6) exterior and interior surface geometry, (7) nutrient exchange, (8) useable carbon or energy source, (9) toxic materials or compounds, (10) surface structure/crystals/tortuosity, (11) compatibility with biofilm formations, (12) surface charge, (13) enzyme activity and (14) sterilization.

1. pH

It is well known that various microbes prefer varying levels of acidity or alkalinity. For example, acidophiles have evolved to inhabit extremely acidic environments. Likewise, alkaliphiles prefer more basic (alkali) environments. It has been clearly shown that the methods outlined for treating biochars can product targeted pH values that can be sustained over long periods of time.

2. Hydrophobicity

There are several common sources of hydrophobicity in porous carbonaceous materials, One of them is the occurrence of hydrophobic organic compounds on the surface of the char—typically residual from the pyrolysis process. Targeted removal of these compounds is a method to improve the hydrophobicity of porous carbonaceous substances. These compounds can be removed in a non-selective way by increasing the pyrolysis temperature of the biomass to a level at which the compounds will disassociate with the material and become gaseous. This method, while useful, is very broad, and can also remove other desirable compounds as well as changing the surface chemistry of the residual carbon, increasing ash percentages, or reducing carbon yield by reacting and removing more carbon than is necessary. These compounds can also be selectively removed by the application of a targeted solvent using the mechanisms previously disclosed to infiltrate liquids into the pore volume of the material. This method is also effective, and has shown to be much more predictable in the removal of certain compounds. Since the vast majority of microbes rely heavily on water for both transport and life, the easy association of water with a material has a large bearing on its ability to sustain microbial lift.

3. Sodium Levels

Differing types of microbes have varying proclivities for the presence of sodium, Some microbes *Halobacterium* spp., *Salinibacter ruber, Wallemia ichthyophaga* prefer high levels of salinity, while others prefer moderate or limited levels of sodium. Sodium can be removed from biochar by either simple washing, or more preferably and effectively, treatment methods which infuse a solvent (most commonly water, although others may be used) into the pores of the material. Sodium can be added, by using the same methods except instead of using a solvent, the liquid being washed with or infused is a solution high in sodium content. Additionally, since sodium usually manifests itself as a cation in solution, temporary or permanent adjustment of the cationic exchange capacity (CEC) of the material through treatment which impacts the ability of the material to exchange cations. Lowering the CEC of the material will in many cases reduce its ability to exchange sodium cations, while raising the CEC will typically enhance the ability of the material to exchange sodium cations, with exceptions occurring if other cations are present in quantities that cause them to preferentially exchange instead of the sodium cations present. Finally, differing biomass feedstock contains differing levels of sodium—selecting an appropriate feedstock prior to pyrolysis will result in a raw or untreated biochar with reasonably controlled levels of sodium. For example, pine wood, when pyrolyzed, results in a raw char with lower levels of sodium, while coconut shells result in char with higher levels of sodium after pyrolysis.

| ASH Composition | Untreated Coconut Shell Biochar | Untreated Pine Biochar #1 | Untreated Pine Biochar #2 |
|---|---|---|---|
| Ultimate Analysis - Moisture free results | | | |
| Ash | 6.7% | 9.2% | 3.6% |
| Ash Composition | | | |
| Sodium Oxide, as Na2O | 5.7% | 1.2% | 0.8% |

Regardless, it should be clear that there are various methods available to produce final product with a targeted sodium level, making it suitable for various microbes depending on their preference for an environment with a certain sodium level.

4. Usable Pore Size Distribution and Usable Pore Volume

One very important quality of a microbial habitat is the availability of shelter from environmental or biological hazards. A few examples of environmental hazards are high temperature, UV radiation, or low moisture, while an example of a biological hazard is the existing of predatory multicellular microbes such as protozoa, including both flagellates and ciliates. In order for a particle or material to provide shelter for microbes, at least two conditions must be present: (i) The material must consist of pores or openings of a size which can be inhabited by the microbe in question (ii) but prevent the hazard from entering (e.g. pore sire smaller than the size of predators, such as protozoa, or deep enough to be shaded from UV rays) and, (iii) the pores mentioned previously must be usable—namely, they should not be occupied by solid matter (clogged) and/or they should not contain substances that are toxic or undesirable for the microbe in question. In some cases, the pore size distribution of a biochar can be adjusted by the selection of the biomass feedstock to be pyrolyzed and the conditions of the pyrolysis process itself. For example, pine wood has a relatively narrow pore size distribution, with most pores falling in the range from 10-70 μm. Coconut shells, on the other hand, have a much wider size distribution, with many pores below 1 μm, and also a high percentage of porosity above 100 μm. It is theorized that materials with pores of a single size or where most pores are of similar size can potentially be good carriers or habitats for certain, targeted microbes, while materials consisting of broader ranges of pore size may be better habitats for communities, consortia or groups of microbes, where each microbe may prefer a slightly different pore size. Furthermore, the pore size of a material may also be controlled during the pyrolysis process by increasing temperature or performing "activation" or other steps common in activated carbon production to react or remove carbon, leaving larger pores, or exposing availability of pores that were once inaccessible from the exterior surface of the material. Adjusting the particle size of the material may also change the pore size distribution in at least two ways: (i) exposing pores that were not available or accessible previously, or (ii) destroying larger pores by fracturing, splitting, or dividing them. In many cases, raw biochar may contain a proper pore size distribution, but for one reason or another, the pores are not usable by the microbes in question. In other cases, the pore size distribution provided by the natural feedstock may be undesirable. Both properties may also be impacted through treatment of the raw biochar itself. Larger pores can be created using strong acids or other caustic substances either by simple washing or through forced or rapid infusion into the pores. Conversely, a material with fewer usable pores may be created by intentionally "clogging" or filling the larger pores with either solids, gums, or liquids designed to stay resident in the pores themselves. This treatment may be done in a controlled way to only partially fill the pores. For example, one could infuse a limited amount of heated liquid, such as a resin, that will become solid at normal atmospheric temperatures, if the volume of liquid used is less than the available pore volume of the material being infused, some of the porosity of the material will be left untreated and available for use. Most importantly, and most commonly, usable pore volume may be increased through the act of simply removing contaminants (physical or chemical) from the pores. Rapid infusion and extraction of liquids may be used to accomplish this. As discussed previously, appropriate solvents may be infused or extracted to remove chemical contaminants. Additionally, gasses or liquids may be driven into or out of the pores to force the removal of many solid obstructions, such as smaller particles of ash or simply smaller particles of raw biochar which may have become lodged in the pore in question. Regardless of the mechanism used, it has been shown that the available, uncontaminated, usable pore volume and pore size has a major role in determining the efficacy of biochars in microbial roles.

Figure 29:
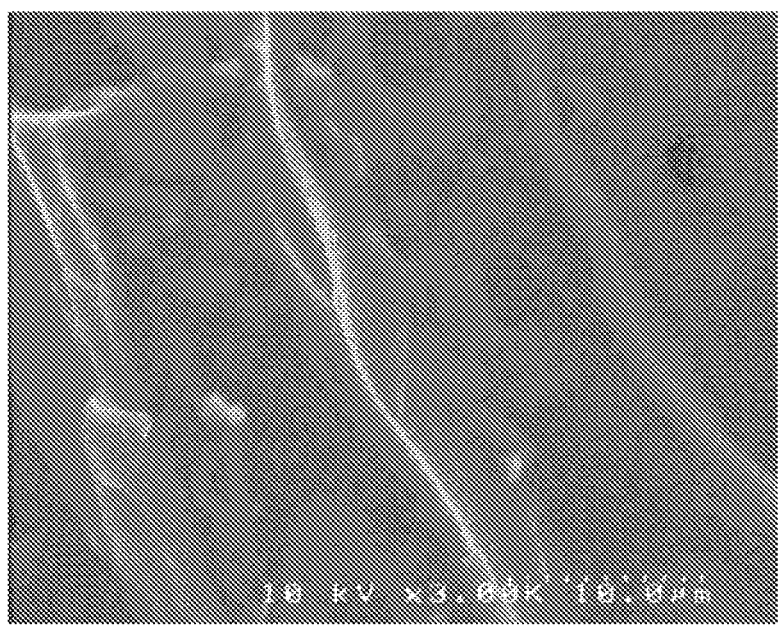
FIGS. 29 and 30 are images that show how different sized bacteria will fit in different biochar Pore size structures.
Figure 30:
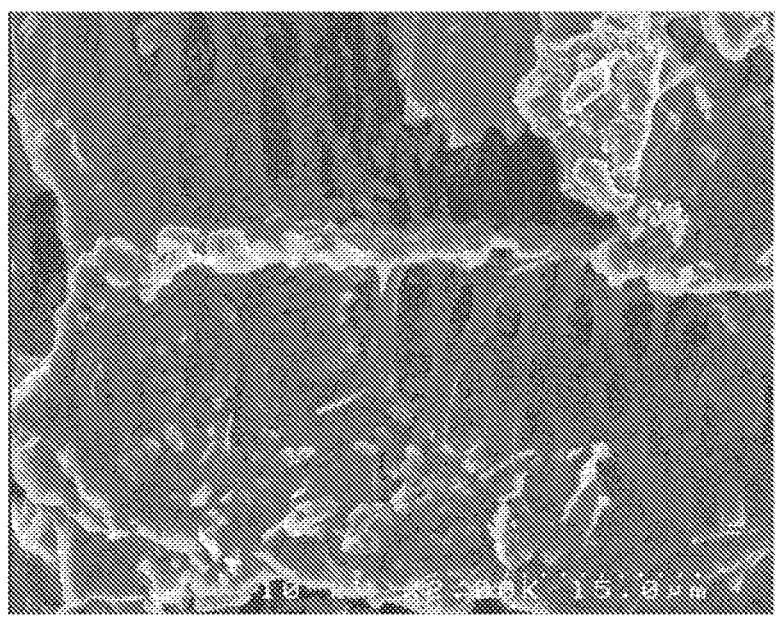
Figure 31:
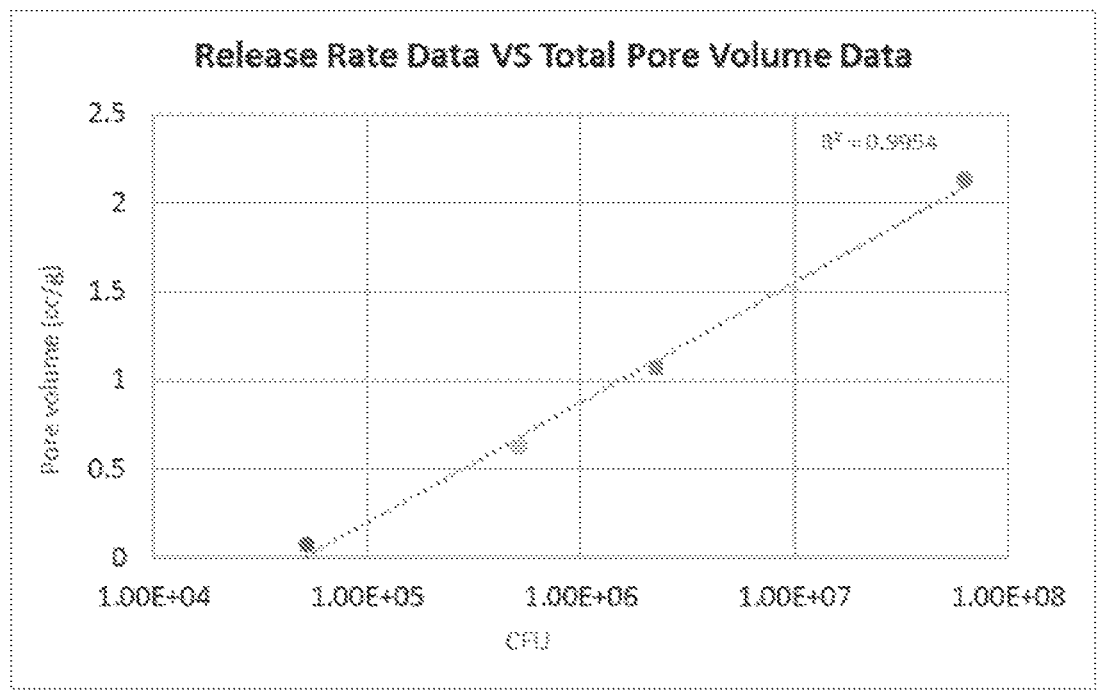
FIG. 31 illustrates release rate data verse total pore, volume data for both coconut shell and pine based treated biochars inoculated with a releasable bacteria.

FIGS. 29 and 30 are images that show how different sized bacteria will fit in different biochar pore size structures. FIG. 29 is rod-shaped gram-positive bacteria, *Bacillus thuringiensis israelensis*, in a treated pine biochar, with pore openings of ~10-20 μm and bacteria of ~2-5 μm. FIG. 30 is rod-shaped gram-negative bacteria, *Serratia liquefaciens*, in a treated coconut shell biochar, with pore openings of ~2-10 μm and bacteria of ~1-2 μm.

In addition, total pore volume in the size of 5-50 μm has been shown to correlate with microbial release rate after inoculation on treated biochar. FIG. 31 illustrates release rate data verse total pore volume data for both coconut shell and pine based treated biochars inoculated with a releasable bacteria. As illustrated in FIG. 31, the data was plotted in a graph, and clearly shows that as pore volume increases so does the release rate, 5. Exterior and Interior Surface Geometry Two important properties of microbial carriers are: (i) their ability to release microbes from their surfaces and (ii) their ability to immobilize or stabilize microbes on their surfaces. Depending on the final application or use of the carrier, one or both of these properties may be desired. For example, for carriers designed to quickly release a microbe into a targeted domain such as a lake, river, or other waterway, the release characteristics of the material are paramount. For other applications, such as applications of certain symbiotic microbes in agriculture, rapid release may be undesirable, rather it may be important to sustain the microbes within the porosity of the material until plant tissue, such as root biomass, is nearby to provide nutrition for the microbes in question. The surface and pore geometry of the material used as a carrier can be critical to determine this behavior. For example, material with generally smooth, uniform surfaces will typically release many microbes much more effectively, while material with more rugged, varied, tortuous pore surfaces and geometry will typically retain and immobilize microbes more effectively. The biomass used in the production of the final material is one of the most important factors in surface geometry. However, even this quality can be altered through treatment. Specifically, smooth surfaces may be etched by implementing the treatment and infusion processes previously disclosed with strong acids, rendering them rougher. Conversely, rough surfaces may be treated with either organic or inorganic compounds to coat and remove contour. Mechanical means may also be used to affect changes in particle geometry. Many forms of charred material have relatively low crush strength and are relatively brittle. The method used to grind, or size particles can have a large impact on the geometry of the final particles. For example, particles milled using a ball mill or other type of grinding technology will typically have a smoother exterior geometry after the milling is complete and may lose a good amount of their porosity through the simple mechanical crushing of pores. However, particles sized using ultrasonic vibrations or even simple physical vibrations to shatter, rather than crush larger particles into smaller ones, will typically retain their geometry, or sometimes result in smaller particles with more rugged geometries than the particles at the beginning. It should be apparent to one skilled in the art that there are various mechanical mechanisms available to effect these changes, but the resulting particles can be tailored to meet a particular microbial release or immobilization outcome.

6. Particle Size and Distribution

It is well known that the particle size and particle size distribution of a material has a key impact on its formulation as a microbial carrier. In many cases, these factors are very different for porous carbonaceous materials than they are for other common microbial carriers. In standard carriers, typically the reduction of particle size is a method used to increase surface area, and thus the area available to support, immobilize, and carry microbes. However, in porous materials, specifically materials with a large volume of usable interior porosity, sometimes a reduction in particle size does not cause a large increase in the usable surface area—specifically because the interior surfaces of the material were already exposed, and reducing the size of the particle does not change that fact. This leads to a somewhat counterintuitive behavior in some cases in which the reduction of the particle size of a porous material actually degrades its performance as a microbial carrier, due to the phenomena that surfaces that were once sheltered inside the material are exposed as exterior surfaces when the material is split or crushed, making the material less desirable as a habitat for microbes that require shelter from the surrounding environment. Additionally, at times the actual distribution of particle sizes can be a key factor in performance. As a simple example, imagine an aggregated material which consists of only two particle sizes: 1 mm and 1 μm. Furthermore, imagine that 50% of the mass of the aggregate resided in the 1 mm particles with the remainder in the 1 μm particles. Lastly, imagine that the 1 mm particles were porous carbonaceous particles with an average pore size of approximately 50 μm. It should be clear that if this aggregate was placed in a container and agitated, that a good portion of the 1 μm particles would end up inhabiting the pore volume of the 1 mm particles, impacting their usability. In fact, this is the behavior that we see in practice. Therefore, for certain microbial applications, it is desirable to remove extremely small particles, often referred to as fines, from the aggregate. This has the additional benefit of reducing dust during application, which is particularly important in aerial applications, and reducing the level of surface runoff for applications in water, which also is important in certain microbial applications. The small particles may be removed through several methods such as sieving, blowing or aerodynamic removal, separation with either stationary or moving liquids (hydrostatic or hydrodynamic separation) of various viscosities, temperatures, flow rates, etc. However, at times, having a mixture of smaller and larger particles can be desirable. The most common cases are when communities of microbes are to be deployed, or the aggregate is to remain generally intact for a period of time (fermentation applications, long term storage applications, or preparation for other formulation uses such as palletization), in which case, the interparticle void space is also an important factor and can be optimized for a particular microbe or set of microbes by providing a range of particle sizes and geometries.

7. Nutrient Exchange

The ability of a material to hold or exchange nutrients is an incredibly important characteristic, not only for microbial, but also for general agricultural applications, There are two primary mechanisms that porous carbonaceous materials can exchange nutrients: (i) sorption or retention of the nutrients on the interior and exterior surfaces of the material, and (ii) retention of the nutrients either in suspension or solution in liquid or gasses residing in the pore volume of the material Both mechanisms are very useful, but also very different in function. Surface sorption or retention is driven by two main properties, among others: (i) ion exchange capacity of the material and. (ii) reactivity or electrical charge of compounds present on or coating the surfaces of the material. Retention of nutrients in solution or suspension are impacted by other, different characteristics of the material, such as hydrophilicity, oil sorption capacity, usable pore volume and pore size distribution, and interior pore geometry and tortuosity. The surface retention of nutrients can be targeted by selecting the feedstock biomass (some materials render a char after pyrolysis with vastly differing ionic exchange capacities (CEC and AEC) than other. It can also be impacted by adjusting pyrolysis conditions, Higher pyrolysis temperatures tend to reduce CEC and nutrient adsorption capability. See Gai, Xiapu et al. "Effects of Feedstock and Pyrolysis Temperature on Biochar Adsorption of Ammonium and Nitrate." Ed. Jonathan A. Coles. *PLoS ONE* 9.12 (2014): e113888. *PMC*. Web. 19 Nov. 2016. In addition, the surface retention of nutrients can be impacted by treating the surfaces of the material with substances targeted towards adjusting the ionic exchange characteristics. For example, using the previously disclosed treatment methods to infuse $H_2O_2$ into the pores of the carbonaceous material and then evaporating the liquid can increase the cationic exchange properties of the material.

Furthermore, another way to exchange nutrients more efficiently is to use the pore volume rather than, or in addition to, the pore surfaces—namely keeping the nutrients in solution or liquid or gaseous form and placing them in the volume of the pores rather than attempting to sorb them on the surfaces of the material. This can be an incredibly useful technique not only for plant life and soil health, but also for microbes. The food sources can vary from simple to complex such as glucose, molasses, yeast extract, kelp meal, or bacteria media (e.g. MacConkey, Tryptic Soy, Luria-Bertani), When using the pore volume to exchange nutrients in this way, it should be clear that a wide variety of nutrients may be used, and targeted combinations of pore volume, size, and nutrition can be produced to assist in the delivery, establishment, or successful colonization of targeted microorganisms or groups of microorganisms. It should be clear by this point that merely immersing the biochar or porous carbonaceous material in a liquid nutrient broth may be partially effective in filling the pore volume or coating the pore surfaces with these nutrients and should be considered within the scope of this invention, however using the treatment techniques outlined in this and related disclosures is much more effective at both coating the surfaces and infusing nutrition into the pore volume of the material itself. Since many microbes rely on liquid for mobility, placing liquid into the pore volume of the material is in many cases a prerequisite for successfully infusing, carrying, or delivering microbes.

8. Usable Carbon or Energy Sources

Related to the ability to improve nutrient exchange is the ability to treat the pore volume, pore surfaces, exterior surfaces, or any combination of these with not only custom broths or growth media, but also other forms of carbon known to be beneficial to microbes and plant life. Some examples of this are carbohydrates (simple and complex), humic substances, plant macro and micronutrients such as nitrogen (in many forms, such as ammonium and nitrates), phosphorous, potassium, iron, magnesium, calcium, and sulfur and trace elements such as manganese, cobalt, zinc, copper, molybdenum. These nutrients may either be infused in liquid or gaseous form, or even as a suspended solid in liquid. The liquid may be left in the pores, or may be removed. If removed through evaporation, nutrients in solution or suspended solids may be left behind, while if removed by mechanical or physical means, a portion of the liquid may be left behind as well as some solids. It should be noted that the various forms of removal have differing advantages and disadvantages and that many energy sources may be added either at the sane time or in sequence, with one, or many, removal steps in between treatment or infusion steps.

9. Toxic Materials or Compounds

The selective addition or removal of materials or substances known to be toxic to a certain microbe or lifeform is a key step in preparation of biochar for use as a microbial habitat or carrier. It has been shown, that through treatment, potentially toxic compounds can be removed with much greater effectiveness than through simple pyrolysis alone. Some examples of the potentially deleterious compounds that may be removed are: volatile organic compounds (VOCs), monoaromatics, polycyclic aromatic hydrocarbons (PAHs), heavy metals, and chlorinated compounds (e.g. dioxins and furans). A proven approach to remove these substances is to wash the exterior surfaces with and/or rapidly infuse a solvent into the pore volume of the material targeted to remove these substances. Following the infusion with either mechanical extraction, drying, or other methods to remove the solvent, laden with the substances in question, from the pores and interparticle spaces is a desirable, but not strictly necessary step to further reduce the levels of toxicity. For example, the following data shows removal of dioxins using the treatment process of the present invention.

|  | Raw coconut shell biochar | Treated coconut shell biochar | Raw pine biochar | Treated pine biochar |
|---|---|---|---|---|
| TEQ ng/kg (method 8290A) | 0.7 | 0.4 | 9.6 | 0.4 |

Another approach for some toxic compounds (benzene as one example) is, rather than removing the compounds in question, to react them in place with other compounds to neutralize the toxicant. This approach can be used either with washing, or forced/assisted infusion, and in these cases a removal step is less necessary—although it still can be used to prepare the material for another, subsequent phase of treatment.

Much attention is given to the removal of toxic compounds, but it should be also be noted that at times, it can be extremely beneficial to actually add or treat the material with toxic compounds. A primary example of this is sterilization, or preparation for selective infusion. Even after pyrolysis, residual biological life has been found to potentially establish itself in biochars given the right conditions. Treating, washing, or infusing the material with antiseptics such as methanol, ethanol, or other antibacterial or antiviral substances can be a key step in removing contamination and preparing the material for use in microbial applications. A variation on this approach is to infuse, treat, or wash the material with a selectively toxic compound, such as a targeted antibiotic or pharmaceutical targeted towards interrupting the lifecycle of a specific set of microorganisms or organisms, thereby giving other microbes, either through infusion or merely contact in situ the opportunity to establish, Some examples of this treatment would be the use of antifungals such as cycloheximide to suppress fungal growth and provide an environment better suited for the establishment of bacteria. As has been stated previously, the methods may be used alone, or in combination with one another. Specifically, a toxic compound such as ethanol, may be infused, removed, and then steps may be taken to remove other toxic compounds, followed by steps to add carbon sources or growth media.

10. Surface Structures/Crystals/Tortuosity

The physical surface and pore structure of the material is critically important to its suitability as a microbial habitat. There are many factors that contribute to the surface structure of the material. The most notable of these factors is the biomass used to produce the carbonaceous material—the cellular structure of the biomass dictates the basic shape of many of the pores. For example, pyrolyzed coconut shells typically have less surface area, and a more diverse distribution of pore sizes than pyrolyzed pine wood, which, when pyrolyzed at the same temperature, has greater surface area, but a more uniform (less diverse) pore size distribution. Tortuosity. or the amount of curvature in a given path through a selected pore volume is also an extremely important characteristic of engineered porous carbonaceous materials.

Figure 32:
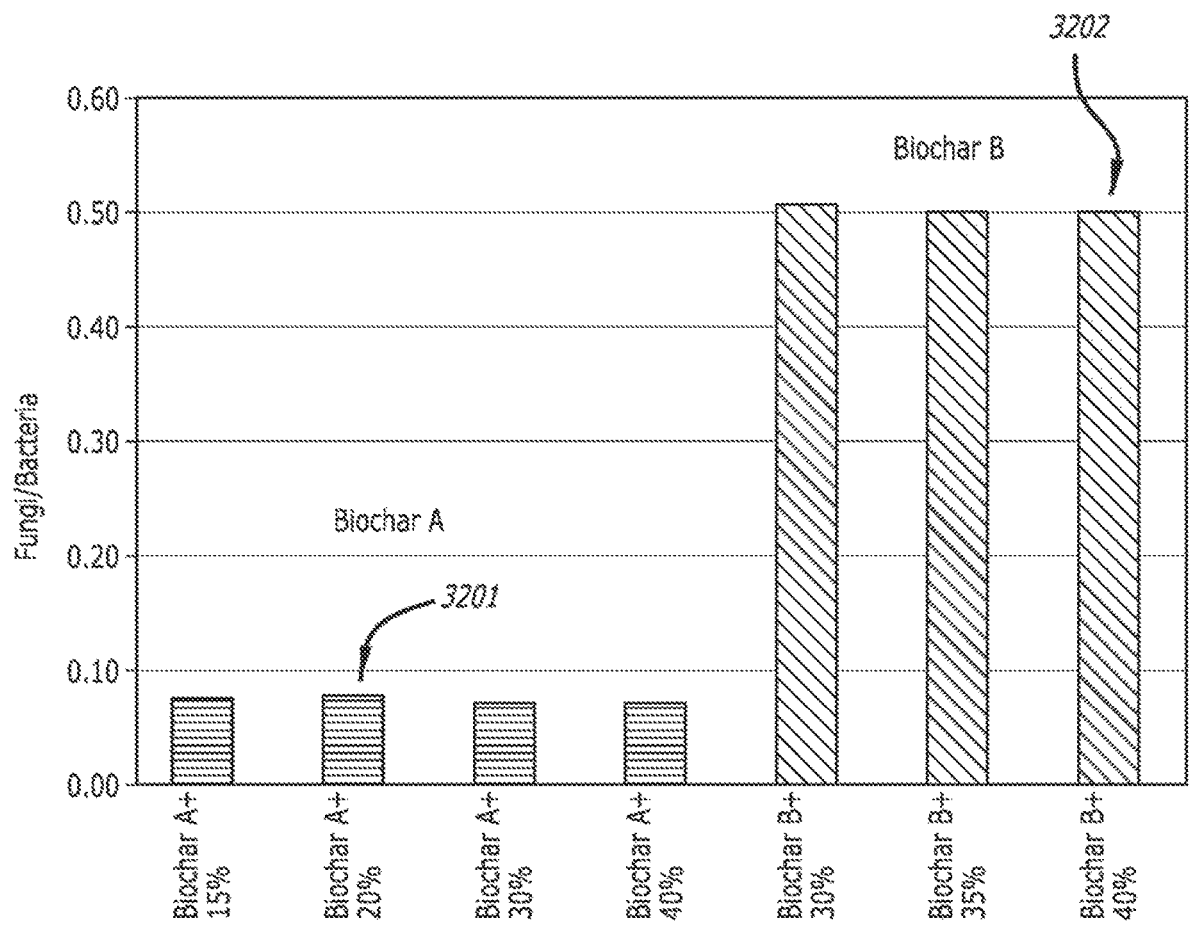
FIG. 32 is a chart comparing examples of biochars.

FIG. 32 shows the total fungi/bacteria ratio for two biochars derived from different biochar starting materials, e.g., feedstocks. Each biochar was loaded with different levels of moisture, and the total fungi/bacteria ratio was monitored during the first week. Biochar A 3201 showed a constant total fungi/bacteria ratio of 0.08 across moisture levels range 5000 ng from 15% to 40%, while Biochar B 2602 showed a constant total fungi/bacteria ratio of 0.50 for moisture levels ranging from 30% to 40%. It is theorized that, a fungi/bacteria ratio between 0.05 and 0.60 is an effective prescription for a stable biochar composition. This composition allows a commercially viable product, which has sufficient shelf life that it can be delivered to storage houses waiting for the proper planting window.

It is theorized that the difference in the observed total fungi/total bacteria ratios of may also be explainable by the structures of the biochars. Biochar's having an open pore structure, e.g., more interconnected pores, promotes more bacteria formation; while closed pores, e.g., relatively non-connected nature of the pores, tends to promote fungi formation. Biochars with differing microbial communities may be beneficial for specific applications in commercial agriculture. Thus, custom or tailored loading of the microbial population may be a desired implementation of the present invention.

Figure 33B:
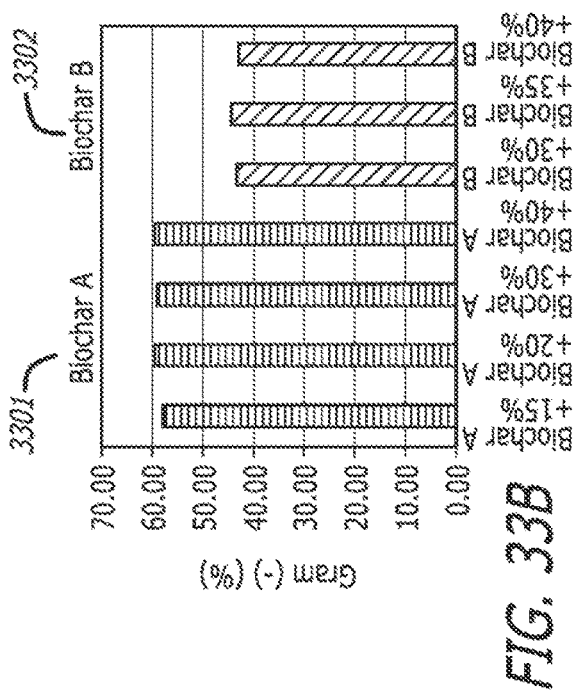
FIGS. 33a, 33b, 33c are charts comparing different examples of biochars.
Figure 33A:
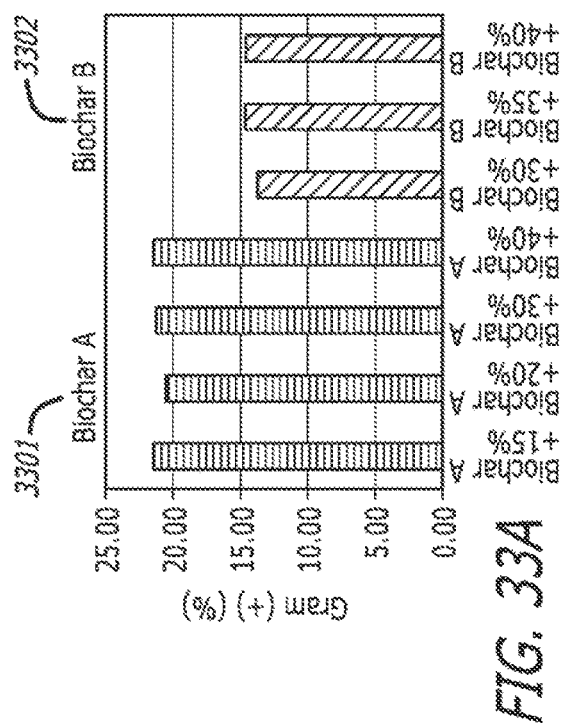
Figure 33C:
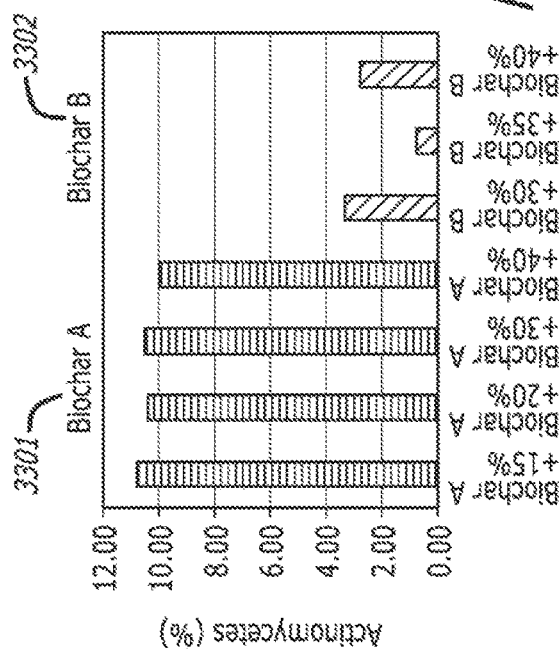

For example, as shown in FIGS. 33a, 33b and 33c, Biochar A 3301 shows that it has a greater population of, i.e., is inhabited by, more gram negative, gram positive and actinomycetes than Biochar B 3302. Thus, for example, Biochar A would be more applicable for use with certain agricultural crops in which Plant Growth Promoting Bacteria (PGPB) species in the actinomycetes, gram (-) *pseudomonas*, and *bacillus* groups are used for nutrient utilization and uptake.

It should be noted that both pyrolysis and post-treatment can be used to further modify the shape of these pores and structures. Pyrolyzing at higher temperatures, injecting select gasses or liquids during pyrolysis, or both typically will increase the pore volume and surface area of the material in question. Steam is the most readily available gas to cause this effect, but hydrogen sulfide, carbon dioxide, carbon monoxide, as well as other reactive gasses can be used. Prior art has clearly shown that the surface area of a biochar changes based on feedstock and pyrolysis temperature. Post treatment focused on a forced infusion of a strong acid, or other reactive substance into the pore space of the carbonaceous material can also be used to modify the pore size and pore volume of material by removing or breaking down the carbon matrix which forms the structure of the biochar, or other porous carbonaceous material. Acid etching or infusion can also be used to make smoother surfaces rougher. Rough surfaces can be very useful in the attachment and immobilization of microbes. Smooth surfaces can be useful for the easy release of carried microbes. Coating the surface area with materials such as starches is a technique to make rough surfaces smoother. Ultrasound, with or without a transmission media (gel, liquid, oil, or other) can also be used to rupture interpore divisions and create more pore space. Flash gasification, either at atmospheric pressure, or under negative or positive pressure, of liquid infused into the pores by the methods previously disclosed can also be used to crack, disrupt, or fracture solid material separating adjacent pores.

While much attention is given to modifying the pore structure by removing carbonaceous material, it should be noted that the pore structure can also be modified by the coating, forced infusion, and/or addition of materials which will bond to the carbon and consume pore volume, smooth surfaces, add tortuosity, change the exterior surfaces, or all of these. In the most simple form, it should be clear that materials may be added to coat surfaces or fill pore volume either through forced infusion, simple contact, or other means. However, if the material is infused or even simply contacted with a super saturated solution of a substance that will crystalize, such as sucrose, sodium chloride, or other common or uncommon substances known to form crystals. It should be noted that the crystals or substances used to create them do not need to be water soluble, and in fact in many cases it is desirable if they are not. The crystals may also be composed of nutrients or substances which may be beneficial to microbial or plant life. Examples of this are sucrose and monoammonium phosphate, both known for their ability to easily crystalize and be beneficial for microbial and plant life respectively. By adding material or even growing crystals on the carbon, a hybrid material is formed which can have many properties that are exceptionally useful for the delivery and establishment of microbial systems. Crystallization is also way to add tortuosity to a carbonaceous material and typically is much more effective in this aspect than coating with solids alone.

11. Compatibility with Biofilm Formation

Biofilms can be an important factor in the survival of a microbe in extreme or challenging conditions. Bacterial communities can shift their morphology to increase nutritional access and decrease predation. One such modification is that the bacteria may attach to surfaces, such as those found in biochar, in a densely compacted community. In this compacted form, they may form an extracellular polymeric substance (EPS) matrix called a biofilm. These communities can contain hundreds of different species which find shelter under the protective EPS coating from predatory protozoa, pathogens, contaminants, and other environmental stressors. In some cases, usually related to public health or healthcare, biofilms are undesirable as they typically allow pathogenic microbes to survive exposure to antiseptics, antibiotics, predatory microbes such as protozoa, or other agents which may eliminate them or negatively impact their prospects for survival. But in agricultural settings, encouraging target biofilm establishment could lead to improved microbe survival and thus improved agricultural or crop benefits.

As outlined in the article titled *The Effect of Environmental Conditions on Biofilm Formation of Burkholderia psudomallei Clinical Isolates*, it can be seen that certain bacteria require certain environmental factors, among them surface pH, for the creation of biofilms. See Ramli, et al., *The Effect of Environmental Conditions on Biofilm Formation of Burkholderia psudomallei Clinical Isolates* (Sep. 6, 2012) (dx.doi.org/10.1371/journal.pone.0044104). It is believed that other surface characteristics (rugged vs. smooth surfaces, surface charge, and more), along with moisture levels and relative humidity also play a large role in biofilm formation.

But for certain microbes requiring deployment into environments known to present survival challenges, optimizing a delivery material to encourage the formation of these protective biofilms can provide the targeted microbes with a significant advantage. Also, many vegetable and short cycle row crops such as tomatoes, lettuce, and celery form mutualistic relationships with bacteria that lead to the formation of biofilms on root hairs that function not only in nutrient uptake but also in plant pathogen resistance.

As outlined in previous disclosure, treatment of raw biochar can be used to adjust the surface pH to a level suitable for biofilm formation. Similarly, adjusting the humidity by selectively leaving a measured or controlled amount of water resident in the pore volume of the material can also provide benefit Lastly, the techniques outlines for modifying the physical surface properties of the material either by smoothing or roughening, can be key factors also.

It should be clear that these factors can also be reversed to create an environment that is unsuitable for biofilm formation in applications where the formation of biofilms on the carrier is not desirable—e.g. delivery or applications where quick release of microbes from the carrier is important.

12. Surface Charge

The surface charge of a porous carbonaceous material can be crucially important in the association and establishment of targeted microbes with or on the material. For example, most bacteria have a net negative surface charge and in certain conditions a specific bacterium may favor attachment to positively charged surfaces. In some biological applications, this attachment may be preferred, in others, attachment may not be preferred. However, modifying the surface charge of the material is clearly a way to impact the suitability for attachment of certain microbes. There are many ways in which the surface charge of a carbonaceous material may be changed or modified. One way to accomplish this is by treating the surface area of the material with a solution containing a metal, such as Mn, Zn, Fe, or Ca. This can be performed either by doping the material with these metals prior to or during pyrolysis, or more preferably, by using a forced infusion or treatment technique after pyrolysis to deposit these substances on the interior and/or exterior surfaces of the carbonaceous material. By controlling the amount and or types of substances infused, the surface charge of the material can be modified by encouraging loading of $O_2^-$ or other anions, or conversely, $N^+$, $NH_2^+$, or other cations. This modification of surface charge can have a profound impact on the ability of certain microorganism to be immobilized on the interior and exterior surfaces of the material.

Another application of surface charge can be found by temporarily charging the carbonaceous material during inoculation with microbes, Carbon is used as a cathode or anode in many industrial applications. Because of its unique electrical properties, carbon, or more specifically porous carbonaceous materials, may be given a temporary surface charge by the application of a difference in electrical potential, One application of this mechanism is to create a temporarily positively charged surface to encourage microbial attachment. Then, while the charge is maintained, allowing the microbes to attach themselves to and colonize the carrier. Once the colonization is complete, the charge can be released and the carrier, laden with microbes can either be deployed as is, or can undergo further treatment to stabilize the microbes such as lyophilization, or freeze drying.

13. Enzyme Activity

For some types of microbes, enzyme activity, or the presence of certain enzymes is every bit as important as the availability of energy or nutrition. Enzymes can be critical in the ability of microbes to metabolize nutrition, which in turn can be a key element of reproduction, survival, and effective deployment. There are six main types of enzymes: hydrolases, isomerases, ligases, lyases, oxidoreductases, and transferases. These enzymes can be important in microbial applications. Through treatment or even simple contact, enzymes, like nutrients and energy sources, can be deposited on the surfaces or within the pore volume of porous carbonaceous materials, either as solids, or in solution/suspension ensuring the enzymes are not degraded through the process. However, forced infusion of enzymes through the treatment processes previously outlined allows for much greater storage capacity and much greater levels of contact with the interior surfaces of the biochar, and as such, is preferable to simple contact. In some cases, the carbonaceous material can be used to deliver enzymes alone into an environment where both a habitat and enzymes are needed to promote or encourage the growth of certain indigenous microbes.

Another important aspect of enzyme activity is that some bacteria make extra-cellular enzymes which could be bound by the biochar or either reduce or even stop biochemical reactions. Thus, in certain situations when application is appropriate the carbonaceous material can be used to inhibit or make certain enzymes ineffective. For example, if the biochar is being used as a carrier for food or certain chemicals that are vulnerable to breakdown by enzymatic degradation and these specific enzymes would be bound by the biochar, then using the carbonaceous material as the carrier would provide for greater shelf-life and viability of the product versus traditional carriers.

14. Sterilization

In many cases, it is desirable to remove potential unwanted microbes from the surfaces and pore volume of the material through sterilization. At outlined above, infusion with antiseptics or antibiotics are a way to accomplish this. Boiling, or more preferably, forced infusion of steam is also a technique that can be used to remove resident microbial life. Heating to a temperature above 100 degrees C., and preferably between 100 and 150 degrees C. is also effective for removing some microbial life. Heating may be required for ideally 30 minutes or more, depending on volume, method, and extent (temperature, radiation). Autoclaving can also be used 30 minutes, 121 degrees C., 20 psig. For applications requiring a high level of sterility, gamma irradiation can be used, with dosages adjusted for the level of sterility needed in ranges of 5 to 10 kGy or even 50 to 100 kGy or even higher dosage levels. For all sterilization methods, the extent of treatment required will depend on the volume of material and the required level of sterilization. In general, sterilization, using heat, should be done for at least 30 minutes, but should be adjusted as needed.

At this point, it should be clear that all of these properties can be controlled and modified to create a treated, controlled biochar that is suitable for use as a microbial carrier, delivery system, habitat, fermentation substrate, or environmental (soil, water or other) enhancement. By controlling these properties and producing a material matched to the application and the microbe(s) in question, effectiveness can be dramatically improved over both traditional biological carriers, and many forms of raw, untreated, uncontrolled biochar. Furthermore, varying materials, with varying properties, may be aggregated to provide delivery systems or habitats targeted towards consortia, communities, or groups of microbes.

F. Inoculating, Applying, or Immobilizing the Microbes on the Biochar

Typically, the prior art teaches either placing biochar on soils alone or combining the biochar with compost and using this mixture as a soil amendment. The nature of the microbial population in this compost mixture is poorly disclosed by the prior art. Thus using more targeted methods to get the desired microbes into the suitable habitat created by the raw biochar, or more preferably treated or controlled biochar is desired. The following are some but not all, methods and systems that can be used to inoculate, deploy, or otherwise associate microbial life with a treated or untreated biochar:

1. Co-Deployment

This method focuses on deploying the microbes at the same time as the biochar. This can be done either by deploying the biochar into the environment first, followed by microbes or by reversing the order, or even deploying the two components simultaneously. An example of this would be the deployment of a commercial brady *rhizobium* inoculant simultaneously with the introduction of a treated biochar into the soil media. The system here is the combination use of a biochar and microbes in the environment, and more preferably a char treated to have suitable properties for a target microbe or group of microbes which it is used with in a targeted application for a specified purpose, for example a symbiotic crop of said microbe(s).

Figure 34:
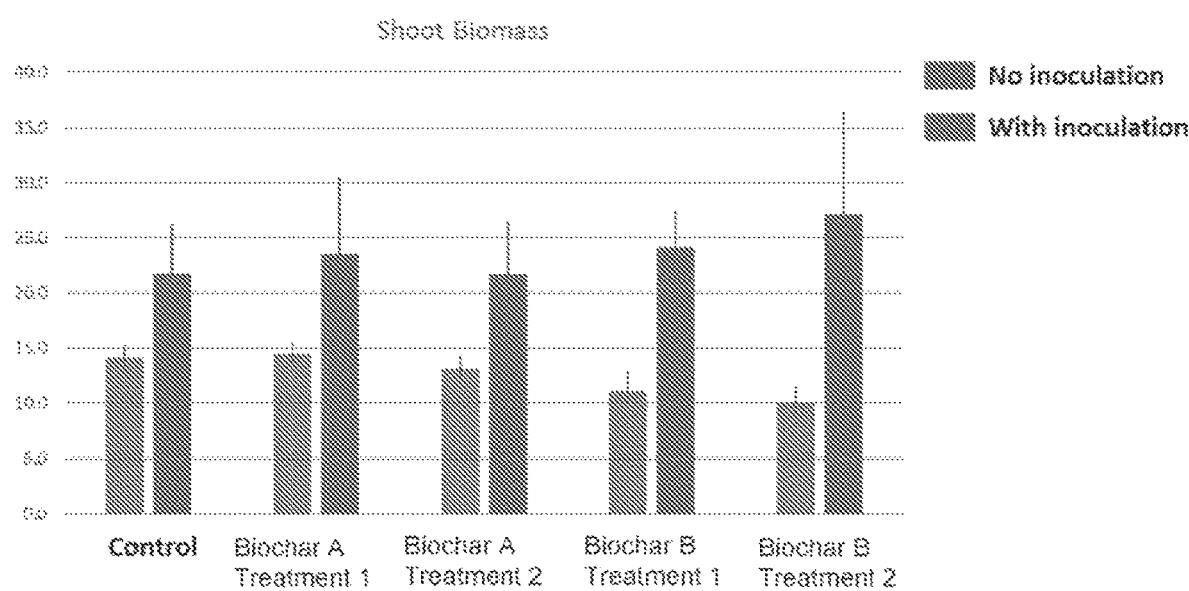
FIG. 34 is a chart comparing shoot biomass when the biochar added to a soilless mix containing soybean seeds is treated with microbial product containing *Bradyrhizobium japonicum*. and when it is untreated.

In one experiment, various biochar feedstocks with various post-treatments were added to a soilless mix containing soybean seeds that had been treated with a commercial microbial product containing *Bradyrhizobium japonicum*. and compared to both a control with microbe inoculant and one without. Some of the treated biochars co-deployed with the inoculant increased seed germination rates, one by 29%. Others increased nodulation measured at 10 weeks, one more than doubled the number of nodules. The use of the microbial inoculant increased shoot biomass in all treatments. FIG. 34 is a chart comparing shoot biomass when the biochar added to a soilless mix containing soybean seeds is treated with microbial product containing *Bradyrhizobium japonicum*. and when it is untreated. As illustrated in FIG. 34, shoot biomass increased with the biochar was treated.

Figure 35:
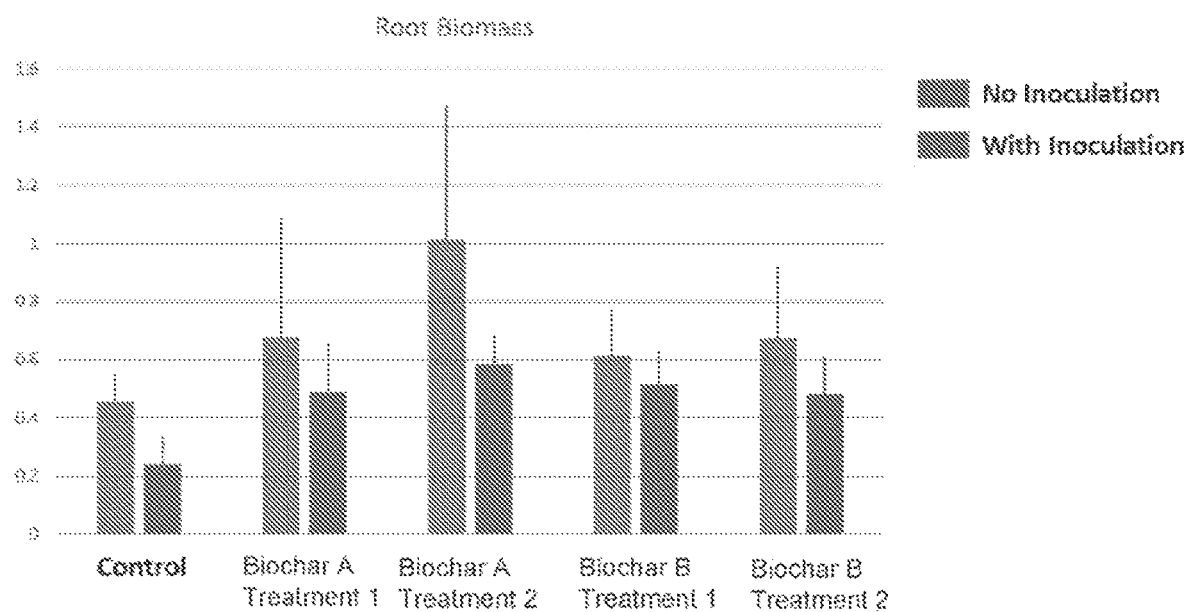
FIG. 35 shows the comparison of root biomass in a treated verses an untreated environment.

FIG. 35 shows the comparison of root biomass in a microbial inoculated environment versus one without inoculation. As illustrated in FIG. 35, when inoculated, root biomass decreased with the inoculant alone yet increased with the use of all the treated biochars with or without inoculant.

Figure 36:
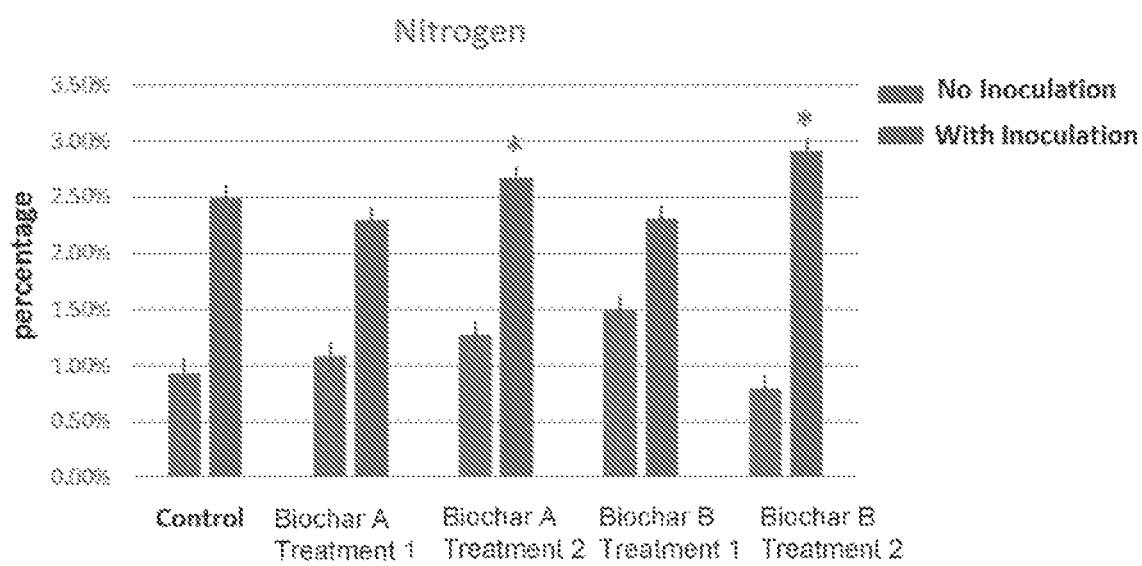
FIG. 36 is a chart comparing the nitrogen levels when the biochar is inoculated with the rhizobial inoculant verses when it is not inoculated.

In addition leaf tissue analysis was done which showed some of the treated biochars co-deployed with the rhizobial inoculant showed a significant increase in nitrogen uptake. FIG. 36 is a chart comparing the nitrogen levels when the biochar is inoculated with the rhizobial inoculant verses when it is not inoculated. Statistical significance in the chart in FIG. 36 is marked with a star. In all cases, nitrogen levels increase with inoculation.

As outlined in these results, the addition of a treated biochar suitable for co-deployment with this particular microbe increased nodulation, increased nitrogen fixation/availability, and resulted in substantially increased root mass. It should be noted that to demonstrate the differing performance of varying formulations, two formulations were tested, each showing different interactions with the microbe in question, along with significant variations in performance. This is just one example to demonstrate the invention of how the specific combination of biochar feedstock, biochar treatment, co-deployed microbe, and application (this case plant species) can lead to improved microbial effectiveness and thus improved results (this case plant vigor), versus no treatment, applying the microbe alone, or applying the biochar alone. Another example of co-deployment benefit could be using a biochar that has strong absorption properties in combination with fertilizer (or infused with fertilizer) and microbes in an agricultural setting. The biochar properties that help retain and then slowly release nutrients and ions will also help the targeted microbe population to establish and grow without being impacted by the high levels of fertilizer salts or nutrients which can often impede and sometimes kill the microbes being deployed.

2. Basic Inoculation

A more advanced method of inoculation centers on mixing the microbe or microbes in question with the treated or untreated biochar before deployment. In some cases, the biochar in question can be treated, produced, or controlled to assist with this deployment, making this case slightly different than merely inoculating a microbe on untreated biochar. In one form, microbes suspended in liquid (either water, growth media, or other liquids) are deposited on the biochar and mixed together until both materials are well integrated and then the material is deployed as a granular solid. It has been shown that materials that have been treated to be more hydrophilic typically accept this inoculation more readily than hydrophobic materials—demonstrating yet another way in which the treatment of biochar can enhance performance. In another form of basic inoculation, the biochar is delivered in suspension in the liquid also carrying the microbes. This biochar/liquid/microbe slurry is then deployed as a liquid. In this form, sizing the biochar particles in such a way that their surface properties and porosity is maintained is a key element of effectiveness. Additionally, ensuring that the pores are treated to allow easy association of both liquid and microbes with the surfaces of the biochar is important. An example of a basic inoculation method of biochar for a bacteria in lab scale is as follows:

1) Isolate *Pseudomonas protegens* on a plate with 1.5% w/v Tryptic Soy Broth solidified with 1.5% w/v agar and incubate at 30° C. for 12 h
2) Take an isolated colony of *Pseudomonas protegens* and grow up in a 1.5% w/v TSB solution (90 ml) along with 10 g sterile biochar (sterilized at 110 C in small batches for 15-20 min) and combine both in a sterile 250 ml Erlenmeyer flask
3) Shake contents of flask at 150 rpm at 30° C. for 12 h, or greater
4) Transfer contents of flask into a sterilized ultracentrifuge tube (250 ml) and spin at 10,000×g for 10 min
5) Carefully remove supernatant liquid fraction by filtering through a Whatman No 4 filter with a vacuum filtration system to separate out the bulk liquid from biochar.

After basic inoculation, the material and the microbes may be deployed immediately, stored for future use, or stabilized using technology such as lyophilization.

3. Assisted Inoculation

Figure 37:
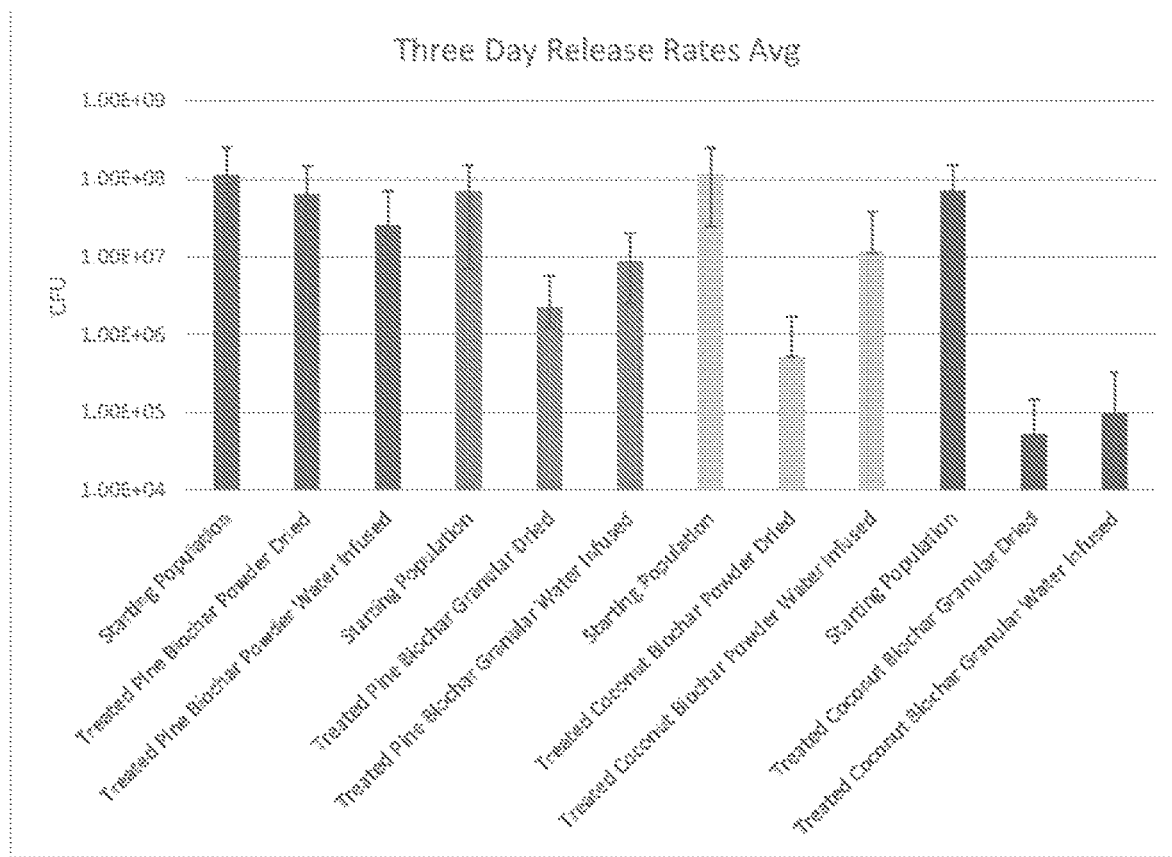
FIG. 37 illustrates the three day release rates of water infused biochar compared to other types of biochar.

Another form of inoculation, which appears to have greater efficacy with some microbial systems, is assisted inoculation. Assisted inoculation involves providing mechanical, chemical, or biological assistance to move the targeted microbe either into the pore volume of the carrier or onto interior surfaces of the material that normally may not be accessible. Realizing that many microbes require liquid, and preferably water, for mobility, the most straightforward method of assisted inoculation requires infiltrating the pore volume of the material with water prior to contact with the targeted microbes. This water infusion can be done using the treatment methods described previously in this disclosure. It has been shown that, with certain microbes, making this change alone will have a positive impact on the ability of microbes to associate with and infiltrate the material. In one experiment, it was shown that water infusion improved release rate on both a treated pine biochar with granular particles and with a coconut biochar powder. FIG. 37 illustrates the three-day release rates of water infused biochar compared to other types of biochar. As illustrated, results vary depending upon the biomass.

Changes can also be made in the media to reduce surface tension and increase flowability through the addition of a surfactant to the water, either into the liquid used to carry the microbes, or into the pores of the material itself, through simple contact, or preferably forced infusion.

Additionally, the microbes themselves may be assisted into the pores using the treatment techniques previously outlined. Care needs to be taken to match the microbe to the technique used, but many microbes are capable of surviving vacuum infiltration if performed at relatively gentle, lower pressure differentials (+/−10% of standard temperature and pressure). Some microbes, and many spores however are capable of surviving vacuum infiltration even at relatively large pressure differentials (+/−50, 75, or even 90 or 95% or more variation from standard temperature and pressure). When this technique is used, a liquid mixture is constructed containing both liquid to be infused and the microbe or microbes in question. The liquid is then used as the "infiltrant" outlined in previous disclosure related to placing liquid into the pore volume of the material. The final material, infiltrated with microbes, may then be heated to incubate the microbes, cooled to slow development of the microbes or stabilize the microbes, or have other techniques applied such as lyophilization. The material may then be delivered in solid granular form, powdered, further sized downward by grinding or milling, upward by agglomerating, aggregating, or bonding, or suspended in a liquid carrier. A clear advantage to this assisted infusion approach is that the material can be processed or handled after inoculation with more microbial stability because the targeted microbes are inhabiting the interior pore volume of the material and are less prone to degradation due to contact with exterior surfaces, or other direct physical or environmental contact. This method may be applied repeatedly, with one or more microbes, and one to many moisture removal steps. It may also be combined with the other inoculation methods disclosed here either in whole or in part.

FIGS. 38*a*, 38*b* and 38*c* show scanning electron microscopy (SEM) images of raw biochar compared to ones that have been processed by being infused under vacuum with bio-extract containing different microbial species.

FIG. 38*a* is a SEM (10 KV×3.00K 10.0 μm) of pore morphology of raw biochar. FIG. 38*b* is a SEM (10 KV×3.00K 10.0 μm) of pore morphology of raw biochar of FIG. 38*a* after it has been infused with microbial species. FIG. 38*c* is a SEM (10 KV×3.00K 10.0 μm) of a pore morphology of another example of raw biochar of FIG. 38*a* after it has been infused with microbial species. The images confirm the ability to incorporate different microbes into the pores of biochar by treatment. In turn, these beneficial microbes can interact with and enhance the performance of the environment they are deployed into, for example the plants' root systems when the inoculated biochar is mixed with the soil in the root zone.

Compared to a biochar that has immersed in a compost tea, which may have a relatively short, e.g., a few days for the life of the microbes, the impregnated populations of examples of the present treated biochars, are stable over substantially longer periods of time, e.g., at least an 8 week period and in some cases 1 year or more as measured by PLFA (Phospholipid-derived fatty acids) analysis. PLFA analysis extracts the fatty acid side chains of phospholipid bilayers and measures the quantity of these biomarkers using GC-MS. An estimate of the microbial community population can thus be determined through PLFA analysis. The microbial activity may also be inferred through PLFA analysis by monitoring the transformation of specific fatty acids. Thus, the impregnation of the biochar with a microbial population provides for extended life of the microbes by at least 5×, 10×, or more over simple contact or immersion. In fact, some microbes may be better suited to surfactant infiltration versus vacuum infiltration and vice versa and this may impact the shelf life, penetration, viability, or other characteristics of the microbes.

As used herein, unless stated otherwise, the stable shelf life of an example of a biochar product having a microbial population is the period of time over which the product can be stored in a warehouse, e.g., dry environment, temperature between 40° F.-90° F., with a less than 50% decrease in microbial population.

4. Integrated Growth/Deployable Substrate

With many microbes, especially fungi, it can be helpful to develop or "grow" the microbes on the material itself. With porous materials, rather than mechanically or chemically assisting the infiltration of the microbes, it can be beneficial to allow the microbes themselves to inhabit the pore volume of the material prior to deployment. In fact, with materials constructed to effectively immobilize microbes, this can be the most efficient technique to stabilize, store, and ultimately deploy the microbes in question.

An example of this method involves preparing the biochar material for the microbes, sometimes through thorough cleansing, other times through addition of either enzymes or energy sources needed by the microbe in question, preferably using the treatment techniques described previously in this disclosure. Once the material is prepared, the microbes are placed onto the material, or infused into the material and then incubated for a period of time. In the case of many microbial systems, the microbes themselves will inhabit the material and form close affiliations with available surfaces and pore volume. At this point, the material can be deployed with the microbes actively attached and affiliated. With many microbes, especially fungi, this is a preferred method of deployment and shows many advantages over co-deployment, or basic inoculation because of the tight integration of biological life with the material itself.

An example of an integrated growth inoculation method of biochar for a fungus in lab scale is as follows:
 1) Make petri dishes containing corn meal agar (17 g/L), glucose (10 g/L), and yeast extract (1 g/L)
 2) Inoculate plates with *Sordaria fimicola* and incubate between 22-30 C for at least 1 day to produce hyphae
 3) Sterilize an inoculating loop and slice "plugs" of the hyphae and agar generating cubes that are agar and hyphal mass
 4) Inoculate a sterile plate with a "plug" in the center of the plate, around perimeter have sterile biochar
 5) Incubate plate for at least a day and remove biochar (that are now covered with grown over hyphae)]

It should be noted that because of this effect, biochars, and specifically treated biochars can also be extremely effective substrates for solid state fermentation—particularly when growth media or energy sources are added to the pore volume of the material. So, once incubation is ongoing, the material can either be removed, with the integrated microbes, and deployed, or it can be stabilized for long term storage, or it can be left in situ and used as a fermentation or growth substrate to develop or grow more microbes—especially those that require a solid to propagate and develop.

5. Media and/or Enzyme Infiltration

As mentioned previously, growth media, energy sources, enzymes, or other beneficial/necessary components for microbial growth may be infused into the pore volume or coated onto the surfaces of the material in question. This method can be combined with any of the other inoculation techniques disclosed here. It has been shown that with certain microbes and certain types of material, inoculation with growth media or enzymes can significant impact the effectiveness of the biochar material as a carrier.

6. Habitat Pre-Establishment (Enhanced Rhizosphere)

There are certain microbes which, because of symbiotic associations with host organisms, such as plants, prefer to develop in the vicinity of the organism, such as the active root or other plant tissue. An effective method for deploying these organisms can be to develop and deploy the plant/microbe/habitat (biochar) system together as a unit.

An example of this is germinating seed or transplanting a seedling or developing juvenile plant in the presence of treated or untreated biochar, and the targeted microbes. Biochar that has been treated to encourage hydrophilicity and neutral pH typically allows for easier affiliation of plant root tissue with the material. As this affiliation occurs, a habitat for symbiotic organisms is developed within the material itself due to the proximity of active plant tissue to microbes reliant on the tissue for energy. As this symbiosis continues, the number, activity, and colony size of the targeted microbes will continue to grow. At this point, the plant and biochar can be deployed together into the target environment, acting as a pre-established habitat and carrying the microbes along with them.

Another option is to develop and then remove the biochar from the "incubation" system either by stripping the biochar material from the symbiotic organism, such as the root mass, or by sieving or sifting the media used to grow the plant. At this point, the microbes can either be deployed directly or stabilized for storage.

Thus, through more controlled inoculation of the biochar particles, one can achieve a predetermined and controllable amount of a microbial community, e.g., population, into the soil. This integration of a microbial community with a biochar particle, and biochar batches provides the ability to have controlled addition, use and release of the microbes in the community. In agricultural applications, this integration c an further enhance, promote and facilitate the growth of roots, e.g., micro-roots, in the biochar pores, e.g., pore morphology, pore volume.

Other methods than those listed above exist for integrating a microbial community with an untreated or previously infused biochar particle. Different manners and methods would be preferred depending on needs to minimize contamination, encourage biochar pore colonization/infiltration, minimize labor and cost and producing a uniform, or mostly uniform, product.

Other methods for integrating a microbial community with a biochar particle may include, but are not be limited to the following: while under vacuum, pulling the microbial solution through a treated biochar bed that is resting on a membrane filter; spraying a microbial solution on top of a treated biochar bed; lyophilizing a microbial solution and then blending said freeze dried solution with the treated biochar; again infusing, as defined previously, the treated biochar with a microbial solution; adding treated biochar to a growth medium, inoculating with the microbe, and incubating to allow the microbe to grow in said biochar containing medium; infusing, as defined previously, the biochar with a food source and then introducing the substrate infused biochar to a microbe and incubating to allow the microbes to grow; blending commercially available strains in dry form with treated biochar; adding the treated biochar to a microbial solution and then centrifuging at a high speed, potentially with a density gradient in order to promote the biochar to spin down with the microbes; densely packing a column with treated biochar and then gravity flowing a microbial solution through the column and possibly repeating this multiple times; or adding the microbe to a solution based binder that is well known to enter the treated biochar pores and then adding said solution to the treated biochar. In order to insure the proper microbial community the treated biochar may need to be sterilized prior to these methods for integrating a microbial community. All or parts of the above manners and methods may be combined to create greater efficacy. In addition, those skilled in the art will recognize that there may be additional manners or methods of infusing biochars with microbials, including those created by the combination of one or more of the manners and methods listed above, without departing from the scope of the present invention. Further, when using any of the above methods for integrating the microbes with the biochar, including but not limited to infusing the microbes in the biochar, it is recognized that such microbes or other MSM or minerals can continue to be deployed in the soil once the biochar is in situ.

G. Using Microbial Inoculated Biochars

Thus, treated biochar can have a microbial community in its pores (macro-, meso-, and combinations and variations of these), on its pore surfaces, embedded in it, located on its surface, and combinations and variations of these. The microbial community can have several different types, e.g., species, of biologics, such as different types of bacteria or fungi, or it may have only a single type. For example, a preferred functional biochar, can have a preferred range for bacterial population of from about 50-5000000 micrograms/g biochar; and for fungi, from about 5 to 500000 micrograms/g biochar. A primary purpose in agricultural settings, among many purposes, in selecting the microbial population is looking toward a population that will initiate a healthy soil, e.g., one that is beneficial for, enhances or otherwise advance the desired growth of plants under particular environmental conditions. Two types of microbial infused biochars will be discussed further for agricultural settings: bacteria and fungi. However, the microbes may also be used in other applications, including but not limited to animal health, either directly or through interactions with other microbes in the animals' digestive tract and public health applications, such as microbial larvicides (e.g. *Bacillus thuringiensis* var. *israelensis* (Bti)) and *Bacillus sphaericus* used to fight Malaria).

H. Bacteria Inoculated Biochars

Another application of using biochar inoculated with bacteria would be in the biofuel industry, where methanotroph inoculated biochar could be used to create methanol. Methanotrophic bacteria are proteobacteria with diverse respiration capabilities, enzyme types, and carbon assimilation pathways. However, *Methylosinus trichosporium* OB3b is one of the few methanotrophs that can be manipulated by environmental conditioning to exclusively produce methanol from methane. *M. trichosporium* OB3b is one of the most well studied aerobic $C_1$ degraders and can be grown in either batch or continuous systems. As mentioned earlier, the large pore volume and surface area of biochar is suitable for bacterial colonization and should subsequently increase substrate access to enzyme activation sites. To improve the conversion rate, copper, nitrate, and phosphate should be included in the system. The use of biochar as a support material for the aerobic bioconversion of methane to methanol provides a pore distribution suitable for both adsorptions of methane and impregnation with bacteria. By providing biological and adsorptive functionality the biochar can intensify the bacteria in the biochar and increases the conversion rate.

In general, bacteria communicate via the distribution of signaling molecules which trigger a variety of behaviors like swarming (rapid surface colonization), nodulation (nitrogen fixation), and virulence. Biochars can bind signaling molecules and in particular it is believed can bind a major signaling molecule to their surface. This binding ability can be dependent upon many factors including on the pyrolysis temperature. This dependency on pyrolysis temperature and other factors can be overcome, mitigated, by the use of examples of the present vacuum infiltration techniques. For example, a signaling molecule that is involved in quorum sensing-multicellular-like cross-talk found in prokaryotes can be bound to the surface of biochars. Concentration of biochars required to bind the signaling molecule decreased as the surface area of biochars increased. These signaling molecules may be added to the surface of a biochar and may be used to manipulate the behavior of the bacteria. An example of such a use would be to bind the molecules which inhibit cell-to-cell communication and could be useful in hindering plant pathogens; using techniques in the present invention signaling molecules may be added to the surface of a biochar to engineer specific responses from various naturally occurring bacteria.

I. Aggregate Biochar Particles

It has been discovered that the same benefits can be achieved through the production and application of biochar aggregate particles as biochar particles that have not been aggregated. The creation of biochar aggregate particles, however, allows for easier product distribution for in various applications including industrial agricultural equipment, and provides a highly beneficial use for the biochar dust and fines, which are generally discarded. In this same manner, biochar aggregate particles may be produced for use for consumption by animals or use in composting.

The biochar, prior to being formed into a solid aggregate (e.g., through agglomeration, extrusion, or pelletization), may be raw or treated, as described above. If the biochar is treated, not only can various characteristics including pH be adjusted as needed, but fertilizers, nutrients, vitamins, supplements, microbes or other additives may be infused into the biochar prior to aggregation (as further described below). However, regardless of whether the biochar is raw or treated, the present application for biochar aggregate particles can be utilized for both.

There are various types of aggregation methods and resulting aggregate particles. FIGS. 39a, 39b and 39c shows three resulting aggregate examples. FIG. 39a shows pellets, FIG. 39b shows extrudates and FIG. 39c shows biochar sulfate prills.

Figure 40:
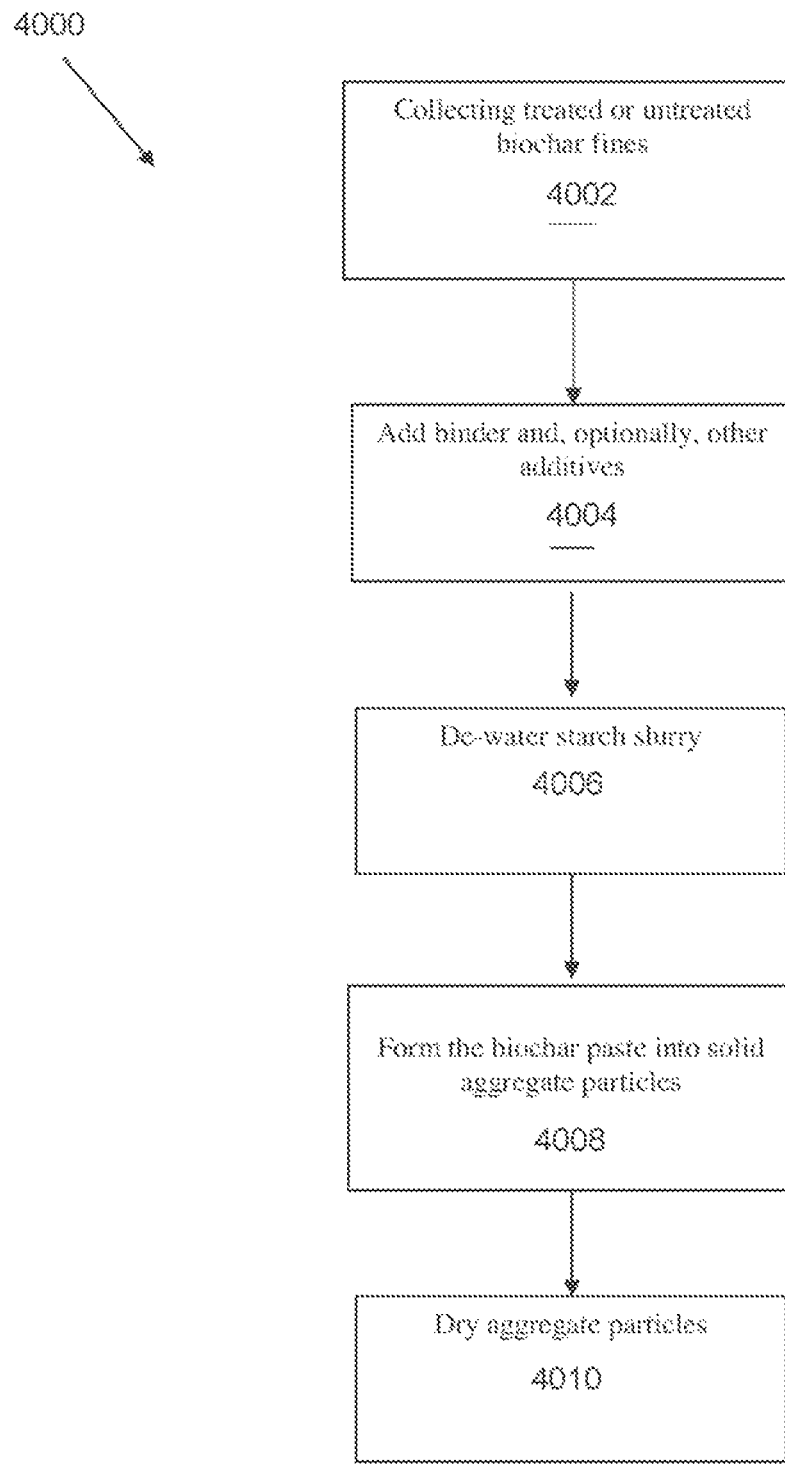
FIG. 40 is a flow diagram of one example of a method for producing biochar aggregate particles.
Figure 41C:
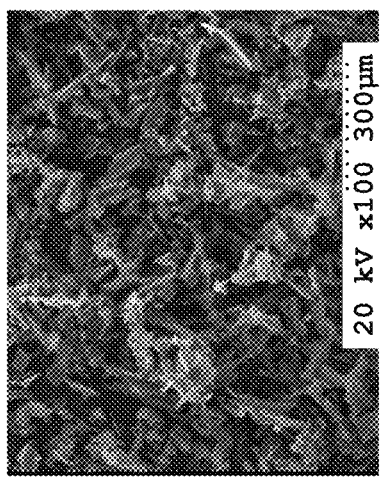
FIGS. 41a-f illustrates the effects of size and grinding on particle structure of a biochar derived from a first biomass.
Figure 41F:
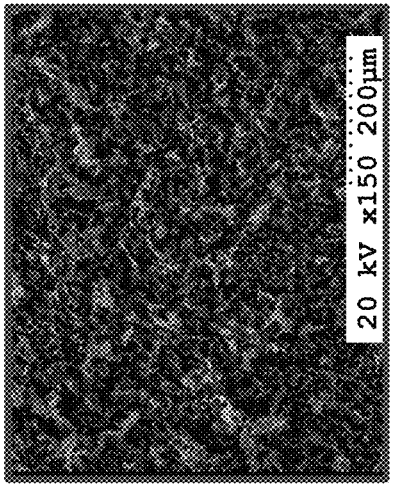
Figure 41B:
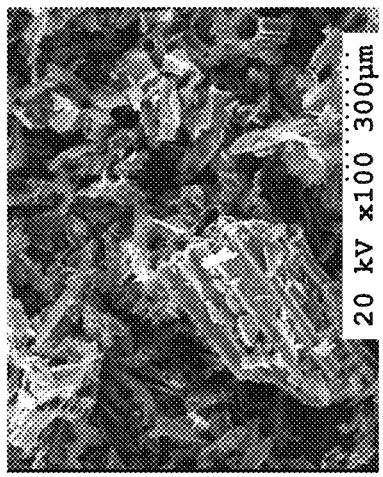
Figure 41E:
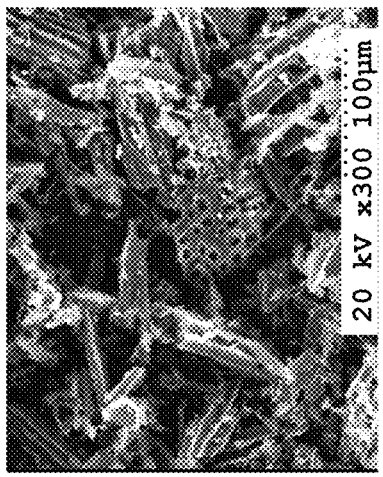
Figure 41A:
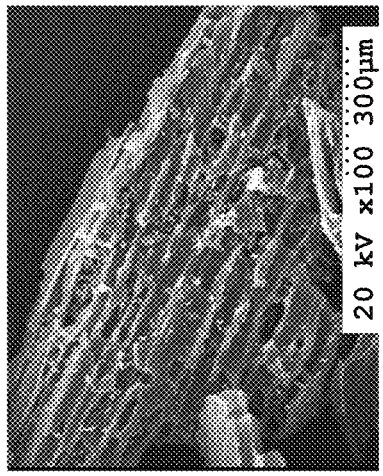
Figure 41D:
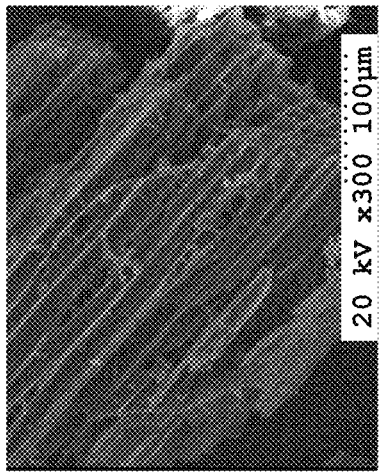

As an example, one method to produce biochar aggregate particles is depicted in the flow diagram shown in FIG. 40. The flow diagram 4000 of FIG. 40 is an example of one method that may be used for producing biochar aggregate particles. In general, the method of producing biochar aggregate particles from biochar may be accomplished by first collecting the treated or untreated biochar fines at step 4002. The fines may be collected by washing the biochar media, which may cause the biochar fines and dust to be placed in suspension in the liquid solution used to wash and/or treat the biochar. The biochar fines can also be produced by grinding, crushing, sieving, or otherwise resizing biochar of a larger particle size to one better suited for extrusion, compression, coagulation, or other forms of pelletization.

For example, the biochar fines may be separated from larger biochar particles by dry-sieving to remove the fine particles followed by wet-sieving with deionized water to remove fine fractions that remained. To separate particles of 0.5 mm or less of equivalent diameter, both the dry-sieving and wet-sieving may be carried out with a US size 35 mesh sieve. Biochar fines or dust may also be created by mechanical means such as grinding cutting or crushing the raw or treated biochar particles. These mechanically created small particles can be separated as set forth above through sieving or may be collected by washing or treating the material and using the resulting solution to recover the smaller particles. The recovery of small biochar particles from the solution can be accomplished by using chemical or physical means of separation or even a combination of multiple chemical and physical separation methods or steps.

While the biochar particles or fines may be treated in advance of collection, it is also possible to treat them once collected or as part of the collection process. Optionally, other physical and chemical properties may be adjusted during the treating step, as needed, or may be adjusted prior to, or during the fines collection process. For example, the biochar fines may be collected during treatment of the biochar media (e.g., to adjust the pH). The fines may then be collected in the treating solution by adding a flocculent and/or coagulant to the treating liquid, which creates a biochar slurry (the "flocculent slurry").

Given the application, it may be necessary to de-water the flocculent slurry before further treatment, as part of the collection process. The flocculent slurry is de-watered, typically using a belt filter press to create a biochar paste. Those skilled in the art will recognize that other de-watering systems, besides a belt filter press may be used to de-water the biochar slurry and that mechanisms other than a flocculent, such as filtration, settling, or other separation technology, may be used to separate the biochar from the minerals, inorganic compounds, and other substances found in the slurry that remain in the washing or treating solution.

Once the biochar fines are collected, a binder is then added to the biochar particles at step 4004. The binder solution used to coagulate the fines may be prepared by mixing a starch, polymer, lignin, clay, or other binder with water or appropriate solvents. The addition of the binder solution creates a biochar slurry or a paste (the "binder slurry"). The binder solution may be prepared by mixing, for example, enough corn starch with deionized H2O to create a solution. For example, the starch may be approximately 2% by weight, but may range from 0.5% to 10% by weight. Those skilled in the art will recognize that another material, besides corn starch may be used as a binder. Additionally, other binders may be used with the restriction that they must be appropriate for the application they will be used in. So for example, they may not be toxic in the quantities used in agriculture or animal feed and must be suitable for introduction into whatever application without profound ill effect. Some examples of other generally non-toxic binders that may be used are gelatins, cellulose, sugars, or combinations thereof. While the above describes adding the binder after the flocculent slurry is dewatered, the binder may also be added to the flocculent slurry before de-watering.

Like the flocculent slurry, the binder slurry is also de-watered before further treatment, step 4006. The binder slurry may be de-watered using a belt filter press to create a biochar paste. Those skilled in the art will recognize that other de-watering systems, besides a belt filter press may be used to de-water the biochar.

Optionally, other growth or beneficial additives may also be added to the slurry at step 4006. The binder and the growth additives may be added together or at separate stages, before or after the de-watering step 4006, with or without de-watering between, depending upon the application, the binder and the additives. In either event, the biochar is de-watered at step 4006 prior to further treatment.

Such growth enhancing additives may include, but are not limited to, fertilizers and beneficial microbes that can withstand the biochar aggregation process. For certain additives, the temperature of the process may need to be adjusted to avoid, for example, the denaturing of the proteins. Such additives can be added to the biochar particles (either with or after de-watering the starch slurry) through mixing. If a fertilizer is desired, the fertilizer may be pulverized to prepare for addition. The fertilizer may be pulverized to an average particle size of <1 mm before dispensing. Liquid fertilizers may also be used in solution. For example, 1000 ppm NO3-N fertilizer solution may be used. Examples of fertilizers that may be added to the paste, include, but are not limited to the following: ammonium nitrate, ammonium sulfate, monoammonium phosphate, ammonium polyphosphate, Cal-Mag fertilizers or micronutrient fertilizers. Other additives, such as fungicides, insecticides, nematicides, plant hormones, beneficial microbial spores, secondary signal activators, vitamins, medications, supplements, or sensory enhancers may also be added to the paste in a similar manner as a fertilizer, the inclusion of which does not depart from the scope of the invention. Additionally, beneficial macro- and micro-nutrients such as nitrogen, phosphorous, potassium, calcium, magnesium, sulfur, boron, zinc, iron, manganese, molybdenum, copper and chloride can be added to the mixture at this time.

Examples of compounds, in addition to fertilizer, that may be blended with, infused into the pores of or coated on the surface of the biochar include, but are not limited to: 2,1,3-Benzothiadiazole (BTH), an inducer of systemic acquired resistance that confers broad spectrum disease resistance (including soil borne pathogens); signaling agents similar to BTH in mechanism or structure that protects against a broad range or specific plant pathogens; biopesticides; herbicides; and fungicides.

As noted above, all the above additives may also be added at various steps in the described processes, including with the flocculant or coagulant, with the binder, or prior to the creation of the slurry or biochar paste. Such additives may be added through a pre-treatment process, such as those treatment processes described above (e.g., vacuum infiltration or surfactant treatment), or other treatment processes that result in the infusion of liquids and/or vapors into the pores of the biochar. It may also be possible to contact the biochar aggregate particles, once they are produced, with additives. Such contact or coating after production of the biochar aggregate particles is within the scope of the present invention.

Once de-watered, at step 4006, the biochar particles become a thicker slurry or paste (the "biochar paste"). The biochar paste, now including a binder and possibly other additives, is then formed into solid shapes, at step 4008 and then dried, at step 4010. To form the biochar paste into solids, alternative forms of processing may be used. For example, the paste may be passed through an extruder, a pelletizer, a briquetter, a granulator and/or other heating, cooling, dehydration, or pressure system capable of forming the paste into solid shapes. Alternatively, the biochar may be mixed with the binder, both in a dry form, and then fed into the equipment used to form the solid shaped biochar aggregates while adding moisture and/or other additives.

In one example of an implementation, the biochar paste is shaped through an extruder that is heated at a temperature of 25-120° C. in order to adequately activate the starch or other binder. The extruder may be specifically set depending on the appointed application to produce an extrudate size, ranging from 1 to 5 mm in diameter. At step 4010, the resulting extrudates are dried using a hot air, tunnel oven dryer, or other dryer known to the art. For some application, e.g., when microbes are added to or inoculated into the biochar particles, it may not be desirable to use heat to activate the binder. Alternatively, lipids or other binders that bind at cold temperatures may be used, with the substitution of cooling equipment in place of heating equipment to activate said binder.

The biochar aggregate particles from the extruder may be cut into predetermined specific sized particles, which may take the form of pellets. The steps of extruding and cutting may be performed together by the extruder, or separately, again depending upon the application and equipment capabilities. In addition larger extrudates can be formed creating a biochar spike, which can be applied by pushing them into soil near existing plants or trees.

In one example of an implementation, the biochar aggregate particles may be created from pyrolyzed wood or cellulosic biomass, as described above. The resulting biochar fines or dust are then removed from the other biochar particles at step 4002. As part of the collection process, the fines may optionally be washed with a treatment solution, as described in detail above. The treatment solution may, for example, be added to neutralize the biochar pH levels, as needed, depending upon the pH of the biochar fines. A neutralized biochar slurry is then exposed to a de-watering station and a flocculent is added to coagulate the fines or dust for de-watering. To dewater the flocculent slurry, a belt filter press or other equipment known to the art may be used. Once dewatered, a starch or another suitable binder is added to the biochar particles, at step 4004. Other additives may also be added to the biochar particles during this step. The biochar particles are again de-watered at step 4006 and the slurry becomes a thicker slurry or paste. The de-watered biochar paste may then be formed into aggregate solids at step 4008, by, for example, the use of an extruder. The aggregate particles are then dried using a hot air, tunnel oven dryer, or other dryer known to the art, at step 4010. The aggregate particles could also be freeze dried (e.g., lyophilized) and/or allowed to air dry, at step 4010. Such drying can be done before or after the biochar paste is subjected to a forming processes.

Treatment of biochar fines or dust is optional, but may be desired for pH adjustment and/or removal of elemental ash and other harmful organics or materials, as described in more detail above. Depending on the chemical properties of the biochar dust or fines, either water or acidic acid can be used to adjust the pH to neutral levels, and obtain a neutralized biochar slurry. The wash may also contain a surfactant or detergent to aid in the penetration of the wash solution into the pores of the char. Those skilled in the art will recognize that other pH adjusting agents, besides acidic acid may be used to neutralize the biochar pH levels. Additionally, other binders may be used with the restriction that they must be suitable for introduction into their particular application, for example not phytotoxic for use in soil or toxic to animals or humans for use in animal feed or maintenance. Some examples of these other pH adjustment agents include, but are not limited to gypsum, sulfur, lime, or combinations thereof. As set forth earlier, treatment can be performed on the fines or on the larger biochar media from which the fines are collected.

The above illustrated example details only one method of how biochar aggregate particles may be produced. As noted above, alternate forming processes may also be used besides passing the biochar paste through an extruder, such as a pelletizer, a briquetter, a granulator and/or other heat, cold, evaporation and/or pressure system capable of forming the paste into solid shapes.

Further, in another implementation, raw or treated biochar fines and/or larger biochar particles may be dried and ground to a smaller particle size or powder. The biochar powder can then be mixed with a binder in a rotary drum to create reasonably uniform spherical biochar aggregate particles.

Further, in another implementation, the biomass, prior to pyrolysis, may be formed into solids shape aggregates, such as pellets, by equipment designed to create pellets, granules and/or briquettes. Further, these pellets may be stabilized by mixing a dry binder or a binder solution with biomass prior to pelletizing to improve the mechanical stability of the formed pellet. These binders may include but are not limited to starches, polymers, clays, or lignins.

By shaping the biomass prior to pyrolysis, the biomass may retain the solid shape. Depending upon the biomass, the biomass aggregate may need to be treated prior to pyrolysis to maintain the original shape with, for example, a binder solution. Wet formed, or solution treated pellets may require drying before handling and pyrolysis. This drying may be done using hot air, a tunnel oven dryer, or other dryer known to the art.

In creating biochar aggregates, it is critical to determine the proper biochar particle size and the proper method to use to create said particles for the biochar aggregate production. Setting the correct size limits and method will ensure the aggregates maintain the physical and chemical characteristics that make the specific biochar effective in the target application. FIGS. 41 and 42 show SEM photos from two different biomass based treated biochars. FIG. 41 shows the effect of size and grinding on particle structure for three different particle size ranges: 0.1-0.3 mm, 0.05-1 mm, and <0.05 mm. These particles were collected using two different methods: (i) sieving the as is treated biochar and (ii) grinding the as is treated biochar and then sieving. FIG. 41 shows one treated biochar ("treated biochar 1") and FIG. 42 shows a second treated biochar ("treated biochar 2"). In the treated biochar 1 SEM photos (FIGS. 41*a, b, c, d, e* and *f*), it is clear that the two methods of collection show no substantial difference in pore structure. It is also clear that the particle structure is destroyed once the particle sizes are less than 0.05 mm. In the treated biochar 2 SEM photos (FIGS. 42*a, b, c, d, e* and *f*), a different observation is noted, when the material is just sieved to 0.3-0.5 mm range, the biochar particle has retained its porous structure, but when the as is treated biochar 2 is ground using a medium grind or a fine grind and then sieved to 0.3-0.5 mm range, then the porous structures have been mostly destroyed. FIGS. 42*d*, 42*e* and 42*f* are zoomed images of FIGS. 42*a*, 42*b* and 42*c*.

Figures 43A, 43B, 43C, 43D:
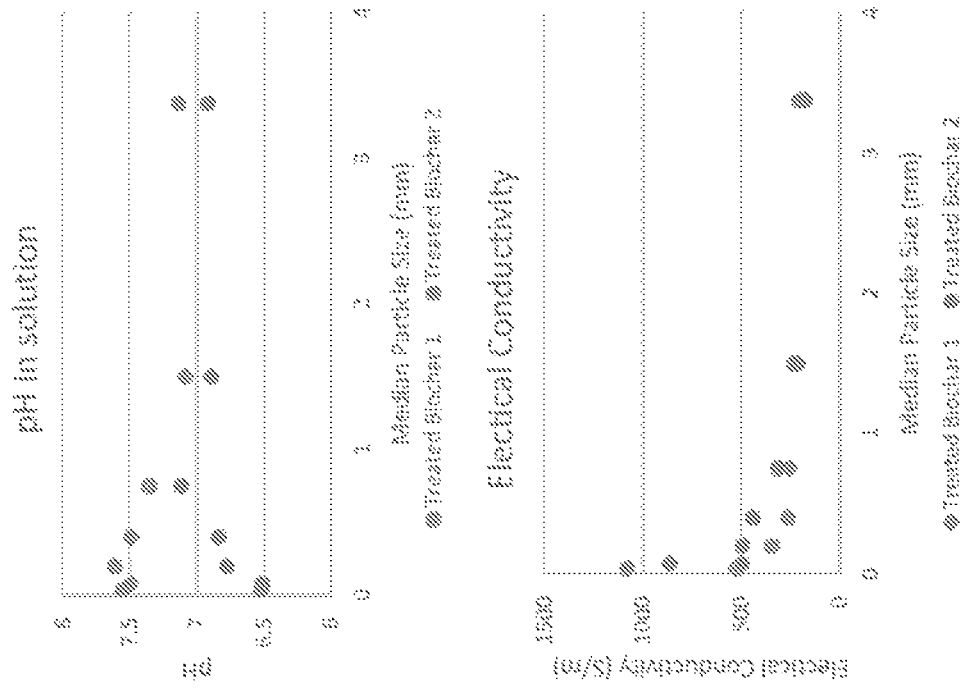
FIG. 43a shows the effect of size fraction on water holding capacity of two different biomass based treated biochars.
FIG. 43b shows the effect of size fraction on pH of two different biomass based treated biochars.
FIG. 43c shows the effect of size fraction on Cl— concentration of two different biomass based treated biochars.
FIG. 43d shows the effect of size fraction on electrical conductivity of two different biomass based treated biochars.

In addition, various particle size ranges from the two treated biochars were further tested to see how biochar characteristics changed with particle size. FIGS. 43*a, b, c* and *d* show the effect of size fraction on four properties, water holding capacity, pH, Cl-concentration, and electrical conductivity of two different biomass based treated biochars. For treated biochar 1, these properties, except pH, were stable across particle sizes except when the particles were smaller than 0.1 mm. This is likely due to the loss of pore structure somewhere below 0.1 mm for this treated biochar. For treated biochar 2, some properties, electrical conductivity and chloride concentration, seemed to correlate to particle size in a similar way to that of treated biochar 1.

But decreasing particle size of treated biochar 2 had the opposite effect on water holding capacity and pH versus treated biochar 1.

These observations show how particle size and the method used to create them can have significant impact on both the pore structure of the particles and the biochars properties. Thus an aggregate's properties and effectiveness can be maintained, adjusted, or harmed based on the method for creating and collecting sized biochar particles in addition to the method of aggregation and may differ based on the biochar feedstock and pyrolysis method.

Further in another implementation, the biomass may be sized prior to pyrolysis so that the aggregate can be made with the as is biochar particles or treated biochar particles without additional sizing. Eliminating the need to size the biochar further, may help to maintain the biochar properties when aggregating as biochar pore structures that are susceptible to being destroyed during sizing post pyrolysis will not be harmed using this method.

As noted above, the biochar aggregate particles can be created with either raw biochar or treated biochar that is treated in the manner or method further described below. Biochar aggregate particles can be applied through a wide range of devices, including agricultural equipment including but not limited to broadcast spreaders, drop spreaders and/or hand distribution means. The application of biochar aggregate particles can be used for trees, row crops, vines, turf grasses, potted plants, flowering plants, annuals, perennials, evergreens and seedlings. The biochar aggregate particles may also be applied to animal pens, bedding, and/or other areas where animal waste is present to reduce odor and emission of unpleasant or undesirable vapors. Furthermore it may be applied to compost piles to reduce odor, emissions, and temperature, such as that taught by co-owned U.S. Patent application 2015/429,104, which is herein incorporated by reference in its entirety. Or it can even be applied to areas where fertilizer or pesticide runoff is occurring to slow or inhibit leaching and runoff. The aggregates may also be integrated with animal feed and/or other substances beneficial to animal health, either whole (biochar pellets mixed with separate feed pellets to form an aggregate, for example), or with animal feed or other beneficial substances mixed into the biochar slurry or paste prior to extrusion. Biochar aggregate particles may be incorporated into or around the root zone of a plant. As most trees, rows, and specialty crops extract greater than 90% of their water from the first twenty-four inches below the soil surface, the above applications will generally be effective incorporating the biochar around the root zone from the top surface of the soil and up to a depth of 24" below the top surface of the soil, depending on the plant type and species, or alternatively, within a 24" radius surrounding the roots regardless of root depth or proximity from the top surface of the soil. When the plant roots are closer to the surface, the incorporation of the biochar within the top 2-6" inches of the soil surface may also be effective. Greater depths are more beneficial for plants having larger root zones, such as trees.

Biochar aggregates are particularly useful, when they will be put into an application that requires mixing with other solid granular products. This is because the aggregates can be designed and created to be similar in shape, size, or density to that which it will be mixed with. When the aggregates are physically similar to the material particles they will be mixed with then the final mixture will stay more uniformly mixed and have better flow properties. When a specific rate of each material in the mixture is needed, say in agriculture or animal feed, then a uniform mixture is critical to ensure the soil or animal consistently gets the correct rate.

J. Biochar Suspended Solution

Another application of biochar for animals and agriculture is biochar suspended in solution. In certain applications, biochar may be more effectively applied if the biochar is in suspension in solution. The biochar, prior to being put in suspension in solution, may be raw or treated, as described above. If the biochar is treated, not only can the pH be adjusted as needed, as discussed above, but also fertilizers, microbes, and host of other additives may be infused in the biochar prior to suspension in solution (as further described below). However, regardless of whether the biochar is raw or treated, the present application for the suspension of biochar in solution can be utilized for both.

Figure 44:
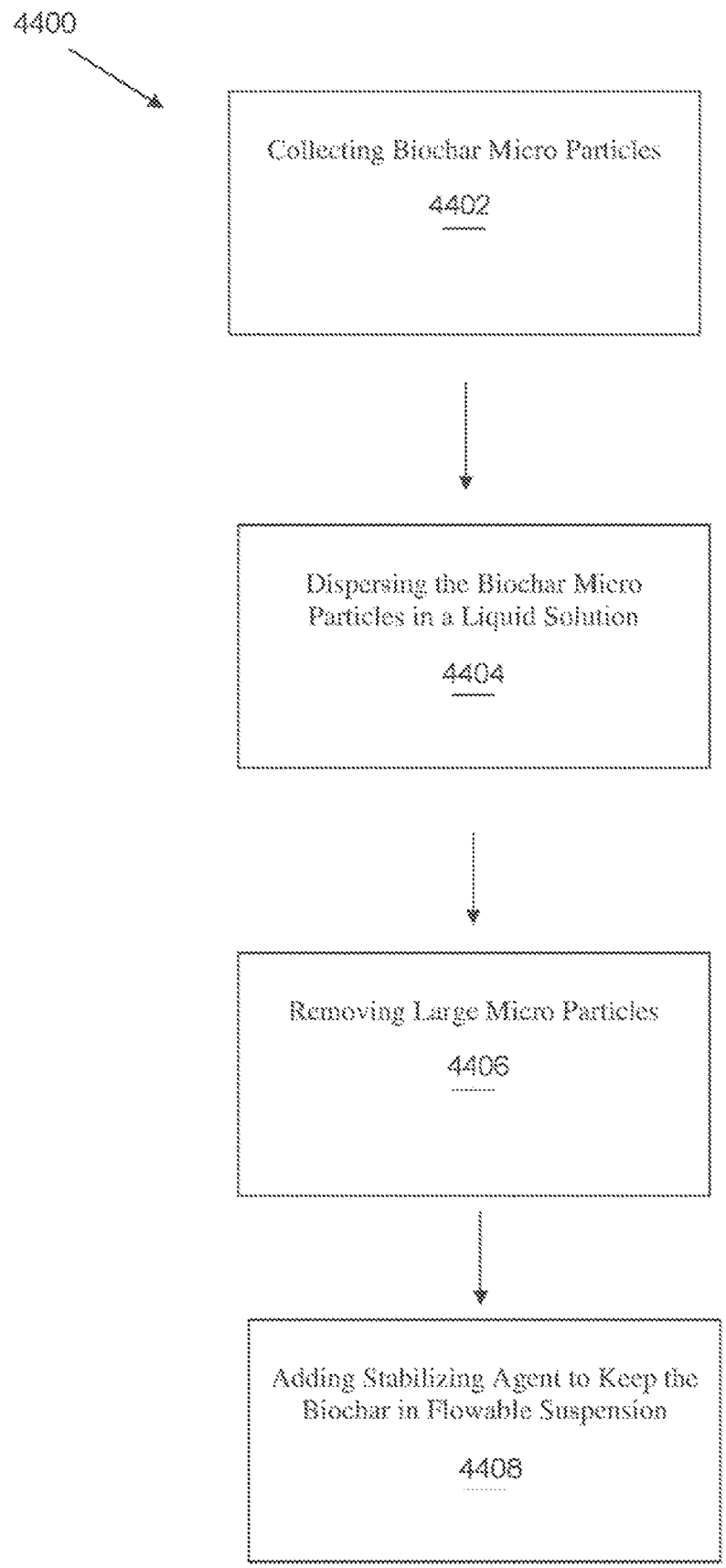
FIG. 44 is a flow diagram of one example of a method for producing a suspended biochar solution.

FIG. 44 is a flow diagram of an example of a method that may be used for producing biochar solutions. For purposes of this application, "biochar solution" or "biochar suspended solution" shall mean biochar that has been added or suspended in a liquid, alone or in combination with other additives. In general, the method of producing liquid products containing biochar may be accomplished by sufficiently de-sizing the biochar to pass through nozzles and/or mesh screens, dispersing the biochar in solution, such as water, and adding xanthan gum and/or other additives to keep the biochar in suspension, in solution.

At step 4402, biochar particles, either treated or raw, are collected for use in solution. The biochar particles may be collected in any number of ways, including but not limited to: (i) flow from a centrifuge effluent, (ii) from biochar granular product, or (ii) a combination of both a centrifuge effluent and granulated product. In all cases, the collected biochar may be passed to a media mill, air impingement, burr grinder, or other grinding, milling, or particle sizing equipment for production of smaller particles. The media mill or other similar equipment (e.g., attritor mill) allows for the de-sizing of the biochar product through dry and/or wet grinding. Micro particles may also be collected directly by traditional desizing equipment, including but not limited to hammer mills and grinders. Those skilled in the art will recognize that other desizing equipment, such as impellers, ultrasonic mechanisms, vibrators, shakers, or other devices besides hammer mills and grinders may be used to produce and collect biochar micro particles. Flocculants such as polyacrylamide can also be used at levels of 1000 ppm or less to collect the micro particles and to create a biochar micro particle cake. The residual amount of flocculant left in the micro particle cake will vary depending on the amount of flocculant that leaves with the liquid. Those skilled in the art will recognize that other flocculants, besides polyacrylamide may be used to clump the biochar particles together and other agents besides flocculants may be used to separate the solid micro particles from liquid for storing, transporting, or other purposes. Differences or variation in liquid or gas flow speed, rate, or pressure may also be used to sort particles based on their hydrodynamic or aerodynamic properties.

At step 4404, the biochar micro particles may then be dispersed in a liquid solution to create a biocarbon solution having a biochar solid content of approximately 1-75%, most desirable ranges between 15-70%. The liquid solution may include, but not be limited to, water, deionized water, liquid fertilizer and/or any combination thereof. Other liquid and/or solid additives may also be included in solution without departing from the scope of the invention. Once mixed in solution, the resulting biochar solution may then be passed through nozzles and mesh screens to remove any large biochar particles from the solution, at step 4406. Filters, such as nozzles and screen may be used to filter particles of sizes greater than about 0.2 mm. For example, mesh screens ranging from 0.2 mm-7.0 mm in size may be used to filter undesired larger particle sizes from solution. For example, a 15 mesh screen having 1.0 mm-1.2 mm openings may be used to filter undesired larger particle sizes from solution. Those skilled in the art will also recognize that the step of filtering out the larger particles may alternatively occur prior to or during the collection process (at step 4402).

To best hold the biochar in suspension, biochar micro particle sizes of about 0.5 mm or less may be desired or may depend on the method of application. For example, if applying biochar suspended solution with irrigation equipment, less than 0.05 mm, 0.025 mm, 0.01 mm, or even less may be desired, whereas less than 1 mm, 0.5 mm, 0.2 mm, or even less than 0.1 mm may be desired if applying biochar suspended solution with varying types of fertilizer equipment.

The following table shows the particle size distribution and physical characteristics of particles when held in suspension to support the efficacy of using biochar held in suspension compared to other mixtures such as solutions and colloids:

| Characteristic | Solution | Colloid | Suspension |
|---|---|---|---|
| Type of particle | individual molecules or ions | very large individual molecules or aggregates of tens to thousands of smaller molecules | very large aggregates of molecules |
| Particle size | <1 nm | ~1 nm to ~200 nm | >100 nm |
| Separation by gravity? | no | no (usually, otherwise, very slowly) | yes |
| Separation by contrifugation? | no | yes, for more massive dispersed particles | yes |
| Captured by filter paper? | no | no | yes |
| Captured by membrane? | no | yes (usually) | yes |
| Precipitatable by flocculation? | no | yes | yes |
| Exhibits Tyndall Effect? | no | yes | yes |
| Affects colligative properties? | yes | no | no |

"*Laboratory 18.0: Colloids and Suspensions—Introduction.*" Table 18-2.makezine.com/laboratory-18-colloids-and-suspensi/

It should be noted that the pH of the biochar solution can affect how much biochar particles will stay in solution and the viscosity of said solution. Thus it may be beneficial to add an acid or base before, during, or after these steps. For example, lowering the viscosity of the solution by adding a base to the solution prior to wet milling will allow for more efficient milling and result in a higher amount of solids fit for the solution, i.e. less particles will be removed during the large particle removal step. Then, after the wet milling an acid could be added to bring the pH back down and provide the viscous stability to ensure the particles stay and solution instead of settling.

At step 4408, a stabilizing agent may then be added to keep the biochar in flowable suspension and prevent it from settling. The stabilizing agent can include xanthan gum at about 0.1% to 0.7% by weight to the solution or it can vary depending on the solids already in solution, the percentage of solids in solution and/or the particle size of the biochar used to create the solution. Alternative natural or synthetic agents with pseudoplastic rheology capable of suspending biocarbon particles in solution may also be added at this step such as alkali swellable acrylic thickeners, inorganic substances, surfactants or other water born thickeners. Isothiazolin type preservatives could also be added to prevent biological degradation of the xanthan gum. For example, 50 ppm of active Kathon™ LX 1.5% biocide may be added to protect the xanthan gum. Those skilled in the art will recognize that other preservatives may be used to prevent biological degradation of the xanthan gum. Those skilled in the art will also recognize that the step of adding stabilizing agents may alternatively occur prior to, during, or after the collection process (at step 4402).

For example, the stabilizing agent could be added prior to the creation of the suspended biochar solution by mixing or spraying the agents on dry biochar particles either prior or post micro particle collection process. In fact, they could even be added or infuse into the biochar during the treatment processes. This could allow for the production, transport, and/or sale of a dry or semi-dry biochar product that could then be turned into a solution after production, for example at the time of sale or just prior to application at say the farm where it will be applied. Similarly, the process of adjusting the density of the biochar can be combined with the process of adding stabilizing agents or thickeners.

Depending on the thickener or stabilizing agent used at step 4408, a preservative may also be added to ensure an optimal product with long shelf life. Choosing the right preservative is important as the biochar itself can absorb certain preservatives and thus allow unwanted microbiological growth in the solution over time. Potential preservatives that may be used are polymeric preservatives such as poly quats or formaldehyde emitter preservatives. Chlorine based preservatives are not generally used as the biochar can degrade chlorine in a short amount of time. Another option to avoid biochar solution degradation is to choose a stabilizing agent that will not rot or encourage microbiological growth in the solution. One example of this is clay based thickeners such as Attagel and Veegum. An exception to this would be cases in which microbial agents are to be inoculated on or suspended with the biochar itself. A third option is to not create the solution until right before it will be used, for example at the time of sale or at the time of application. The shorter shelf-life reduces chances of solution degradation.

Optionally, growth enhancing additives, including but not limited to, fertilizers, liquid micronutrients, liquid manure, liquefied compost or compost "tea", compost extract and beneficial microbes can be added to the biochar solution. These additives may be added either prior, during, or after the suspended biochar solution is created. For example, the additive may be infused into the biochar prior to creating the solution using vacuum infiltration or a surfactant as further described above. Alternatively, or in addition to infusing the biochar with additives, additives may be included with the biochar solution described above prior, during or after creation of the biochar solution.

For example, fertilizers may be pulverized to an average particle size of <1 mm and included with the solid biochar or added to solution. Liquid fertilizers may also be used in solution. For example, 1000 ppm NO3-N fertilizer solution may be used. Examples of fertilizers that may be added to the solution, include, but are not limited to the following: ammonium nitrate, ammonium sulfate, monoammonium phosphate, ammonium polyphosphate, Cal-Mag fertilizers or micronutrient fertilizers. Other additives, such as fungicides, insecticides, nematicides, plant hormones, beneficial microbial spores, or secondary signal activators, may also be added to the solution in a similar manner as a fertilizer, the inclusion of which does not depart from the scope of the invention. Additionally, beneficial macro- and micro-nutrients such as nitrogen, phosphorous, potassium, calcium, magnesium, sulfur, boron, zinc, iron, manganese, molybdenum, copper and chloride can be added to the suspended biochar solution. As set forth above, in addition to adding these to solution, such additives can be infused into the biochar prior to creating the solution.

Examples of compounds, in addition to fertilizer, that may be mixed with the biochar solution or infused into the biochar prior to creating the solution include, but are not limited to: 2,1,3-Benzothiadiazole (BTH), an inducer of systemic acquired resistance that confers broad spectrum disease resistance (including soil borne pathogens); signaling agents similar to BTH in mechanism or structure that protects against a broad range or specific plant pathogens; biopesticides; herbicides; and fungicides.

Those skilled in the art will recognize that there are many other mechanisms and processes that may be used to produce biochar solutions without departing from the scope of the invention. Those skilled in the art will further recognize that the present invention can be used on any type of soil application, including, but not limited to, the following: crops, turf grasses, potted plants, flowering plants, annuals, perennials, evergreens and seedlings.

By putting the biochar solution, as taught above, a variety of equipment may be used for the application of the suspended biochar solution. The ability to uniformly apply the biochar solution is also enhanced by allowing the use of pumps, sprays and various other types of equipment capable of handling liquid dispersion. For example, Sprayers, booms, and misting heads can be an efficient way to apply the biochar solution to a large area, while backpacks or hose sprayers can be sufficient for smaller applications. Aside from spraying applications, biochar solution may also be pumped through the ground to eliminate the potential for wind erosion while allowing for faster infiltration into the soil. Furthermore, biochar solution can be used in connection with a variety of equipment used for hydroseeding, manure spreading (either solid or liquid), foliar spraying, irrigation, or other liquid application technologies. As there are so many different options to apply biochar suspended solutions or solution, much time and expense can be saved.

In addition, the use of a biochar suspended solution can allow for more efficient and focused applications to ensure the biochar treatment stays in the root zone, or is deployed in the vicinity of juvenile or developing root tissue, thus reducing the amount of biochar needed on a cubic yard per acre basis. For example, if the biochar solution is put through irrigation tape that is laid directly in a row crop bed the biochar will only be treating the root zones of said crop in the beds and not the row crop furrows nor above or below the root zone in the bed. Not only does this lessen the cost by reducing the amount of biochar needed it also can lessen the cost of the application method itself as it can be applied using the same equipment that may already be available for irrigation and liquid fertilizer application.

The application of the biochar solution can be used for trees, row crops, vines, turf grasses, potted plants, flowering plants, annuals, perennials, evergreens and seedlings. The biochar solution may be incorporated into or around the root zone of a plant at ratios of between 1:999 to 1:1. However, an application does not necessarily need to be restricted or limited to these ratios. Biochar can be added to soil at a concentration of 0.01% up to 99% depending upon the application, plant type and plant size. As most trees, rows, and specialty crops extract greater than 90% of their water from the first twenty-four inches below the soil surface, the above applications will generally be effective incorporating the biochar around the root zone from the top surface of the soil and up to a depth of 24" below the top surface of the soil, depending on the plant type and species, or alternatively, within a 24" radius surrounding the roots regardless of root depth or proximity from the top surface of the soil. When the plant roots are closer to the surface, the incorporation of the biochar within the top 2-6" inches of the soil surface may also be effective. Greater depths are more beneficial for plants having larger root zones, such as trees.

The biochar suspended solution may also be applied to animal pens, bedding, and/or other areas where animal waste is present to reduce odor and emission of unpleasant or undesirable vapors. Furthermore it may be applied to compost piles to reduce odor, emissions, and temperature or even to areas where fertilizer or pesticide runoff is occurring to slow or inhibit leaching and runoff. In some instances, it may even be mixed with animal feed, fed to animals directly as a liquid, or used in aquaculture applications.

Biochar solution may also be utilized and applied through irrigation equipment for both low flow and high flow irrigation systems. For the purpose of this application, "low flow system" includes but is not limited to micro sprays, drip emitters, and drip lines and "high flow systems" includes but is not limited to fixed sprays, rotors, bubblers, and soaker hoses. Although the utilization of the chemical and physical properties of biochar for optimal plant growth would ideally be most effective when applied to plants during their peak growing cycle, all of the applications discussed above can be applied at any time during the different stages of plant growth or ground preparation as needed. Similarly, the methods of application can be repeated as many times as needed from year to year depending on factors not limited to plant type, climate, soil properties, topography, and light. In summary, when any type of liquid is applied to the plants such as water or liquid fertilizer, the suspended biochar solution can be added to the liquid in order to provide further soil enhancement characteristics.

An alternative method for creating a biochar solution is to instead make a biochar slurry using a process similar to hydromulching or hydroseeding. With this method the size reduction step can be reduced or eliminated since the process is typically applicable for larger particle sizes in which the resulting slurry is applied through pumps and sprays. For this application method typically the granular biochar will be mixed with water, fiber mulch, and optionally a tackifier at time of application and then sprayed to area needed. In addition, it can be mixed with fertilizer, seeds, or other additives including dyes to help aid in uniform distribution. Typical hydroseeding and hydromulching equipment may be used and generally include a tank mounted truck that is equipped with a special pump and continuous agitation system. The pump then pushes the slurry though a hose and nozzle for application. To create a biochar slurry for this application the fiber mulch is usually a cellulose based material which can be made from shredded waste paper sources and can include dyes, binders, or other additives. The optional tackifier can include but is not limited to guar gum, xanthan gum, plantago gum, methyl cellulose, pectin, lignin, seedmeals, such as camelina or lesquerella, polysaccharide gums, or starches, such as corn starch. The addition of a tackifier increases the biochar slurry's effectiveness especially when applied on a slope, on an area that is erosion prone, or other areas that would cause concern of the biochar application being washed away due to rain or irrigation. If the slurry is to be made significantly prior to application then a preservative would likely be needed as well to ensure a longer shelf life. Otherwise the biochar, fiber, and tackifier can be mixed dry and then turned into a slurry just prior to application or even onsite, similarly to current practices of hydromulching and hydroseeding. This biochar slurry may be particularly useful in turf and landscape applications where hydroseeding or hydromulching is already being used. In the case of turf particularly, it could be either mixed with grass seeds prior to application or applied immediately prior to the hydroseeding application. A process similar to this can be used for mixing the biochar with manure to create a manure slurry, either in lagoons, or at any point prior to application of the manure.

K. Animal Applications

Generally, treated biochar of the present inventions can be used with numerous animal species, large and small scale farming, and in a variety of animal management applications and systems, and combinations and variations of these. In fact, this particular solution provides the capability to custom-manufacture biochar for a particular species, physiology, nutritional need, pathogen susceptibility, illness, environment, geographical area or other application by more precisely controlling key characteristics.

The fundamental benefit of treated biochar use in animal applications is the fact that deleterious characteristics can be adjusted and toxic materials left over from the biomass and its pyrolysis can be removed. For example, pH can be adjusted, and undesirable ash, inorganic compounds, toxins or heavy metals, and organic compounds such as acids, esters, ethers, ketones, alcohols, sugars, phenyls, alkanes, alkenes, phenols, polychlorinated biphenyls or poly or mono aromatic hydrocarbons, can be removed. As described previously, one major concern with charcoals or raw biochars used in animal applications is the potential for dioxins which are released from combustion processes and are an example of toxic material that the treatment of the present invention can remove. Thus, a treated biochar can be used in animal applications where ingestion may be possible such as bedding, or specifically as a feed additive, whether it be for general purpose such as color, manure odor control, or roughage replacement or as a technical additive as a binding agent or carrier as it can be made without toxins, specifically dioxins, consistently with various feedstocks and various pyrolysis methods without risk of harm to the animals or humans that consume the animal products/meat from said animals.

Through the use of detoxified treated biochars, the other benefits of biochar qualities can be realized in applications related to the care, maintenance and feeding of animals. These benefits can include increase in animals' uptake of foodstuffs and the energy contained within them; reduction in the amount of nutrients lost into excrement and manure; detoxification of the animal and enrichment of the beneficial microbes in the digestive track that are key to maintaining an animal's metabolism and helping it to resist dangerous pathogens; reduction in methane production; better odor control of stalls, pens, cages, lagoons and other animal enclosures; and any combination and variation of these and other benefits. The results are increased growth rates for animals consuming treated biochar, as well as better overall health of the animals that consume it, greater efficiencies in animal care and maintenance, and improved odor. As an additional benefit, manure produced by an animal that consumes biochar contains biochar, making this manure better for agricultural purposes than ordinary manure.

For animal applications, in the same way that biochars are known to bind organic contaminants in soil environments due to hydrophobic-hydrophobic interactions, treated biochar may bind organic toxins as they pass through an animal's digestive system, for example, when cattle are suffering from botulism or diarrhea.

Another toxin binding application could be with commercial farm pollinating bee hives. Bee species have been on the decline in the US and this year, the first species of bees in the continental US was placed on the endangered species list. Bee species decline appears to be in part due to fungicides, and insecticides, including neonicotinoids, leading to bees becoming more susceptible to disease. See Pettis et al., Crop Pollination Exposes Honey Bees to Pesticides Which Alters Their Susceptibility to the Gut Pathogen Nosema ceranae, PLOS, Jul. 24, 2013 (journals.plos.org/plosone/article?id=10.1371/journal.pone.0070182).

Adding small particle treated biochar to a commercial hive feed patty, which generally consist of sugar and protein and may have additional vitamins or probiotics, may allow the insects to ingest said treated biochar and allow for it to help bind the pesticide toxins and help lessen their sub-lethal effects to keep the bees more resistant to pathogens even when they have been and continue to be exposed to these pesticides.

Figure 45:
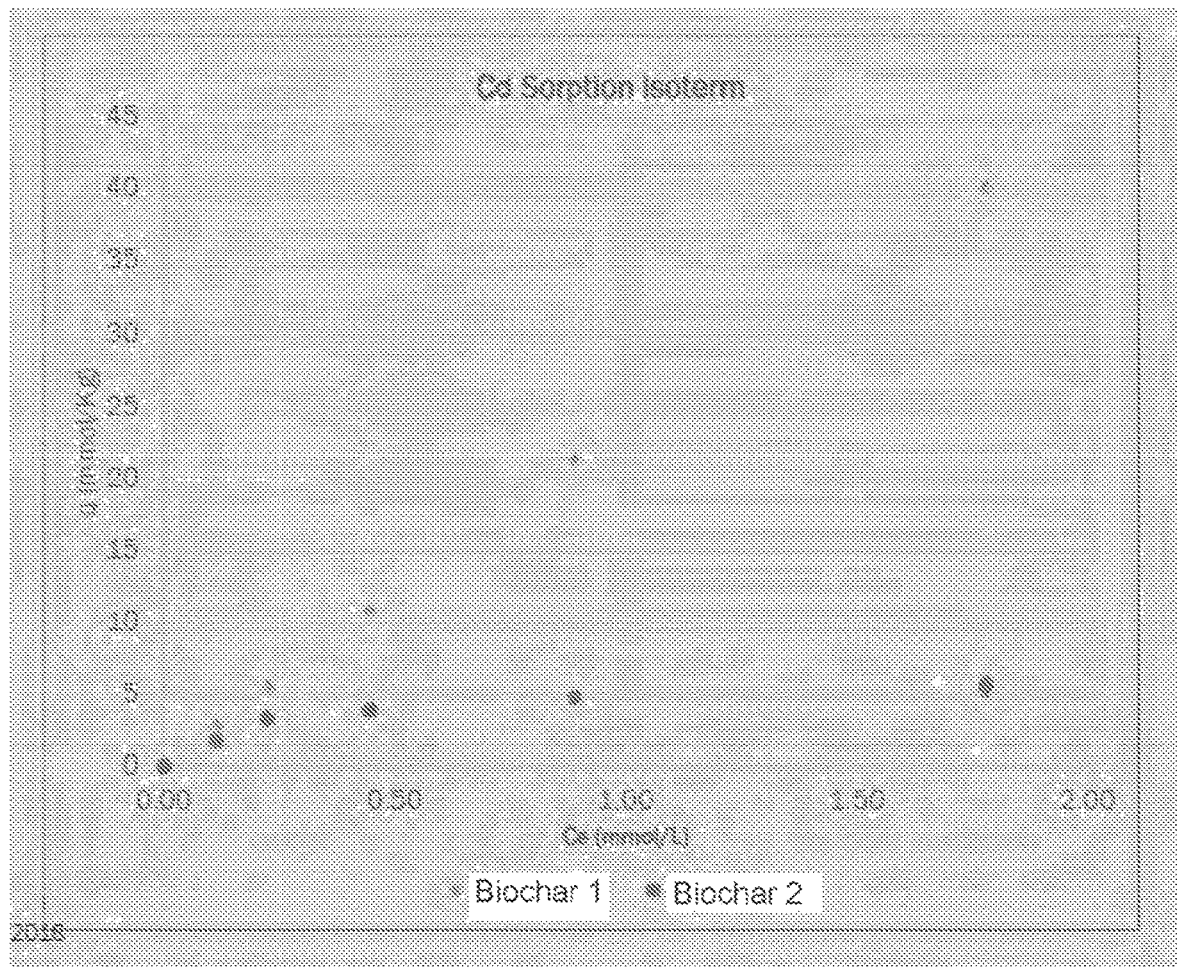
FIG. 45 is chart illustrating biochar capacity to absorb Cadmium.

In another example, biochars were shown to absorb Cadmium, a heavy metal, but the absorption capacity was dependent on the biochar properties including the biomass feedstock type. FIG. 45 is chart illustrating biochar capacity to absorb Cadmium. Thus a specific treated biochar formulation can be developed for each toxin binding animal application to ensure optimum results for the specific toxin(s) of concern.

Another application is to use the treated biochar as bedding in order to reduce odors, absorb ammonia, and absorb toxins and thus lead to an environment that will lead to healthier animals and also lead to a better secondary product of quality manure by reduced nutrient leaching. A bedding trial was conducted with broiler chickens. After decaking the houses, the test houses had treated biochar spread evenly over the entire house at various rates while one was left as a control. The flock produced over the two sets of trials was above normal. After the first trial, manure samples were tested from each house for nutrient content and estimated 1st year availability of said nutrients. The estimated manure value was then calculated off of the estimated 1st year availability. Results showed higher value for the bedding with treated biochar, as seen in table below:

|  | 1st Year Availability (lbs/ton) | |
| --- | --- | --- |
|  | Control | With Treated Biochar |
| Total N | 37 | 35 |
| P (P2O5) | 31 | 34 |
| K (K2O) | 56 | 61 |
| Total Est. Value | $56.40 | $58.90 |

Further, mixing treated biochar in while composting can reduce odors, these same mechanisms can be used to reduce odors when treated biochar is mixed with animal bedding, manure, swine lagoons, etc.

Typically, the prior art teaches mixing raw biochar with animal feed without 'precharging' with nutrients, microbes, etc. Through impregnation of the biochar particles, one can achieve a predetermined and controllable amount of a particular nutrient, medication, foodstuff, microbial community, etc. being ingested by the animal. In ruminants, once the additive laden biochar is in the rumen, data indicates that these infused additives will also be released more slowly over time, yielding yet another benefit over additives mixed directly into the feed. This integration of a beneficial additive with a biochar particle and biochar batches provides the ability to have controlled addition, use and release of the additive or additives. This integration may further enhances, promotes and facilitate animal growth and health, aid in digestion and digestibility of food, improvement hygiene, increase intestinal health, reduces the amount of nutrients lost into excrement and manure and reduces methane discharge.

Enhancing treated biochar with an additive, including infusing liquids into the pores of biochar, can provide additional benefits in animal applications, by making it an effective delivery mechanism for beneficial nutrients, pharmaceuticals, enzymes, microbes, or other substances. Additionally a sensory enhancer, such as a smell or flavor (e.g. salt), could be infused to increase the animal's desire to ingest said biochar.

The additive may include, but not be limited to, water, water solutions of salts, inorganic and organic liquids of different polarities, liquid organic compounds or combinations of organic compounds and solvents, vitamins, supplements and/or medications, nutrients, minerals, oils, probiotics, amino acids, fatty acids, supercritical liquids, growth promotants, proteins and enzymes, phytogenics, carbohydrates, antimicrobial additives and sensory additives (e.g. flavor enhancers salt or sweeteners or smell enhancers), among others, to provide nutrition, promote the overall health of the animal, and increase the animal's desire to ingest said biochar. Vitamins, supplements, minerals, nutritional and/or medications may be used to prevent, treat or cure animal illnesses and diseases and/or control the nutritional value of the animals overall diet.

For example, dietary supplementation with certain nutrients (e.g., arginine, glutamine, zinc, and conjugated linoleic acid) can regulate gene expression and key metabolic pathways to improve fertility, pregnancy outcome, immune function, neonatal survival and growth, feed efficiency, and meat quality. Such additives in the biochar can help provide the proper balance of protein, energy, vitamins and nutritionally important minerals in animal diets. Additionally, for poultry, the additive may include, for example, coccidiostats and/or histomonostats, which are both shown to control the health of the poultry. The present invention can be used to help correct deficiencies in basal diets (e.g., corn- and soybean meal-based diets for swine; milk replacers for calves and lambs; and available forage for ruminants).

The treated biochar can also have a microbial community infused in its pores (macro-, meso-, and combinations and variations of these), on its pore surfaces, embedded in it, located on its surface, and combinations and variations of these. The microbial community can have several different types, e.g., species, of biologics, such as different types of bacteria or fungi, or it may have only a single type. A primary purpose, among many purposes, in selecting the microbial population is looking toward a population that will promote animal health either directly or through interactions with other microbes in the animals digestive tract. These types of beneficial microbes are essential to a functional gastrointestinal tract and immune system in many types of animals, serving many functional roles, including degradation of ingesta, pathogen exclusion, production of short-chain fatty acids, compound detoxification, vitamin supplementation, and immunodevelopment. As noted above, beneficial bacteria include *Lactobacillus acidophilus* LA1 (which decreases adhesion of diarrheagenic *Escherichia coli* to Caco-2 cells by 85% and prevents invasion of the same cells by *E. coli* (95%), *Yersinia* pseudo-tuberculosis (64%) and *Salmonella enterica* serovar *Typhimurium*) and *Lactobacillus rhamnosus* GG to prevent *E. coli* O157:H7-induced lesions in Caco-2 cells.

Further, biochar may be impregnated with probiotic bacteria to treat diseases in farm-raised fish. Infectious diseases pose one of the most significant threats to successful aquaculture. The maintenance of large numbers of fish crowded together in a small area provides an environment conducive for the development and spread of infectious diseases. In this crowded, relatively unnatural environment, fish are stressed and more susceptible to disease. Moreover, the water environment, and limited water flow, facilitates the spread of pathogens within crowded populations. There is thus an urgent need in aquaculture to develop microbial control strategies, since disease outbreaks are recognized as important constraints to aquaculture production and trade and since the development of antibiotic resistance has become a matter of growing concern. One alternative disease control relies on the use of probiotic bacteria as microbial control agents. Another implementation of the invention therefore involves the impregnation of biochar for consumption by aquatic animals as a treatment or preventative for disease.

Additionally, biochar may be infused with bacteria which prove helpful in methane reduction. An example of this is to infuse the biochar with methanotrophic bacteria (bacteria which are able to metabolize methane as a source of carbon and energy). Bacteria which metabolize methane are useful in two regards—they can reduce the environmental methane emissions from the rumen and they (the bacteria) also serve as nutrition for the animal itself, leading to increased weight gain. Infusing biocarbon with microbes such as these can lead to methane reduction in cattle applications that exceeds the methane reduction of solely untreated biochar itself.

Additive infused biochars may be mixed with the animals regular feeds or may be included within a salt or mineral block and made available for animals to self-feed or self-administer the additives.

While this discussion focuses mainly on applications of infused biochars in connection with farm-raised animals, those skilled in the art will also recognize that the invention could also be applied more generally for veterinary purposes for many types of animals other than livestock, poultry, fish or horses, including pets, as well as in a wide variety of environments and contexts, for example, for zoo or aquarium animals or for other penned or caged animals, insects such as bees, or for wild animals.

Furthermore, the treated or additive infused biochar can be sized, agglomerated, or suspended in solution to optimize its use in a specific animal application. For example, if using as a feed additive with smaller animals or very young animals, small particles will be required and being able to suspend these small particles in a solution will make for an easier application.

In addition, if the treated or additive infused biochar is being used to deliver its specific benefit in a targeted location in the animals' digestive tract, it can be mixed with an additive or coated to allow for a slower release or a targeted release in said location. So, for example if the additive or biochar is being targeted for use in the intestines or after rumens a specific coating substance and thickness can be chosen so as to degrade at the required specified rate leading to the biochar or additive being available after the stomach or rumens. This could be specifically useful for getting beneficial microbes to targeted organs in the digestive tract. If the microbe is infused into the pores to a significant depth of at least approximately 10 to 20 microns, then both the biochar structure itself and a coating could be used to protect the microbe through harsh conditions, such as stomach acid, prior to getting to the targeted organ location. In addition the coating can help to make the particle smoother to aid in digestion or could be flavored to increase the animal's acceptance of it for ingestion.

Treated biochar and additive infused treated biochar can be used in promoting growth and health in livestock (dairy and beef cattle, sheep, goats and swine); poultry; farm-raised wild animals (e.g. bison, deer and elk); farm-raised fish and other aquatic animals; horses and other members of the horse family; for controlling levels of certain pathogens, e.g. *salmonella* in poultry; for veterinary uses, such as delivery systems for medications, supplements and/or vitamins; for maintenance and welfare of zoo animals or other caged, penned or contained animals; for pets; for zoos and aquaria; for wild animals; for insects, such as bees, and for combinations and variations of these.

Treated biochars and practices and methods provide for healthier animals, increase food intake efficiency, promote better digestion and reduce methane emissions, and combinations and variations of these, and other features that relate to the increased holding, retention and time discharge features of the present biochars and processes.

Treated biochar may also be used in other applications, for example, such mixing with manure in holding ponds to potentially reduce gaseous nitrogen losses, soil remediation (for example absorption and capture of pesticide, contaminates, heavy metals, or other undesirable, disadvantageous soil components), ground water remediation, other bioremediations, storm water runoff remediation, mine remediation and mercury remediation.

In summary, the treatment processes of the present information may be used to clean the pores of the biochar, ridding the pores of dioxins or other detrimental substances, or infiltrating the pores of biochar with a variety of substances, for a number of purposes, including but not limited to, infiltrating the pores of biochar with nutrients, vitamins, drugs, microbes, and/or other supplements, or a combination of any of the foregoing, for consumption by animals. The treated biochar may also be applied to animal pens, bedding, and/or other areas where animal waste is present to reduce odor and emission of unpleasant or undesirable vapors. Furthermore it may be applied to compost piles to reduce odor, emissions, and temperature to enable the use of the food waste and animal feed in composting. Biochar can also be applied to areas where fertilizer or pesticide runoff is occurring to slow or inhibit leaching and runoff. The biochar may also be treated with additives which make it easier to dispense or apply, such as non-toxic oils, anti-clumping/binding additives, surface drying agents, or other materials.

While the above teaches a treatment process for biochar that increases the amount of additives that can be retained within the pores of the biochar, it is within the scope of the present invention to contact raw or treated biochar with additives (e.g. by submersion) for purposes of creating a delivery system for additives useful for animal health and consumption.

As set forth above, the treated biochar of the present invention may be used in various agriculture activities, as well as other activities and in other fields. Additionally, the treated biochar may be used, for example, with: farming systems and technologies, operations or activities that may be developed in the future; and with such existing systems, operations or activities which may be modified, in part, based on the teachings of this specification. Further, the various treated biochar and treatment processes set forth in this specification may be used with each other in different and various combinations. Thus, for example, the processes and resulting biochar compositions provided in the various examples provided in this specification may be used with each other; and the scope of protection afforded the present inventions should not be limited to any particular example, process, configuration, application or arrangement that is set forth in a particular example or figure.

Although this specification focuses on applications related to the maintenance, care, feeding and health of animals, it should be understood that the materials, compositions, structures, apparatus, methods, and systems, taught and disclosed herein, may have applications and uses for many other activities in addition to agriculture for example, as filters, additives, and in remediation activities, among other things.

L. Biochars to Address Specific Environmental Impacts of Farming

Farms, and especially factory farms, including Animal Feeding Operations (AFOs) and Concentrated Animal Feeding Operations (CAFOs), can have a significant negative impact on the environment in a number of areas. For example, excessive use of fertilizers in crop farming can lead to the leaching of dangerous chemicals into waterways and water supplies, polluting these and affecting, or even killing, fauna growing in and around them.

Of perhaps even greater significance is the effect on the environment resulting from the raising of animals. With over nine billion animals raised and slaughtered for human consumption each year in the U.S. alone, modem animal agriculture puts an incredible strain on natural resources like land, water, and fossil fuel. Factory farms yield a relatively small amount of meat, dairy, and eggs for this input, and in return produce staggering quantities of waste and greenhouse gases, polluting the land, air and water and contributing to climate change.

Farms, especially factory farms generate massive amounts of waste. According to the U.S. Department of Agriculture (USDA), animal feeding operations produce approximately 500 million tons of manure annually. This staggering number is three times the amount of sewage produced by humans in the U.S. Over the past two decades, shifts in animal agribusiness have exacerbated existing waste management problems, with more animals being intensively confined in fewer, but larger, operations. The USDA's Natural Resources Conservation Service and the U.S. Environmental Protection Agency (EPA) outline the changes as including: the move toward intensive confinement; the steady replacement of small- and medium-sized operations with large confinement operations; the continued consolidation of all aspects of production; the increase in numbers of confined animals per operation; and the spatial concentration of operations in high production areas. (An HSUS Report—*The Impact of Industrialized Animal Agriculture on the Environment, The Humane Society of the United States,* 2)(HSUS Report).

These developments have resulted in industrial animal agriculture facilities producing more manure than can be assimilated by available land, particularly in high production areas. Farms, especially factory farms, do not treat the sewage they produce. Instead, they dump animal feces, urine, and antibiotic-laden waste into gigantic open-air lagoons, often as big as several football fields. These open-air lagoons are prone to leaks and spills. In 2011, an Illinois hog farm spilled 200,000 gallons of manure into a creek, killing over 110,000 fish. When lagoons reach capacity, farmers will often opt to apply manure to surrounding areas rather than pay to have the waste transported off-site.

In order to prevent the spread of disease in the crowded, filthy conditions of confinement operations, and to promote faster growth, producers feed farm animals a number of antibiotics. Upwards of 75 percent of the antibiotics fed to farm animals end up undigested in their urine and manure. Through this waste, the antibiotics may contaminate crops and waterways and ultimately be ingested by humans.

While festering in these lagoons, liquefied animal waste often leaches into the groundwater, contaminating neighboring wells and rendering water unsafe for humans and farm animals. When factory farms spread their waste onto available land, it is generally over-applied. As a consequence, that waste frequently runs off into waterways. The resulting overload of nutrients causes rapid algae growth, which depletes the water of oxygen and kills large numbers of fish and other aquatic life.

Waste runoff also transports dangerous fecal bacteria, such as *E. coli*, into waterways and wells. For example, a heavy rain caused manure to infiltrate a municipal well in Walkerton (Ontario, Canada) in May 2000. Even though the water was being chlorinated, the amount of *E. coli* overwhelmed the treatment system. Seven people died, and more than 2,300 people became ill due to drinking tap water. In 2003, California's Chino basin estimated that it would spend more than $1 million per year to remove nitrates from its drinking water due to the abundance of local dairies and the relatively rapid transformation of nitrogen in manure into nitrates, which were ultimately transported into the community's drinking water supply. In February 2008, a group of Tulare County, California, residents filed a lawsuit over pollution permits the state water quality control board had issued to 1,600 dairies in the area after learning that wells and public water systems in the county contained unsafe amounts of nitrates. Tulare County has the country's highest concentration of cows used for the dairy industry. (HSUS Report, 3)

In addition to contaminating water, farm waste pollutes the air. Liquefied animal waste emits 160 known toxic gases, including hydrogen sulfide, a deadly gas with the characteristic stench of rotten eggs. Small droplets of waste also become airborne, carrying a plethora of microorganisms and pathogens into surrounding communities. For example, the Excel Dairy CAFO in Minnesota emitted so much hydrogen sulfide that the Minnesota Department of Health recommended neighbors evacuate the area. After years of violations, the Minnesota Pollution Control Agency closed the CAFO in 2009, but the lagoons full of manure remained.

In addition, during digestion, ruminants like cattle, sheep, and goats emit methane, an infamous "greenhouse gas" and key contributor to global warming. Livestock production is the largest methane source emitter in the world and the third largest in the United States (Shepherd, J. M. (2011, July) "Carbon, Climate Change, and Controversy," *Animal Frontiers*, 1(1), 5-13 2011). Most of this methane is a result of manure storage and enteric fermentation, which is methane produced in the digestive tract of an animal (Hermansen, J. E. & Kristensen, T., "Management Options to Reduce the Carbon Footprint of Livestock Products, *Animal Frontiers*, 1(1) 33-39 (7-2011). The EPA has estimated that, between 1990 and 2005, methane emissions from pig and cow operations rose 37 percent and 50 percent respectively, largely due to the greater amount and concentration of manure in lagoons and related storage systems. Decomposing farm waste releases greenhouse gases too, including methane and nitrous oxide, which contribute to climate change. Worldwide, agricultural emissions comprise nearly 20% of all greenhouse gas emissions generated by human activities.

Aquaculture also has a significant negative impact on the surrounding environment. Nutrients and effluents build up on the sea floor below the cages in which fish are farmed because the fish are contained in a confined space at high densities. Their waste, which includes both solids and dissolved nutrients like nitrogen, has the potential to build up below the cages and in the surrounding area. This creates the potential for algal blooms, which deplete the water of oxygen and can create damaging dead zones near aquaculture sites. Another environmental concern is the effect of the farmed fish on local wild fisheries. Disease and parasite outbreaks in fish farms can spread rapidly among farmed fish because of the high densities at which they are kept, and disease may spread to wild fish populations.

Generally, treated biochar of the present invention can be used in numerous applications to ameliorate a wide variety of these negative environmental impacts.

In connection with the raising of crops, biochars may be treated to increase or decrease hydrophilicity/hydrophobicity and/or impregnated with various fertilizers and other nutrients beneficial to healthy plant growth. As noted above, by infusing liquids into the pores of biochar, it has been discovered that additives infused within the pores of the biochar provide a time release effect or steady flow of some beneficial substances to the root zones of the plants and also can improve and provide a more beneficial environment for microbes which may reside or take up residence within the pores of the biochar. In particular, additive infused biochars placed in the soil prior to or after planting can dramatically reduce the need for high frequency application of additives, minimize losses caused by leaching and runoff and/or reduce or eliminate the need for controlled release fertilizers.

As previously noted, the utility of infusing the biochar with fertilizer is that the pores in biochar create a protective "medium" for carrying the nutrients to the soil that provides a more constant supply of available nutrients to the soil and plants and continues to act beneficially, potentially sorbing more nutrients or nutrients in solution even after introduction to the soil. By infusing the nutrients in the pores of the biochar, immediate oversaturation of the soil with the nutrients is prevented and a time released effect is provided, as illustrated in connection with FIGS. 20 and 21. As demonstrated in connection with FIGS. 20 and 21, biochars having pores infused with additives, using the infusion methods described above, have been shown to increase nutrient retention, increase crop yields and provide a steadier flow of fertilizer to the root zones of the plants.

In connection with animal raising, treated biochars and practices and methods provide for healthier animals, increase food intake efficiency, promote better digestion and reduce greenhouse gases, and combinations and variations of these, and other features that relate to the increased holding, retention and time discharge features of the present biochars and processes. In connection with the raising of animals, applications include: (1) use in providing nutrients for promoting growth and health in livestock, poultry, farm-raised wild animals (e.g. bison, deer and elk), farm-raised fish and other aquatic animals and horses and other members of the horse family; (2) the controlling of levels of certain pathogens, e.g. *salmonella* in poultry; (3) for veterinary uses, such as delivery systems for medications, supplements and/or vitamins; (4) promoting animal health by improving stalls, pens and bedding for animals by reducing noxious compounds and odors; (5) reducing or controlling emissions of noxious and greenhouse gases, such as ammonia, hydrogen sulfide and methane; (6) for manure treatment, including odor and emissions control in manure holding ponds; and for combinations and variations of these.

Figure 46:
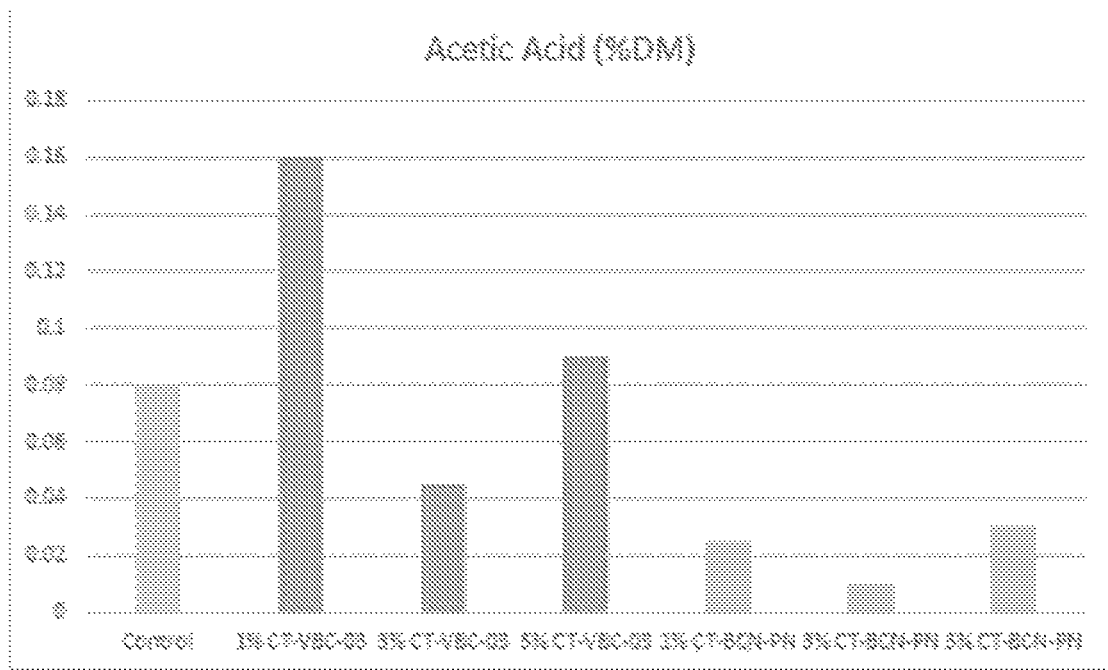
FIG. 46 is a chart showing the impact of biochars of different biomasses on acetic acid in manure.
Figure 47:
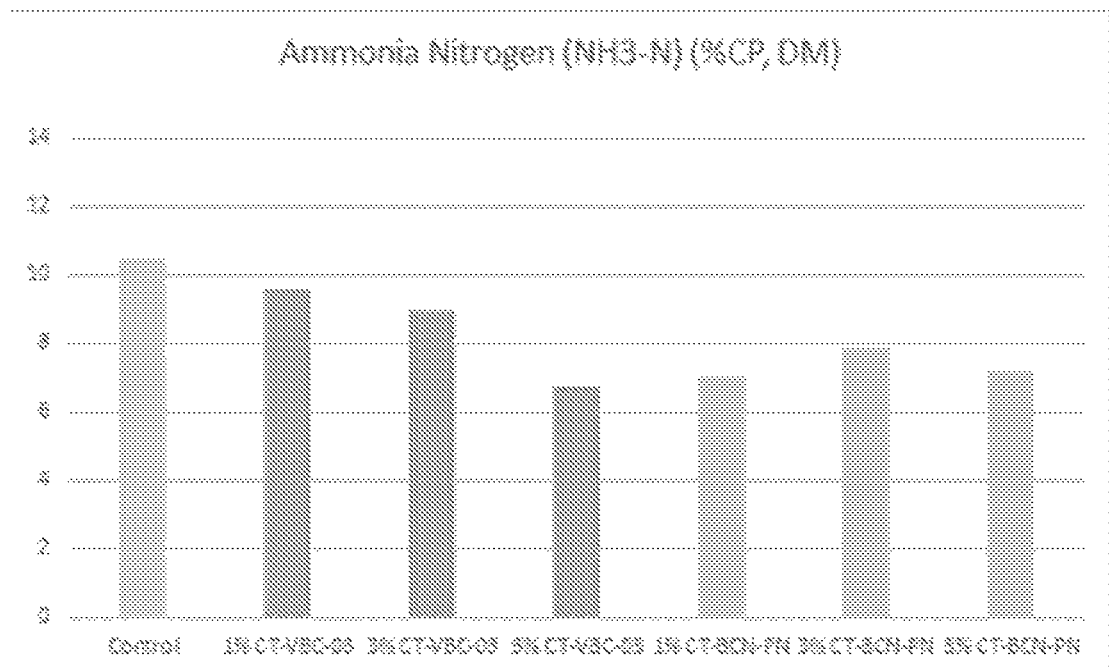
FIG. 47 is a chart showing the impact of biochars of different biomasses on ammonia nitrogen in manure.

For example, data from recent tests indicate a positive impact from the use of biochar on the control of ammonia and odors from VOCs in manures. In one test, a manure mixture was first made by mixing 1:1 w/w steer manure and chicken litter. Next, 50 g of urea (46-0-0) was added to 5 liters of distilled water. A control batch was created, and biochars derived from different biomasses were mixed into the remaining batches in ratios of 1%, 3% and 5% respectively. The treatments the treatments were kept in large 4 L flasks in an anaerobic environment for up to 2 weeks at a temperature up to 35 C. Results from the test, shown in FIGS. 46 and 47, strongly indicate that the biochars resulted in a reduction in both acetic acid content and ammonia, and dosages as low as 1% are efficacious. The charts in FIGS. 46 and 47 also show that different formulations and different treatments of biochar create efficacy in differing situations, in this case reduction of acetic acid and ammonia nitrogen.

In another test, treated biochar in differing amounts was spread over the entire floor of several chicken barns. Ammonia levels were monitored after seven and 14 days. Litter samples were taken prior to the initial application and at the end of each cycle to compare nutrient level retention and compare to prior samples taken. Results from the test indicated significant ammonia control and better overall chicken health due to better living conditions, even from the barns for which a lesser amount of biochar was spread. This reduction in ammonia benefits animal health, even without odor control.

In yet another test, research was conducted to determine the impact of the use of the biochar on enteric methane production, in vitro. Dr. Matthias Hess conducted the test by placing raw and treated biochars of various sizes at an inclusion rate of 1% to a vessel containing rumen fluid, artificial saliva, Ig of rumen solids, and 1 g super basic ration. Five different types of biochar were included in the experiment, with each different type being added to one treatment vessel. The sixth treatment was the control and had no added biochar. Biochar material used in treatments 1 through 5 are outlined in the table below to understand similarities and differences between the biochars used based on feedstock, post-treatment, and particle size. Post-treated biochars were treated in accordance with the methods taught above.

| Treatment | #1 | #2 | #3 | #4 | #5 |
|---|---|---|---|---|---|
| Biochar Feedstock | A | A | A | B | A |
| Biochar Treatment | X | X | None | X | Y |
| Biochar Particle Size | <0.3 mm | 0.3-1 mm | 0.3-1 mm | <0.3 mm | 0.3-1 mm |

Figure 48:
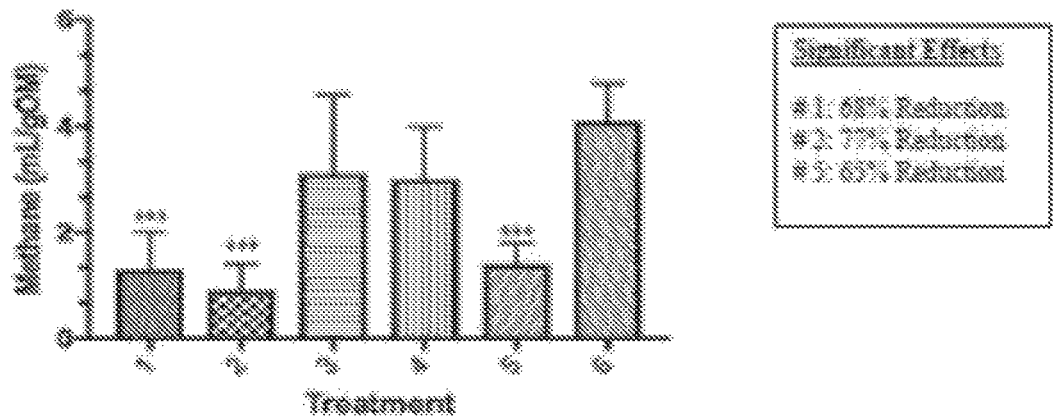
FIG. 48 illustrates a chart measuring the amount of methane collected per g of organic matter in a vessel designed to simulate methane production.
Figure 49:
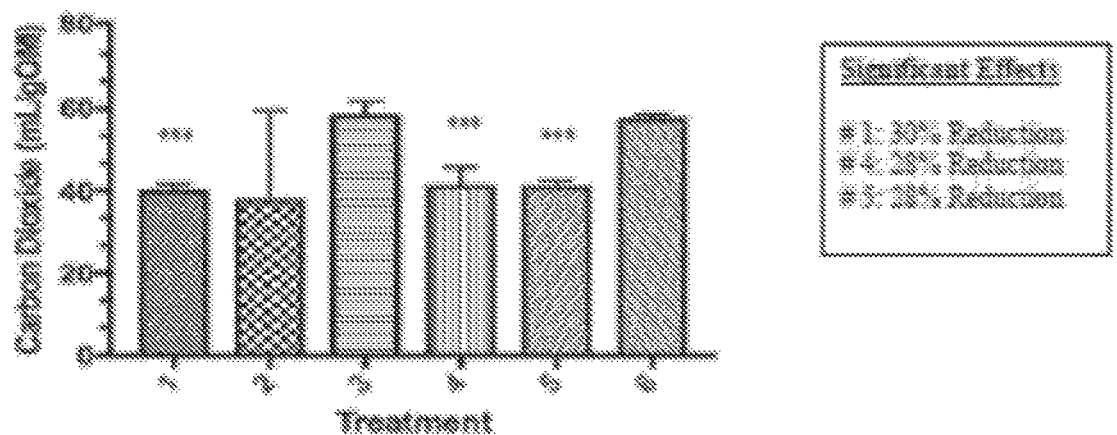
FIG. 49 illustrates a chart measuring the amount of carbon dioxide produced per g of Organic Matter.

Twenty-four ours after complete vessel set up, the amounts of methane, CO2 and total gas volume collected in the vessel were measured. FIG. 48 illustrates a chart measuring the amount of methane collected per g of organic matter and FIG. 49 illustrates a chart measuring the amount of carbon dioxide produced per g of Organic Matter. In both cases, the use of treated biochars reduced, and most of the time significantly reduced, the production of methane and carbon dioxide over that of the control (treatment #6). In addition in both cases, a the use of treated biochars vs raw biochar (treatment #3) reduced the amount of meth and carbon dioxide. Thus, establishing that through the addition of biochar treated in accordance with the present invention, the amount of methane and carbon dioxide produced by ruminant farm animals can be significantly reduced.

In addition, biochar treated as taught above, may provide an improvement over current methods of treating liquid manure. In its raw form, liquid manure gives off an acrid stench, which comes mainly from ammonia formed from the urea contained in the manure. Hans Peter Schmidt, in his article "Treating Liquid Manure with Biochar," *The Biochar Journal* available at www.biochar-journal.org/en/ct/29, September 2014 (cited as "Schmidt"), argues for the treatment of liquid manure using lactic acid bacteria in order to lower the pH in liquid manure to 3.5-4.5 by fermentation (which results in a highly acidic environment below the survival conditions for most types of bacteria, spore-forming organisms and enzymes), coupled with the biochar to fix toxic substances like ammonia. Schmidt notes that while treatment with biochar alone is effective, it is only by combining it with lactic acid fermentation that the liquid manure is disinfected and pathogenic bacteria killed off, and that to maintain the fermentative microbial environment, the liquid manure has to be regularly inoculated with lactic acid bacteria. Biochar treated as taught above, including inoculation with *Lactobacillus* species, can provide a more efficient way to combine the beneficial effects of both lactic acid fermentation with biochar fixation of toxic substances, as well as a more beneficial environment for these microbes so as to reduce the need for high frequency applications of these beneficial bacteria in the manure pit.

Further, biochar can be applied to clean lagoon water in accordance with the teaching of U.S. patent application Ser. No. 15/641,040 titled "TREATED BIOCHAR FOR USE IN WATER TREATMENT SYSTEMS" filed Jul. 3, 2017 (which is incorporated herein by reference in its entirety), to reduced nutrient loading, and to filter valuable nutrients from lagoon effluent.

In addition, biochar can potentially reduce gaseous nitrogen losses, soil remediation (for example absorption and capture of pesticide, contaminates, heavy metals or other undesirable, disadvantageous soil components), ground water remediation, other bioremediations, storm water run-off remediation and mercury remediation.

In summary, the treatment processes of the present information may be used to clean the pores of the biochar, ridding the pores of dioxins or other detrimental substances, or infiltrating the pores of biochar with a variety of substances, for a number of purposes, including but not limited to, infiltrating the pores of biochar with nutrients, vitamins, drugs, microbes, and/or other supplements, or a combination of any of the foregoing, for consumption by animals. The treated biochar may also be applied to animal pens, bedding, and/or other areas where animal waste is present to reduce odor and emission of unpleasant or undesirable VOCs. Furthermore it may be applied to compost piles to reduce odor, emissions, and temperature to enable the use of the food waste and animal feed in composting, such as that taught by co-owned U.S. Patent application 2015/429,104, which is herein incorporated by reference in its entirety. Biochar can also be applied to areas where fertilizer or pesticide runoff is occurring to slow or inhibit leaching and runoff. The biochar may also be treated with additives which make it easier to dispense or apply, such as non-toxic oils, anti-clumping/binding additives, surface drying agents, or other materials.

M. Systemic Benefits in Farm and Ranch Environments

Figure 50B:
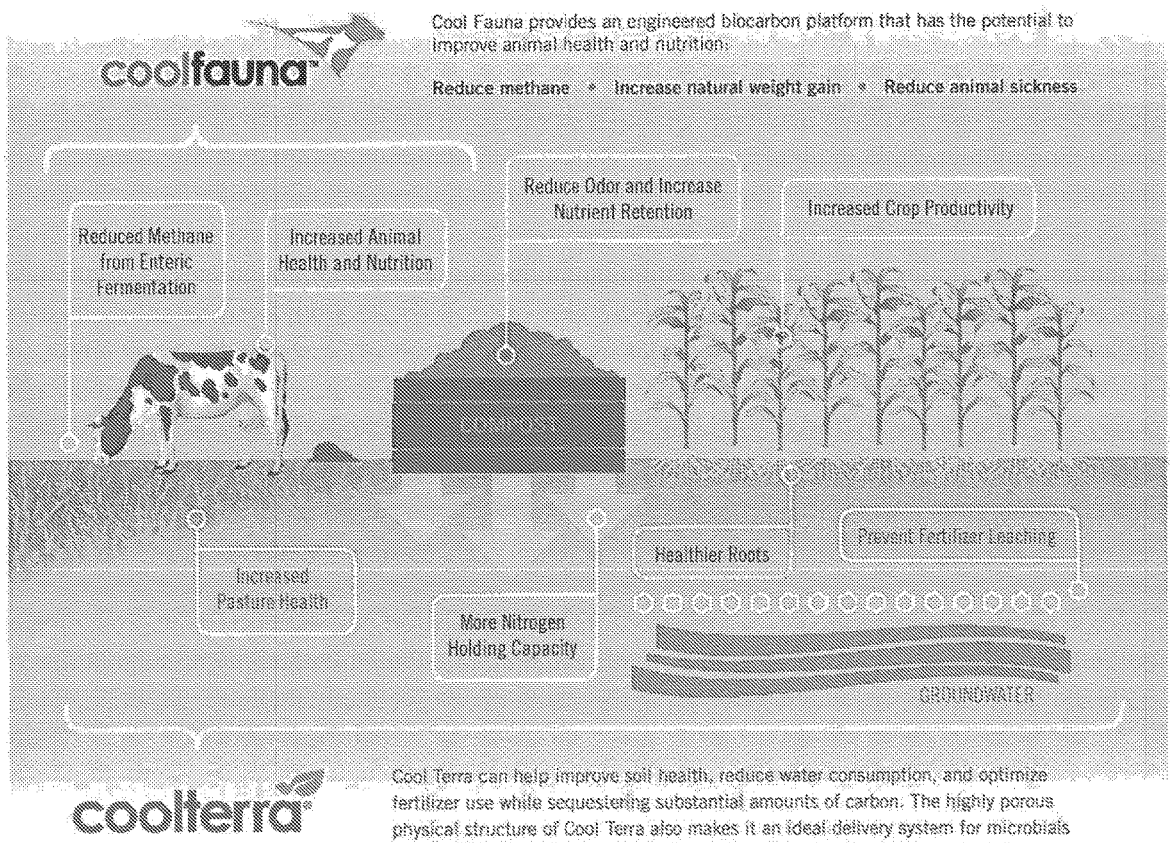
Figure 50C:

As previously discussed, in many cases the application of biochar or treated biochar is done to optimize a particular facet of an agricultural system—for example, application of biochar to improve crop yield or the care and maintenance of farm animals. However, if properly processed, treated, and deployed, biochar can be used in such a way that productivity of the entire farm or ranch system is improved, as illustrated by FIGS. 50a, 50b and 50c.

Typically, a working livestock farm involves several key process steps: (1) Livestock are bred and grown to maturity while consuming nutritional inputs (feed). During this process step, the growth rate, health, and emissions associated with the livestock all need to be managed and ideally optimized. The feed conversion rate of the livestock in question is key as ultimately the amount of biomass, or other marketable product such as milk, produced per unit of feed is key to the profitability and viability of the particular farm. Furthermore, livestock produce significant waste products during this phase, which can cause significant environmental impact if not managed correctly. (2) In some systems, these waste products, such as manure, are deployed into fields where feed or feed supplements are grown in order to improve productivity. (3) Sources of feed or feed supplements are grown using conventional agronomic techniques. During this stage, it is beneficial to optimize yield and improve soil health and quality, while reducing runoff and other environmental impacts, such as leaching, carbon emissions, and runoff. In systems designed to produce livestock for food, the livestock are slaughtered, but in systems involving milk or egg production, or production of other animal byproducts such as wool, the livestock remain alive and health/efficiency of feed remain key.

One manifestation of the present invention is as follows: (i) Producing a biochar or treated biochar with characteristics suitable for feeding to livestock or other animals. This biochar can optionally be produced from waste agricultural feedstock or biosolids found on the same farm—representing recycling of agricultural waste. (ii) Feeding the biochar to animals with the goal of increasing feed efficiency, improving animal health, removing/binding toxins, improving animal growth rates, reducing methane emissions, or any combination of these items. The biochar can be fed either separately, in many forms, or mixed with or incorporated with existing feed products. In some applications, the biochar can also be added to drinking water with a particle size amenable to suspension in water, or the biochar can be incorporated with the litter, which some animals consume. (iii) Allowing the material to pass through the digestive tracts of the animals in question and be expelled as a component of the manure or animal waste. Because biochar is a highly recalcitrant form of carbon, a large percentage of the material survives digestion and exists in manure. The properties of a properly engineered biochar will allow for greater adsorption or retention of nutrients in the manure as well as a potential reduction in the mobility of those nutrients and reductions in leaching and runoff from manure holding ponds, lagoons, or other facilities. The biochar has also been shown to alter the composition of the microbiome in said manure, reducing odor and other emissions of greenhouse gasses such as methane. Additional biochar, raw or treated in the same or different ways can be added to the manure at this step to improve the targeted outcomes. Furthermore, the biochar may be removed from the manure at this step also. This biochar, removed from the manure and laden with nutrients, can be used in a variety of agricultural applications. (iv) redeploying the biochar, either separately, or as a component of manure, for agronomic uses as a crop input or soil amendment e.g. as taught by U.S. patent application Ser. No. 15/393,176, titled ADDITIVE INFUSED BIOCHAR filed on Dec. 30, 2016 (which is incorporated herein by reference in its entirety), or adding the biochar (either as a component of manure or not) to either to other agricultural waste in an effort to produce compost, or enhance existing compost, e.g. as taught by U.S. patent application Ser. No. 15/429,104, titled BIOCHARS FOR USE IN COMPOSTING filed on Feb. 9, 2017 (which is incorporated herein by reference in its entirety) or to silage, to enhance the quality of the final silage product. It should be noted that at this stage, additional biochar may be added, or there may be processing steps involved to prepare the biochar to be deployed more effectively—these processing steps may include, but are not limited to, pelletizing, forming slurries, mixing or blending with other agricultural inputs, drying, wetting, adding further treatment steps as outlined above to either remove compounds, modify the properties of the biochar, or to introduce new compounds to improve the agronomic performance or the applicability of the material. (v) Growing and harvesting crops that have been treated with the biochar, and (vi) optionally feeding those crops to the livestock with or without the introduction of additional biochar. It should be noted that improving crop yield in this way directly reduces feed costs and improves systemwide efficiency. Additionally, the crop residue from this step that is unused or not suitable for consumption by animals can be pyrolyzed, optionally treated, and made into additional biochar which can then be used in one of the steps of this invention. This approach has the added benefit of sequestering carbon from the crop residues and improving overall farm efficiency.

Carbon sequestration in the form of biochar, is a topic that has had much focus in recent years, particularly as it relates to being produced to make carbon-negative biofuels or to reduce the carbon footprint of a conversion process, such as that taught by co-owned U.S. Patent application 2015/429, 104, which is herein incorporated by reference in its entirety. But, if the biochar production process is not connected to a conversion process nor is it being used to make biofuels, the user of said biochar can use it to reduce their carbon footprint. Thus, similar accounting method approaches can be used to determine the carbon-negativity of the produced biochar, untreated or treated. Then the biochar end-user who has a carbon positive farm, for example a farm or ranch, can apply that negative $CO_2e$ emissions to their net emissions, thus reducing their overall carbon footprint.

Not all biochars produced are carbon negative. In fact, creating a carbon-negative biochar can be difficult and more expensive, particularly the more advanced the biochar in production capacity, treatment, or formulation as additional processing steps require more energy and thus increase the carbon footprint of the production process. In order to create a carbon-negative biochar, particularly when using a continuous production process, the pyrolysis vapors often need to be recycled back to be combusted and used for pyrolysis, thus replacing natural gas. Sometimes replacing as much as 50% or even 80% or more of the natural gas needed.

Figure 52:
FIG. 52 illustrates the results of the analysis by showing a pictorial representation of how emissions are accounted for at each life cycle step in the production of the treated biochar.

To show that carbon-negative treated biochar can be produced, a heat and material balance created for a wood-based treated biochar plant, in which 80% of the natural gas requirement was replaced with pyrolysis vapors, was used in a Life Cycle Analysis (LCA) based on emission method. The LCA was completed using CARB 2.0 & GREET standards to determine the Carbon intensity and $CO_2$ Equivalent ($CO_2e$) per ton of treated biochar produced. The life of the treated biochar in soil was determined using data fit in literature (*Biochar for Environmental Management: Science, Technology, and Implementation*, $2^{nd}$ Edition edited by Lehman, Joseph) by using the resulting biochar's H:C ratio. The resulting carbon loss at 100 years was calculated to be 7.9%. The carbon intensity was calculated to be $-51.5$ $gCO_2/MJ_{treated\ biochar}$, which equates to 1.5 tons $CO_2e$ sequestered per ton of treated biochar placed in soil. FIG. 52 illustrates the results of the analysis by showing a pictorial representation of how emissions are accounted for at each life cycle step in the production of the treated biochar.

Also depicted in FIG. 52, is that the final step is the carbon sequestration of the treated biochar. This particular example assumed it was placed directly into a crop agricultural farm, but any use outlined previously could be modeled as long as that the final step includes sequestration into the ground.

Like other industries, the agricultural industry and the farmers/ranchers in it are starting to focus on understanding their carbon footprint and reducing it. In fact, Colorado State University in conjunction with the USDA NRCS has created a free online tool for farmers and ranchers to determine their carbon footprint. The tool known as COMET Farm, is a whole farm & ranch carbon and greenhouse gas accounting system. By way of example, two demo projects that are in the system will be considered to understand how use of a carbon negative biochar can reduce a cropland farm or an animal agricultural ranch.

The cropland demo was based on the 60-acre Allee Farm run by Iowa State University that is a non-irrigated corn-soybean rotated farm that uses conventional nitrogen fertilizer. It's baseline emissions are modeled to be 115.7 tonnes $CO_2e/yr$ (or 127.5 tons $CO_2e/yr$). The tool allows farmers to then project future carbon sequestration and greenhouse gas emission reductions if they adopt NRCS conservation practices. Currently biochar is not included in the NRCS nutrient management—replacing nitrogen fertilizer with soil amendments (Conservation Practice Standard 590) but it could be envisioned that a carbon negative biochar could fit well here or in its own future standard. Again by example, if this demo farm began applying 100 lbs/A of the treated biochar modeled in FIG. 52 annually, they would reduce their overall footprint by 4.5 tons $CO_2e/yr$ or by 3.5%. If the treated biochar also allows for reduced fertilizer use or run-off, as discussed previously, then the footprint can be reduced further.

The animal agriculture demo depicts a hypothetical feeding based on the fact sheet Grain Finishing Beef:Alternative Rations, Cattle Performance & Feeding Costs for small Feeders developed by Utah State University and the same university's Science Farm which is 500 head of cattle housed in dry lots June through November and fed 10 lbs corn and 16 lbs alfalfa/grass hay per head daily. Manure is temporarily stacked and then stored in long-term stockpiles. The Beef-Steer Stockers demos baseline emissions based on enteric production and solid storage are 332.5 tonnes $CO_2e/yr$ (or 366.5 tons $CO_2e/yr$). If this demo ranch began using the carbon-negative treated biochar modeled in FIG. 52 either in the animal feed or mixing into their manure their carbon footprint would be reduced as the carbon of the biochar would eventually be sequestered to the land through the manure stockpiles or use as fertilizer. Again by example, if this demo ranch began adding said biochar at 0.2% of feed, they would reduce their overall footprint by 3.51 tons $CO_2e/yr$ or by 1%. In addition if the treated biochar also reduced enteric emissions and volatile organic emissions in the manure solid storage, as discussed previously, the footprint can be reduced further.

N. Biochar to Control Airborne or Waterborne Pollutants

Many farms have to deal with the migration of pollutants from a source of emission to neighboring properties. This migration can either occur through the air or through the water. Some examples of common airborne pollutants from livestock farms are ammonia gas ($NH_3$), methane ($CH_4$), and hydrogen sulfide ($H_2S$). Of these, ammonia and hydrogen sulfide are malodorous, while methane is odorless. Biochar, when deployed into the systems that generate these pollutants has shown the ability to reduce the levels of airborne ammonia and other odor causing gasses. However, treated biochar has the potential to address these airborne substances in even more profound ways. For example, biochar can be infused with sodium hydroxide (NaOH) which improves its capacity to solubilize hydrogen sulfide ($H_2S$). Other compounds such as sodium hypochlorite (NaClO) can be infused to target other odors. Furthermore, the actual physical structure of the biochar can be targeted to control odors through the creation of materials with higher surface areas—either by adjusting pyrolysis conditions, activation processes, or treatment processes that cause cavitation or surface erosion. These methods can be combined with the infiltration of compounds designed to react with odor causing gasses. The biochar can also be infused or inoculated with biological systems designed to consume or degrade airborne pollutants. For example, biochar may be infused with methane assimilating bacteria (MAB), methanotrophs, or ammonia oxidizing bacteria (AAOB) to assist in this degradation process. Once prepared, the biochar may be used directly in filtration applications such as routing exhaust gasses from a chicken production facility over a bed or multiple beds of biochar, or by adding the biochar to the environment itself, either to a manure pile or lagoon, animal bedding, compost heap or pile, or other point of odor emission. To reduce the mobility of pollutants in liquid form, several approaches can be taken, and biochar can be constructed or treated to target differing pollutants. The most direct method for reducing pollutants from liquid effluent is to pass the liquid over the biochar (either treated or untreated) and allow the biochar to sorb the targeted compounds. It has been shown that varying treatments offer varying performance levels with respect to common pollutants For example, Dr. Jim Ippolito with the Department of Soil and Crop Sciences at Colorado State University and formerly with the USDA-Agricultural Research Service in Kimberly, Idaho in conjunction with Dr. Mark G. Johnson with the US EPA in Corvallis, Oregon compared different treated and raw biochars to determine their effectiveness on sorbing metals from solid mine-waste leaching. The metal sorption experiment was done using metal-laden soil from the Tri-State Mining District in Southwestern Missouri and the Synthetic Precipitation Leaching Procedure (SPLP) to extract the metals from the soil. The SPLP extract was then contacted with the biochars for 24 hours. Cadmium, copper, and zinc concentration of the extract prior and post contact was then compared to determine the percent removal of the metals. The results depicted in FIG. 51 show that different treated biochar formulations had different removal efficiencies. Formulation 3, showed the best results removing greater than 99% of all three metals tested. These results show treated biochars potential benefits, particularly realizing that Cadmium is considered a difficult metal to remove.

However, there are also indirect methods to remove or reduce the mobility of liquid pollutants from farm systems. One of these methods is to improve the uptake of soluble nutrients by plant systems, which in turn will allow reductions in application of nutrients and also reduction of leachable pollutants. It has been shown that biochar treated in a particular way can delay the mobility of several forms of soluble nutrients in the root zone, allowing the plant system greater time to uptake these nutrients, effectively removing them from the soil and sequestering them in the plant tissue. Alternatively, biochar can be deployed as a component of other liquid pollutant control mechanisms such as biofilters to improve their efficiency. When deployed as a component of a biofilter, biochar can improve or enhance the microbial activity while still allowing acceptable infiltration/flow rates which ultimately can improve the effectiveness or efficiency of the biofilter. Where tile drainage is used commonly, biochar can be deployed at the outlets in conjunction with plant systems to remove soluble nutrients. Finally, in heavy soils, certain forms of treated biochar have been shown to improve infiltration, which can allow nutrition (or other inputs such as pesticides) to more effectively penetrate the soil and progress to the root zone of the plants, thereby reducing pollution due to runoff of agricultural inputs.

While the above teaches the use of treated biochar to reduce the environmental impact of farming, it is within the scope of the present invention to employ either raw or treated biochar for such purposes.

As set forth above, the treated biochar of the present invention may be used in various agriculture activities, as well as other activities and in other fields. Additionally, the treated biochar may be used, for example, with: farming systems and technologies, operations or activities that may be developed in the future; and with such existing systems, operations or activities which may be modified, in part, based on the teachings of this specification. Further, the various treated biochar and treatment processes set forth in this specification may be used with each other in different and various combinations. Thus, for example, the processes and resulting biochar compositions provided in the various examples provided in this specification may be used with each other; and the scope of protection afforded the present inventions should not be limited to any particular example, process, configuration, application or arrangement that is set forth in a particular example or figure. Although this specification focuses on applications related to the reduction of the negative environmental impact of farming, it should be understood that the materials, compositions, structures, apparatus, methods, and systems, taught and disclosed herein, may have applications and uses for many other activities in addition to agriculture for example, as filters, additives, and in remediation activities, among other things.

Although this specification focuses on applications related to the reduction of the negative environmental impact of farming, it should be understood that the materials, compositions, structures, apparatus, methods, and systems, taught and disclosed herein, may have applications and uses for many other activities in addition to agriculture for example, as filters, additives, and in remediation activities, among other things.

It is understood that one or more of these may be preferred for one application, and another of these may be preferred for a different application. Thus, these are only a general list of preferred features and are not required, necessary and may not be preferred in all applications and uses.

It is noted that there is no requirement to provide or address the theory underlying the novel and groundbreaking functionality, performance or other beneficial features and properties that are the subject of, or associated with, implementations of the present inventions. Nevertheless, to the extent that various theories are provided in this specification it is done to further advance the art in this important area. These theories put forth in this specification, unless expressly stated otherwise, in no way limit, restrict or narrow the scope of protection to be afforded the claimed inventions. These theories many not be required or practiced to utilize the present inventions. It is further understood that the present inventions may lead to new, and heretofore unknown theories to explain the functionality, performance or other beneficial features and properties that are the subject of, or associated with, embodiments of the methods, articles, materials, and devices of the present inventions; and such later developed theories shall not limit the scope of protection afforded the present inventions.

Those skilled in the art will recognize that there are other methods that may be used to treat biochar in a manner that forces the infusion of liquids into the pores of the biochar without departing from the scope of the invention. The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A method for reducing an overall environmental impact of farming or ranching, the method comprising:
   (i) obtaining treated biochar, wherein the treated biochar is produced from a treatment process on biochar to remove a dioxin from pores of the biochar and infuse a liquid additive into the pores of the biochar for ingestion by farm animals; and
   (ii) causing the farm animals to ingest the treated biochar, thereby producing ingested treated biochar wherein the causing is achieved by combining the treated biochar with animal bedding for the farm animals, thereby reducing an odor emanating from the animal bedding and reducing a toxicity to the farm animals.

2. The method of claim 1, wherein the treatment process does not exclusively comprise submersing the biochar in a liquid solution to achieve infusing of the liquid additive into the pores of the biochar and does not exclusively comprise using steam to achieve infusing of the liquid additive into the pores of the biochar.

3. The method of claim 2, wherein the infusing of the liquid additive into the pores of the biochar is achieved using a surfactant.

4. The method of claim 2, wherein the infusing of the liquid additive into the pores of the biochar is achieved by combining the biochar and the liquid additive in a vessel and pulling a vacuum on the vessel or applying positive pressure on the content of the vessel.

5. The method of claim 1, wherein the treatment process comprises immersing the biochar in a treating liquid, varying a pressure in a vessel for a predetermined period of time, and returning the pressure in the vessel to its original pressure.

6. The method of claim 1, wherein the treatment process comprises immersing the biochar in a solution containing a surfactant.

7. The method of claim 1, wherein the liquid additive comprises at least one nutrient, vitamin, drug, microbe, or supplement for the farm animals.

8. The method of claim 1, further comprising: redeploying the treated biochar, wherein the redeploying is achieved by combining the ingested treated biochar with the animal bedding or applying the ingested treated biochar to lagoons.

9. The method of claim 1, wherein the liquid additive comprises at least one coloring, flavor agent, or coating.

10. A method for reducing an overall environmental impact of farming or ranching, the method comprising:
   obtaining treated biochar, wherein the treated biochar is produced from a treatment process on biochar to detoxify the biochar and infuse an additive into pores of the biochar; and
   combining the treated biochar with animal bedding for farm animals, thereby (i) causing the farm animals to ingest the treated biochar, thereby producing ingested treated biochar, and thereby reducing methane from enteric fermentation and (ii) reducing a toxicity to the farm animals.

11. The method of claim 10, wherein the treatment process does not exclusively comprise submersing the biochar in a liquid solution to achieve infusing of the additive into the pores of the biochar and does not exclusively comprise using steam to achieve infusing of the additive into the pores of the biochar.

12. The method of claim 11, wherein the infusing of the additive into the pores of the biochar is achieved using a surfactant.

13. The method of claim 11, wherein the infusing of the additive into the pores of the biochar is achieved by combining the biochar and the additive in a vessel and pulling a vacuum on the vessel or applying positive pressure on the content of the vessel.

14. The method of claim 10, wherein the treatment process comprises immersing the biochar in a treating liquid, varying a pressure in a vessel for a predetermined period of time, and returning the pressure in the vessel to its original pressure.

15. The method of claim 10, wherein the treatment process comprises immersing the biochar in a solution containing a surfactant.

16. The method of claim 10, wherein the additive comprises at least one nutrient, vitamin, drug, microbe, supplement, coloring, or flavor agent for the farm animals.

17. The method of claim 10, further comprising:
   redeploying the treated biochar, wherein the redeploying is achieved by combining the ingested treated biochar with the animal bedding or applying the ingested treated biochar to lagoons.

18. The method of claim 10, wherein the treatment process to detoxify the biochar removes dioxins from the pores of the biochar, thereby reducing toxicity to the farm animals.

19. A method for using treated biochar to reduce an overall environmental impact of farming or ranching, the method comprising:
   obtaining treated biochar, wherein the treated biochar is produced from a treatment process, wherein the treatment process infuses a liquid additive into pores of biochar and removes dioxins from the pores of the biochar, and
   combining the treated biochar with compost, animal bedding, or manure piles, thereby reducing odor and increasing nutrient retention.

20. The method of claim 19, wherein the treated biochar is treated to reduce methane from enteric fermentation when ingested by a farm animal.

* * * * *